US009924721B2

(12) United States Patent
Hillebrand et al.

(10) Patent No.: US 9,924,721 B2
(45) Date of Patent: Mar. 27, 2018

(54) MALONIC ESTER DERIVATIVES OF HETEROARYLPIPERIDINES AND -PIPERAZINES AS FUNGICIDES

(71) Applicant: BAYER CROPSCIENCE AKTIENGESELLSCHAFT, Monheim am Rhein (DE)

(72) Inventors: Stefan Hillebrand, Neuss (DE); Matthias Riedrich, Cologne (DE); Sebastian Hoffmann, Neuss (DE); Mark James Ford, Schmitten (GB); Joachim Telser, Wuppertal (DE); Mazen Es-Sayed, Langenfeld (DE); Guenter Hoemberger, Eppstein (DE); Pierre Wasnaire, Duesseldorf (DE); Ulrike Wachendorff-Neumann, Neuwied (DE); Tomoki Tsuchiya, Lyons (FR); Valerie Toquin, Saint-Romain-au-Mont-d'Or (FR)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 18 days.

(21) Appl. No.: 14/914,230

(22) PCT Filed: Aug. 26, 2014

(86) PCT No.: PCT/EP2014/068053
§ 371 (c)(1),
(2) Date: Feb. 24, 2016

(87) PCT Pub. No.: WO2015/028457
PCT Pub. Date: Mar. 5, 2015

(65) Prior Publication Data
US 2016/0198713 A1 Jul. 14, 2016

(30) Foreign Application Priority Data
Aug. 28, 2013 (EP) .................... 13182045

(51) Int. Cl.
| C07D 401/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 421/00 | (2006.01) |
| A01N 43/80 | (2006.01) |
| A01N 43/82 | (2006.01) |
| A01N 43/78 | (2006.01) |
| C07D 417/14 | (2006.01) |

(52) U.S. Cl.
CPC ............. *A01N 43/80* (2013.01); *A01N 43/78* (2013.01); *A01N 43/82* (2013.01); *C07D 417/14* (2013.01)

(58) Field of Classification Search
None
See application file for complete search history.

(56) References Cited

U.S. PATENT DOCUMENTS

| 7,943,774 | B2 | 5/2011 | Cristau et al. |
| 8,349,870 | B2 * | 1/2013 | Kamireddy .......... C07D 417/14 514/326 |
| 8,748,420 | B2 | 6/2014 | Cristau et al. |
| 9,029,549 | B2 | 5/2015 | Cristau et al. |
| 9,150,565 | B2 | 10/2015 | Tsuchiya et al. |
| 9,220,266 | B2 | 12/2015 | Cristau et al. |
| 9,247,748 | B2 | 2/2016 | Cristau et al. |
| 2010/0292275 | A1 * | 11/2010 | Kamireddy .......... C07D 417/14 514/326 |
| 2012/0122928 | A1 | 5/2012 | Tsuchiya et al. |

(Continued)

FOREIGN PATENT DOCUMENTS

| WO | 2007/014290 A2 | 2/2007 |
| WO | 2008/013622 A2 | 1/2008 |
| WO | 2008/013925 A2 | 1/2008 |
| WO | 2008/091580 A2 | 7/2008 |
| WO | 2008/091594 A2 | 7/2008 |
| WO | 2009/055514 A2 | 4/2009 |
| WO | 2009/094407 A2 | 7/2009 |
| WO | 2009/094445 A2 | 7/2009 |
| WO | 2009132785 A1 | 11/2009 |
| WO | 2010/037479 A1 | 4/2010 |
| WO | 2010/065579 A2 | 6/2010 |

(Continued)

OTHER PUBLICATIONS

Ivashchenko et al., "Synthesis and study of 2-1(pyrazoly) purine derivatives." Database CA [Online] XP002720037, 1978.

(Continued)

*Primary Examiner* — Andrew D Kosar
*Assistant Examiner* — Ben S Michelson
(74) *Attorney, Agent, or Firm* — McBee Moore Woodward & Vanik IP, LLC

(57) ABSTRACT

Malonic ester derivatives of the formula (I)

in which the symbols $A^1$, $A^2$, Y, $R^{10}$, p, X, $R^2$, G, Q, $L^2$ and $R^1$ are each as defined in the description, and salts, metal complexes and N-oxides of the compounds of the formula (I), and the use thereof for controlling phytopathogenic harmful fungi and processes for preparing compounds of the formula (I).

11 Claims, No Drawings

(56) References Cited

U.S. PATENT DOCUMENTS

2015/0218152 A1    8/2015    Hillebrand et al.

FOREIGN PATENT DOCUMENTS

| WO | 2011/018415 A2 | 2/2011 |
|---|---|---|
| WO | 2011018401 A1 | 2/2011 |
| WO | 2011/076510 A1 | 6/2011 |
| WO | 2011/076699 A1 | 6/2011 |
| WO | 2011/134969 A1 | 11/2011 |
| WO | 2011/146182 A1 | 11/2011 |
| WO | 2011/147765 A1 | 12/2011 |
| WO | 2012/020060 A1 | 2/2012 |
| WO | 2012/025557 A1 | 3/2012 |
| WO | 2012/055837 A1 | 5/2012 |
| WO | 2012/082580 A2 | 6/2012 |
| WO | 2012/104273 A1 | 8/2012 |
| WO | 2013/037768 A1 | 3/2013 |
| WO | 2013/098229 A2 | 7/2013 |

OTHER PUBLICATIONS

Hu et al., "Synthesis and herbicidal activities of novel 4-(4-(5-methyl-3-arylisoxazol-4-yl) thiazol-2-yl) piperidyl carboxamides and thiocarboxamides." Molecules, 2009, 14(3), 1288-1303, XP002609686.

International Search Report dated Dec. 19, 2014, issued in PCT/EP2014/068053.

* cited by examiner

MALONIC ESTER DERIVATIVES OF HETEROARYLPIPERIDINES AND -PIPERAZINES AS FUNGICIDES

CROSS REFERENCE TO RELATED APPLICATIONS

This application is a § 371 National Stage Application of PCT/EP2014/068053, filed 26 Aug. 2014 which claims priority to EP 13182045.8, filed 28 Aug. 2013.

BACKGROUND

Field of the Invention

The invention relates to malonic ester derivatives of heteroarylpiperidines and -piperazines, to agrochemically active salts thereof, to use thereof and to methods and compositions for controlling phytopathogenic harmful fungi in and/or on plants or in and/or on seed of plants, to processes for producing such compositions and treated seed, and to use thereof for controlling phytopathogenic harmful fungi in agriculture, horticulture and forestry, in animal health, in the protection of materials and in the domestic and hygiene sector. The present invention further relates to a process for preparing malonic ester derivatives of heteroarylpiperidines and -piperazines.

Description of Related Art

It is already known that particular heterocyclically substituted piperidines and piperazines can be used as fungicidal crop protection compositions (see WO 07/014290, WO 08/013925, WO 08/013622, WO 08/091594, WO 08/091580, WO 09/055514, WO 09/094407, WO 09/094445, WO 09/132785, WO 10/037479, WO 10/065579, WO 11/076510, WO 11/018415, WO 11/018401, WO 11/076699, WO 11/134969, WO 11/146182, WO 11/147765, WO 12/020060, WO 12/055837, WO 12/025557, WO 12/082580, WO 12/104273, WO 13/037768, WO13/098229). However, specifically at relatively low application rates, the fungicidal efficacy of these compounds is not always adequate.

Since the ecological and economical demands made on modern crop protection agents are increasing constantly, for example with respect to activity spectrum, toxicity, selectivity, application rate, formation of residues and favourable manufacture, and there can furthermore be problems, for example, with resistances, there is a constant need to develop novel crop protection compositions, in particular fungicides, which, at least in some areas, have advantages over the known ones.

SUMMARY

It has now been found that, surprisingly, the present malonic ester derivatives of heteroarylpiperidines and -piperazines achieve at least some aspects of the objects mentioned and are suitable for use as crop protection compositions, especially as fungicides.

The invention provides compounds of the formula (I)

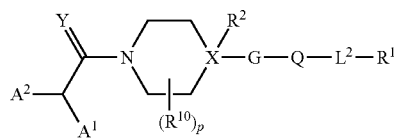

(I)

in which the radicals are each defined as follows:
$A^1$ is cyano, $—C(=O)R^{L1}$ or $—C(=S)R^{L1}$,
$A^2$ is hydrogen, halogen, nitro, cyano, alkoxy, haloalkoxy, $—NR^3R^4$, formylamino, alkylcarbonylamino, haloalkylcarbonylamino, alkylthio, haloalkylthio, arylthio, alkylsulphinyl, haloalkylsulphinyl, arylsulphinyl, alkylsulphonyl, haloalkylsulphonyl, arylsulphonyl, alkylsulphinyloxy, haloalkylsulphinyloxy, arylsulphinyloxy, alkylsulphonyloxy, haloalkylsulphonyloxy, or arylsulphonyloxy, wherein aryl is optionally substituted by one, two or three groups independently selected from halogen, CN, $NH_2$, $NO_2$, OH, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_3$-$C_6$-cycloalkyl, or $C_3$-$C_6$-cycloalkoxy, or
$A^2$ is an optionally benzofused, unsubstituted or substituted 5- or 6-membered heteroaryl which may contain up to four substituents, where the substituents on carbon are each independently selected from $Z^{A-1}$ and the substituents on nitrogen are each independently selected from $Z^{A-2}$,
$Z^{A-1}$ and $R^{G1}$ are the same or different and are each independently hydrogen, halogen, hydroxyl, thiol, nitro, cyano, $—C(=O)H$, $—C(=O)OH$, alkyl, alkenyl, alkynyl, haloalkyl, haloalkenyl, haloalkynyl, cycloalkyl, halocycloalkyl, hydroxyalkyl, formylalkyl, alkoxyalkyl, alkylcarbonylalkyl, alkylcycloalkyl, alkoxy, alkylcycloalkylalkyl, alkylthio, haloalkylthio, alkynylthio, alkenyloxy, alkynyloxy, haloalkoxy, alkoxyalkoxy, alkylcarbonyloxy, haloalkylcarbonyloxy, cycloalkylcarbonylamino, alkylsulphonylamino, haloalkylsulphonylamino, phenylsulphonylamino, cycloalkylalkyl, halocycloalkylalkyl, cycloalkylcycloalkyl, alkoxycarbonyloxy, alkylcarbonylthio, alkylsulphinyl, haloalkylsulphinyl, alkylsulphonyl, haloalkylsulphonyl, alkylcarbonyl, haloalkylcarbonyl, alkoxycarbonyl, alkylaminocarbonyloxy, $—C(=O)NR^3R^4$ or $—NR^3R^4$,
$Z^{A-2}$ is the same or different and are each independently hydrogen, $—C(=O)H$, $—C(=O)NR^3R^4$, alkyl, alkenyl, alkynyl, haloalkyl, haloalkenyl, haloalkynyl, cycloalkyl, halocycloalkyl, alkylcycloalkyl, cycloalkylalkyl, alkoxyalkyl, alkylsulphonyl, haloalkylsulphonyl, cycloalkylsulphonyl, phenylsulphonyl, alkylcarbonyl, haloalkylcarbonyl, alkoxycarbonyl, haloalkoxycarbonyl, cycloalkoxycarbonyl, phenyl or benzyl,
$R^3$ and $R^4$ are the same or different and are each independently hydrogen, alkyl, alkenyl, alkynyl, haloalkyl, cycloalkyl, benzyl or phenyl,
Y are sulfur or oxygen,
$R^{L1}$ is amino, $NR^3R^4$, hydroxyamine, alkylthio, haloalkylthio, alkylcarbonyloxy, haloalkylcarbonyloxy, alkylcarbonylamino, haloalkylcarbonylamino, cyano, $C_2$-$C_{10}$-alkoxy, haloalkoxy, cycloalkoxy, halocycloalkoxy, alkenyloxy, alkynyloxy, phenyloxy, or benzyloxy, or a 5- or 6-membered heterocyclyloxy containing one to three heteroatoms independently selected from O, S and N, providing that the heterocycle does not contain adjacent oxygen atoms, adjacent sulphur atoms, or adjacent sulphur and oxygen atoms, wherein alkoxy, haloalkoxy, cycloalkoxy, halocycloalkoxy, alkenyloxy, alkynyloxy, alkoxyalkoxy are optionally substituted by one or more groups independently selected from halogen, CN, $NH_2$, $NO_2$, OH, $=O$, $=S$, $C_1$-$C_4$-alkyl, $C_1$-$C_4$-haloalkyl, $C_1$-$C_4$-alkoxy, $C_1$-$C_4$-haloalkoxy, and $C_1$-$C_4$-alkoxy-$C_1$-$C_4$-alkyl, and wherein phenyloxy, benzyloxy, heterocyclyloxy are optionally substituted by one or more groups independently selected from halogen, CN, $NH_2$, $NO_2$, OH, $C_1$-$C_4$-alkyl, $C_1$-$C_4$-haloalkyl, $C_1$-$C_4$-alkoxy, $C_1$-$C_4$- haloalkoxy, $C_1$-$C_4$-alkoxy-$C_1$-$C_4$-alkyl, $C_3$-$C_6$-cycloalkyl, or $C_3$-$C_6$-cycloalkoxy, X is carbon or nitrogen, $R^2$ is hydrogen, alkyl, alkenyl, haloalkyl, alkoxy, halogen, cyano or hydroxyl, $R^{10}$ is the same or different and is independently hydrogen, alkyl, alkenyl, haloalkyl, alkoxy, halogen, cyano or hydroxyl, p is 0, 1 or 2, G is

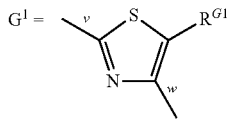

where the bond identified by "v" is bonded directly to the piperidine or piperazine ring and where the bond identified by "w" is bonded directly to Q, Q is saturated or partly or fully unsaturated 5-membered heterocyclyl which is substituted by $L^2$-$R^1$ according to the general formula (I) and may otherwise be unsubstituted or substituted, where the substituents are each independently selected from $R^5$, $R^5$ is the same or different and is independently:

bonded to carbon of the 5-membered heterocyclyl of Q: oxo, thioxo, hydrogen, halogen, cyano, hydroxyl, nitro, amino, —CHO, —C(=O)OH, —C(=O)NH$_2$, —NR$^7$R$^8$, alkyl, alkenyl, alkynyl, haloalkyl, haloalkenyl, haloalkynyl, cycloalkyl, halocycloalkyl, alkylcycloalkyl, cycloalkylalkyl, cycloalkylcycloalkyl, halocycloalkylalkyl, alkylcycloalkylalkyl, cycloalkenyl, halocycloalkenyl, alkoxyalkyl, cycloalkoxyalkyl, alkoxyalkoxyalkyl, alkylthioalkyl, alkylsulphinylalkyl, alkylsulphonylalkyl, alkylaminoalkyl, dialkylaminoalkyl, haloalkylaminoalkyl, cycloalkylaminoalkyl, alkylcarbonyl, haloalkylcarbonyl, cycloalkylcarbonyl, alkoxycarbonyl, cycloalkoxycarbonyl, cycloalkylalkoxycarbonyl, alkylaminocarbonyl, dialkylaminocarbonyl, cycloalkylaminocarbonyl, haloalkoxyalkyl, hydroxyalkyl, alkoxy, haloalkoxy, cycloalkoxy, halocycloalkoxy, cycloalkylalkoxy, alkenyloxy, haloalkenyloxy, alkynyloxy, haloalkynyloxy, alkoxyalkoxy, alkylcarbonyloxy, haloalkylcarbonyloxy, cycloalkylcarbonyloxy, alkylcarbonylalkoxy, alkylthio, haloalkylthio, cycloalkylthio, alkylsulphinyl, haloalkylsulphinyl, alkylsulphonyl, haloalkylsulphonyl, cycloalkylsulphonyl, trialkylsilyl, alkylsulphonylamino, haloalkylsulphonylamino, bonded to nitrogen of the 5-membered heterocyclvl of Q: hydrogen, alkyl, alkenyl, alkynyl, haloalkyl, haloalkenyl, haloalkynyl, cycloalkyl, halocycloalkyl, alkylcycloalkyl, cycloalkylalkyl, phenyl, benzyl, alkylsulphonyl, —C(=O)H, alkoxycarbonyl or alkylcarbonyl, m is 0, 1 or 2, $R^7$ is hydrogen, alkyl, haloalkyl, cycloalkyl, alkylcarbonyl, haloalkylcarbonyl, alkoxycarbonyl or haloalkoxycarbonyl, $R^8$ is alkyl, haloalkyl, cycloalkyl, alkylcarbonyl, haloalkylcarbonyl, alkoxycarbonyl, haloalkoxycarbonyl or -$L^5$$R^1$, $L^5$ is —O—, —C(=O)—, S(=O)$_m$ or CHR$^{20}$, $L^2$ is a direct bond, —O—, —C(=O)—, —S(=O)$_m$—, —CHR$^{20}$— or —NR$^{21}$—

$R^{20}$ is hydrogen, alkyl or haloalkyl, $R^{21}$ is hydrogen, alkyl, haloalkyl, cycloalkyl, alkylcarbonyl, haloalkylcarbonyl, alkoxycarbonyl or haloalkoxycarbonyl, $R^1$ is phenyl, benzyl, naphthalenyl, an optionally benzofused, substituted 5- or 6-membered heteroaryl which is substituted at least once by a substituent $Z^4$ and may otherwise be unsubstituted or substituted, where the substituents are each independently selected from $Z^4$ and optionally from $Z^1$, or $R^1$ is a 5- to 8-membered nonaromatic (saturated or partially saturated) carbocyclic ring, a 5-, 6- or 7-membered nonaromatic heterocyclyl radical or an 8- to 11-membered carbocyclic or heterocyclic bicyclic ring, each of which is substituted at least once by a substituent $Z^4$ and may otherwise be unsubstituted or substituted, where the substituents are each independently selected from $Z^4$ and optionally from oxo, thio or $Z^1$, $Z^1$ is bonded to carbon of $R^1$:

hydrogen, halogen, hydroxyl, amino, nitro, amino, cyano, alkyl, alkenyl, alkynyl, haloalkyl, haloalkenyl, haloalkynyl, cycloalkyl, halocycloalkyl, hydroxyalkyl, alkoxyalkyl, alkylcycloalkyl, alkoxy, alkylcycloalkylalkyl, alkylthio, haloalkylthio, haloalkoxy, alkylcarbonyloxy, alkylamino, dialkylamino, cycloalkylalkyl, cycloalkylcycloalkyl, alkylcarbonylthio, alkylsulphinyl, haloalkylsulphinyl, alkylsulphonyl, haloalkylsulphonyl, alkylcarbonyl, alkoxycarbonyl, alkylaminocarbonyl, dialkylaminocarbonyl, trialkylsilyl, and cycloalkylamino, cycloalkenyl, halocycloalkenyl, cycloalkoxyalkyl, halocycloalkoxy, cycloalkylthio, cycloalkoxy, cycloalkylalkoxy, cycloalkylamino, halocycloalkylalkyl, cycloalkylcarbonyl, cycloalkylsulphonyl, or -$L^3$$Z^3$, bonded to nitrogen of $R^1$:

alkyl, alkylcarbonyl, alkoxycarbonyl or alkoxy, $L^3$ is a direct bond, —C(=O)—, sulfur, oxygen, —NR$^{21}$—, —C(=S)—, —S(=O)$_m$—, —CHR$^{20}$—, —CHR$^{20}$—CHR$^{20}$—, —CR$^{20}$=CR$^{20}$—, —OCHR$^{20}$—, —CHR$^{20}$O—, $L^4$ is —C(=O)O—, —C(=O)NR$^3$—, —OC(=O)—, —NR$^3$C(=O)—, —OCH$_2$C≡C— or —OCH$_2$CH=CH—, $Z^3$ is a phenyl radical, naphthalenyl radical or a 5- or 6-membered heteroaryl radical, each of which may contain 0, 1, 2 or 3 substituents, where the substituents are each independently selected from the following list:

substituents on carbon: halogen, cyano, nitro, hydroxyl, amino, —SH, alkyl, alkenyl, alkynyl, haloalkyl, haloalkenyl, haloalkynyl, cycloalkyl, halocycloalkyl, alkoxyalkyl, alkylcarbonyl, haloalkylcarbonyl, alkoxycarbonyl, alkoxy, haloalkoxy, cycloalkoxy, halocycloalkoxy, alkenyloxy, alkynyloxy, alkoxyalkoxy, alkylamino, dialkylamino, alkylthio, haloalkylthio, alkylsulphinyl, haloalkylsulphinyl, alkylsulphonyl, haloalkylsulphonyl, trisilylalkyl or phenyl, substituents on nitrogen: hydrogen, —C(=O)H, alkyl, alkenyl, alkynyl, haloalkyl, haloalkenyl, haloalkynyl, cycloalkyl, halocycloalkyl, alkylcycloalkyl, cycloalkylalkyl, alkoxyalkyl, alkylsulphonyl, haloalkylsulphonyl, cycloalkylsulphonyl, phenylsulphonyl, alkylcarbonyl, haloalkylcarbonyl, alkoxycarbonyl, haloalkoxycarbonyl, cycloalkoxycarbonyl, —C(=O) NR$^{11}$R$^{12}$, phenyl or benzyl, $Z^4$ is —SH, —C(=O)H, haloalkoxyalkyl, alkylthioalkyl, alkylsulphinylalkyl, alkylaminoalkyl, haloalkylaminoalkyl, cycloalkylaminoalkyl, dialkylaminoalkyl, alkylsulphonylalkyl, alkenyloxy, alkynyloxy, haloalkenyloxy, haloalkynyloxy, alkoxyalkoxy, haloalkylcarbonyloxy, cycloalkylcarbonyloxy, alkylsulphonylamino, haloalkylsulphonylamino, alkoxyalkoxyalkyl, alkylcarbonylalkoxy, cycloalkylaminocarbonyl, cycloalkylalkoxycarbonyl, haloalkylcarbonyl, cycloalkoxycarbonyl, $C_4$-$C_6$-alkylcarbonyl, $C_5$-$C_6$-alkoxy, $C_5$-$C_6$-haloalkoxy, $C_5$-$C_6$-alkylthio, $C_5$-$C_6$-haloalkylthio, $C_5$-$C_6$-haloalkylsulphinyl, $C_5$-$C_6$-haloalkylsulphonyl, cyanoalkyl, alkenylcarbonyloxy, alkoxyalkylthio, haloalkenylcarbonyloxy, alkoxycarbonylalkyl, alkoxyalkynyl, alkynylthio, halocycloalkylcarbonyloxy, alkenylamino, alkynylamino, haloalkylamino, cycloalkylalkylamino, alkoxyamino, haloalkoxyamino, alkylcarbonylamino, haloalkylcarbonylamino, alkoxycarbonylamino, alkylcarbonyl(alkyl)amino, haloalkylcarbonyl(alkyl)amino, alkoxycarbonyl(alkyl)amino, alkenylthio, haloalkoxycarbonyl, alkoxyalkylcarbonyl, —$SF_5$, haloalkoxycarbonylamino, di(haloalkyl)aminoalkyl, halocycloalkenyloxyalkyl, alkoxy(alkyl)aminocarbonyl, haloalkylsulphonylaminocarbonyl, alkoxycarbonylalkoxy, alkylaminothiocarbonylamino, cycloalkylalkylaminoalkyl, alkylthiocarbonyl, cycloalkenyloxyalkyl, alkoxyalkoxycarbonyl, dialkylaminothiocarbonylamino, alkylsulphonylaminocarbonyl, haloalkoxyhaloalkoxy, halocycloalkoxyalkyl, dialkylaminocarbonylamino, alkoxyalkenyl, alkoxyhaloalkoxy, alkylthiocarbonyloxy, haloalkoxyalkoxy, haloalkylsulphonyloxy, alkylsulphonyloxy, alkoxyhaloalkyl, di(haloalkyl)amino, dialkoxyalkyl, alkylaminocarbonylamino, haloalkoxyhaloalkyl, alkylaminocarbonylalkylamino, trialkylsilylalkynyloxy, trialkylsilyloxy, trialkylsilylalkynyl, cyano(alkoxy)alkyl, dialkylthioalkyl, alkoxysulphonyl, cycloalkylsulphinyl, halocycloalkoxycarbonyl, alkylcycloalkylcarbonyl, halocycloalkylcarbonyl, alkenyloxycarbonyl, alkynyloxycarbonyl, cyanoalkoxycarbonyl, alkylthioalkoxycarbonyl, alkynylcarbonyloxy, haloalkynylcarbonyloxy, cyanocarbonyloxy, cyanoalkylcarbonyloxy, cycloalkylsulphonyloxy, cycloalkylalkylsulphonyloxy, halocycloalkylsulphonyloxy, alkenylsulphonyloxy, alkynylsulphonyloxy, cyanoalkylsulphonyloxy, haloalkenylsulphonyloxy, haloalkynylsulphonyloxy, alkynylcycloalkyloxy, cyanoalkenyloxy, cyanoalkynyloxy, alkoxycarbonyloxy, alkenyloxycarbonyloxy, alkynyloxycarbonyloxy, alkylalkylcarbonyloxy, —O(C=O)H, —SCN, —NHC(=O)H, —C(=NOR$^9$)R$^{13}$, —NR$^{12}$SO$_2$Z$^3$, —O(C=S)NR$^{11}$R$^{12}$, —O(C=S)SR$^6$, —N=C(R$^6$)$_2$, —OSO$_2$Z$^3$, —NHCN, —SO$_2$NHCN, —C(=O)OH, —C(=O)NH$_2$, —C(=S)NR$^{11}$R$^{12}$, —C(=O)NHCN, —OC(=O)NR$^{11}$R$^{12}$, —NR$^{11}$R$^{12}$, —C(=O)NR$^{11}$R$^{12}$, —SO$_2$NR$^{11}$R$^{12}$ or -L$^4$Z$^3$, or Z$^4$ is alkyl which contains 1 or 2 substituents, where the substituents are each independently selected from the following list:
cyano, alkoxycarbonyl, —C(=N—R$^6$)R$^{13}$, —C(=N—NR$^3$R$^4$)R$^{13}$, alkylcarbonylamino, haloalkylcarbonylamino, dialkylcarbonylamino, alkylcarbonyloxy, —C(=O)H, benzyloxy, benzoyloxy, —C(=O)OH, alkenyloxy, alkynyloxy, haloalkenyloxy, haloalkynyloxy, halocycloalkoxy, alkoxyamino, alkenylthio, alkynylthio, cycloalkylthio, haloalkoxyamino, haloalkylthio, alkenylsulphinyl, alkynylsulphinyl, cycloalkylsulphinyl, haloalkylsulphinyl, alkenylsulphonyl, alkynylsulphonyl, cycloalkylsulphonyl, haloalkylsulphonyl, alkoxycarbonyloxy, alkylcarbonyloxy, cycloalkylcarbonyloxy, haloalkylcarbonyloxy, haloalkenylcarbonyloxy, —SCN, alkylaminocarbonyloxy, alkylcarbonyl(alkyl)amino, alkoxycarbonyl(alkyl)amino, alkylaminocarbonylamino, alkylsulphonyloxy, haloalkoxycarbonylamino, haloalkylcarbonyl(alkyl)amino, haloalkylsulphonyloxy, alkylsulphonylamino, haloalkylsulphonylamino, alkylthiocarbonyloxy, cyanoalkoxy, cycloalkylalkoxy, benzyloxyalkoxy, alkoxyhaloalkoxy, alkoxyalkylthio, alkoxyalkylsulphinyl, alkoxyalkylsulphonyl, alkoxyalkylcarbonyloxy, cycloalkoxyalkoxy, haloalkoxyalkoxy, haloalkoxyhaloalkoxy, alkoxycarbonylalkoxy, alkylcarbonylalkoxy, alkylthioalkoxy, dialkylaminocarbonylamino, alkoxyalkoxyalkoxy, trialkylsilyloxy, trialkylsilylalkynyloxy, alkynylcycloalkyloxy, cycloalkylalkynyloxy, alkoxycarbonylalkynyloxy, arylalkynyloxy, alkylaminocarbonylalkynyloxy, dialkylaminocarbonylalkynyloxy, alkenylcarbonyloxy, alkynylcarbonyloxy, haloalkynylcarbonyloxy, cyanoalkylcarbonyloxy, cycloalkylsulphonyloxy, cycloalkylalkylsulphonyloxy, halocycloalkylsulphonyloxy, alkenylsulphonyloxy, alkynylsulphonyloxy, cyanoalkylsulphonyloxy, haloalkenylsulphonyloxy, haloalkynylsulphonyloxy, dialkylaminocarbonyloxy, haloalkylaminocarbonyloxy, N-alkyl-N-haloalkylaminocarbonyloxy, alkenyloxycarbonyl, alkynyloxycarbonyl, haloalkynyloxycarbonyl, cyanoalkyloxycarbonyl, alkenyloxysulphonyl, alkynyloxysulphonyl, or Z$^4$ is alkenyl which contains 1 or 2 substituents, where the substituents are each independently selected from the following list:
trialkylsilyl, cycloalkyl, cyclopropylidenyl, alkoxy, trialkylsilyloxy, alkylcarbonyloxy or Z$^4$ is alkynyl which contains 1 or 2 substituents, where the substituents are each independently selected from the following list:
cycloalkyl, cyclopropylidenyl, or Z$^4$ is alkoxy which contains 1 or 2 substituents, where the substituents are each independently selected from the following list:
alkoxycarbonyl, cycloalkoxy, alkylcarbonyloxy, —O(C=O)H, alkylthio, hydroxyalkyl, trialkylsilyl, cycloalkylsulphonyl, haloalkylsulphonyl, benzyloxy, alkoxyalkoxy, alkylsulphonyl, cyano, or Z$^4$ is alkenyloxy which contains 1 or 2 substituents, where the substituents are each independently selected from the following list:
cycloalkyl, hydroxyl, alkoxy, alkenyloxy, alkynyloxy, haloalkoxy, haloalkenyloxy, haloalkynyloxy, cycloalkoxy, cyclohaloalkoxy, alkoxycarbonyl, haloalkoxycarbonyl, cycloalkoxycarbonyl, alkenyloxycarbonyl, haloalkenyloxycarbonyl, alkynyloxycarbonyl, haloalkynyloxycarbonyl, alkylcarbonyl, haloalkylcarbonyl, cycloalkylcarbonyl, cyclohaloalkylcarbonyl, alkenylcarbonyl, haloalkenylcarbonyl, alkynylcarbonyl, haloalkynylcarbonyl, or Z$^4$ is alkynyloxy which contains 1 or 2 substituents, where the substituents are each independently selected from the following list:
cycloalkyl, alkoxycarbonyl, —Z$^3$, alkylaminocarbonyl, dialkylaminocarbonyl, R$^6$ is alkyl, alkenyl, alkynyl, haloalkyl, cycloalkyl, benzyl or phenyl, R$^9$ is hydrogen, alkyl, haloalkyl, benzyl or Z$^3$, R$^{13}$ is hydrogen, alkyl, haloalkyl, cycloalkylalkyl, cycloalkyl, alkylcycloalkyl, haloalkylcycloalkyl, alkoxylalkyl, haloalkoxyalkyl, benzyl or phenyl R$^{11}$ and R$^{12}$ are the same or different and are each independently hydrogen, alkyl, alkenyl, alkynyl, haloalkyl, cycloalkyl, alkoxyalkyl, cyanoalkyl, formyl, alkylcarbonyl, cycloalkoxycarbonyl, alkoxycarbonyl, alkenyloxycarbonyl, alkynyloxycarbonyl, haloalkylcarbonyl, halocycloalkylcarbonyl, cycloalkoxycarbonyl, cycloalkylcarbonyl, dialkylaminocarbonyl, dialkylaminothiocarbonyl, benzyl or phenyl, and salts, metal complexes and N-oxides of the compounds of the formula (I).

The invention also provides compounds of the formula (II)

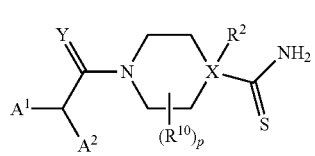

in which the radicals $A^1$, $A^2$, X, Y, $R^{10}$, $R^2$ and p are as defined as the formula (I),
and salts, metal complexes and N-oxides of the compounds of the formula (II).

The invention also provides compounds of the formula (IV)

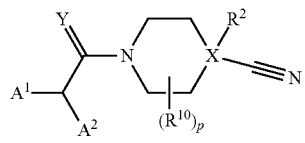

in which the radicals $A^1$, $A^2$, X, Y, $R^{10}$, $R^2$ and p are as defined as the formula (I), and salts, metal complexes and N-oxides of the compounds of the formula (IV).

The invention further provides for the use of the compounds of the formula (I) as fungicides.

Inventive malonic ester derivatives of heteroarylpiperidines and -piperazines of the formula (I) and the salts, metal complexes and N-oxides thereof are very suitable for controlling phytopathogenic harmful fungi. The aforementioned inventive compounds exhibit, in particular, potent fungicidal activity and can be used in crop protection, in the domestic and hygiene sector and in the protection of materials.

The compounds of the formula (I) may be present either in pure form or as mixtures of different possible isomeric forms, especially of stereoisomers, such as E and Z, threo and erythro, and also optical isomers, such as R and S isomers or atropisomers, and, if appropriate, also of tautomers.

Both the E and Z isomers, and the threo and erythro isomers, and also the optical isomers, any desired mixtures of these isomers, and the possible tautomeric forms are claimed.

DETAILED DESCRIPTION OF A PREFERRED EMBODIMENT

The radical definitions of the inventive compounds of the formula (I) preferably, more preferably and most preferably have the following definitions:
$A^1$ is preferably cyano or —C(=O)$R^{L1}$, and more preferably —C(=O)$R^{L1}$, $A^2$ is preferably hydrogen, halogen, alkylsulphonyl, haloalkylsulphonyl, arylsulphonyl, alkylsulphonyloxy, haloalkylsulphonyloxy, or arylsulphonyloxy, wherein aryl is optionally substituted by one, two or three groups independently selected from halogen, CN, $NH_2$, $NO_2$, OH, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_3$-$C_6$-cycloalkyl, or $C_3$-$C_6$-cycloalkoxy, or $A^2$ is preferably a heteroaromatic radical selected from the following group: furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,3-triazol-1-yl, 1,2,4-triazol-1-yl, pyridin-2-yl, pyridin-3-yl, pyridin-4-yl, pyridazin-3-yl, pyridazin-4-yl, pyrazin-2-yl, pyrazin-3-yl, pyrimidin-2-yl, pyrimidin-4-yl or pyrimidin-5-yl which may contain up to two substituents, where the substituents are each independently selected from the following list:

substituents on carbon:
halogen, cyano, hydroxyl, nitro, —NR$^3$R$^4$, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-alkylsulphonyl, $C_1$-$C_4$-haloalkylthio, $C_1$-$C_4$-haloalkylsulphonyl, $C_1$-$C_4$-alkoxy-$C_1$-$C_4$-alkyl, hydroxy-$C_1$-$C_4$-alkyl, $C_1$-$C_6$-alkylcarbonyl, $C_1$-$C_6$-alkoxycarbonyl, $C_1$-$C_6$-alkylcarbonyloxy or phenyl, substituents on nitrogen:
$C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_{10}$-cycloalkyl-$C_1$-$C_6$-alkyl, $C_1$-$C_6$-haloalkylcarbonyl, phenyl, benzyl, $C_1$-$C_4$-alkylsulphonyl, $C_1$-$C_4$-haloalkylsulphonyl, phenylsulphonyl, —C(=O)H, or $C_1$-$C_6$-alkylcarbonyl, $A^2$ is more preferably hydrogen, chloro, bromine, iodine, $C_1$-$C_4$-alkylsulphonyl, $C_1$-$C_4$-haloalkylsulphonyl, phenylsulphonyl, $C_1$-$C_4$-alkylsulphonyloxy, $C_1$-$C_4$-haloalkylsulphonyloxy, or phenylsulphonyloxy, wherein phenyl is optionally substituted by one, two or three groups independently selected from halogen, $C_1$-$C_4$-alkyl, $C_1$-$C_4$-haloalkyl, $C_1$-$C_4$-alkoxy, or $C_1$-$C_4$-haloalkoxy, or $A^2$ is more preferably a heteroaromatic radical selected from the following group: furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,3-triazol-1-yl, 1,2,4-triazol-1-yl, pyridin-2-yl, pyridin-3-yl, pyridin-4-yl, pyridazin-3-yl, pyridazin-4-yl, pyrimidin-2-yl, pyrimidin-4-yl or pyrimidin-5-yl, which may contain up to two substituents, where the substituents are the same or different and are each independently selected from the following list:

substituents on carbon:
fluorine, chlorine, bromine, iodine, cyano, nitro, methyl, ethyl, n-propyl, 1-methylethyl, 1,1-dimethylethyl, chlorofluoromethyl, dichloromethyl, dichlorofluoromethyl, difluoromethyl, trichloromethyl, trifluoromethyl, cyclopropyl, ethoxy, 1-methylethoxy, n-propoxy, methoxy, trifluoromethoxy, difluoromethoxy, 1-methylethylthio, methylthio, ethylthio, n-propylthio, difluoromethylthio, trifluoromethylthio or phenyl, substituents on nitrogen:
methyl, ethyl, n-propyl, 1-methylethyl, methylsulphonyl, trifluoromethylsulphonyl, methylcarbonyl, trifluoromethylcarbonyl, chloromethylcarbonyl, 2,2-trifluoroethyl, 2,2-difluoroethyl, 2,2-dichloro-2-fluoroethyl, 2-chloro-2-difluoroethyl or 2-chloro-2-fluoroethyl, $A^2$ is most preferably hydrogen, chlorine, bromine, iodine, methylsulfonyloxy, trifluoromethylsulfonyloxy, phenylsulfonyloxy or 4-methylphenylsulfonyloxy, or $A^2$ is most preferably pyrazol-1-yl which may contain up to two substituents, where the substituents are each independently selected from the following list: methyl, ethyl, chlorine, chloromethyl, dichloromethyl, bromine, fluorine, fluoromethyl, difluoromethyl or trifluoromethyl, $R^3$ and $R^4$ are preferably the same or different and are each independently hydrogen, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, benzyl or phenyl, and more preferably hydrogen, methyl, ethyl, n-propyl, 1-methylethyl, n-butyl or 1,1-dimethylethyl, Y are preferably sulfur or oxygen, and more preferably oxygen, $R^{L1}$ is preferably amino, $NR^3R^4$, hydroxyamine, $C_1$-$C_4$-alkylthio, $C_1$-$C_4$-haloalkylthio, $C_1$-$C_4$-alkylcarbonyloxy, $C_1$-$C_4$-haloalkylcarbonyloxy, $C_1$-$C_4$-alkylcarbonylamino, $C_1$-$C_4$-haloalkylcarbonylamino, cyano, $C_2$—C-alkoxy, $C_1$-$C_4$-haloalkoxy, $C_3$-$C_6$-cycloalkoxy, $C_2$-$C_6$-alkenyloxy, $C_1$-$C_4$-alkoxy-$C_1$-$C_4$-alkoxy, phenoxy, or benzyloxy, wherein phenyloxy, benzyloxy, are optionally substituted by one or two groups independently selected from halogen, CN, OH, methyl, ethyl, n-propyl, 1-methylethyl, n-butyl, 2,2,2-trifluoromethyl, difluoromethyl, methoxy, ethoxy, n-propoxy, and more preferably amino, ethoxy, n-propoxy, 1-methylethoxy, n-butoxy, 1,1-dimethylethoxy, 1,2-dimethylethoxy, n-pentyloxy, n-hexyloxy, n-octyloxy, 2-ethylhexyloxy, 2,2,2-trifluoroethoxy, 2-methoxy-ethoxy, 2-ethoxyethoxy, allyloxy, but-2-en-1-yloxy, prop-2-yn-1-yloxy, phenoxy, 2,6-dimethylphenoxy, 2,6-diisopropylphenoxy, 2,6-di-tert-butylphenoxy, benzyloxy, 4-methoxybenzyloxy, or 3,4-dimethoxybenzyloxy, X is preferably carbon or nitrogen, and more preferably carbon, $R^2$ is preferably hydrogen, $C_1$-$C_4$-alkyl, $C_1$-$C_2$-haloalkyl, $C_1$-$C_2$-alkoxy, halogen, cyano or hydroxyl, and more preferably hydrogen, fluorine, methoxy or hydroxyl, and most preferably hydrogen, $R^{10}$ is preferably the same or different and is independently hydrogen, $C_1$-$C_4$-alkyl, $C_1$-$C_2$-haloalkyl, $C_1$-$C_2$-alkoxy, halogen, cyano or hydroxyl, and more preferably hydrogen, fluorine, methoxy or hydroxyl, p is preferably 0 to 1, and more preferably 0, G is preferably $G^1$ $R^{G1}$ is preferably hydrogen, $C_1$-$C_3$-alkyl or halogen and more preferably hydrogen, Q is preferably

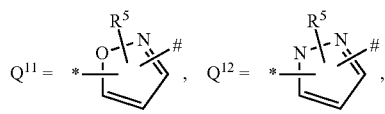

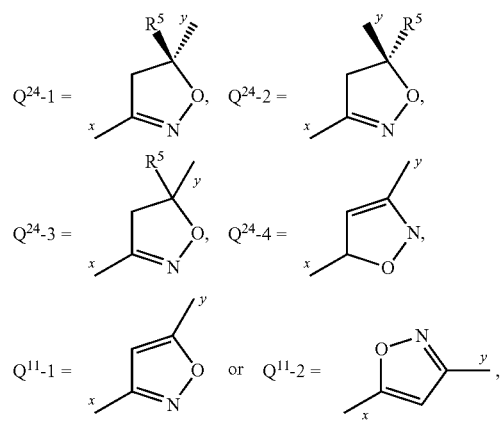

where the bond identified by "*" is bonded directly to G or $L^2$, and where the bond identified by "#" is bonded directly to $L^2$ or G, or where the bond identified by "*" is bonded directly to $L^2$, and the bond identified by "#" is at the same time bonded directly to G, Q is more preferably where the bond identified by "x" is bonded directly to G, and where the bond identified by "y" is bonded directly to $L^2$, $R^5$ is preferably the same or different and is independently bonded to carbon of the 5-membered heterocyclyl of Q: hydrogen, halogen, cyano, —$NR^7R^8$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_3$-$C_8$-halocycloalkyl, $C_1$-$C_4$-alkyl-$C_3$-$C_8$-cycloalkyl, $C_3$-$C_8$-cycloalkyl-$C_1$-$C_4$-alkyl, $C_1$-$C_4$-alkoxy-$C_1$-$C_4$-alkyl, $C_3$-$C_8$-cycloalkoxy-$C_1$-$C_4$-alkyl, $C_1$-$C_4$-alkoxy-$C_1$-$C_4$-alkoxy-$C_1$-$C_4$-alkyl, $C_1$-$C_4$-alkylthio-$C_1$-$C_4$-alkyl, $C_1$-$C_6$-alkoxy, $C_1$-$C_6$-haloalkoxy, $C_3$-$C_8$-cycloalkoxy, $C_3$-$C_8$-halocycloalkoxy, $C_3$-$C_8$-cycloalkyl-$C_1$-$C_4$-alkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkoxy-$C_1$-$C_4$-alkoxy, $C_1$-$C_6$-alkylcarbonyloxy, $C_1$-$C_6$-haloalkylcarbonyloxy, $C_3$-$C_8$-cycloalkylcarbonyloxy, $C_1$-$C_6$-alkylcarbonyl-$C_1$-$C_6$-alkoxy, $C_1$-$C_6$-alkylthio, $C_1$-$C_6$-haloalkylthio, $C_3$-$C_8$-cycloalkylthio, tri($C_1$-$C_4$-alkyl) silyl, bonded to nitrogen of the 5-membered heterocyclyl of Q: hydrogen, —C(=O)H, $C_1$-$C_3$-alkyl, $C_1$-$C_6$-alkylcarbonyl, $C_1$-$C_6$-alkoxycarbonyl or benzyl, $R^5$ is more preferably hydrogen, cyano, methyl, trifluoromethyl, difluoromethyl or methoxymethyl, or $R^5$ is most preferably hydrogen, $R^7$ is preferably hydrogen, $C_1$-$C_6$-alkyl, $C_1$-$C_6$-haloalkyl, $C_3$-$C_8$-cycloalkyl, $C_1$-$C_4$-alkylcarbonyl, $C_1$-$C_4$-haloalkylcarbonyl, $C_1$-$C_4$-alkoxycarbonyl or $C_1$-$C_4$-haloalkoxycarbonyl, $R^8$ is preferably $C_1$-$C_3$-alkyl or -$L^5R^1$, $L^5$ is preferably —C(=O)— or S(=O)$_2$, $L^2$ is preferably a direct bond, —O—, —C(=O)—, —S(=O)$_2$—, —CHR$^{20}$— or —NR$^{21}$—, and more preferably a direct bond, —C(=O)—, —CHR$^{20}$— or —NR$^{21}$—, and most preferably a direct bond, $R^{20}$ is preferably hydrogen, $C_1$-$C_4$-alkyl, $C_1$-$C_4$-haloalkyl, and more preferably hydrogen, methyl, ethyl, trifluoromethyl, $R^{21}$ is preferably hydrogen, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxycarbonyl or $C_1$-$C_6$-haloalkoxycarbonyl, and more preferably hydrogen or methyl, $R^1$ is preferably $C_5$-$C_6$-cycloalkenyl or $C_3$-$C_8$-cycloalkyl, where the $C_5$-$C_6$-cycloalkenyl or $C_3$-$C_8$-cycloalkyl is in each case substituted at least once by a substituent $Z^4$ and may otherwise be unsubstituted or substituted, where the substituents are each independently selected from $Z^4$ and optionally from $Z^{1-1}$, and more preferably substituted cyclopentenyl, cyclohexenyl, cyclopentyl, cyclohexyl or cycloheptyl, each of which may contain 1 or 2 substituents, where the substituents are each independently selected at least once from $Z^4$ and optionally from the following list: methyl, ethyl, methoxy, ethoxy, trifluoromethoxy, ethynyl, 2-propenyloxy, 2-propynyloxy, methylcarbonyloxy, ethylcarbonyloxy, trifluorocarbonyloxy, methylthio, ethylthio or trifluoromethylthio, or $R^1$ is preferably phenyl which is substituted at least once by a substituent $Z^4$ and may otherwise be unsubstituted or substituted, where the substituents are each independently selected from $Z^4$ and optionally from $Z^{1-2}$, and more preferably phenyl which may contain 1, 2 or 3 substituents, where the substituents are each independently selected at least once from $Z^4$ and optionally from the following list: fluorine, chlorine, bromine, iodine, cyano, nitro, hydroxyl, amino, —SH, —C(=O)H, methyl, ethyl, n-propyl, 1-methylethyl, n-butyl, 1,1-dimethylethyl, 1,2-dimethylethyl, ethenyl, ethynyl, trifluoromethyl, difluoromethyl, trichloromethyl, dichloromethyl, cyclopropyl, methoxy, ethoxy, n-propoxy, 1-methyl-ethoxy, 1,1-dimethylethoxy, methylcarbonyl, ethylcarbonyl, trifluoromethylcarbonyl, methoxycarbonyl, ethoxycarbonyl, n-propoxycarbonyl, 1-methylethoxycarbonyl, 1,1-dimethylethoxycarbonyl, 1-ethenyloxy, 2-propenyloxy, 2-propynyloxy, methylcarbonyloxy, trifluoromethylcarbonyloxy, chloromethylcarbonyloxy, methylthio, ethylthio, methylsulphonyl, or -$L^3Z^3$, and most preferably phenyl which is substituted at least once by a substituent selected from the following list:

formyl, methoxymethoxy, 2-methoxyethoxy, allyloxy, 2-fluoroprop-2-en-1-yloxy, 2-chloroprop-2-en-1-yloxy, 3-chloroprop-2-en-1-yloxy, 2-bromoprop-2-en-1-yloxy, 2-methylprop-2-en-1-yloxy, 3,3-dichloroprop-2-en-1-yloxy, 3,3-dichloro-2-fluoroprop-2-en-1-yloxy, but-2-en-1-yloxy, but-3-en-2-yloxy, but-3-en-1-yloxy, 3-chlorobut-2-en-1-yloxy, 3-methylbut-2-en-1-yloxy, 4,4,4-trifluorobut-2-en-1-yloxy, prop-2-yn-1-yloxy, 3-chloroprop-2-yn-1-yloxy, 3-bromoprop-2-yn-1-yloxy, but-2-yn-1-yloxy, pent-2-yn-1-yloxy, 2-fluoro-2-methylpropanoyloxy, 3,3,3-trifluoropropanoyloxy, cyclopropylcarbonyloxy, cyclohexylcarbonyloxy, (1-chlorocyclopropyl)carbonyloxy, but-2-enoyloxy, acryloyloxy, benzoyloxy, 2-fluorobenzoyloxy, 3-fluorobenzoyloxy, 4-fluorobenzoyloxy, cyanomethoxy, methylsulphonyloxy, ethylsulphonyloxy, trifluoromethylsulphonyloxy, cyclopropylsulphonyloxy, 2-methoxyethoxymethyl, allyloxymethyl, prop-2-yn-1-yloxymethyl, methylsulphonylmethyl, methylcarbonylaminomethyl, methylsulphonylaminomethyl, —C(=NOH)H, —C(=NOCH$_3$)H, —C(=NOCH$_2$CH$_3$)H, —C(=NOCH(CH$_3$)CH$_3$)H, —C(=NOH)CH$_3$, —C(=NOCH$_3$)CH$_3$, —C(=NOCH$_2$CH$_3$)CH$_3$, —C(=NOCH(CH$_3$)CH$_3$)CH$_3$, dimethylaminosulphonyl, —C(=O)NH$_2$, ethylaminosulphonyl, trimethylsilylethynyl, diethylaminosulphonyl, methylaminosulphonyl, trimethylsilyloxy, trimethylsilylprop-2-yn-1-yloxy, trifluoromethylamino, dimethylaminocarbonylamino, —C(=O)OH, 1,1-dimethylethylcarbonylamino, chloromethylcarbonylamino, trifluoromethylcarbonylamino, 1,1-dimethylethoxycarbonylamino, ethylcarbonylamino, 1-methylethoxycarbonylamino, trifluoromethylcarbonylamino, methylcarbonylamino, methoxycarbonylamino, ethoxycarbonylamino, iso-propoxycarbonylamino, 1-methylethylcarbony lamino, methylsulphonylamino or phenylsulphonylamino, 3-bromoprop-2-en-1-yloxy, and additional substituents are optionally selected from the following list: fluorine, chlorine, methyl, trifluoromethyl, methoxy, $R^1$ is preferably naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 2,3-dihydro-1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl or indan-5-yl, where these are each substituted at least once by a substituent $Z^4$ and may otherwise be unsubstituted or substituted, where the substituents are each independently selected from $Z^4$ and optionally from $Z^{1-3}$, $R^1$ is more preferably naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 2,3-dihydro-1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl or indan-5-yl, where these are each substituted at least once by a substituent $Z^4$ and may otherwise contain further substituents each independently selected from $Z^4$ and optionally the group consisting of methyl, methoxy, cyano, fluorine, chlorine, bromine and iodine, where a total of at most three substituents are present in the particularly preferred variant, $R^1$ is preferably a 5- or 6-membered heteroaryl radical which is substituted at least once by a substituent $Z^4$ and may otherwise be unsubstituted or substituted, where the substituents on carbon are each independently selected from $Z^4$ and optionally from $Z^{1-4}$, and the substituents on nitrogen are each independently selected from $Z^2$, $R^1$ is more preferably furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol- 1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl or pyrazin-2-yl, each of which may contain 1 or 2 substituents, where the substituents are each independently selected at least once from $Z^4$ and may otherwise be unsubstituted or substituted, where the substituents are each independently selected from $Z^4$ and optionally from the following list:
  substituents on carbon: fluorine, chlorine, bromine, iodine, cyano, nitro, hydroxyl, amino, methyl, ethyl, n-propyl, 1-methylethyl, n-butyl, 1,1-dimethylethyl, 1,2-dimethylethyl, ethenyl, ethynyl, trifluoromethyl, difluoromethyl, trichloromethyl, dichloromethyl, cyclopropyl, methoxy, ethoxy, n-propoxy, 1-methylethoxy, 1,1-dimethylethoxy, methylcarbonyl, ethylcarbonyl, methoxycarbonyl, ethoxycarbonyl, n-propoxycarbonyl, 1-methylethoxycarbonyl, 1,1-dimethylethoxycarbonyl, methylcarbonyloxy, methylthio, ethylthio or methylsulphonyl,
  substituents on nitrogen: methyl, ethyl, n-propyl, —C(=O)H, methylcarbonyl, trifluoromethylcarbonyl, chloromethylcarbonyl, methylsulphonyl, trifluoromethyl-sulphonyl, phenylsulphonyl, phenyl or 2-propynyl, or
$R^1$ is preferably benzofused substituted 5- or 6-membered heteroaryl which is substituted by at least one substituent $Z^4$ and may otherwise be unsubstituted or substituted, where the substituents on carbon are each independently selected from $Z^4$ and $Z^{1-5}$, and the substituents on nitrogen are each independently selected from $Z^2$, and more preferably indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl, each of which is substituted at least once by a substituent $Z^4$ and may otherwise be unsubstituted or substituted, where the substituents are each independently selected from $Z^4$ and optionally from the following list:
  substituents on carbon: fluorine, chlorine, bromine, iodine, methyl, methoxy,
  substituents on nitrogen: methyl, ethyl, n-propyl, —C(=O)H, methylcarbonyl, trifluoromethylcarbonyl, chloromethylcarbonyl, methylsulphonyl, trifluoromethylsulphonyl, phenylsulphonyl, phenyl or 2-propynyl, or
$R^1$ is preferably $C_5$-$C_{15}$-heterocyclyl which is substituted on carbon at least once by a substituent $Z^4$ and may otherwise be unsubstituted or substituted, where the substituents, on carbon, are each independently selected from $Z^4$, oxo, thioxo or $Z^{1-6}$ and the substituents on nitrogen are each independently selected from $Z^2$,
$R^1$ is more preferably piperidin-1-yl, piperidin-2-yl, piperidin-3-yl, piperidin-4-yl, piperazin-1-yl, piperazin-2-yl, piperazin-3-yl, morpholin-1-yl, morpholin-2-yl, morpholin-3-yl, tetrahydropyran-2-yl, tetrahydropyran-3-yl, tetrahydropyran-4-yl, 1,2,3,4-tetrahydroquinolin-1-yl, 1,2,3,4-tetrahydroisoquinolin-2-yl, 1,2,3,4-tetrahydroquinoxalin-1-yl, indolin-1-yl, isoindolin-2-yl, decahydroquinolin-1-yl oder decahydroisoquinolin-2-yl, each of which is substituted at least once by a substituent $Z^4$ and may otherwise be unsubstituted or substituted, where the substituents are each independently selected from $Z^4$ and optionally from the following list:
  substituents on carbon: fluorine, chlorine, bromine, iodine, methyl, methoxy, oxo, thioxo
  substituents on nitrogen: methyl, ethyl, n-propyl, —C(=O)H, methylcarbonyl, trifluoromethylcarbonyl, chloromethylcarbonyl, methylsulphonyl, trifluoromethylsulphonyl, phenylsulphonyl, phenyl or 2-propynyl,
$Z^{1-1}$ are the same or different and are each independently hydrogen, cyano, halogen, $C_1$-$C_6$-alkyl, $C_1$-$C_6$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, hydroxyl, $C_1$-$C_6$-alkoxy, $C_1$-$C_6$-haloalkoxy, $C_1$-$C_6$-alkylcarbonyloxy, $C_1$-$C_6$-alkylthio or $C_1$-$C_6$-haloalkylthio,
$Z^{1-2}$ is hydrogen, halogen, cyano, hydroxyl, amino, nitro, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_3$-$C_8$-cycloalkenyl, $C_3$-$C_8$-halocycloalkenyl, $C_1$-$C_6$-alkoxy-$C_1$-$C_6$-alkyl, $C_1$-$C_6$-alkylcarbonyl, $C_3$-$C_8$-cycloalkylcarbonyl, $C_1$-$C_6$-alkoxycarbonyl, $C_1$-$C_6$-alkoxy, $C_1$-$C_6$-haloalkoxy, $C_3$-$C_8$-cycloalkoxy, $C_3$-$C_8$-halocycloalkoxy, $C_1$-$C_6$-alkylcarbonyloxy, $C_1$-$C_6$-alkylthio, $C_1$-$C_6$-haloalkylthio, $C_3$-$C_6$-cycloalkylthio, $C_1$-$C_6$-alkylsulphonyl, $C_1$-$C_6$-haloalkylsulphonyl, $C_3$-$C_8$-cycloalkylsulphonyl, tri($C_1$-$C_4$-alkyl)silyl, or -$L^3Z^3$,
$Z^{1-3}$ and $Z^{1-5}$ are the same or different and are each independently hydrogen, halogen, cyano, nitro, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_6$-alkylcarbonyl, $C_1$-$C_6$-alkoxycarbonyl, $C_1$-$C_4$-alkoxy, $C_1$-$C_4$-haloalkoxy, $C_1$-$C_6$-alkylcarbonyloxy, $C_1$-$C_6$-alkylcarbonylthio, $C_1$-$C_4$-alkylthio, $C_1$-$C_4$-haloalkylthio, $C_1$-$C_4$-alkylsulphonyl or $C_1$-$C_4$-haloalkylsulphonyl,
$Z^{1-4}$ is hydrogen, halogen, cyano, hydroxyl, amino, nitro, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_3$-$C_8$-cycloalkenyl, $C_3$-$C_8$-halocycloalkenyl, $C_1$-$C_6$-alkoxy-$C_1$-$C_6$-alkyl, $C_1$-$C_6$-alkylcarbonyl, $C_3$-$C_8$-cycloalkylcarbonyl, $C_1$-$C_6$-alkoxycarbonyl, $C_1$-$C_6$-alkoxy, $C_1$-$C_6$-haloalkoxy, $C_3$-$C_8$-cycloalkoxy, $C_3$-$C_8$-halocycloalkoxy, $C_1$-$C_6$-alkylcarbonyloxy, $C_1$-$C_6$-alkylthio, $C_1$-$C_6$-haloalkylthio, $C_3$-$C_6$-cycloalkylthio, $C_1$-$C_6$-alkylsulphonyl, $C_1$-$C_6$-haloalkylsulphonyl or $C_3$-$C_8$-cycloalkylsulphonyl,
$Z^{1-6}$ are the same or different and are each independently hydrogen, cyano, halogen, $C_1$-$C_6$-alkyl, $C_1$-$C_6$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkylthio, $C_1$-$C_6$-alkylcarbonyl, $C_1$-$C_6$-alkoxycarbonyl, $C_1$-$C_6$-alkylcarbonyloxy, $C_1$-$C_6$-haloalkylthio or phenyl, $Z^2$ is the same or different and is independently hydrogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, phenyl, benzyl, $C_1$-$C_4$-haloalkylsulphonyl, $C_1$-$C_6$-alkoxycarbonyl, $C_1$-$C_6$-haloalkoxycarbonyl, phenylsulphonyl, $C_1$-$C_4$-alkylsulphonyl, —C(=O)H, $C_1$-$C_3$-haloalkylcarbonyl or $C_1$-$C_3$-alkylcarbonyl, $L^3$ is preferably a direct bond, —CH$_2$—, sulphur, oxygen or —(S=O)$_2$— and more preferably a direct bond, $L^4$ is preferably —C(=O)O—, —C(=O)NH—, —OC(=O)—, —NHC(=O)— or —OCH$_2$C≡C—, and more preferably —OCH$_2$C≡C— or —C(=O)O—, $Z^3$ is preferably a phenyl radical, naphthalenyl or a 5- or 6-membered heteroaryl radical which may contain up to two substituents, where the substituents are each independently selected from the following list:

halogen, cyano, nitro, hydroxyl, amino, —SH, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$-haloalkynyl, $C_2$-$C_4$-alkoxyalkyl, $C_1$-$C_6$-alkylcarbonyl, $C_1$-$C_6$-haloalkylcarbonyl, $C_1$-$C_6$-alkoxycarbonyl, $C_1$-$C_4$-alkoxy, $C_1$-$C_4$-haloalkoxy, $C_2$-$C_6$-alkenyloxy, $C_2$-$C_6$-alkynyloxy, $C_1$-$C_4$-alkylthio, $C_1$-$C_4$-haloalkylthio, $C_1$-$C_4$-alkylsulphonyl, $C_1$-$C_4$-haloalkylsulphonyl or $C_1$-$C_4$-alkylamino, di($C_1$-$C_4$-alkyl)amino, substituents on nitrogen: hydrogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, phenyl, benzyl, $C_1$-$C_4$-haloalkylsulphonyl, $C_1$-$C_6$-alkoxycarbonyl, $C_1$-$C_6$-haloalkoxycarbonyl, phenylsulphonyl, $C_1$-$C_4$-alkylsulphonyl, —C(=O)H, or $C_1$-$C_3$-alkylcarbonyl, and $Z^3$ is more preferably a phenyl radical which may contain up to two substituents, where the substituents are each independently selected from the following list:

chlorine, bromine, iodine, fluorine, cyano, nitro, hydroxyl, amino, —SH, methyl, ethyl, n-propyl, 1-methylethyl, 1,1-dimethylethyl, ethenyl, propen-2-yl, ethynyl, propyn-2-yl, trifluoromethyl, difluoromethyl, methoxymethyl, methylcarbonyl, ethylcarbonyl, trifluoromethylcarbonyl, methoxycarbonyl, ethoxycarbonyl, n-propoxycarbonyl, 1-methylethoxycarbonyl, 1,1-dimethylethoxycarbonyl, methoxy, ethoxy, n-propoxy, 1-methylethoxy, 1,1-dimethylethoxy, trifluoromethoxy, ethenyloxy, 2-propenyloxy, ethynyloxy, 2-propynyloxy, methylthio, ethylthio, trifluoromethylthio, methylsulphonyl, ethylsulphonyl, propylthionyl, 1-methylethylthio, trifluoromethylsulphonyl, methylamino, ethylamino, n-propylamino, 1-methylethylamino, 1,1-dimethylethylamino or dimethylamino, or $Z^3$ is more preferably naphthalenyl, $Z^4$ is preferably —SH, —C(=O)H, $C_1$-$C_6$-alkoxy-$C_1$-$C_6$-alkoxy-$C_1$-$C_6$-alkyl, $C_1$-$C_6$-alkylthioalkyl, $C_1$-$C_6$-alkylsulphinyl-$C_1$-$C_6$-alkyl, $C_1$-$C_6$-alkylsulphonyl-$C_1$-$C_6$-alkyl, $C_4$-$C_6$-alkylcarbonyl, $C_1$-$C_6$-haloalkylcarbonyl, $C_3$-$C_6$-cycloalkoxycarbonyl, $C_3$-$C_6$-cycloalkyl-$C_1$-$C_6$-alkoxycarbonyl, $C_3$-$C_6$-cycloalkylaminocarbonyl, $C_1$-$C_6$-haloalkoxy-$C_1$-$C_6$-alkyl, $C_5$-$C_6$-alkoxy, $C_5$-$C_6$-haloalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkoxy-$C_1$-$C_6$-alkoxy, $C_1$-$C_6$-haloalkylcarbonyloxy, $C_3$-$C_6$-cycloalkylcarbonyloxy, $C_1$-$C_6$-alkylcarbonyl-$C_1$-$C_6$-alkoxy, $C_5$-$C_6$-alkylthio, $C_5$-$C_6$-haloalkylthio, $C_5$-$C_6$-haloalkylsulphinyl, $C_5$-$C_6$-haloalkylsulphonyl, $C_1$-$C_6$-alkylsulphonylamino, $C_1$-$C_6$-haloalkylsulphonylamino, cyano-$C_1$-$C_6$-alkyl, $C_2$-$C_6$-alkenylcarbonyloxy, $C_2$-$C_6$-alkynylthio, $C_3$-$C_8$-halocycloalkylcarbonyloxy, $C_2$-$C_6$-alkenylamino, $C_2$-$C_6$-alkynylamino, $C_1$-$C_6$-haloalkylamino, $C_3$-$C_8$-cycloalkyl-$C_1$-$C_6$-alkylamino, $C_1$-$C_6$-alkoxyamino, $C_1$-$C_6$-haloalkoxyamino, $C_1$-$C_6$-alkylcarbonylamino, $C_1$-$C_6$-haloalkylcarbonylamino, $C_1$-$C_6$-alkoxycarbonylamino, $C_1$-$C_6$-alkylcarbonyl($C_1$-$C_6$-alkyl)amino, $C_1$-$C_6$-haloalkylcarbonyl($C_1$-$C_6$-alkyl)amino, $C_1$-$C_6$-alkoxycarbonyl($C_1$-$C_6$-alkyl)amino, $C_2$-$C_6$-alkenylthio, $C_1$-$C_6$-haloalkoxycarbonyl, $C_1$-$C_6$-alkoxy-$C_1$-$C_4$-alkylcarbonyl, —SF$_5$, $C_1$-$C_6$-haloalkoxycarbonylamino, —NHC(=O)H, $C_1$-$C_6$-alkoxy($C_1$-$C_4$-alkyl)aminocarbonyl, $C_1$-$C_6$-alkoxycarbonyl-$C_1$-$C_6$-alkoxy, di($C_1$-$C_6$-alkyl)aminocarbonylamino, di($C_1$-$C_6$-alkyl)aminosulphonyl, di($C_1$-$C_6$-haloalkyl)amino, $C_1$-$C_6$-alkylaminosulphonyl, $C_1$-$C_6$-alkylaminocarbonylamino, tri($C_1$-$C_4$-alkyl)silyloxy, $C_1$-$C_6$-haloalkylsulphonyloxy, $C_1$-$C_6$-alkylsulphonyloxy, tri($C_1$-$C_4$-alkyl)silyl-$C_2$-$C_4$-alkynyloxy, tri($C_1$-$C_4$-alkyl)silyl-$C_2$-$C_4$-alkynyl, $C_2$-$C_4$-alkynylcarbonyloxy, cyano-$C_1$-$C_3$-alkylcarbonyloxy, $C_3$-$C_8$-cycloalkylsulphonyloxy, $C_3$-$C_8$-halocycloalkylsulphonyloxy, $C_2$-$C_4$-alkenylsulphonyloxy, $C_1$-$C_3$-alkylaminocarbonyloxy, $C_2$-$C_4$-alkynyl-$C_3$-$C_8$-cycloalkyloxy, cyanocarbonyloxy, cyano-$C_2$-$C_4$-alkenyloxy, —C(=NOR)R$^{13}$, —C(=O)OH, —C(=O)NH$_2$, —C(=S)NR$^{11}$R$^{12}$, —NR$^{11}$R$^{12}$, —C(=O)NR$^{11}$R$^{12}$, —SO$_2$NR$^{11}$R$^{12}$, —NR$^{12}$SO$_2$Z$^3$, —O(C=O)H, —SCN, $C_1$-$C_3$-alkoxysulphonyl, $C_3$-$C_8$-cycloalkylsulphinyl, cyano($C_1$-$C_3$-alkoxy)-$C_1$-$C_3$-alkyl or -L$^4$Z$^3$, or $Z^4$ is preferably $C_1$-$C_3$-alkyl which contains 1 or 2 substituents, where the substituents are each independently selected from the following list:

cyano, —C(=O)H, $C_2$-$C_4$-alkenyloxy, $C_2$-$C_4$-alkynyloxy, $C_2$-$C_4$-alkenylthio, $C_2$-$C_4$-alkynylthio, $C_1$-$C_3$-haloalkylthio, $C_2$-$C_4$-alkenylsulphinyl, $C_2$-$C_4$-alkynylsulphinyl, $C_1$-$C_3$-haloalkylsulphinyl, $C_2$-$C_4$-alkenylsulphonyl, $C_2$-$C_4$-alkynylsulphonyl, $C_1$-$C_3$-haloalkylsulphonyl, $C_1$-$C_3$-alkylcarbonyloxy, $C_1$-$C_3$-haloalkylcarbonyloxy, $C_1$-$C_3$-alkylaminocarbonyloxy, $C_1$-$C_3$-alkylcarbonylamino, $C_1$-$C_3$-alkylaminocarbonylamino, $C_1$-$C_3$-haloalkylcarbonylamino, $C_1$-$C_3$-alkylsulphonylamino, $C_1$-$C_3$-haloalkylsulphonylamino, $C_1$-$C_3$-alkylthiocarbonyloxy, cyano-$C_1$-$C_3$-alkoxy, $C_3$-$C_8$-cycloalkyl-$C_1$-$C_3$-alkoxy, $C_1$-$C_3$-alkoxy-$C_1$-$C_3$-alkylthio, $C_1$-$C_3$-alkoxy-$C_1$-$C_3$-alkylsulphinyl, $C_1$-$C_3$-alkoxy-$C_1$-$C_3$-alkylsulphonyl, $C_1$-$C_3$-haloalkoxy-$C_1$-$C_3$-alkoxy, $C_1$-$C_3$-alkylcarbonyl-$C_1$-$C_3$-alkoxy, $C_2$-$C_4$-alkylthio-$C_1$-$C_3$-alkoxy, di($C_1$-$C_3$-alkyl)aminocarbonylamino, tri($C_1$-$C_4$-alkyl)silyloxy, or $Z^4$ is preferably $C_1$-$C_3$-alkoxy which contains 1 or 2 substituents, where the substituents are each independently selected from the following list:

cyano, $C_1$-$C_3$-alkylcarbonyloxy $C_1$-$C_3$-alkoxycarbonyl, $C_3$-$C_8$-cycloalkoxy, $C_1$-$C_3$-alkylcarbonyloxy, —O(C=O)H, $C_1$-$C_3$-alkylthio, hydroxyl-$C_1$-$C_3$-alkyl, $C_3$-$C_8$-cycloalkylsulphonyl, $C_1$-$C_3$-haloalkylsulphonyl, $C_1$-$C_3$-alkoxy-$C_1$-$C_3$-alkoxy, $C_1$-$C_3$-alkylsulphonyl, or $Z^4$ is preferably $C_2$-$C_4$-alkenyloxy which contains 1 or 2 substituents, where the substituents are each independently selected from the following list:

$C_3$-$C_8$-cycloalkyl, hydroxyl, $C_1$-$C_3$-alkoxy, $C_1$-$C_3$-alkoxycarbonyl, $C_1$-$C_3$-alkylcarbonyl, or $Z^4$ is preferably $C_2$-$C_4$-alkynyloxy which contains 1 or 2 substituents, where the substituents are each independently selected from the following list:
$C_3$-$C_8$-cycloalkyl, —$Z^3$, $Z^4$ is more preferably—formyl, methoxymethoxy, 2-methoxyethoxy, allyloxy, 2-fluoroprop-2-en-1-yloxy, 2-chloroprop-2-en-1-yloxy, 3-chloroprop-2-en-1-yloxy, 2-bromoprop-2-en-1-yloxy, 2-methylprop-2-en-11-yloxy, 3,3-dichloroprop-2-en-1-yloxy, 3,3-dichloro-2-fluoroprop-2-en-1-yloxy, but-2-en-1-yloxy, but-3-en-2-yloxy, but-3-en-1-yloxy, 3-chlorobut-2-en-1-yloxy 3-methylbut-2-en-1-yloxy, 4,4,4-trifluorobut-2-en-1-yloxy, prop-2-yn-1-yloxy, 3-chloroprop-2-yn-1-yloxy, 3-bromoprop-2-yn-1-yloxy, but-2-yn-1-yloxy, pent-2-yn-1-yloxy, 2-fluoro-2-methylpropanoyloxy, 3,3,3-trifluoropropanoyloxy, cyclopropylcarbonyloxy, cyclohexylcarbonyloxy, (1-chlorocyclopropyl)carbonyloxy, but-2-enoyloxy, acryloyloxy, cyanomethoxy, methylsulphonyloxy, ethylsulphonyloxy, trifluoromethylsulphonyloxy, cyclopropylsulphonyloxy, 2-methoxyethoxymethyl, allyloxymethyl, prop-2-yn-1-yloxymethyl, methylsulphonylmethyl, methylcarbonylaminomethyl, methylsulphonylaminomethyl, —C(=NOR$^9$)R$^{13}$, dimethylaminosulphonyl, ethylaminosulphonyl, trimethylsilylethynyl, diethylaminosulphonyl, methylaminosulphonyl, trimethylsilyloxy, trimethylsilylprop-2-yn-1-yloxy, trifluoromethylamino, dimethylaminocarbonylamino, —C(=O)OH, —NHC(=O)H, —C(=O)NH$_2$, —C(=S)NR$^{11}$R$^{12}$ 1,1-dimethylethylcarbonylamino, chloromethylcarbonylamino, trifluoromethylcarbonylamino, 1,1-dimethylethoxycarbonylamino, ethylcarbonylamino, 1-methylethoxycarbonylamino, trifluoromethylcarbonylamino, methylcarbonylamino, methoxycarbonylamino, ethoxycarbonylamino, iso-propoxycarbonylamino, 1-methylethylcarbonylamino, methylsulphonylamino or phenylsulphonylamino, 3-bromoprop-2-en-1-yloxy, or -L$^4$Z$^3$, R$^9$ is preferably hydrogen, $C_1$-$C_6$-alkyl, $C_1$-$C_6$-haloalkyl, benzyl or Z$^3$, R$^{13}$ is preferably hydrogen, $C_1$-$C_6$-alkyl, $C_1$-$C_6$-haloalkyl, $C_3$-$C_8$-cycloalkyl-$C_1$-$C_4$-alkyl, $C_3$-$C_8$-cycloalkyl, $C_1$-$C_4$-alkyl-$C_3$-$C_8$-cycloalkyl, $C_1$-$C_4$-haloalkyl-$C_3$-$C_8$-cycloalkyl, $C_1$-$C_4$-alkoxy-$C_1$-$C_4$-alkyl, $C_1$-$C_4$-haloalkoxy-$C_1$-$C_4$-alkyl, benzyl or phenyl, more preferably hydrogen, methyl, ethyl, n-propyl, 1-methylethyl, n-butyl, 1,1-dimethylethyl or 2-methylpropyl, R$^{11}$ and R$^{12}$ are the same or different and are preferably hydrogen, $C_3$-$C_4$-alkenyl, $C_3$-$C_4$-alkynyl, cyano-$C_1$-$C_3$-alkyl, formyl, $C_1$-$C_3$-haloalkyl, phenyl, $C_1$-$C_3$-alkylcarbonyl, $C_3$-$C_8$-cycloalkoxycarbonyl, $C_1$-$C_3$-alkoxycarbonyl, $C_3$-$C_4$-alkenyloxycarbonyl, $C_3$-$C_4$-alkynyloxycarbonyl, $C_1$-$C_3$-haloalkylcarbonyl, $C_3$-$C_8$-halocycloalkylcarbonyl, $C_3$-$C_8$-cycloalkoxycarbonyl, $C_3$-$C_8$-cycloalkylcarbonyl, di($C_1$-$C_3$-alkyl)aminocarbonyl.

The malonic ester derivatives of heteroarylpiperidines and -piperazines usable in accordance with the invention are defined in general terms by the formula (I). The radical definitions of the radical definitions above and specified below of the formula (I) apply to the end products of the formula (I), and also equally to all intermediates (see also below under "Elucidations of the processes and intermediates").

The radical definitions and elucidations listed above and below, in general terms or in areas of preference, can be combined with one another as desired, i.e. including combinations between the particular areas and areas of preference. They apply both to the end products and correspondingly to precursors and intermediates. Moreover, individual definitions may not apply.

The radical definitions specified above can be combined with one another as desired. Moreover, individual definitions may not apply.

According to the type of substituents defined above, the compounds of the formula (I) have acidic or basic properties and can form salts, possibly also internal salts or adducts, with inorganic or organic acids or with bases or with metal ions. If the compounds of the formula (I) bear amino, alkylamino or other groups which induce basic properties, these compounds can be reacted with acids to give salts, or they are obtained directly as salts by the synthesis. If the compounds of the formula (I) bear hydroxyl, carboxyl or other groups which induce acidic properties, these compounds can be reacted with bases to give salts. Suitable bases are, for example, hydroxides, carbonates, hydrogencarbonates of the alkali metals and alkaline earth metals, especially those of sodium, potassium, magnesium and calcium, and also ammonia, primary, secondary and tertiary amines having $C_1$-$C_4$-alkyl groups, mono-, di- and trialkanolamines of $C_1$-$C_4$-alkanols, choline and chlorocholine.

The salts thus obtainable likewise have fungicidal properties.

Examples of inorganic acids are hydrohalic acids, such as hydrogen fluoride, hydrogen chloride, hydrogen bromide and hydrogen iodide, sulfuric acid, phosphoric acid and nitric acid, and acidic salts, such as NaHSO$_4$ and KHSO$_4$. Useful organic acids include, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated $C_6$-$C_{20}$ fatty acids, alkylsulphuric monoesters, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

Useful metal ions are especially the ions of the elements of the second main group, especially calcium and magnesium, of the third and fourth main group, especially aluminium, tin and lead, and also of the first to eighth transition groups, especially chromium, manganese, iron, cobalt, nickel, copper, zinc and others. Particular preference is given to the metal ions of the elements of the fourth period. Here, the metals can be present in the various valencies that they can assume.

Optionally substituted groups may be mono- or polysubstituted, where the substituents in the case of polysubstitutions may be identical or different.

In the definitions of the symbols given in the above formulae, collective terms were used, which are generally representative of the following substituents:

Halogen: fluorine, chlorine, bromine and iodine and preferably fluorine, chlorine, bromine and more preferably fluorine, chlorine.

Alkyl: saturated, straight-chain or branched hydrocarbyl radicals having 1 to 8, preferably 1 to 6 and more preferably 1 to 3 carbon atoms, for example (but not limited to) $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. This definition also applies to alkyl as part of a composite substituent, for example cycloalkylalkyl, hydroxyalkyl etc., unless defined elsewhere like, for example, alkylthio, alkylsufinyl, alkylsulphonyl, haloalkyl or haloalkylthio. If the alkyl is at the end of a composite substituent, as, for example, in alkylcycloalkyl, the part of the composite substituent at the start, for example the cycloalkyl, may be mono- or polysubstituted identically or differently and independently by alkyl. The same also applies to composite substituents in which other radicals, for example alkenyl, alkynyl, hydroxyl, halogen, formyl etc., are at the end.

Alkenyl: unsaturated, straight-chain or branched hydrocarbyl radicals having 2 to 8, preferably 2 to 6, carbon atoms and one double bond in any position, for example (but not limited to) $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1,-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl. This definition also applies to alkenyl as part of a composite substituent, for example haloalkenyl etc., unless defined elsewhere.

Alkynyl: straight-chain or branched hydrocarbyl groups having 2 to 8, preferably 2 to 6, carbon atoms and one triple bond in any position, for example (but not limited to) $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl. This definition also applies to alkynyl as part of a composite substituent, for example haloalkynyl etc., unless defined elsewhere.

Alkoxy: saturated, straight-chain or branched alkoxy radicals having 1 to 8, preferably 1 to 6 and more preferably 1 to 3 carbon atoms, for example (but not limited to) $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. This definition also applies to alkoxy as part of a composite substituent, for example haloalkoxy, alkynylalkoxy, etc., unless defined elsewhere.

Alkylthio: saturated, straight-chain or branched alkylthio radicals having 1 to 8, preferably 1 to 6 and more preferably 1 to 3 carbon atoms, for example (but not limited to) $C_1$-$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio. This definition also applies to alkylthio as part of a composite substituent, for example haloalkylthio etc., unless defined elsewhere.

Alkoxycarbonyl: an alkoxy group which has 1 to 6, preferably 1 to 3, carbon atoms (as specified above) and is bonded to the skeleton via a carbonyl group (—CO—). This definition also applies to alkoxycarbonyl as part of a composite substituent, for example cycloalkylalkoxycarbonyl etc., unless defined elsewhere.

Alkylsulphinyl: saturated, straight-chain or branched alkylsulphinyl radicals having 1 to 8, preferably 1 to 6 and more preferably 1 to 3 carbon atoms, for example (but not limited to) $C_1$-$C_6$-alkylsulphinyl such as methylsulphinyl, ethylsulphinyl, propylsulphinyl, 1-methylethylsulphinyl, butylsulphinyl, 1-methylpropylsulphinyl, 2-methylpropylsulphinyl, 1,1-dimethylethylsulphinyl, pentylsulphinyl, 1-methylbutylsulphinyl, 2-methylbutylsulphinyl, 3-methylbutylsulphinyl, 2,2-dimethylpropylsulphinyl, 1-ethylpropylsulphinyl, hexylsulphinyl, 1,1-dimethylpropylsulphinyl, 1,2-dimethylpropylsulphinyl, 1-methylpentylsulphinyl, 2-methylpentylsulphinyl, 3-methylpentylsulphinyl, 4-methylpentylsulphinyl, 1,1-dimethylbutylsulphinyl, 1,2-dimethylbutylsulphinyl, 1,3-dimethylbutylsulphinyl, 2,2-dimethylbutylsulphinyl, 2,3-dimethylbutylsulphinyl, 3,3-dimethylbutylsulphinyl, 1-ethylbutylsulphinyl, 2-ethylbutylsulphinyl, 1,1,2-trimethylpropylsulphinyl, 1,2,2-trimethylpropylsulphinyl, 1-ethyl-1-methylpropylsulphinyl and 1-ethyl-2-methylpropylsulphinyl. This definition also applies to alkylsulphinyl as part of a composite substituent, for example haloalkylsulphinyl etc., unless defined elsewhere.

Alkylsulphonyl: saturated, straight-chain or branched alkylsulphonyl radicals having 1 to 8, preferably 1 to 6 and more preferably 1 to 3 carbon atoms, for example (but not limited to) $C_1$-$C_6$-alkylsulphonyl such as methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1,1-dimethylpropylsulphonyl, 1,2-dimethylpropylsulphonyl, 1-methylpentylsulphonyl, 2-methylpentylsulphonyl, 3-methylpentylsulphonyl, 4-methylpentylsulphonyl, 1,1-dimethylbutylsulphonyl, 1,2-dimethylbutylsulphonyl, 1,3-dimethylbutylsulphonyl, 2,2-dimethylbutylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl. This definition also applies to alkylsulphonyl as part of a composite substituent, for example alkylsulphonylalkyl etc., unless defined elsewhere.

Cycloalkyl: monocyclic, saturated hydrocarbyl groups having 3 to 10, preferably 3 to 8 and more preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

Cycloalkenyl: monocyclic, partially unsaturated hydrocarbyl groups having 3 to 10, preferably 3 to 8 and more preferably 3 to 6 carbon ring members, for example (but not limited to) cyclopropenyl, cyclopentenyl and cyclohexenyl. This definition also applies to cycloalkenyl as part of a composite substituent, for example cycloalkenylalkyl etc., unless defined elsewhere.

Cycloalkoxy: monocyclic, saturated cycloalkyloxy radicals having 3 to 10, preferably 3 to 8 and more preferably 3 to 6 carbon ring members, for example (but not limited to) cyclopropyloxy, cyclopentyloxy and cyclohexyloxy. This definition also applies to cycloalkoxy as part of a composite substituent, for example cycloalkoxyalkyl etc., unless defined elsewhere.

Haloalkyl: straight-chain or branched alkyl groups having 1 to 8, preferably 1 to 6 and more preferably 1 to 3 carbon atoms (as specified above), where some or all of the hydrogen atoms in these groups may be replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent, for example haloalkylaminoalkyl etc., unless defined elsewhere.

Haloalkenyl and haloalkynyl are defined analogously to haloalkyl except that, instead of alkyl groups, alkenyl and alkynyl groups are present as part of the substituent.

Haloalkoxy: straight-chain or branched alkoxy groups having 1 to 8, preferably 1 to 6 and more preferably 1 to 3 carbon atoms (as specified above), where some or all of the hydrogen atoms in these groups may be replaced by halogen atoms as specified above, for example (but not limited to) $C_1$-$C_3$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy. This definition also applies to haloalkoxy as part of a composite substituent, for example haloalkoxyalkyl etc., unless defined elsewhere.

Haloalkylthio: straight-chain or branched alkylthio groups having 1 to 8, preferably 1 to 6 and more preferably 1 to 3 carbon atoms (as specified above), where some or all of the hydrogen atoms in these groups may be replaced by halogen atoms as specified above, for example (but not limited to) $C_1$-$C_3$-haloalkylthio such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio. This definition also applies to haloalkylthio as part of a composite substituent, for example haloalkylthioalkyl etc., unless defined elsewhere.

Heteroaryl: 5 or 6-membered, fully unsaturated monocyclic ring system containing one to four heteroatoms from the group of oxygen, nitrogen and sulphur; if the ring contains more than one oxygen atom, they are not directly adjacent;

5-membered heteroaryl containing one to four nitrogen atoms or one to three nitrogen atoms and one sulphur or oxygen atom: 5-membered heteroaryl groups which, in addition to carbon atoms, may contain one to four nitrogen atoms or one to three nitrogen atoms and one sulphur or oxygen atom as ring members, for example (but not limited thereto) 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

nitrogen-bonded 5-membered heteroaryl containing one to four nitrogen atoms, or benzofused nitrogen-bonded 5-membered heteroaryl containing one to three nitrogen atoms: 5-membered heteroaryl groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-diene-1,4-diyl group in which one or two carbon atoms may be replaced by nitrogen atoms, where these rings are attached to the skeleton via one of the nitrogen ring members, for example (but not limited to) 1-pyrrolyl, 1-pyrazolyl, 1,2,4-triazol-1-yl, 1-imidazolyl, 1,2,3-triazol-1-yl and 1,3,4-triazol-1-yl;

6-membered heteroaryl which contains one to four nitrogen atoms: 6-membered heteroaryl groups which, in addition to carbon atoms, may contain, respectively, one to three and one to four nitrogen atoms as ring members, for example (but not limited thereto) 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzofused 5-membered heteroaryl containing one to three nitrogen atoms or one nitrogen atom and one oxygen or sulphur atom: for example (but not limited to) indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl and 1,3-benzoxazol-7-yl;

benzofused 6-membered heteroaryl which contains one to three nitrogen atoms: for example (but not limited to) quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl and isoquinolin-8-yl.

This definition also applies to heteroaryl as part of a composite substituent, for example heteroarylalkyl etc., unless defined elsewhere.

Heterocyclyl: three- to fifteen-membered, preferably three- to nine-membered, saturated or partially unsaturated heterocycle containing one to four heteroatoms from the group of oxygen, nitrogen and sulphur: mono, bi- or tricyclic heterocycles which contain, in addition to carbon ring members, one to three nitrogen atoms and/or one oxygen or sulphur atom or one or two oxygen and/or sulphur atoms; if the ring contains more than one oxygen atom, they are not directly adjacent; for example (but not limited to) oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl. This definition also applies to heterocyclyl as part of a composite substituent, for example heterocyclylalkyl etc., unless defined elsewhere.

Leaving group: $S_N1$ or $S_N2$ leaving group, for example chlorine, bromine, iodine, alkylsulphonates (—$OSO_2$-alkyl, e.g. —$OSO_2CH_3$, —$OSO_2CF_3$) or arylsulphonates (—$OSO_2$-aryl, e.g. —$OSO_2Ph$, —$OSO_2PhMe$).

Not included are combinations which are against natural laws and which the person skilled in the art would therefore exclude based on his/her expert knowledge. Ring structures having three or more adjacent oxygen atoms, for example, are excluded.

Elucidation of the Preparation Processes and Intermediates

The piperidinecarboxylic acid derivatives of the formula (I) can be prepared in different ways. First of all, the possible processes are shown schematically below. Unless indicated otherwise, the radicals given have the meanings given above.

The processes according to the invention for preparing compounds of the formula (I) are optionally performed using one or more reaction auxiliaries.

Useful reaction auxiliaries are, as appropriate, inorganic or organic bases or acid acceptors. These preferably include alkali metal or alkaline earth metal acetates, amides, carbonates, hydrogencarbonates, hydrides, hydroxides or alkoxides, for example sodium acetate, potassium acetate or calcium acetate, lithium amide, sodium amide, potassium amide or calcium amide, sodium carbonate, potassium carbonate or calcium carbonate, sodium hydrogencarbonate, potassium hydrogencarbonate or calcium hydrogencarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; and also basic organic nitrogen compounds, for example trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, 1,4-diazabicyclo[2.2.2]octane (DABCO), 1,5-diazabicyclo[4.3.0]non-5-ene (DBN) or 1,8-diazabicyclo[5.4.0]-undec-7-ene (DBU).

Useful reaction auxiliaries are, as appropriate, inorganic or organic acids. These preferably include inorganic acids, for example hydrogen fluoride, hydrogen chloride, hydrogen bromide and hydrogen iodide, sulphuric acid, phosphoric acid and nitric acid, and acidic salts such as $NaHSO_4$ and $KHSO_4$, or organic acids, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated $C_6$-$C_{20}$ fatty acids, alkylsulphuric monoesters, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

The processes according to the invention are optionally performed using one or more diluents. Useful diluents are virtually all inert organic solvents. These preferably include aliphatic and aromatic, optionally halogenated hydrocarbons, such as pentane, hexane, heptane, cyclohexane, methyl cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether, methyl tert-butyl ether and dibutyl ether, glycol dimethyl ether and diglycol dimethyl ether, tetrahydrofuran, 2-methyltetrahydrofuran and dioxane, ketones such as acetone, methyl ethyl ketone, methyl isopropyl ketone and methyl isobutyl ketone, esters, such as methyl acetate, ethyl acetate and butyl acetate, nitriles, for example acetonitrile, propionitrile and butyronitrile, alcohols, for example methanol, ethanol, propanol, iso-propanol, butanol, tert-butanol, amides, for example dimethylformamide, dimethylacetamide and N-methylpyrrolidone, and also dimethyl sulphoxide, tetramethylenesulphone and hexamethylphosphoramide and DMPU.

In the processes according to the invention, the reaction temperatures can be varied within a relatively wide range. In general, the temperatures employed are between −50° C. and 250° C., preferably temperatures between −20° C. and 185° C.

The reaction time varies as a function of the scale of the reaction and of the reaction temperature, but is generally between a few minutes and 48 hours.

The processes according to the invention are generally performed under standard pressure. However, it is also possible to work under elevated or reduced pressure.

For performance of the processes according to the invention, the starting materials required in each case are generally used in approximately equimolar amounts. However, it is also possible to use one of the components used in each case in a relatively large excess.

Process A

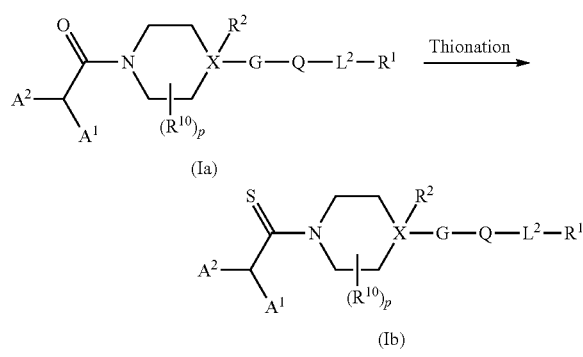

Scheme 1: Process A

The amides (Ia) can be converted by means of methods described in the literature to the corresponding thioamides (Ib) (e.g. *Bioorganic & Medicinal Chemistry Letters*, 2009, 19(2), 462-468) (Process A, Scheme 1). This involves reacting the compounds of the formula (Ia) typically with phosphorus pentasulphide or 2,4-bis(4-methoxyphenyl)-1,3-dithia-2,4-diphosphetane 2,4-disulphide (Lawesson's reagent).

Process A according to the invention is preferably carried out using one or more diluents. The preferred solvents are toluene, tetrahydrofuran, 1,4-dioxane and 1,2-dimethoxyethane.

After the reaction has ended, the compounds (Ib) are separated from the reaction mixture by one of the customary separation techniques. If necessary, the compounds are purified by recrystallization or chromatography.

Process B

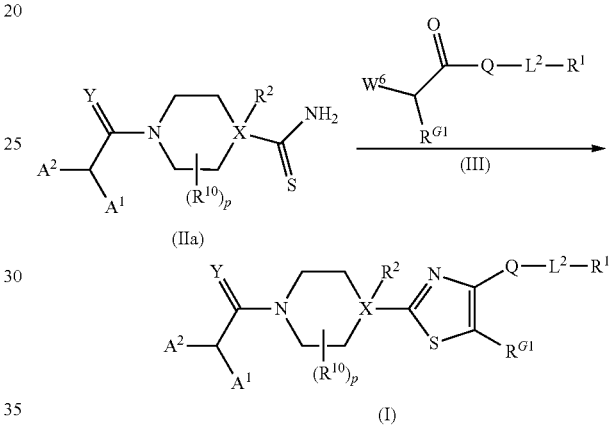

Scheme 2: Process B

One means of preparing compounds of the formula (I) from a corresponding thioamide of the formula (IIa) is shown in Scheme 2 (process B).

A thioamide of the formula (IIa) is converted in the presence of a compound of the formula (III) to a compound of the formula (I) by Hantzch thiazole synthesis described in the literature (Organic & Biomolecular Chemistry, 2012, 10, 1093-1101; Journal of *Medicinal Chemistry*, 1991, 34, 600-605).

The compound with the general formula (III) can be synthesised analogously to methods well described in the literature (see, for example WO 2008/013925 or WO 2013/098229).

After the reaction has ended, the compounds (I) are separated from the reaction mixture by one of the customary separation techniques. If necessary, the compounds are purified by recrystallization or chromatography, or can, if desired, also be used in the next step without prior purification.

Process C

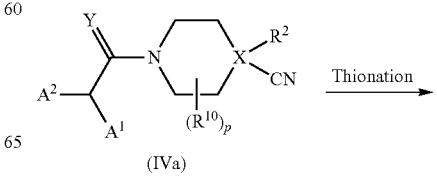

Scheme 3: Process C

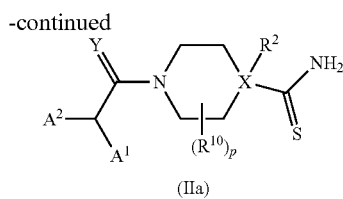

(IIa)

A nitrile of the formula (IVa) can be converted to the corresponding thioamides (IIa) by thionation (Process C, Scheme 3). The reaction can be performed under appropriate reaction conditions described in the literature (for example, see Synlett, 2009, 2338-2340; Synthesis, 2006, 224-226; Synlett, 2011, 2807-2810; EP696581), and it involves reacting the compounds of the formula (IVa) in the presence of a thionating reagent, for example, hydrogen sulphide or its bisulfide salt with an alkali metal or ammonia, and if necessary in the presence of an acid or a base.

In addition, a nitrile of the formula (IVa) can be hydrolysed first under acidic or basic conditions (for example, with aqueous sodium, potassium or lithium hydroxide solution or with aqueous hydrochloric acid) to a corresponding amide, then converted under an appropriate thionating conditions similar to Process A to a thioamide of the general formula (IIa).

After the reaction has ended, the compounds (IIa) are separated from the reaction mixture by one of the customary separation techniques. If necessary, the compounds are purified by recrystallization or chromatography.

Process D

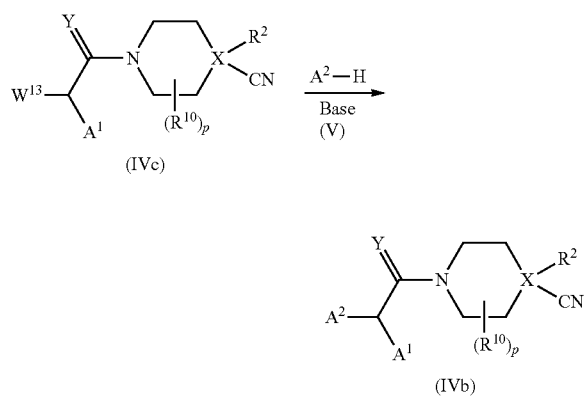

In general, it is possible to prepare compounds of the formula (IVb) from corresponding compounds (IVc) which bear a suitable leaving group $W^{13}$ for a substitution reaction with a substrate such as $A^2$-H (V), where $A^2$ is defined as above and H is hydrogen (see Scheme 4, Process D).

For the substitution reaction, at least one equivalent of a base (e.g. sodium hydride, potassium carbonate) or an acid scavenger is used in relation to the starting material of the general formula (IVc).

After the reaction has ended, the compounds (IVb) are separated from the reaction mixture by one of the customary separation techniques. If necessary, the compounds are purified by recrystallization or chromatography.

Process E

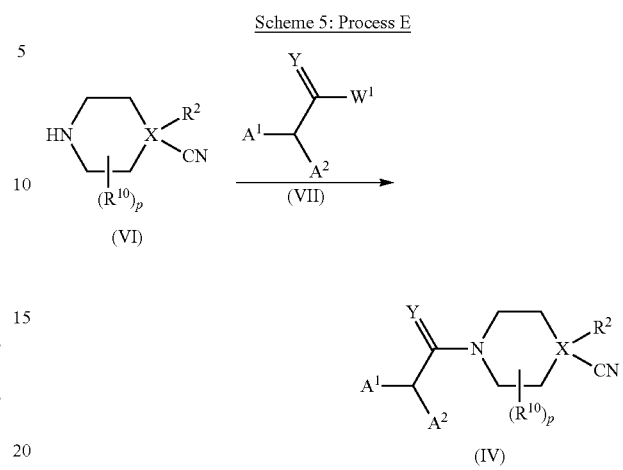

One means of preparing compounds of the formula (IV) from corresponding compounds (VI) with the compounds (VII) is shown in Scheme 5 (process E).

A compound with the general formula (IV) can be synthesized analogously to methods described in the literature (see, for example WO2008091594), by a coupling reaction of a compound with the corresponding general formula (VI) with a substrate of the general formula (VII) where $W^1$ is chlorine or fluorine, optionally in the presence of an acid scavenger/base.

At least one equivalent of an acid scavenger/a base (for example Hünig's base, triethylamine or commercially available polymeric acid scavengers) is used, in relation to the starting material of the general formula (VI). If the starting material is a salt, at least two equivalents of the acid scavenger are required.

Alternatively, a compound of the formula (IV) can also be synthesized from the corresponding compound of the formula (VI) with a substrate of the formula (VII) where $W^1$ is hydroxyl in the presence of a coupling agent, analogously to methods described in the literature (for example Tetrahedron, 2005, 61, 10827-10852, and references cited therein).

Suitable coupling reagents are, for example, peptide coupling reagents (for example N-(3-dimethylaminopropyl)-N'-ethylcarbodiimide mixed with 4-dimethylaminopyridine, N-(3-dimethylaminopropyl)-N'-ethylcarbodiimide mixed with 1-hydroxybenzotriazole, bromotripyrrolidinophosphonium hexafluorophosphate, O-(7-azabenzotriazol-1-yl)-N,N,N',N'-tetramethyluronium hexafluorophosphate, etc.).

A compound of the formula (VII) is either commercially available or can be prepared by processes described in the literature (see, for example, WO 2008013925, WO2008091580, WO2007014290 and WO2008091594).

Compounds of formula (VI) are either commercially available or can be synthesized analogously to methods described in the literature (for example, Polish Journal of Chemistry, 1988, 62, 451-5; WO2012045124).

After the reaction has ended, the compounds (IV) are separated from the reaction mixture by one of the customary separation techniques. If necessary, the compounds are purified by recrystallization or chromatography.

Process F

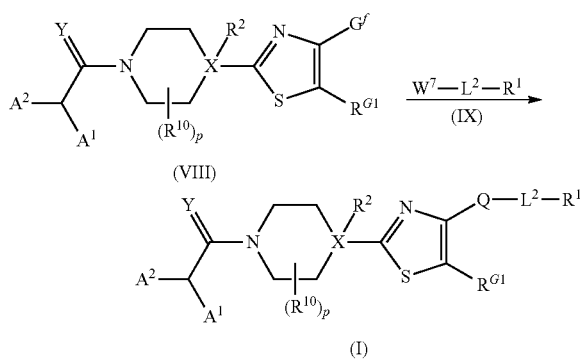

In general, it is also possible to prepare compounds of the formula (I) from corresponding compounds (VIII) and (IX) with suitable functional groups $G^f$ and $W^7$ (Scheme 6, Process F). There are numerous literature methods for the preparation of heterocycles (see WO 2008/013622; Comprehensive Heterocyclic Chemistry vol. 4-6, editors: A. R. Katritzky and C. W. Rees, Pergamon Press, New York, 1984; Comprehensive Heterocyclic Chemistry II, vol. 2-4, editors: A. R. Katritzky, C. W. Rees and E. F. Scriven, Pergamon Press, New York, 1996; The Chemistry of Heterocyclic Compounds, editor: E. C. Taylor, Wiley, New York; Rodd's Chemistry of Carbon Compounds, vol. 2-4, Elsevier, New York; Synthesis, 1982, 6, 508-509; Tetrahedron, 2000, 56, 1057-1064).

Compounds with the general formula (IX), for example styrenes, are generally commercially available or can be prepared by methods described in the literature.

After the reaction has ended, the compounds (I) are separated from the reaction mixture by one of the customary separation techniques. If necessary, the compounds are purified by recrystallization or chromatography.

Process G

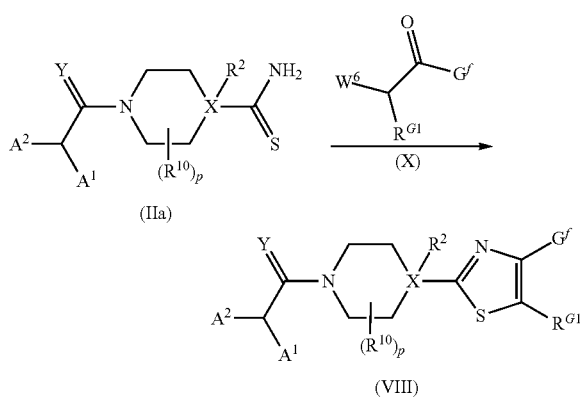

One means of preparing compounds of the formula (VIII) from a corresponding thioamide of the formula (IIa) is shown in Scheme 7 (process G).

A thioamide of the formula (IIa) is converted in the presence of a compound of the formula (X) to a compound of the formula (VIII) by Hantzch thiazole synthesis analogously to Process B (Scheme 2).

The compound with the general formula (X) can be synthesized analogously to methods well described in the literature (see, for example WO 2008013925).

After the reaction has ended, the compounds (VIII) are separated from the reaction mixture by one of the customary separation techniques. If necessary, the compounds are purified by recrystallization or chromatography, or can, if desired, also be used in the next step without prior purification.

It is recognized that the substituent $R^2$ can be converted from one substituent definition to another as specified above, at any appropriate stage of the synthesis, in one or more steps, by synthetic methods commonly used by the person skilled in the art of chemical synthesis. For example, an intermediate or a final product that bears an ester as $R^2$ can be saponified in the presence of an aqueous base or an acid to its corresponding carboxylic acid that can be in turn converted to an amide or another ester by amidation or by esterification.

Furthermore, it is also recognized that some reagents and reaction conditions described above for preparation of compounds of the formula (I) may not be compatible with particular functionalities present in the intermediate compounds. In these cases, the introduction of protection/deprotection sequences or of mutual conversions of functional groups into the synthesis helps to obtain the desired products. The use and selection of the protecting groups is obvious to the person skilled in the art of chemical synthesis (see, for example, "Protective Groups in Organic Synthesis"; Third Edition; 494-653, and literature cited therein). The person skilled in the art will recognize that, in some cases, after the introduction of a given reagent as shown in an individual scheme, it may be necessary to perform additional routine synthesis steps not described individually in order to complete the synthesis of compounds of the formula (I). The person skilled in the art will likewise recognize that it may be necessary to perform a combination of the steps illustrated in the above schemes in a sequence other than the implied sequence shown specifically, in order to prepare the compounds of the formula (I).

The workup is carried out by customary methods. If necessary, the compounds are purified by recrystallization or chromatography.

The invention also relates to a method for controlling unwanted microorganisms, characterized in that the inventive heteroarylpiperidine and -piperazine derivatives are applied to the microorganisms and/or in their habitat.

The invention further relates to seed which has been treated with at least one inventive heteroarylpiperidine or -piperazine derivative.

The invention finally provides a method for protecting seed against unwanted microorganisms by using seed treated with at least one inventive heteroarylpiperidine or -piperazine derivative according to the present invention.

The inventive substances have potent microbicidal activity and can be used for control of unwanted microorganisms, such as fungi and bacteria, in crop protection and in the protection of materials.

The inventive piperidinecarboxylic acid derivatives of the formula (I) have very good fungicidal properties and can be used in crop protection, for example for control of Plasmodiophoromycetes, Oomycetes, Chytridiomycetes, Zygomycetes, Ascomycetes, Basidiomycetes and Deuteromycetes.

Bactericides can be used in crop protection, for example, for control of Pseudomonadaceae, Rhizobiaceae, Enterobacteriaceae, Corynebacteriaceae and Streptomycetaceae.

The inventive fungicidal compositions can be used for curative or protective control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

The inventive compositions for controlling phytopathogenic fungi in crop protection comprise an effective but non-phytotoxic amount of the inventive active ingredients. An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds.

Composition/Formulation

The present invention further relates to a crop protection composition for controlling harmful microorganisms, especially unwanted fungi and bacteria, comprising an effective and non-phytotoxic amount of the inventive active ingredients. These are preferably fungicidal compositions which comprise agriculturally suitable auxiliaries, solvents, carriers, surfactants or extenders.

In the context of the present invention, "control of harmful microorganisms" means a reduction in infestation by harmful microorganisms, compared with the untreated plant measured as fungicidal efficacy, preferably a reduction by 25-50%, compared with the untreated plant (100%), more preferably a reduction by 40-79%, compared with the untreated plant (100%); even more preferably, the infection by harmful microorganisms is entirely suppressed (by 70-100%). The control may be curative, i.e. for treatment of already infected plants, or protective, for protection of plants which have not yet been infected.

An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

Suitable organic solvents include all polar and non-polar organic solvents usually employed for formulation purposes. Preferable the solvents are selected from ketones, e.g. methyl-isobutyl-ketone and cyclohexanone, amides, e.g. dimethyl formamide and alkanecarboxylic acid amides, e.g. N,N-dimethyl decaneamide and N,N-dimethyl octanamide, furthermore cyclic solvents, e.g. N-methyl-pyrrolidone, N-octyl-pyrrolidone, N-dodecyl-pyrrolidone, N-octyl-caprolactame, N-dodecyl-caprolactame and butyrolactone, furthermore strong polar solvents, e.g. dimethylsulfoxide, and aromatic hydrocarbons, e.g. xylol, Solvesso™, mineral oils, e.g. white spirit, petroleum, alkyl benzenes and spindle oil, also esters, e.g. propyleneglycol-monomethylether acetate, adipic acid dibutylester, acetic acid hexylester, acetic acid heptylester, citric acid tri-n-butylester and phthalic acid di-n-butylester, and also alcohols, e.g. benzyl alcohol and 1-methoxy-2-propanol.

According to the invention, a carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. Mixtures of such carriers can likewise be used.

Suitable solid filler and carrier include inorganic particles, e.g. carbonates, silicates, sulphates and oxides with an average particle size of between 0.005 and 20 μm, preferably of between 0.02 to 10 μm, for example ammonium sulphate, ammonium phosphate, urea, calcium carbonate, calcium sulphate, magnesium sulphate, magnesium oxide, aluminium oxide, silicium dioxide, so-called fine-particle silica, silica gels, natural or synthetic silicates, and alumosilicates and plant products like cereal flour, wood powder/sawdust and cellulose powder.

Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Useful liquefied gaseous extenders or carriers are those liquids which are gaseous at standard temperature and under standard pressure, for example aerosol propellants such as halohydrocarbons, and also butane, propane, nitrogen and carbon dioxide.

In the formulations, it is possible to use tackifiers such as carboxymethylcellulose, and natural and synthetic polymers in the form of powders, granules or latices, such as gum arabic, polyvinyl alcohol and polyvinyl acetate, or else natural phospholipids, such as cephalins and lecithins, and synthetic phospholipids. Further additives may be mineral and vegetable oils.

If the extender used is water, it is also possible to employ, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

Suitable surfactants (adjuvants, emulsifiers, dispersants, protective colloids, wetting agent and adhesive) include all common ionic and non-ionic substances, for example ethoxylated nonylphenols, polyalkylene glycolether of linear or branched alcohols, reaction products of alkyl phenols with ethylene oxide and/or propylene oxide, reaction products of fatty acid amines with ethylene oxide and/or propylene oxide, furthermore fattic acid esters, alkyl sulfonates, alkyl sulphates, alkyl ethersulphates, alkyl etherphosphates, arylsulphate, ethoxylated arylalkylphenols, e.g. tristyrylphenol-ethoxylates, furthermore ethoxylated and propoxylated arylalkylphenols like sulphated or phosphated arylalkylphenol-ethoxylates and -ethoxy- and -propoxylates. Further examples are natural and synthetic, water soluble polymers, e.g. lignosulphonates, gelatine, gum arabic, phospholipides, starch, hydrophobic modified starch and cellulose derivatives, in particular cellulose ester and cellulose ether, further polyvinyl alcohol, polyvinyl acetate, polyvinyl pyrrolidone, polyacrylic acid, polymethacrylic acid and co-polymerisates of (meth)acrylic acid and (meth)acrylic acid esters, and further co-polymerisates of methacrylic acid and methacrylic acid esters which are neutralized with alkali-metal hydroxide and also condensation products of optionally substituted naphthalene sulfonic acid salts with formaldehyde. The presence of a surfactant is necessary if one of the active ingredients and/or one of the inert carriers is insoluble in water and when application is effected in water. The proportion of surfactants is between 5 and 40 percent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Antifoams which may be present in the formulations include e.g. silicone emulsions, longchain alcohols, fattiy acids and their salts as well as fluoroorganic substances and mixtures therof.

Examples of thickeners are polysaccharides, e.g. xanthan gum or veegum, silicates, e.g. attapulgite, bentonite as well as fine-particle silica.

If appropriate, it is also possible for other additional components to be present, for example protective colloids, binders, adhesives, thickeners, thixotropic substances, penetrants, stabilizers, sequestrants, complexing agents. In general, the active ingredients can be combined with any solid or liquid additive commonly used for formulation purposes.

The inventive active ingredients or compositions can be used as such or, depending on their particular physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, gas (under pressure), gas generating product, foams, pastes, pesticide coated seed, suspension concentrates, suspoemulsion concentrates, soluble concentrates, suspensions, wettable powders, soluble powders, dusts and granules, water-soluble and water-dispersible granules or tablets, water-soluble and water-dispersible powders for the treatment of seed, wettable powders, natural products and synthetic substances impregnated with active ingredient, and also microencapsulations in polymeric substances and in coating materials for seed, and also ULV cold-fogging and warm-fogging formulations.

The inventive compositions include not only formulations which are already ready for use and can be applied with a suitable apparatus to the plant or the seed, but also commercial concentrates which have to be diluted with water prior to use. Customary applications are for example dilution in water and subsequent spraying of the resulting spray liquor, application after dilution in oil, direct application without dilution, seed treatment or soil application of granules.

The inventive compositions and formulations generally contain between 0.05 and 99% by weight, 0.01 and 98% by weight, preferably between 0.1 and 95% by weight, more preferably between 0.5 and 90% of active ingredient, most preferably between 10 and 70% by weight. For special applications, e.g. for protection of wood and derived timber products the inventive compositions and formulations generally contain between 0.0001 and 95% by weight, preferably 0.001 to 60% by weight of active ingredient.

The contents of active ingredient in the application forms prepared from the commercial formulations may vary in a broad range. The concentration of the active ingredients in the application forms is generally between 0.000001 to 95% by weight, preferably between 0.0001 and 2% by weight.

The formulations mentioned can be prepared in a manner known per se, for example by mixing the active ingredients with at least one customary extender, solvent or diluent, adjuvant, emulsifier, dispersant, and/or binder or fixative, wetting agent, water repellent, if appropriate desiccants and UV stabilizers and, if appropriate, dyes and pigments, antifoams, preservatives, inorganic and organic thickeners, adhesives, gibberellins and also further processing auxiliaries and also water. Depending on the formulation type to be prepared further processing steps are necessary, e.g. wet grinding, dry grinding and granulation.

The inventive active ingredients may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The inventive treatment of the plants and plant parts with the active ingredients or compositions is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching), drip irrigating and, in the case of propagation material, especially in the case of seeds, also by dry seed treatment, wet seed treatment, slurry treatment, incrustation, coating with one or more coats, etc. It is also possible to deploy the active ingredients by the ultra-low volume method or to inject the active ingredient preparation or the active ingredient itself into the soil.

Plant/Crop Protection

The inventive active ingredients or compositions have potent microbicidal activity and can be used for control of unwanted microorganisms, such as fungi and bacteria, in crop protection and in the protection of materials.

The invention also relates to a method for controlling unwanted microorganisms, characterized in that the inventive active ingredients are applied to the phytopathogenic fungi, phytopathogenic bacteria and/or their habitat.

Fungicides can be used in crop protection for control of phytopathogenic fungi. They are characterized by an outstanding efficacy against a broad spectrum of phytopathogenic fungi, including soilborne pathogens, which are in particular members of the classes Plasmodiophoromycetes, Peronosporomycetes (Syn. Oomycetes), Chytridiomycetes, Zygomycetes, Ascomycetes, Basidiomycetes and Deuteromycetes (Syn. Fungi imperfecti). Some fungicides are systemically active and ca be used in plant protection as foliar, seed dressing or soil fungicide. Furthermore, they are suitable for combating fungi, which inter alia infest wood or roots of plant.

Bactericides can be used in crop protection for control of Pseudomonadaceae, Rhizobiaceae, Enterobacteriaceae, Corynebacteriaceae and Streptomycetaceae.

Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* and *Phakopsora meibomiae*; *Puccinia* species, for example *Puccinia recondite, P. triticina, P. graminis* or *P. striiformis*; *Uromyces* species, for example *Uromyces appendiculatus*;

diseases caused by pathogens from the group of the Oomycetes, for example *Albugo* species, for example *Albugo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidia form: *Drechslera*, Syn: *Helminthosporium*), *Cochliobolus miyabeanus*; *Colletotrichum* species, for example *Colletotrichum lindemuthanium*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans, Leptosphaeria nodorum*; *Magnaporthe* species, for example *Magnaporthe grisea*; *Microdochium* species, for example *Microdochium nivale*; *Mycosphaerella* species, for example *Mycosphaerella graminicola, M. arachidicola* and *M. fijiensis*; *Phaeosphaeria* species, for example *Phaeosphaeria nodorum*; *Pyrenophora* species, for example *Pyrenophora teres, Pyrenophora tritici repentis*; *Ramularia* species, for example *Ramularia collo-cygni, Ramularia areola*; *Rhynchosporium* species, for example *Rhynchosporium secalis*; *Septoria* species, for example *Septoria apii, Septoria lycopersii*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, such as, for example *Rhizoctonia solani*; *Sarocladium* diseases caused for example by *Sarocladium oryzae*; *Sclerotium* diseases caused for example by *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example *Septoria nodorum*;

diseases caused by smut fungi, for example *Sphacelotheca* species, for example *Sphacelotheca reiliana*; *Tilletia* species, for example *Tilletia caries, T. controversa*; *Urocystis* species, for example *Urocystis occulta*; *Ustilago* species, for example *Ustilago nuda, U. nuda tritici*;

fruit rot caused, for example, by *Aspergillus* species, for example *Aspergillus flavus*; *Botrytis* species, for example *Botrytis cinerea*; *Penicillium* species, for example *Penicillium expansum* and *P. purpurogenum*; *Sclerotinia* species, for example *Sclerotinia sclerotiorum*; *Verticilium* species, for example *Verticilium alboatrum*;

seed and soilborne decay, mould, wilt, rot and damping-off diseases caused, for example, by *Alternaria* species, caused for example by *Alternaria brassicicola*; *Aphanomyces* species, caused for example by *Aphanomyces euteiches*; *Ascochyta* species, caused for example by *Ascochyta lentis*; *Aspergillus* species, caused for example by *Aspergillus flavus*; *Cladosporium* species, caused for example by *Cladosporium herbarum*; *Cochliobolus* species, caused for example by *Cochliobolus sativus*; (Conidiaform: *Drechslera, Bipolaris* Syn: *Helminthosporium*); *Colletotrichum* species, caused for example by *Colletotrichum coccodes*; *Fusarium* species, caused for example by *Fusarium culmorum*; *Gibberella* species, caused for example by *Gibberella zeae*; *Macrophomina* species, caused for example by *Macrophomina phaseolina*; *Monographella* species, caused for example by *Monographella nivalis*; *Penicillium* species, caused for example by *Penicillium expansum*; *Phoma* species, caused for example by *Phoma lingam*; *Phomopsis* species, caused for example by *Phomopsis sojae*; *Phytophthora* species, caused for example by *Phytophthora cactorum*; *Pyrenophora* species, caused for example by *Pyrenophora graminea*; *Pyricularia* species, caused for example by *Pyricularia oryzae*; *Pythium* species, caused for example by *Pythium ultimum*; *Rhizoctonia* species, caused for example by *Rhizoctonia solani*; *Rhizopus* species, caused for example by *Rhizopus oryzae*; *Sclerotium* species, caused for example by *Sclerotium rolfsii*; *Septoria* species, caused for example by *Septoria nodorum*; *Typhula* species, caused for example by *Typhula incarnata*; *Verticillium* species, caused for example by *Verticillium dahliae*;

cancers, galls and witches' broom caused, for example, by *Nectria* species, for example *Nectria galligena*;

wilt diseases caused, for example, by *Monilinia* species, for example *Monilinia laxa*;

leaf blister or leaf curl diseases caused, for example, by *Exobasidium* species, for example *Exobasidium vexans*; *Taphrina* species, for example *Taphrina deformans*;

decline diseases of wooden plants caused, for example, by Esca disease, caused for example by *Phaemoniella clamydospora*, *Phaeoacremonium aleophilum* and *Fomitiporia mediterranea*; Eutypa dyeback, caused for example by *Eutypa lata*; *Ganoderma* diseases caused for example by *Ganoderma boninense*; *Rigidoporus* diseases caused for example by *Rigidoporus lignosus*;

diseases of flowers and seeds caused, for example, by *Botrytis* species, for example *Botrytis cinerea*;

diseases of plant tubers caused, for example, by *Rhizoctonia* species, for example *Rhizoctonia solani*; *Helminthosporium* species, for example *Helminthosporium solani*;

Club root caused, for example, by *Plasmodiophora* species, for example Plamodiophora *brassicae*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllosticta leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*, *Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The inventive fungicidal compositions can be used for curative or protective/preventive control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

The fact that the active ingredients are well tolerated by plants at the concentrations required for controlling plant diseases allows the treatment of above-ground parts of plants, of propagation stock and seeds, and of the soil.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

The inventive active ingredients, when they are well tolerated by plants, have favourable homeotherm toxicity and are well tolerated by the environment, are suitable for protecting plants and plant organs, for enhancing harvest yields, for improving the quality of the harvested material. They can preferably be used as crop protection compositions. They are active against normally sensitive and resistant species and against all or some stages of development.

Plants which can be treated in accordance with the invention include the following main crop plants: maize, soya bean, alfalfa, cotton, sunflower, *Brassica* oil seeds such as *Brassica napus* (e.g. canola, rapeseed), *Brassica rapa, B. juncea* (e.g. (field) mustard) and *Brassica carinata*, Arecaceae sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. Rosaceae sp. (e.g. pome fruits such as apples and pears, but also stone fruits such as apricots, cherries, almonds, plums and peaches, and berry fruits such as strawberries, raspberries, red and black currant and gooseberry), Ribesioidae sp., Juglandaceae sp., Betulaceae sp., Anacardiaceae sp., Fagaceae sp., Moraceae sp., Oleaceae sp. (e.g. olive tree), Actinidaceae sp., Lauraceae sp. (e.g. avocado, cinnamon, camphor), Musaceae sp. (e.g. banana trees and plantations), Rubiaceae sp. (e.g. coffee), Theaceae sp. (e.g. tea), Sterculiceae sp., Rutaceae sp. (e.g. lemons, oranges, mandarins and grapefruit); Solanaceae sp. (e.g. tomatoes, potatoes, peppers, *capsicum*, aubergines, tobacco), Liliaceae sp., Compositae sp. (e.g. lettuce, artichokes and chicory—including root chicory, endive or common chicory), Umbelliferae sp. (e.g. carrots, parsley, celery and celeriac), Cucurbitaceae sp. (e.g. cucumbers—including gherkins, pumpkins, watermelons, calabashes and melons), Alliaceae sp. (e.g. leeks and onions), Cruciferae sp. (e.g. white cabbage, red cabbage, broccoli, cauliflower, Brussels sprouts, pak choi, kohlrabi, radishes, horseradish, cress and chinese cabbage), Leguminosae sp. (e.g. peanuts, peas, lentils and beans—e.g. common beans and broad beans), Chenopodiaceae sp. (e.g. Swiss chard, fodder beet, spinach, beetroot), Linaceae sp. (e.g. hemp), Cannabeacea sp. (e.g. cannabis), Malvaceae sp. (e.g. okra, cocoa), Papaveraceae (e.g. poppy), Asparagaceae (e.g. asparagus); useful plants and ornamental plants in the garden and woods including turf, lawn, grass and *Stevia rebaudiana*; and in each case genetically modified types of these plants.

Plant Growth Regulation

In some cases, the inventive compounds can, at particular concentrations or application rates, also be used as herbicides, safeners, growth regulators or agents to improve plant properties, or as microbicides, for example as fungicides, antimycotics, bactericides, viricides (including compositions against viroids) or as compositions against MLO (*Mycoplasma*-like organisms) and RLO (*Rickettsia*-like organisms). If appropriate, they can also be used as intermediates or precursors for the synthesis of other active ingredients.

The inventive active ingredients intervene in the metabolism of the plants and can therefore also be used as growth regulators.

Plant growth regulators may exert various effects on plants. The effect of the substances depends essentially on the time of application in relation to the developmental stage of the plant, and also on the amounts of active ingredient applied to the plants or their environment and on the type of application. In each case, growth regulators should have a particular desired effect on the crop plants.

Plant growth-regulating compounds can be used, for example, to inhibit the vegetative growth of the plants. Such inhibition of growth is of economic interest, for example, in the case of grasses, since it is thus possible to reduce the frequency of grass cutting in ornamental gardens, parks and sport facilities, on roadsides, at airports or in fruit crops. Also of significance is the inhibition of the growth of herbaceous and woody plants on roadsides and in the vicinity of pipelines or overhead cables, or quite generally in areas where vigorous plant growth is unwanted.

Also important is the use of growth regulators for inhibition of the longitudinal growth of cereal. This reduces or completely eliminates the risk of lodging of the plants prior to harvest. In addition, growth regulators in the case of cereals can strengthen the culm, which also counteracts lodging. The employment of growth regulators for shortening and strengthening culms allows the deployment of higher fertilizer volumes to increase the yield, without any risk of lodging of the cereal crop.

In many crop plants, inhibition of vegetative growth allows denser planting, and it is thus possible to achieve higher yields based on the soil surface. Another advantage of the smaller plants obtained in this way is that the crop is easier to cultivate and harvest.

Inhibition of the vegetative plant growth may also lead to enhanced yields because the nutrients and assimilates are of more benefit to flower and fruit formation than to the vegetative parts of the plants.

Frequently, growth regulators can also be used to promote vegetative growth. This is of great benefit when harvesting the vegetative plant parts. However, promoting vegetative growth may also promote generative growth in that more assimilates are formed, resulting in more or larger fruits.

In some cases, yield increases may be achieved by manipulating the metabolism of the plant, without any detectable changes in vegetative growth. In addition, growth regulators can be used to alter the composition of the plants, which in turn may result in an improvement in quality of the harvested products. For example, it is possible to increase the sugar content in sugar beet, sugar cane, pineapples and in citrus fruit, or to increase the protein content in soya or cereals. It is also possible, for example, to use growth regulators to inhibit the degradation of desirable ingredients, for example sugar in sugar beet or sugar cane, before or after harvest. It is also possible to positively influence the production or the elimination of secondary plant ingredients. One example is the stimulation of the flow of latex in rubber trees.

Under the influence of growth regulators, parthenocarpic fruits may be formed. In addition, it is possible to influence the sex of the flowers. It is also possible to produce sterile pollen, which is of great importance in the breeding and production of hybrid seed.

Use of growth regulators can control the branching of the plants. On the one hand, by breaking apical dominance, it is possible to promote the development of side shoots, which may be highly desirable particularly in the cultivation of ornamental plants, also in combination with an inhibition of growth. On the other hand, however, it is also possible to inhibit the growth of the side shoots. This effect is of particular interest, for example, in the cultivation of tobacco or in the cultivation of tomatoes.

Under the influence of growth regulators, the amount of leaves on the plants can be controlled such that defoliation of the plants is achieved at a desired time. Such defoliation plays a major role in the mechanical harvesting of cotton, but is also of interest for facilitating harvesting in other crops, for example in viticulture. Defoliation of the plants can also be undertaken to lower the transpiration of the plants before they are transplanted.

Growth regulators can likewise be used to regulate fruit dehiscence. On the one hand, it is possible to prevent premature fruit dehiscence. On the other hand, it is also possible to promote fruit dehiscence or even flower abortion to achieve a desired mass ("thinning"), in order to eliminate alternation. Alternation is understood to mean the characteristic of some fruit species, for endogenous reasons, to deliver very different yields from year to year. Finally, it is possible to use growth regulators at the time of harvest to reduce the forces required to detach the fruits, in order to allow mechanical harvesting or to facilitate manual harvesting.

Growth regulators can also be used to achieve faster or else delayed ripening of the harvested material before or after harvest. This is particularly advantageous as it allows optimal adjustment to the requirements of the market. Moreover, growth regulators in some cases can improve the fruit colour. In addition, growth regulators can also be used to concentrate maturation within a certain period of time. This establishes the prerequisites for complete mechanical or manual harvesting in a single operation, for example in the case of tobacco, tomatoes or coffee.

By using growth regulators, it is additionally possible to influence the resting of seed or buds of the plants, such that plants such as pineapple or ornamental plants in nurseries, for example, germinate, sprout or flower at a time when they are normally not inclined to do so. In areas where there is a risk of frost, it may be desirable to delay budding or germination of seeds with the aid of growth regulators, in order to avoid damage resulting from late frosts.

Finally, growth regulators can induce resistance of the plants to frost, drought or high salinity of the soil. This allows the cultivation of plants in regions which are normally unsuitable for this purpose.

Resistance Induction/Plant Health and Other Effects

The active compounds according to the invention also exhibit a potent strengthening effect in plants. Accordingly, they can be used for mobilizing the defenses of the plant against attack by undesirable microorganisms.

Plant-strengthening (resistance-inducing) substances are to be understood as meaning, in the present context, those substances which are capable of stimulating the defence system of plants in such a way that the treated plants, when subsequently inoculated with undesirable microorganisms, develop a high degree of resistance to these microorganisms.

The active compounds according to the invention are also suitable for increasing the yield of crops. In addition, they show reduced toxicity and are well tolerated by plants.

Further, in context with the present invention plant physiology effects comprise the following:

Abiotic stress tolerance, comprising temperature tolerance, drought tolerance and recovery after drought stress, water use efficiency (correlating to reduced water consumption), flood tolerance, ozone stress and UV tolerance, tolerance towards chemicals like heavy metals, salts, pesticides (safener) etc.

Biotic stress tolerance, comprising increased fungal resistance and increased resistance against nematodes, viruses and bacteria. In context with the present invention, biotic stress tolerance preferably comprises increased fungal resistance and increased resistance against nematodes Increased plant vigor, comprising plant health/plant quality and seed vigor, reduced stand failure, improved appearance, increased recovery, improved greening effect and improved photosynthetic efficiency.

Effects on plant hormones and/or functional enzymes.

Effects on growth regulators (promoters), comprising earlier germination, better emergence, more developed root system and/or improved root growth, increased ability of tillering, more productive tillers, earlier flowering, increased plant height and/or biomass, shorting of stems, improvements in shoot growth, number of kernels/ear, number of ears/m$^2$, number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

Increased yield, referring to total biomass per hectare, yield per hectare, kernel/fruit weight, seed size and/or hectoliter weight as well as to increased product quality, comprising:
improved processability relating to size distribution (kernel, fruit, etc.), homogenous riping, grain moisture, better milling, better vinification, better brewing, increased juice yield, harvestability, digestibility, sedimentation value, falling number, pod stability, storage stability, improved fiber length/strength/uniformity, increase of milk and/or meet quality of silage fed animals, adaption to cooking and frying; further comprising improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;
further comprising increased desired ingredients such as e.g. protein content, fatty acids, oil content, oil quality, aminoacid composition, sugar content, acid content (pH), sugar/acid ratio (Brix), polyphenols, starch content, nutritional quality, gluten content/index, energy content, taste, etc.;
and further comprising decreased undesired ingredients such as e.g. less mycotoxines, less aflatoxines, geosmin level, phenolic aromas, lacchase, polyphenol oxidases and peroxidases, nitrate content etc.

Sustainable agriculture, comprising nutrient use efficiency, especially nitrogen (N)-use efficiency, phosphours (P)-use efficiency, water use efficiency, improved transpiration, respiration and/or $CO_2$ assimilation rate, better nodulation, improved Ca-metabolism etc.

Delayed senescence, comprising improvement of plant physiology which is manifested, for example, in a longer grain filling phase, leading to higher yield, a longer duration of green leaf colouration of the plant and thus comprising colour (greening), water content, dryness etc. Accordingly, in the context of the present invention, it has been found that the specific inventive application of the active compound combination makes it possible to prolong the green leaf area duration, which delays the maturation (senescence) of the plant. The main advantage to the farmer is a longer grain filling phase leading to higher yield. There is also an advantage to the farmer on the basis of greater flexibility in the harvesting time.

Therein "sedimentation value" is a measure for protein quality and describes according to Zeleny (Zeleny value) the degree of sedimentation of flour suspended in a lactic acid solution during a standard time interval. This is taken as a measure of the baking quality. Swelling of the gluten fraction of flour in lactic acid solution affects the rate of sedimentation of a flour suspension. Both a higher gluten content and a better gluten quality give rise to slower sedimentation and higher Zeleny test values. The sedimentation value of flour depends on the wheat protein composition and is mostly correlated to the protein content, the wheat hardness, and the volume of pan and hearth loaves. A stronger correlation between loaf volume and Zeleny sedimentation volume compared to SDS sedimentation volume could be due to the protein content influencing both the volume and Zeleny value (*Czech J. Food Sci*. Vol. 21, No. 3: 91-96, 2000).

Further the "falling number" as mentioned herein is a measure for the baking quality of cereals, especially of wheat. The falling number test indicates that sprout damage may have occurred. It means that changes to the physical properties of the starch portion of the wheat kernel has already happened. Therein, the falling number instrument analyzes viscosity by measuring the resistance of a flour and water paste to a falling plunger. The time (in seconds) for this to happen is known as the falling number. The falling number results are recorded as an index of enzyme activity in a wheat or flour sample and results are expressed in time as seconds. A high falling number (for example, above 300 seconds) indicates minimal enzyme activity and sound quality wheat or flour. A low falling number (for example, below 250 seconds) indicates substantial enzyme activity and sprout-damaged wheat or flour.

The term "more developed root system"/"improved root growth" refers to longer root system, deeper root growth, faster root growth, higher root dry/fresh weight, higher root volume, larger root surface area, bigger root diameter, higher root stability, more root branching, higher number of root hairs, and/or more root tips and can be measured by analyzing the root architecture with suitable methodologies and Image analysis programmes (e.g. WinRhizo).

The term "crop water use efficiency" refers technically to the mass of agriculture produce per unit water consumed and economically to the value of product(s) produced per unit water volume consumed and can e.g. be measured in terms of yield per ha, biomass of the plants, thousand-kernel mass, and the number of ears per m$^2$.

The term "nitrogen-use efficiency" refers technically to the mass of agriculture produce per unit nitrogen consumed and economically to the value of product(s) produced per unit nitrogen consumed, reflecting uptake and utilization efficiency.

Improvement in greening/improved colour and improved photosynthetic efficiency as well as the delay of senescence can be measured with well-known techniques such as a HandyPea system (Hansatech). Fv/Fm is a parameter widely used to indicate the maximum quantum efficiency of photosystem II (PSII). This parameter is widely considered to be a selective indication of plant photosynthetic performance with healthy samples typically achieving a maximum Fv/Fm value of approx. 0.85. Values lower than this will be observed if a sample has been exposed to some type of biotic or abiotic stress factor which has reduced the capacity for photochemical quenching of energy within PSII. Fv/Fm is presented as a ratio of variable fluorescence (Fv) over the maximum fluorescence value (Fm). The Performance Index is essentially an indicator of sample vitality. (See e.g. *Advanced Techniques in Soil Microbiology,* 2007, 11, 319-341; *Applied Soil Ecology,* 2000, 15, 169-182.)

The improvement in greening/improved colour and improved photosynthetic efficiency as well as the delay of senescence can also be assessed by measurement of the net photosynthetic rate (Pn), measurement of the chlorophyll content, e.g. by the pigment extraction method of Ziegler and Ehle, measurement of the photochemical efficiency (Fv/Fm ratio), determination of shoot growth and final root and/or canopy biomass, determination of tiller density as well as of root mortality.

Within the context of the present invention preference is given to improving plant physiology effects which are selected from the group comprising: enhanced root growth/more developed root system, improved greening, improved water use efficiency (correlating to reduced water consumption), improved nutrient use efficiency, comprising especially improved nitrogen (N)-use efficiency, delayed senescence and enhanced yield.

Within the enhancement of yield preference is given as to an improvement in the sedimentation value and the falling number as well as to the improvement of the protein and sugar content—especially with plants selected from the group of cereals (preferably wheat).

Preferably the novel use of the fungicidal compositions of the present invention relates to a combined use of a) preventively and/or curatively controlling pathogenic fungi and/or nematodes, with or without resistance management, and b) at least one of enhanced root growth, improved greening, improved water use efficiency, delayed senescence and enhanced yield. From group b) enhancement of root system, water use efficiency and N-use efficiency is particularly preferred.

Seed Treatment

The invention further comprises a method for treating seed.

The invention further relates to seed which has been treated by one of the methods described in the previous paragraph. The inventive seeds are employed in methods for the protection of seed from harmful microorganisms. In these methods, seed treated with at least one inventive active ingredient is used.

The inventive active ingredients or compositions are also suitable for treating seed. A large part of the damage to crop plants caused by harmful organisms is triggered by the infection of the seed during storage or after sowing, and also during and after germination of the plant. This phase is particularly critical since the roots and shoots of the growing plant are particularly sensitive, and even minor damage may result in the death of the plant. There is therefore a great interest in protecting the seed and the germinating plant by using appropriate compositions.

The control of phytopathogenic fungi by treating the seed of plants has been known for a long time and is the subject of constant improvements. However, the treatment of seed entails a series of problems which cannot always be solved in a satisfactory manner. For instance, it is desirable to develop methods for protecting the seed and the germinating plant, which dispense with, or at least significantly reduce, the additional deployment of crop protection compositions after planting or after emergence of the plants. It is also desirable to optimize the amount of the active ingredient used so as to provide the best possible protection for the seed and the germinating plant from attack by phytopathogenic fungi, but without damaging the plant itself by the active ingredient employed. In particular, methods for the treatment of seed should also take account of the intrinsic fungicidal properties of transgenic plants in order to achieve optimal protection of the seed and the germinating plant with a minimum expenditure of crop protection compositions.

The present invention therefore also relates to a method for protection of seed and germinating plants from attack by phytopathogenic fungi, by treating the seed with an inventive composition. The invention likewise relates to the use of the inventive compositions for treatment of seed to protect the seed and the germinating plant from phytopathogenic fungi. The invention further relates to seed which has been treated with an inventive composition for protection from phytopathogenic fungi.

The control of phytopathogenic fungi which damage plants post-emergence is effected primarily by treating the soil and the above-ground parts of plants with crop protection compositions. Owing to the concerns regarding a possible influence of the crop protection compositions on the environment and the health of humans and animals, there are efforts to reduce the amount of active ingredients deployed.

One of the advantages of the present invention is that the particular systemic properties of the inventive active ingredients and compositions mean that treatment of the seed with these active ingredients and compositions not only protects the seed itself, but also the resulting plants after emergence, from phytopathogenic fungi. In this way, the immediate treatment of the crop at the time of sowing or shortly thereafter can be dispensed with.

It is likewise considered to be advantageous that the inventive active ingredients or compositions can especially also be used with transgenic seed, in which case the plant growing from this seed is capable of expressing a protein which acts against pests. By virtue of the treatment of such seed with the inventive active ingredients or compositions, merely the expression of the protein, for example an insecticidal protein, can control certain pests. Surprisingly, a further synergistic effect can be observed in this case, which additionally increases the effectiveness for protection against attack by pests.

The inventive compositions are suitable for protecting seed of any plant variety which is used in agriculture, in greenhouses, in forests or in horticulture and viticulture. In particular, this is the seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cocoa, sugar cane, tobacco, vegetables (such as tomato, cucumbers, onions and lettuce), turf and ornamentals (see also below). The treatment of the seed of cereals (such as wheat, barley, rye, triticale and oats), maize and rice is of particular significance.

As also described below, the treatment of transgenic seed with the inventive active ingredients or compositions is of particular significance. This relates to the seed of plants containing at least one heterologous gene. Definition and examples of suitable heterologous genes are given below.

In the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

When treating the seed, care must generally be taken that the amount of the inventive composition applied to the seed and/or the amount of further additives is selected such that the germination of the seed is not impaired, or that the resulting plant is not damaged. This has to be borne in mind in particular in the case of active ingredients which can have phytotoxic effects at certain application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. No. 4,272,417, U.S. Pat. No. 4,245,432, U.S. Pat. No. 4,808,430, U.S. Pat. No. 5,876,739, US 2003/0176428 A1, WO 2002/080675, WO 2002/028186.

The active ingredients usable in accordance with the invention can be converted to the customary seed dressing formulations, such as solutions, emulsions, suspensions, powders, foams, slurries or other coating compositions for seed, and also ULV formulations.

These formulations are prepared in a known manner, by mixing the active ingredients with customary additives, for example customary extenders and also solvents or diluents, dyes, wetting agents, dispersants, emulsifiers, antifoams, preservatives, secondary thickeners, adhesives, gibberellins and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Preference is given to using alkyl naphthalenesulphonates, such as diisopropyl or diisobutyl naphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are non-ionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The gibberellins which may be present in the seed dressing formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz-und Schädlingsbekäimpfungsmittel" [Chemistry of the Crop Protection Compositions and Pesticides], vol. 2, Springer Verlag, 1970, p. 401-412).

The seed dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For treatment of seed with the seed dressing formulations usable in accordance with the invention, or the preparations prepared therefrom by adding water, all mixing units usable customarily for the seed dressing are useful. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying process.

Mycotoxins

In addition, the inventive treatment can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum*, *F. asiaticum*, *F. avenaceum*, *F. crookwellense*, *F. culmorum*, *F. graminearum* (*Gibberella zeae*), *F. equiseti*, *F. fujikoroi*, *F. musarum*, *F. oxysporum*, *F. proliferatum*, *F. poae*, *F. pseudograminearum*, *F. sambucinum*, *F. scirpi*, *F. semitectum*, *F.*

*solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana, Stachybotrys* spec. and others.

Material Protection

The inventive active ingredients or compositions can also be used in the protection of materials, for protection of industrial materials against attack and destruction by harmful microorganisms, for example fungi and insects.

In addition, the inventive compounds can be used as antifouling compositions, alone or in combinations with other active ingredients.

Industrial materials in the present context are understood to mean inanimate materials which have been prepared for use in industry. For example, industrial materials which are to be protected by inventive active ingredients from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The inventive active ingredients or compositions may prevent adverse effects, such as rotting, decay, discoloration, decoloration or formation of mould.

In the case of treatment of wood the compounds/compositions according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention or a composition according to the invention; this includes for example direct application, spraying, dipping, injection or any other suitable means.

In addition, the inventive compounds can be used to protect objects which come into contact with saltwater or brackish water, especially hulls, screens, nets, buildings, moorings and signalling systems, from fouling.

The inventive method for controlling unwanted fungi can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive active ingredients may prevent adverse effects, such as rotting, decay, discoloration, decoloration or formation of mould.

Microorganisms capable of degrading or altering the industrial materials include, for example, bacteria, fungi, yeasts, algae and slime organisms. The inventive active ingredients preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis; Aspergillus*, such as *Aspergillus niger; Chaetomium*, such as *Chaetomium globosum; Coniophora*, such as *Coniophora puetana; Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma viride; Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli; Pseudomonas*, such as *Pseudomonas aeruginosa; Staphylococcus*, such as *Staphylococcus aureus, Candida* spp. and *Saccharomyces* spp., such as *Saccharomyces cerevisae*.

Antimycotic Activity

In addition, the inventive active ingredients also have very good antimycotic activity. They have a very broad antimycotic activity spectrum, especially against dermatophytes and yeasts, moulds and diphasic fungi (for example against *Candida* species, such as *C. albicans, C. glabrata*), and *Epidermophyton floccosum, Aspergillus* species, such as *A. niger* and *A. fumigatus, Trichophyton* species, such as *T. mentagrophytes, Microsporon* species such as *M. canis* and *M. audouinii*. The list of these fungi by no means constitutes a restriction of the mycotic spectrum covered, and is merely of illustrative character.

The inventive active ingredients can therefore be used both in medical and in non-medical applications.

Application Rates and Timing

When using the inventive active ingredients as fungicides, the application rates can be varied within a relatively wide range, depending on the kind of application. The application rate of the inventive active ingredients is in the case of treatment of plant parts, for example leaves: from 0.1 to 10 000 g/ha, preferably from 10 to 1000 g/ha, more preferably from 10 to 800 g/ha, even more preferably from 50 to 300 g/ha (in the case of application by watering or dripping, it is even possible to reduce the application rate, especially when inert substrates such as rockwool or perlite are used);

in the case of seed treatment: from 2 to 200 g per 100 kg of seed, preferably from 3 to 150 g per 100 kg of seed, more preferably from 2.5 to 25 g per 100 kg of seed, even more preferably from 2.5 to 12.5 g per 100 kg of seed;

in the case of soil treatment: from 0.1 to 10 000 g/ha, preferably from 1 to 5000 g/ha.

These application rates are merely by way of example and are not limiting for the purposes of the invention.

The inventive active ingredients or compositions comprising a compound according to formula (I) can thus be used to protect plants from attack by the pathogens mentioned for a certain period of time after treatment. The period for which protection is provided extends generally for 1 to 28 days, preferably for 1 to 14 days, more preferably for 1 to 10 days, most preferably for 1 to 7 days, after the treatment of the plants with the active ingredients, or for up to 200 days after a seed treatment.

The plants listed can particularly advantageously be treated in accordance with the invention with the compounds of the general formula (I) and the inventive compositions. The preferred ranges stated above for the active ingredients or compositions also apply to the treatment of these plants. Particular emphasis is given to the treatment of plants with the compounds or compositions specifically mentioned in the present text.

The invention is illustrated by the examples below. However, the invention is not limited to the examples.

PREPARATION EXAMPLES

General Notes

Unless stated otherwise, all chromatographic purification and separation steps are carried out on silica gel and using a solvent gradient from 0:100 ethyl acetate/cyclohexane to 100:0 ethyl acetate/cyclohexane.

Example 1: Preparation of ethyl 2-[3,5-bis(difluoromethyl)-1H-pyrazol-1-yl]-3-oxo-3-[4-(4-{5-[2-(prop-2-yn-1-yloxy)phenyl]-4,5-dihydro-1,2-oxazol-3-yl}-1,3-thiazol-2-yl)piperidin-1-yl]propanoate (I-15)

Step 1

Preparation of tert-butyl 4-(4-{5-[2-(prop-2-yn-1-yloxy)phenyl]-4,5-dihydro-1,2-oxazol-3-yl}-1,3-thiazol-2-yl)piperidine-1-carboxylate To a solution of tert-butyl 4-{4-[5-(2-hydroxyphenyl)-4,5-dihydro-1,2-oxazol-3-yl]-1,3-thiazol-2-yl}piperidine-1-carboxylate (5.00 g) and potassium carbonate (3.22 g) in N,N-dimethylformamide (75 ml) was added 3-bromoprop-1-yne (3.46 g, 80% in toluene) and potassium iodide (1.93 g) at room temperature. The reaction mixture was stirred at 72° C. for 12 hours. After cooling down to room temperature water was added to the reaction mixture, and the aqueous phase was extracted with dichloromethane. The combined organic phases were dried over sodium sulphate and concentrated under reduced pressure. The residue was then purified by column chromatography to obtain tert-butyl 4-(4-{5-[2-(prop-2-yn-1-yloxy)phenyl]-4,5-dihydro-1,2-oxazol-3-yl}-1,3-thiazol-2-yl)piperidine-1-carboxylate (4.50 g, purity 96%).
Log P (pH2.7): 4.07[a]

Step 2

Preparation of 4-(4-{5-[2-(prop-2-yn-1-yloxy)phenyl]-4,5-dihydro-1,2-oxazol-3-yl}-1,3-thiazol-2-yl)piperidinium chloride To a solution of tert-butyl 4-(4-{5-[2-(prop-2-yn-1-yloxy)phenyl]-4,5-dihydro-1,2-oxazol-3-yl}-1,3-thiazol-2-yl)piperidine-1-carboxylate (5.50 g) in 1,4-dioxane (120 ml) was added a solution of hydrogen chloride in 1,4-dioxane (14.6%, 28 ml) at room temperature. The reaction mixture was stirred at room temperature until the starting material was completely consumed. Then the reaction mixture was concentrated under reduced pressure to obtain 4-(4-{5-[2-(prop-2-yn-1-yloxy)phenyl]-4,5-dihydro-1,2-oxazol-3-yl}-1,3-thiazol-2-yl)piperidinium chloride (5.10 g, purity 93%).
Log P (pH2.7): 1.26[a]

Step 3

Preparation of ethyl 3-oxo-3-[4-(4-{5-[2-(prop-2-yn-1-yloxy)phenyl]-4,5-dihydro-1,2-oxazol-3-yl}-1,3-thiazol-2-yl)piperidin-1-yl]propanoate (I-41)

To a solution of 4-(4-{5-[2-(prop-2-yn-1-yloxy)phenyl]-4,5-dihydro-1,2-oxazol-3-yl}-1,3-thiazol-2-yl)piperidinium chloride (1.00 g) and triethylamine (0.63 g) in dichloromethane (30 ml) was added ethyl 3-chloro-3-oxopropanoate (0.41 g) at 0° C. The reaction mixture was stirred at room temperature for 16 hours. Then water was added to the reaction mixture, and the aqueous phase was separated and extracted with dichloromethane. The combined organic phases were dried over sodium sulphate and concentrated under reduced pressure. The residue was then purified by column chromatography to obtain ethyl 3-oxo-3-[4-(4-{5-[2-(prop-2-yn-1-yloxy)phenyl]-4,5-dihydro-1,2-oxazol-3-yl}-1,3-thiazol-2-yl)piperidin-1-yl]propanoate (I-41) (0.57 g, purity 92%).
Log P (pH2.7): 2.70[a]

Step 4

Preparation of ethyl 2-bromo-3-oxo-3-[4-(4-{5-[2-(prop-2-yn-1-yloxy)phenyl]-4,5-dihydro-1,2-oxazol-3-yl}-1,3-thiazol-2-yl)piperidin-1-yl]propanoate (I-30)

To a solution of ethyl 3-oxo-3-[4-(4-{5-[2-(prop-2-yn-1-yloxy)phenyl]-4,5-dihydro-1,2-oxazol-3-yl}-1,3-thiazol-2-yl)piperidin-1-yl]propanoate (I-41, 0.49 g) in ethyl acetate (10 ml) was added 1-bromopyrrolidine-2,5-dione (0.18 g) at room temperature. The reaction mixture was stirred at room temperature until the starting material was completely consumed. Then water was added to the reaction mixture, and the aqueous phase was separated and extracted with ethyl acetate. The combined organic phases were dried over sodium sulphate and concentrated under reduced pressure. The residue was then purified by column chromatography to obtain ethyl 2-bromo-3-oxo-3-[4-(4-{5-[2-(prop-2-yn-1-yloxy)phenyl]-4,5-dihydro-1,2-oxazol-3-yl}-1,3-thiazol-2-yl)piperidin-1-yl]propanoate (I-30) (0.29 g, purity 80%).
Log P (pH2.7): 3.18[a]

Step 5

Preparation of ethyl 2-[3,5-bis(difluoromethyl)-1H-pyrazol-1-yl]-3-oxo-3-[4-(4-{5-[2-(prop-2-yn-1-yloxy)phenyl]-4,5-dihydro-1,2-oxazol-3-yl}-1,3-thiazol-2-yl)piperidin-1-yl]propanoate (I-15)

A mixture of ethyl 2-bromo-3-oxo-3-[4-(4-{5-[2-(prop-2-yn-1-yloxy)phenyl]-4,5-dihydro-1,2-oxazol-3-yl}-1,3-thiazol-2-yl)piperidin-1-yl]propanoate (I-30) (50 mg), 3,5-bis(difluoromethyl)-1H-pyrazole (34 mg), potassium carbonate (56 mg) and potassium iodide (3 mg) in acetonitrile (10 ml) was stirred at 40° C. for an hour. Then water was added to the reaction mixture, and the aqueous phase was separated and extracted with dichloromethane. The combined organic phases were dried over sodium sulphate and concentrated to obtain ethyl 2-[3,5-bis(difluoromethyl)-1H-pyrazol-1-yl]-3-oxo-3-[4-(4-{5-[2-(prop-2-yn-1-yloxy)phenyl]-4,5-dihydro-1,2-oxazol-3-yl}-1,3-thiazol-2-yl)piperidin-1-yl]propanoate (I-15) (70 mg, 88% pure) as colorless solid.
Log P (pH2.7): 3.69[a]

Example 2: Preparation of benzyl 2-[3,5-bis(difluoromethyl)-1H-pyrazol-1-yl]-3-{4-[4-(5-{2-[(methylsulfonyl)oxy]phenyl}-4,5-dihydro-1,2-oxazol-3-yl)-1,3-thiazol-2-yl]piperidin-1-yl}-3-oxopropanoate (I-60)

Step 1

Preparation of benzyl 3-chloro-3-oxopropanoate

To a solution of 3-(benzyloxy)-3-oxopropanoic acid (2.1 g) in dichloromethane (30 ml) was added ethanedioyl dichloride (1.89 ml) and N,N-dimethylformamide (0.05 ml) at room temperature. The reaction mixture was stirred at room temperature for 2 hours. The reaction mixture was concentrated under reduced pressure. The residue, benzyl 3-chloro-3-oxopropanoate (2.4 g), was used for the following step without any further purification.

Step 2

Preparation of benzyl 3-(4-cyanopiperidin-1-yl)-3-oxopropanoate

To a solution of benzyl 3-chloro-3-oxopropanoate (2.4 g) and N,N-diethylethanamine (1.9 ml) in dichloromethane (20 ml) was added piperidine-4-carbonitrile (1.0 g) as solution in dichloromethane (10 ml) at 0° C. The reaction mixture was stirred at room temperature for 16 hours. Thereafter water was added to the reaction mixture, and the aqueous phase was extracted with dichloromethane. The combined organic phases were dried over sodium sulphate and concentrated under reduced pressure. The residue was then purified by column chromatography to obtain benzyl 3-(4-cyanopiperidin-1-yl)-3-oxopropanoate (2.0 g).
Log P (pH2.7): 1.85[a]

Step 3

Preparation of benzyl 2-bromo-3-(4-cyanopiperidin-1-yl)-3-oxopropanoate

To a solution of benzyl 3-(4-cyanopiperidin-1-yl)-3-oxopropanoate (1.9 g) in ethyl acetate (100 ml) was added 1-bromopyrrolidine-2,5-dione (1.18 g) at room temperature. The reaction mixture was stirred at room temperature for 16 hours. Thereafter, water was added to the reaction mixture, and the aqueous phase was extracted with ethyl acetate. The combined organic phases were dried over sodium sulphate and concentrated under reduced pressure. The residue was then purified by column chromatography to obtain benzyl 2-bromo-3-(4-cyanopiperidin-1-yl)-3-oxopropanoate (1.50 g).
Log P (pH2.7): 2.24[a]

Step 4

Preparation of benzyl 2-[3,5-bis(difluoromethyl)-1H-pyrazol-1-yl]-3-(4-cyanopiperidin-1-yl)-3-oxopropanoate (IV-1)

To a solution of benzyl 2-bromo-3-(4-cyanopiperidin-1-yl)-3-oxopropanoate (1.30 g) and 3,5-bis(difluoromethyl)-1H-pyrazole (0.60 g) in N,N-dimethylformamide (12 ml) was added potassium carbonate (0.59 g) at room temperature. The reaction mixture was stirred at room temperature for 16 hours. Then, the reaction mixture was filtered, water was added to the filtrate, and the aqueous phase was extracted with ethyl acetate. The combined organic phases were dried over sodium sulphate and concentrated under reduced pressure. The residue was then purified by column chromatography to obtain benzyl 2-[3,5-bis(difluoromethyl)-1H-pyrazol-1-yl]-3-(4-cyanopiperidin-1-yl)-3-oxopropanoate (1.10 g).
Log P (pH2.7): 2.94[a]

Step 5

Preparation of benzyl 2-[3,5-bis(difluoromethyl)-1H-pyrazol-1-yl]-3-(4-carbamothioyl-piperidin-1-yl)-3-oxopropanoate (II-1)

To a solution of benzyl 2-[3,5-bis(difluoromethyl)-1H-pyrazol-1-yl]-3-(4-cyanopiperidin-1-yl)-3-oxopropanoate (6.70 g) in pyridine (67 ml) was added a solution of diammonium sulfide (5.77 g, 21% in water) at 0° C. The reaction mixture was stirred at room temperature for 16 hours. Then, ice-cold water was added to the reaction mixture, and the aqueous phase was extracted with ethyl acetate. The combined organic phases were washed with brine, dried over sodium sulphate and concentrated under reduced pressure. The residue was then purified by column chromatography to obtain benzyl 2-[3,5-bis(difluoromethyl)-1H-pyrazol-1-yl]-3-(4-carbamothioylpiperidin-1-yl)-3-oxopropanoate (2.90 g).
Log P (pH2.7): 2.65[a]

Step 6

Preparation of 2-[3-(chloroacetyl)-4,5-dihydro-1,2-oxazol-5-yl]phenyl methanesulfonate To a solution of 2-vinylphenyl methanesulfonate (12.5 g) in acetonitrile (300 ml) were added sodium hydrogencarbonate (42.4 g) and 3-chloro-N-hydroxy-2-oxopropanimidoyl chloride (9.8 g) at room temperature under argon. The reaction mixture was stirred at room temperature for 16 hours. The solids were filtered off with suction and the filtrate was concentrated under reduced pressure. The residue was purified by column chromatography to obtain 2-[3-(chloroacetyl)-4,5-dihydro-1,2-oxazol-5-yl]phenyl methanesulfonate (5.9 g).
Log P (pH2.7): 2.37[a]

Step 7

Preparation of benzyl 2-[3,5-bis(difluoromethyl)-1H-pyrazol-1-yl]-3-{4-[4-(5-{2-[(methylsulfonyl)oxy]phenyl}-4,5-dihydro-1,2-oxazol-3-yl)-1,3-thiazol-2-yl]piperidin-1-yl}-3-oxopropanoate (I-60)

A solution of benzyl 2-[3,5-bis(difluoromethyl)-1H-pyrazol-1-yl]-3-(4-carbamothioylpiperidin-1-yl)-3-oxopropanoate (2.90 g) and 2-[3-(chloroacetyl)-4,5-dihydro-1,2-oxazol-5-yl]phenyl methanesulfonate (1.45 g) in ethanol (100 ml) was stirred at 78° C. for 16 hours. After cooling down to room temperature the reaction mixture was concentrated under reduced pressure. The residue was then purified by column chromatography to obtain benzyl 2-[3,5-bis(difluoromethyl)-1H-pyrazol-1-yl]-3-{4-[4-(5-{2-[(methylsulfonyl)oxy]phenyl}-4,5-dihydro-1,2-oxazol-3-yl)-1,3-thiazol-2-yl]piperidin-1-yl}-3-oxopropanoate (1.30 g).
Log P (pH2.7): 3.77[a]

COMPOUND EXAMPLES

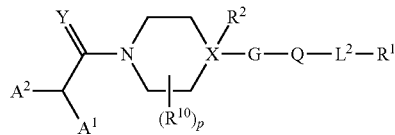

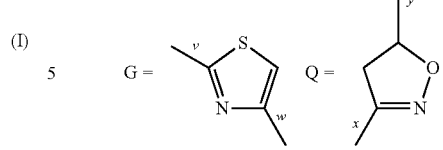

The structural elements G and Q listed in Table 1 are defined as follows:

For all compounds listed in Table 1, $A^1$ is —C(=O)$R^{L1}$, Y is an oxygen atom, X is C, $R^2$ is H, p=0 and $L^2$=direct bond.

TABLE 1

| Ex. | $A^2$ | $R^1$ | $R^{L1}$ | Log P[a] |
|---|---|---|---|---|
| I-01 | 3,5-bis(difluoromethyl)-1H-pyrazol-1-yl | 2-[(methylsulfonyl)oxy]phenyl | isopropoxy | 3.53[a] |
| I-02 | 3,5-bis(difluoromethyl)-1H-pyrazol-1-yl | 2-fluoro-6-(prop-2-yn-1-yloxy)phenyl | 2-methoxyethoxy | 3.37[a] |
| I-03 | 3,5-bis(difluoromethyl)-1H-pyrazol-1-yl | 2-fluoro-6-[(methylsulfonyl)oxy]phenyl | ethoxy | 3.29[a] |
| I-04 | 3,5-bis(difluoromethyl)-1H-pyrazol-1-yl | 2-fluoro-6-(prop-2-yn-1-yloxy)phenyl | ethoxy | 3.57[a] |
| I-05 | 3,5-bis(difluoromethyl)-1H-pyrazol-1-yl | 2-[(methylsulfonyl)oxy]phenyl | 2-methoxyethoxy | 3.14[a] |
| I-06 | 5-methyl-3-(trifluoromethyl)-1H-1,2,4-triazol-1-yl | 2-[(methylsulfonyl)oxy]phenyl | ethoxy | 3.14[a] |
| I-07 | 3,5-bis(difluoromethyl)-1H-pyrazol-1-yl | 2-fluoro-6-(prop-2-yn-1-yloxy)phenyl | isopropoxy | 3.81[a] |
| I-08 | 3,5-bis(difluoromethyl)-1H-pyrazol-1-yl | 2-chloro-6-[(methylsulfonyl)oxy]phenyl | ethoxy | 3.50[a] |
| I-09 | 3,5-bis(difluoromethyl)-1H-pyrazol-1-yl | 2-(prop-2-yn-1-yloxy)phenyl | isopropoxy | 3.93[a] |
| I-10 | 3,5-bis(difluoromethyl)-1H-pyrazol-1-yl | 2-[(methylsulfonyl)oxy]phenyl | octan-3-yloxy | 4.96[a] |
| I-11 | 3,5-bis(difluoromethyl)-1H-pyrazol-1-yl | 2-[(methylsulfonyl)oxy]phenyl | ethoxy | 3.28[a] |
| I-12 | 2-methyl-4-(trifluoromethyl)-1H-imidazol-1-yl | 2-[(methylsulfonyl)oxy]phenyl | ethoxy | 2.99[a] |
| I-13 | 3,5-bis(difluoromethyl)-1H-pyrazol-1-yl | 2-formylphenyl | isopropoxy | 3.70[a] |
| I-14 | 3,5-bis(difluoromethyl)-1H-pyrazol-1-yl | 2-formylphenyl | ethoxy | 3.40[a] |
| I-15 | 3,5-bis(difluoromethyl)-1H-pyrazol-1-yl | 2-(prop-2-yn-1-yloxy)phenyl | ethoxy | 3.69[a] |
| I-16 | 3,5-bis(difluoromethyl)-1H-pyrazol-1-yl | 2-chloro-6-(prop-2-yn-1-yloxy)phenyl | ethoxy | 3.82[a] |
| I-17 | 3,5-bis(difluoromethyl)-1H-pyrazol-1-yl | 2-fluoro-6-[(methylsulfonyl)oxy]phenyl | isopropoxy | 3.49[a] |
| I-18 | 3,5-bis(difluoromethyl)-1H-pyrazol-1-yl | 2-fluoro-6-(prop-2-yn-1-yloxy)phenyl | octan-3-yloxy | 5.22[a] |
| I-19 | 5-methyl-3-(trifluoromethyl)-1H-pyrazol-1-yl | 2-[(methylsulfonyl)oxy]phenyl | ethoxy | 3.42[a] |
| I-20 | 3,5-dimethyl-1H-1,2,4-triazol-1-yl | 2-[(methylsulfonyl)oxy]phenyl | ethoxy | 2.24[a] |
| I-21 | 3,5-bis(difluoromethyl)-1H-pyrazol-1-yl | 2-formylphenyl | octan-3-yloxy | 5.20[a] |
| I-22 | 3,5-bis(difluoromethyl)-1H-pyrazol-1-yl | 2-fluoro-6-[(methylsulfonyl)oxy]phenyl | octan-3-yloxy | 4.04[a] |
| I-23 | bromo | 2-fluoro-6-[(methylsulfonyl)oxy]phenyl | isopropoxy | 2.97[a] |
| I-24 | bromo | 2-fluoro-6-(prop-2-yn-1-yloxy)phenyl | 2-methoxyethoxy | 2.85[a] |
| I-25 | bromo | 2-formylphenyl | ethoxy | 2.82[a] |
| I-26 | bromo | 2-fluoro-6-(prop-2-yn-1-yloxy)phenyl | ethoxy | 2.98[a] |
| I-27 | bromo | 2-fluoro-6-[(methylsulfonyl)oxy]phenyl | ethoxy | 2.72[a] |
| I-28 | bromo | 2-formylphenyl | octan-3-yloxy | 4.83[a] |
| I-29 | bromo | 2-formylphenyl | isopropoxy | 3.11[a] |
| I-30 | bromo | 2-(prop-2-yn-1-yloxy)phenyl | ethoxy | 3.18[a] |
| I-31 | bromo | 2-chloro-6-(prop-2-yn-1-yloxy)phenyl | ethoxy | 3.20[a] |
| I-32 | bromo | 2-(prop-2-yn-1-yloxy)phenyl | isopropoxy | 3.43[a] |
| I-33 | bromo | 2-[(methylsulfonyl)oxy]phenyl | ethoxy | 2.72[a] |
| I-34 | bromo | 2-chloro-6-[(methylsulfonyl)oxy]phenyl | ethoxy | 2.92[a] |
| I-35 | bromo | 2-fluoro-6-(prop-2-yn-1-yloxy)phenyl | octan-3-yloxy | 4.89[a] |
| I-36 | bromo | 2-[(methylsulfonyl)oxy]phenyl | 2-methoxyethoxy | 2.53[a] |
| I-37 | bromo | 2-[(methylsulfonyl)oxy]phenyl | isopropoxy | 2.99[a] |
| I-38 | bromo | 2-fluoro-6-(prop-2-yn-1-yloxy)phenyl | isopropoxy | 3.30[a] |
| I-39 | bromo | 2-[(methylsulfonyl)oxy]phenyl | octan-3-yloxy | 4.55[a] |
| I-40 | H | 2-fluoro-6-(prop-2-yn-1-yloxy)phenyl | octan-3-yloxy | 4.42[a] |
| I-41 | H | 2-(prop-2-yn-1-yloxy)phenyl | ethoxy | 2.70[a] |

TABLE 1-continued

| Ex. | A² | R¹ | R^{L1} | Log P[a] |
|---|---|---|---|---|
| I-42 | H | 2-fluoro-6-(prop-2-yn-1-yloxy)phenyl | ethoxy | 2.58[a] |
| I-43 | H | 2-fluoro-6-(prop-2-yn-1-yloxy)phenyl | 2-methoxyethoxy | 2.43[a] |
| I-44 | H | 2-fluoro-6-(prop-2-yn-1-yloxy)phenyl | isopropoxy | 2.85[a] |
| I-45 | H | 2-[(methylsulfonyl)oxy]phenyl | octan-3-yloxy | 4.07[a] |
| I-46 | H | 2-[(methylsulfonyl)oxy]phenyl | 2-methoxyethoxy | 2.11[a] |
| I-47 | H | 2-fluoro-6-[(methylsulfonyl)oxy]phenyl | isopropoxy | 2.53[a] |
| I-48 | H | 2-fluoro-6-[(methylsulfonyl)oxy]phenyl | octan-3-yloxy | 4.03[a] |
| I-49 | H | 2-chloro-6-[(methylsulfonyl)oxy]phenyl | ethoxy | 2.53[a] |
| I-50 | H | 2-[(methylsulfonyl)oxy]phenyl | ethoxy | 2.30[a] |
| I-51 | H | 2-chloro-6-(prop-2-yn-1-yloxy)phenyl | ethoxy | 2.81[a] |
| I-52 | H | 2-(prop-2-yn-1-yloxy)phenyl | isopropoxy | 2.94[a] |
| I-53 | H | 2-formylphenyl | ethoxy | 2.34[a] |
| I-54 | H | 2-fluoro-6-[(methylsulfonyl)oxy]phenyl | ethoxy | 2.29[a] |
| I-55 | H | 2-formylphenyl | octan-3-yloxy | 4.27[a] |
| I-56 | H | 2-formylphenyl | isopropoxy | 2.57[a] |
| I-57 | H | 2-(prop-2-yn-1-yloxy)phenyl | octan-3-yloxy | 4.56[a] |
| I-58 | H | 2-[(methylsulfonyl)oxy]phenyl | isopropoxy | 2.56[a] |
| I-59 | 3,5-bis(difluoromethyl)-1H-pyrazol-1-yl | 2-chloro-6-(prop-2-yn-1-yloxy)phenyl | benzyloxy | 4.28[a] |
| I-60 | 3,5-bis(difluoromethyl)-1H-pyrazol-1-yl | 2-[(methylsulfonyl)oxy]phenyl | benzyloxy | 3.77[a] |
| I-61 | 3,5-bis(difluoromethyl)-1H-pyrazol-1-yl | 2-chloro-6-[(methylsulfonyl)oxy]phenyl | benzyloxy | 3.98[a] |
| I-62 | 3,5-bis(difluoromethyl)-1H-pyrazol-1-yl | 2-(prop-2-yn-1-yloxy)phenyl | benzyloxy | 4.16[a] |
| I-63 | 3,5-bis(difluoromethyl)-1H-pyrazol-1-yl | 2-chloro-6-(prop-2-yn-1-yloxy)phenyl | tert-butoxy | 4.31[a] |
| I-64 | 3,5-bis(difluoromethyl)-1H-pyrazol-1-yl | 2-chloro-6-[(methylsulfonyl)oxy]phenyl | tert-butoxy | 4.00[a] |
| I-65 | 3,5-bis(difluoromethyl)-1H-pyrazol-1-yl | 2-(prop-2-yn-1-yloxy)phenyl | tert-butoxy | 4.16[a] |
| I-66 | 3,5-bis(difluoromethyl)-1H-pyrazol-1-yl | 2-[(methylsulfonyl)oxy]phenyl | tert-butoxy | 3.74[a] |
| I-67 | bromo | 2-chloro-6-[(methylsulfonyl)oxy]phenyl | benzyloxy | 3.54[a] |
| I-68 | bromo | 2-[(methylsulfonyl)oxy]phenyl | benzyloxy | 3.31[a] |
| I-69 | bromo | 2-chloro-6-(prop-2-yn-1-yloxy)phenyl | benzyloxy | 3.85[a] |
| I-70 | bromo | 2-(prop-2-yn-1-yloxy)phenyl | benzyloxy | 3.72[a] |
| I-71 | bromo | 2-chloro-6-(prop-2-yn-1-yloxy)phenyl | tert-butoxy | 3.84[a] |
| I-72 | bromo | 2-chloro-6-[(methylsulfonyl)oxy]phenyl | tert-butoxy | 3.50[a] |
| I-73 | bromo | 2-(prop-2-yn-1-yloxy)phenyl | tert-butoxy | 3.68[a] |
| I-74 | bromo | 2-[(methylsulfonyl)oxy]phenyl | tert-butoxy | 3.24[a] |
| I-75 | H | 2-[(methylsulfonyl)oxy]phenyl | benzyloxy | 2.89[a] |
| I-76 | H | 2-chloro-6-[(methylsulfonyl)oxy]phenyl | benzyloxy | 3.12[a] |
| I-77 | H | 2-(prop-2-yn-1-yloxy)phenyl | benzyloxy | 3.30[a] |
| I-78 | H | 2-chloro-6-(prop-2-yn-1-yloxy)phenyl | benzyloxy | 3.45[a] |
| I-79 | H | 2-chloro-6-[(methylsulfonyl)oxy]phenyl | tert-butoxy | 3.04[a] |
| I-80 | H | 2-chloro-6-(prop-2-yn-1-yloxy)phenyl | tert-butoxy | 3.36[a] |
| I-81 | H | 2-[(methylsulfonyl)oxy]phenyl | tert-butoxy | 2.80[a] |
| I-82 | H | 2-(prop-2-yn-1-yloxy)phenyl | tert-butoxy | 3.22[a] |

(IV)

![Structure IV]

For all compounds listed in Table 2, A¹ is —C(=O)R^{L1}, Y is an oxygen atom, X is C, R² is H and p represents 0.

TABLE 2

| Ex. | A² | R^{L1} | Log P[a] |
|---|---|---|---|
| IV-01 | 3,5-bis(difluoromethyl)-1H-pyrazol-1-yl | ethoxy | 2.28[a] |
| IV-02 | H | benzyloxy | 1.85[a] |
| IV-03 | bromo | benzyloxy | 2.24[a] |
| IV-04 | 3,5-bis(difluoromethyl)-1H-pyrazol-1-yl | benzyloxy | 2.94[a] |
| IV-05 | H | tert-butoxy | |
| IV-06 | bromo | tert-butoxy | 2.02[a] |
| IV-07 | 3,5-bis(difluoromethyl)-1H-pyrazol-1-yl | tert-butoxy | 2.81[a] |

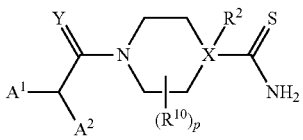

(II)

For all compounds listed in Table 3, A¹ is —C(=O)R^{L1}, Y is an oxygen atom, X is C, R² is H and p represents 0.

TABLE 3

| Ex. | A² | R^L1 | Log P[a] |
|---|---|---|---|
| II-01 | 3,5-bis(difluoromethyl)-1H-pyrazol-1-yl | benzyloxy | 2.65[a] |
| II-02 | 3,5-bis(difluoromethyl)-1H-pyrazol-1-yl | tert-butoxy | 2.54[a] |

The log P values were measured according to EEC directive 79/831 Annex V.A8 by HPLC (High Performance Liquid Chromatography) on reversed-phase columns (C18), using the methods below:

[a] The LC-MS determination in the acidic range is effected at pH 2.7 with 0.1% aqueous formic acid and acetonitrile (contains 0.1% formic acid) as eluents; linear gradient from 10% acetonitrile to 95% acetonitrile.

The calibration is effected with unbranched alkan-2-ones (having 3 to 16 carbon atoms) with known log P values (log P values determined on the basis of the retention times by linear interpolation between two successive alkanones).

The lambda-max values were determined in the maxima of the chromatographic signals using the UV spectra from 200 nm to 400 nm.

NMR Data of Selected Examples

NMR Peak List Method

The 1H NMR data of selected examples are stated in the form of 1H NMR peak lists. For each signal peak, first the δ-value in ppm and then the signal intensity in round brackets are listed. The δ value-signal intensity number pairs for different signal peaks are listed with separation from one another by semicolons.

The peak list for one example therefore takes the form of:
$\delta_1$ (intensity$_1$); $\delta_2$ (intensity$_2$); . . . ; $\delta_i$ (intensity$_i$); . . . ; $\delta_n$ (intensity$_n$)

Example I-01: ¹H-NMR (400.0 MHz, d$_6$-DMSO)

δ=8.055 (4.0); 8.022 (4.8); 7.503 (1.1); 7.486 (1.9); 7.466 (1.5); 7.462 (1.4); 7.451 (6.0); 7.447 (4.8); 7.436 (0.7); 7.432 (0.8); 7.425 (1.0); 7.419 (1.7); 7.413 (1.0); 7.400 (2.0); 7.385 (0.7); 7.379 (0.5); 7.370 (0.6); 7.266 (1.1); 7.237 (1.1); 7.218 (0.8); 7.212 (0.6); 7.205 (0.5); 7.134 (0.8); 7.104 (0.6); 7.082 (1.8); 7.076 (1.3); 7.069 (1.2); 7.054 (2.9); 6.947 (0.8); 6.941 (0.6); 6.934 (0.5); 6.794 (2.3); 6.729 (3.2); 6.009 (0.7); 5.999 (0.9); 5.990 (0.8); 5.980 (1.5); 5.971 (1.0); 5.962 (0.7); 5.952 (0.9); 5.044 (0.4); 5.035 (0.8); 5.028 (1.1); 5.019 (1.2); 5.013 (1.5); 5.004 (0.9); 4.997 (1.1); 4.988 (0.4); 4.981 (0.4); 4.458 (0.6); 4.426 (0.6); 4.398 (0.4); 4.364 (0.4); 4.056 (0.3); 4.038 (1.0); 4.020 (1.0); 4.003 (0.4); 3.994 (0.5); 3.968 (1.2); 3.950 (0.7); 3.940 (1.0); 3.925 (1.4); 3.897 (0.9); 3.795 (0.4); 3.764 (0.4); 3.728 (0.5); 3.695 (0.6); 3.554 (12.5); 3.548 (16.0); 3.357 (1.1); 3.349 (0.8); 3.337 (2.5); 3.325 (32.8); 3.294 (1.8); 3.274 (0.9); 3.258 (0.4); 3.228 (0.7); 3.198 (0.4); 2.947 (0.5); 2.920 (0.9); 2.891 (2.3); 2.856 (0.6); 2.732 (1.1); 2.525 (1.1); 2.511 (20.2); 2.507 (40.2); 2.502 (52.6); 2.498 (38.0); 2.493 (18.4); 2.329 (0.3); 2.118 (0.4); 2.082 (0.8); 2.046 (0.5); 1.989 (4.4); 1.945 (0.5); 1.838 (0.7); 1.825 (0.5); 1.808 (0.6); 1.615 (0.3); 1.504 (0.5); 1.495 (0.5); 1.473 (0.5); 1.464 (0.4); 1.397 (0.9); 1.250 (0.5); 1.222 (13.1); 1.207 (12.8); 1.193 (1.6); 1.175 (2.4); 1.157 (1.2); 0.902 (0.4); 0.894 (0.5); 0.871 (0.5); 0.863 (0.4); 0.008 (0.4); 0.000 (13.2); −0.009 (0.5)

Example I-02: ¹H-NMR (400.0 MHz, d$_6$-DMSO)

δ=7.972 (3.8); 7.944 (4.9); 7.432 (0.7); 7.411 (1.7); 7.401 (1.0); 7.393 (1.9); 7.372 (1.0); 7.269 (1.2); 7.235 (1.1); 7.217 (0.9); 7.213 (1.0); 7.136 (0.8); 7.103 (0.6); 7.082 (2.0); 7.077 (2.2); 7.065 (2.4); 7.056 (2.0); 7.009 (2.8); 6.987 (2.5); 6.947 (1.0); 6.942 (1.1); 6.905 (3.4); 6.884 (1.9); 6.856 (3.5); 6.071 (0.6); 6.060 (0.8); 6.049 (0.8); 6.038 (1.2); 6.029 (0.9); 6.019 (0.7); 6.006 (0.8); 4.843 (5.5); 4.839 (5.6); 4.453 (0.6); 4.419 (0.7); 4.370 (0.5); 4.355 (0.5); 4.345 (0.6); 4.332 (0.6); 4.325 (0.8); 4.314 (1.5); 4.302 (1.7); 4.292 (1.0); 4.280 (1.0); 4.272 (1.1); 4.262 (1.2); 4.250 (0.9); 4.242 (0.5); 4.234 (0.5); 4.229 (0.5); 4.220 (0.4); 3.828 (0.4); 3.804 (0.7); 3.794 (0.5); 3.777 (1.0); 3.761 (1.0); 3.746 (1.2); 3.735 (1.4); 3.707 (0.8); 3.534 (5.0); 3.521 (5.2); 3.496 (1.6); 3.474 (1.2); 3.454 (1.1); 3.431 (0.6); 3.368 (0.6); 3.360 (0.5); 3.337 (1.2); 3.321 (38.5); 3.279 (0.5); 3.238 (16.0); 3.219 (0.5); 3.187 (11.6); 3.009 (0.3); 2.982 (0.5); 2.940 (0.6); 2.908 (1.1); 2.874 (0.6); 2.675 (0.4); 2.670 (0.5); 2.666 (0.4); 2.541 (30.1); 2.524 (1.1); 2.506 (61.8); 2.501 (79.0); 2.497 (56.9); 2.493 (27.6); 2.333 (0.4); 2.328 (0.5); 2.324 (0.4); 2.145 (0.4); 2.108 (0.6); 2.074 (6.3); 2.006 (0.3); 1.974 (0.5); 1.873 (0.8); 1.845 (0.8); 1.643 (0.4); 1.618 (0.3); 1.514 (0.4); 1.485 (0.4); 0.945 (0.4); 0.915 (0.4); 0.146 (0.3); 0.008 (3.4); 0.000 (80.8); −0.009 (3.6); −0.150 (0.4)

Example I-03: ¹H-NMR (400.0 MHz, d$_6$-DMSO)

δ=8.040 (3.4); 8.011 (4.5); 7.953 (2.3); 7.590 (0.7); 7.569 (1.5); 7.553 (1.6); 7.532 (0.9); 7.406 (0.7); 7.380 (0.5); 7.345 (1.1); 7.329 (3.5); 7.308 (2.4); 7.273 (1.2); 7.247 (1.1); 7.220 (0.7); 7.213 (0.6); 7.141 (0.8); 7.114 (0.6); 7.085 (1.6); 7.077 (1.4); 7.073 (1.4); 7.061 (2.7); 6.950 (0.8); 6.942 (0.6); 6.939 (0.6); 6.839 (2.2); 6.793 (3.0); 6.049 (0.6); 6.039 (0.7); 6.026 (0.8); 6.017 (1.2); 6.009 (0.9); 5.996 (0.6); 5.986 (0.7); 4.459 (0.6); 4.426 (0.6); 4.404 (0.5); 4.372 (0.5); 4.259 (0.4); 4.250 (0.9); 4.242 (1.1); 4.232 (2.9); 4.228 (2.1); 4.225 (2.1); 4.214 (3.1); 4.197 (1.3); 4.038 (0.8); 4.020 (0.8); 3.898 (0.4); 3.870 (0.8); 3.854 (0.6); 3.842 (0.6); 3.827 (1.0); 3.800 (0.9); 3.769 (0.5); 3.750 (0.6); 3.715 (0.7); 3.548 (10.9); 3.541 (13.4); 3.506 (1.3); 3.484 (1.2); 3.463 (1.0); 3.440 (0.6); 3.379 (0.4); 3.369 (0.6); 3.360 (0.6); 3.350 (0.9); 3.339 (1.2); 3.324 (20.9); 3.274 (0.4); 3.244 (0.7); 3.214 (0.4); 2.967 (0.6); 2.936 (0.9); 2.901 (1.4); 2.891 (16.0); 2.872 (0.7); 2.731 (13.6); 2.506 (35.4); 2.502 (45.1); 2.498 (33.5); 2.138 (0.4); 2.104 (0.8); 2.065 (0.6); 1.989 (3.4); 1.969 (0.5); 1.869 (0.8); 1.841 (0.8); 1.633 (0.4); 1.603 (0.3); 1.510 (0.5); 1.501 (0.3); 1.490 (0.3); 1.480 (0.5); 1.397 (0.5); 1.250 (0.3); 1.224 (3.9); 1.220 (3.3); 1.206 (7.9); 1.202 (6.4); 1.188 (4.0); 1.184 (3.1); 1.175 (1.9); 1.157 (0.9); 0.934 (0.5); 0.903 (0.5); 0.000 (18.3); −0.008 (0.9)

Example I-04: ¹H-NMR (400.0 MHz, d$_6$-DMSO)

δ=7.973 (4.1); 7.953 (2.2); 7.945 (5.5); 7.432 (0.7); 7.411 (1.7); 7.394 (1.7); 7.380 (0.7); 7.374 (0.9); 7.272 (1.2); 7.247 (1.1); 7.221 (0.8); 7.215 (0.9); 7.141 (0.8); 7.115 (0.6); 7.086 (1.9); 7.080 (2.1); 7.064 (2.4); 7.009 (2.6); 6.988 (2.4); 6.951 (0.9); 6.945 (1.0); 6.907 (1.1); 6.885 (1.7); 6.860 (1.0); 6.839 (2.3); 6.794 (3.0); 6.071 (0.6); 6.059 (0.8); 6.049 (0.7); 6.038 (1.1); 6.029 (0.8); 6.018 (0.6); 6.006 (0.7); 4.845 (5.2); 4.840 (5.3); 4.459 (0.5); 4.425 (0.6); 4.405 (0.4); 4.372 (0.4); 4.259 (0.4); 4.250 (0.9); 4.246 (0.7); 4.242 (1.0); 4.232 (2.9); 4.229 (1.9); 4.224 (2.0); 4.215 (3.2); 4.211 (1.9); 4.207 (1.8); 4.197 (1.3); 4.189 (0.6); 4.056 (0.4); 4.038 (1.2); 4.020 (1.2); 4.002 (0.4); 3.806 (0.5); 3.777 (1.1); 3.762 (1.1); 3.749 (1.0); 3.735 (1.1); 3.708 (0.9); 3.540 (0.9); 3.535 (1.9); 3.529 (1.8); 3.522 (2.3); 3.496 (1.3); 3.473 (1.0); 3.454 (1.0); 3.430

(0.6); 3.375 (0.4); 3.366 (0.5); 3.356 (0.6); 3.347 (1.0); 3.337 (1.2); 3.323 (27.1); 3.308 (0.6); 3.276 (0.4); 3.245 (0.7); 3.215 (0.4); 2.968 (0.5); 2.939 (0.8); 2.905 (1.1); 2.890 (16.0); 2.873 (0.6); 2.731 (12.9); 2.671 (0.4); 2.524 (1.2); 2.511 (22.7); 2.506 (44.7); 2.502 (57.7); 2.497 (40.9); 2.493 (19.2); 2.328 (0.4); 2.139 (0.4); 2.103 (0.7); 2.066 (0.5); 1.989 (5.3); 1.971 (0.4); 1.871 (0.6); 1.839 (0.7); 1.511 (0.4); 1.481 (0.4); 1.397 (1.1); 1.224 (4.3); 1.220 (3.4); 1.206 (9.0); 1.202 (6.8); 1.192 (2.1); 1.188 (4.3); 1.185 (3.3); 1.175 (2.8); 1.157 (1.3); 0.940 (0.4); 0.909 (0.4); 0.008 (2.5); 0.000 (61.9); −0.009 (2.0)

Example I-05: $^1$H-NMR (400.0 MHz, d$_6$-DMSO)

δ=8.056 (3.6); 8.024 (4.1); 7.508 (1.3); 7.489 (1.9); 7.466 (1.2); 7.462 (1.2); 7.451 (5.2); 7.447 (4.1); 7.436 (0.6); 7.432 (0.7); 7.424 (0.9); 7.419 (1.4); 7.413 (0.8); 7.400 (1.6); 7.385 (0.6); 7.379 (0.4); 7.365 (0.5); 7.266 (1.0); 7.233 (0.9); 7.216 (0.7); 7.205 (0.4); 7.134 (0.7); 7.100 (0.5); 7.081 (1.6); 7.077 (1.2); 7.069 (1.6); 7.062 (2.2); 6.946 (0.7); 6.942 (0.6); 6.934 (0.5); 6.902 (2.0); 6.852 (2.6); 6.009 (0.6); 5.999 (0.8); 5.989 (0.7); 5.980 (1.3); 5.971 (0.9); 5.961 (0.6); 5.951 (0.8); 4.450 (0.4); 4.415 (0.5); 4.398 (0.4); 4.363 (0.4); 4.354 (0.5); 4.344 (0.5); 4.340 (0.5); 4.330 (0.6); 4.324 (0.7); 4.310 (1.3); 4.300 (1.4); 4.287 (0.8); 4.277 (0.8); 4.270 (0.9); 4.260 (1.0); 4.258 (1.0); 4.247 (0.8); 4.240 (0.7); 4.231 (0.4); 4.227 (0.4); 3.994 (0.5); 3.968 (1.0); 3.951 (0.7); 3.941 (0.8); 3.925 (1.2); 3.897 (0.8); 3.782 (0.4); 3.745 (0.6); 3.712 (0.5); 3.554 (11.2); 3.547 (14.4); 3.531 (2.8); 3.518 (2.4); 3.509 (0.9); 3.506 (0.8); 3.358 (1.1); 3.338 (2.2); 3.324 (33.8); 3.295 (1.5); 3.275 (1.0); 3.237 (16.0); 3.209 (0.4); 3.204 (0.4); 3.183 (11.3); 2.967 (0.4); 2.933 (0.5); 2.927 (0.5); 2.917 (0.3); 2.895 (0.8); 2.869 (0.4); 2.862 (0.4); 2.671 (0.4); 2.541 (1.0); 2.524 (1.1); 2.520 (1.8); 2.511 (22.2); 2.506 (45.2); 2.502 (59.7); 2.497 (43.0); 2.493 (20.5); 2.329 (0.4); 2.086 (0.5); 2.075 (4.9); 2.051 (0.5); 2.049 (0.5); 1.954 (0.4); 1.857 (0.7); 1.826 (0.6); 1.507 (0.4); 1.498 (0.4); 1.476 (0.4); 1.467 (0.4); 0.921 (0.4); 0.913 (0.4); 0.891 (0.4); 0.882 (0.3); 0.008 (0.5); 0.000 (15.3); −0.009 (0.5)

Example I-06: $^1$H-NMR (400.0 MHz, d$_6$-DMSO)

δ=8.057 (4.7); 8.043 (4.8); 7.954 (0.9); 7.515 (1.0); 7.500 (1.7); 7.486 (1.7); 7.467 (1.6); 7.464 (1.5); 7.452 (6.4); 7.435 (0.9); 7.426 (1.2); 7.420 (1.8); 7.414 (1.0); 7.404 (1.5); 7.402 (1.5); 7.386 (0.8); 7.380 (0.4); 7.014 (7.3); 6.011 (0.8); 6.004 (0.9); 5.992 (1.0); 5.984 (1.8); 5.976 (1.1); 5.964 (0.9); 5.957 (0.9); 5.756 (0.6); 4.453 (0.6); 4.422 (1.1); 4.391 (0.6); 4.315 (0.5); 4.307 (1.0); 4.302 (0.8); 4.296 (1.0); 4.289 (3.1); 4.285 (2.0); 4.278 (2.0); 4.271 (3.3); 4.267 (2.0); 4.260 (1.7); 4.253 (1.3); 4.242 (0.6); 4.233 (0.3); 4.038 (0.6); 4.021 (0.6); 4.003 (0.4); 3.997 (0.7); 3.974 (1.0); 3.970 (1.0); 3.954 (0.9); 3.946 (1.0); 3.930 (1.2); 3.903 (0.8); 3.823 (0.5); 3.786 (0.9); 3.750 (0.6); 3.555 (14.5); 3.548 (16.0); 3.400 (0.4); 3.391 (0.7); 3.381 (0.5); 3.371 (1.0); 3.362 (2.1); 3.353 (1.0); 3.342 (2.1); 3.325 (38.5); 3.298 (1.4); 3.279 (1.1); 3.250 (0.8); 3.220 (0.4); 3.092 (0.4); 3.062 (0.7); 3.035 (0.4); 2.957 (0.6); 2.948 (0.5); 2.925 (1.1); 2.891 (7.6); 2.732 (5.7); 2.672 (0.3); 2.525 (1.1); 2.512 (20.2); 2.507 (38.5); 2.503 (49.7); 2.498 (36.3); 2.494 (17.5); 2.457 (12.4); 2.445 (11.0); 2.330 (0.3); 2.142 (0.5); 2.111 (0.8); 2.096 (0.8); 2.034 (0.4); 2.005 (0.5); 1.989 (3.0); 1.971 (0.5); 1.941 (0.5); 1.839 (0.4); 1.830 (0.4); 1.808 (0.4); 1.800 (0.3); 1.619 (0.4); 1.611 (0.4); 1.589 (0.4); 1.580 (0.4); 1.518 (0.5); 1.510 (0.3); 1.496 (0.3); 1.488 (0.5); 1.337 (1.3); 1.253 (4.8); 1.250 (5.5); 1.236 (9.5); 1.232 (8.2); 1.218 (4.4); 1.214 (3.8); 1.193 (0.9); 1.175 (1.5); 1.158 (0.7); 1.106 (0.5); 1.075 (0.5); 0.000 (0.4)

Example I-07: $^1$H-NMR (400.0 MHz, d$_6$-DMSO)

δ=7.973 (3.2); 7.944 (4.4); 7.432 (0.7); 7.412 (1.6); 7.403 (1.0); 7.394 (1.8); 7.374 (1.3); 7.271 (1.2); 7.241 (1.0); 7.219 (0.8); 7.214 (0.9); 7.138 (0.8); 7.108 (0.6); 7.084 (1.7); 7.078 (2.0); 7.059 (2.6); 7.009 (2.6); 6.988 (2.4); 6.949 (0.9); 6.943 (1.0); 6.907 (1.2); 6.884 (1.8); 6.860 (1.0); 6.797 (2.2); 6.734 (2.9); 6.071 (0.6); 6.059 (0.7); 6.049 (0.7); 6.038 (1.1); 6.029 (0.9); 6.019 (0.6); 6.006 (0.7); 5.045 (0.4); 5.037 (0.8); 5.030 (1.0); 5.022 (1.1); 5.014 (1.3); 5.006 (0.8); 4.998 (1.0); 4.991 (0.4); 4.983 (0.4); 4.844 (5.1); 4.840 (5.3); 4.463 (0.6); 4.429 (0.6); 4.401 (0.4); 4.368 (0.4); 4.038 (0.5); 4.020 (0.5); 3.803 (0.7); 3.775 (1.1); 3.762 (0.9); 3.747 (1.0); 3.735 (1.4); 3.705 (1.2); 3.539 (0.9); 3.533 (1.8); 3.527 (1.9); 3.522 (2.5); 3.496 (1.3); 3.473 (1.0); 3.453 (0.9); 3.430 (0.6); 3.369 (0.5); 3.332 (24.4); 3.303 (0.5); 3.268 (0.4); 3.237 (0.8); 3.206 (0.4); 2.957 (0.5); 2.931 (0.9); 2.901 (1.3); 2.891 (2.6); 2.871 (0.7); 2.732 (1.9); 2.671 (0.4); 2.506 (53.2); 2.502 (66.2); 2.497 (48.3); 2.329 (0.4); 2.137 (0.4); 2.098 (0.8); 2.063 (0.6); 1.989 (2.6); 1.964 (0.5); 1.868 (0.8); 1.836 (0.8); 1.636 (0.4); 1.607 (0.4); 1.512 (0.5); 1.482 (0.4); 1.398 (2.6); 1.224 (16.0); 1.209 (15.8); 1.193 (1.0); 1.175 (1.3); 1.157 (0.7); 0.925 (0.5); 0.894 (0.5); 0.008 (1.6); 0.000 (34.8)

Example I-08: $^1$H-NMR (400.0 MHz, d$_6$-DMSO)

δ=8.050 (5.5); 8.021 (7.2); 7.581 (1.3); 7.577 (1.2); 7.564 (2.9); 7.561 (4.6); 7.557 (5.0); 7.554 (3.3); 7.534 (4.0); 7.517 (1.6); 7.514 (1.9); 7.489 (2.3); 7.485 (4.1); 7.481 (2.5); 7.469 (1.3); 7.465 (2.2); 7.461 (1.4); 7.404 (1.0); 7.378 (0.7); 7.271 (1.6); 7.245 (1.4); 7.219 (1.0); 7.210 (0.9); 7.139 (1.1); 7.113 (0.9); 7.084 (2.3); 7.074 (2.0); 7.072 (2.1); 7.061 (3.3); 6.949 (1.1); 6.939 (0.9); 6.836 (2.9); 6.791 (4.1); 6.190 (0.9); 6.178 (1.2); 6.162 (1.4); 6.160 (1.3); 6.151 (1.8); 6.132 (1.0); 6.121 (1.2); 4.457 (0.7); 4.424 (0.8); 4.403 (0.6); 4.369 (0.6); 4.258 (0.6); 4.249 (1.3); 4.241 (1.5); 4.231 (4.2); 4.227 (2.7); 4.224 (3.0); 4.213 (4.6); 4.209 (2.7); 4.206 (2.7); 4.196 (1.8); 4.179 (0.4); 4.056 (0.4); 4.038 (1.2); 4.020 (1.2); 4.002 (0.4); 3.857 (0.9); 3.826 (1.0); 3.813 (1.2); 3.800 (1.4); 3.786 (1.5); 3.756 (1.5); 3.714 (0.8); 3.586 (1.1); 3.564 (1.4); 3.559 (1.2); 3.542 (1.4); 3.529 (14.5); 3.519 (16.0); 3.494 (1.0); 3.379 (0.6); 3.368 (0.7); 3.360 (0.8); 3.350 (1.3); 3.340 (1.7); 3.323 (66.4); 3.273 (0.6); 3.242 (0.9); 3.213 (0.5); 2.993 (0.4); 2.964 (0.7); 2.935 (1.1); 2.903 (1.4); 2.891 (2.8); 2.877 (0.7); 2.870 (0.8); 2.731 (1.7); 2.675 (0.5); 2.671 (0.7); 2.666 (0.5); 2.565 (1.0); 2.524 (2.1); 2.511 (38.2); 2.506 (76.0); 2.502 (99.2); 2.497 (71.1); 2.493 (33.5); 2.333 (0.5); 2.329 (0.7); 2.324 (0.5); 2.137 (0.5); 2.101 (1.0); 2.066 (0.7); 1.989 (5.5); 1.967 (0.6); 1.867 (0.9); 1.840 (1.0); 1.631 (0.4); 1.601 (0.5); 1.508 (0.6); 1.499 (0.4); 1.486 (0.4); 1.477 (0.6); 1.468 (0.4); 1.398 (1.4); 1.336 (0.5); 1.250 (0.7); 1.223 (5.7); 1.219 (4.4); 1.205 (11.7); 1.201 (8.7); 1.193 (2.6); 1.188 (5.6); 1.183 (4.1); 1.175 (3.1); 1.157 (1.4); 0.929 (0.6); 0.899 (0.6); 0.890 (0.4); 0.008 (2.4); 0.000 (66.2); −0.009 (2.1)

Example I-09: $^1$H-NMR (400.0 MHz, d$_6$-DMSO)

δ=8.012 (3.6); 7.979 (3.8); 7.398 (0.7); 7.368 (0.6); 7.341 (1.1); 7.320 (3.1); 7.313 (1.9); 7.300 (2.7); 7.294 (1.9);

7.264 (1.3); 7.235 (1.1); 7.216 (0.8); 7.205 (0.6); 7.148 (3.0); 7.128 (2.6); 7.102 (0.7); 7.081 (1.8); 7.076 (1.4); 7.069 (1.3); 7.051 (3.4); 7.014 (1.3); 6.996 (2.3); 6.977 (1.1); 6.946 (0.9); 6.941 (0.7); 6.934 (0.5); 6.794 (2.4); 6.726 (3.1); 5.884 (0.7); 5.875 (0.9); 5.867 (0.8); 5.857 (1.6); 5.847 (1.0); 5.839 (0.8); 5.830 (0.9); 5.051 (0.3); 5.042 (0.5); 5.036 (0.9); 5.027 (1.2); 5.020 (1.2); 5.011 (1.5); 5.004 (0.9); 4.996 (1.2); 4.989 (0.4); 4.980 (0.4); 4.878 (4.0); 4.873 (7.5); 4.868 (5.0); 4.454 (0.6); 4.422 (0.6); 4.394 (0.5); 4.360 (0.5); 4.038 (0.7); 4.020 (0.7); 3.893 (0.6); 3.866 (1.2); 3.850 (0.8); 3.839 (1.0); 3.824 (1.5); 3.796 (1.3); 3.763 (0.5); 3.727 (0.6); 3.691 (0.6); 3.586 (0.9); 3.580 (2.0); 3.576 (1.9); 3.571 (2.4); 3.566 (1.1); 3.323 (23.2); 3.301 (0.8); 3.282 (0.5); 3.260 (1.1); 3.242 (1.7); 3.223 (1.8); 3.199 (1.5); 3.180 (1.0); 2.945 (0.6); 2.915 (0.9); 2.890 (1.6); 2.883 (1.3); 2.851 (0.7); 2.731 (0.6); 2.675 (0.3); 2.671 (0.4); 2.666 (0.3); 2.511 (27.2); 2.506 (52.9); 2.502 (68.6); 2.497 (50.8); 2.333 (0.3); 2.329 (0.5); 2.324 (0.3); 2.111 (0.4); 2.074 (0.9); 2.041 (0.6); 1.989 (2.9); 1.938 (0.5); 1.833 (0.7); 1.806 (0.7); 1.606 (0.4); 1.581 (0.3); 1.492 (0.5); 1.462 (0.5); 1.397 (8.4); 1.336 (0.4); 1.249 (0.5); 1.242 (0.6); 1.222 (16.0); 1.206 (15.7); 1.193 (1.3); 1.175 (1.7); 1.157 (0.8); 0.901 (0.5); 0.893 (0.5); 0.872 (0.5); 0.008 (1.6); 0.000 (39.5); −0.008 (1.7)

Example I-10: $^1$H-NMR (400.0 MHz, $d_6$-DMSO)

δ=8.057 (2.4); 8.020 (3.9); 7.506 (1.5); 7.487 (2.4); 7.466 (1.3); 7.462 (1.5); 7.450 (5.2); 7.447 (5.1); 7.432 (0.9); 7.419 (1.6); 7.414 (1.6); 7.401 (1.5); 7.385 (0.6); 7.379 (0.5); 7.364 (0.4); 7.280 (0.9); 7.238 (0.5); 7.230 (0.5); 7.209 (0.6); 7.202 (0.4); 7.194 (0.4); 7.148 (0.7); 7.073 (1.3); 7.055 (3.7); 6.938 (0.6); 6.929 (0.4); 6.924 (0.4); 6.870 (0.8); 6.863 (0.8); 6.757 (2.3); 6.011 (0.6); 5.998 (0.9); 5.993 (0.8); 5.979 (1.1); 5.970 (1.0); 5.964 (0.7); 5.951 (0.8); 4.819 (1.0); 4.811 (0.9); 4.806 (0.9); 4.463 (0.5); 4.429 (0.5); 4.403 (0.4); 4.371 (0.4); 4.056 (0.4); 4.038 (1.4); 4.020 (1.4); 4.002 (0.5); 3.991 (0.5); 3.966 (1.0); 3.948 (0.6); 3.939 (0.9); 3.923 (1.2); 3.895 (0.8); 3.720 (0.5); 3.686 (0.5); 3.550 (13.4); 3.546 (16.0); 3.515 (0.4); 3.512 (0.6); 3.368 (0.3); 3.350 (1.2); 3.331 (1.8); 3.322 (38.7); 3.291 (1.3); 3.273 (0.9); 3.230 (0.6); 3.199 (0.3); 2.985 (0.3); 2.957 (0.4); 2.917 (0.6); 2.891 (3.0); 2.854 (0.6); 2.731 (1.7); 2.676 (0.4); 2.671 (0.5); 2.667 (0.4); 2.524 (1.5); 2.511 (30.6); 2.507 (61.5); 2.502 (82.0); 2.497 (60.7); 2.493 (29.8); 2.333 (0.4); 2.329 (0.6); 2.324 (0.4); 2.122 (0.4); 2.080 (0.6); 2.044 (0.5); 1.989 (6.1); 1.944 (0.4); 1.825 (0.6); 1.803 (0.5); 1.598 (0.7); 1.592 (0.7); 1.575 (1.1); 1.563 (1.3); 1.557 (1.1); 1.543 (1.5); 1.524 (2.1); 1.506 (2.9); 1.488 (2.3); 1.406 (1.1); 1.398 (0.6); 1.336 (0.8); 1.299 (0.8); 1.250 (2.7); 1.236 (3.3); 1.225 (2.7); 1.215 (2.8); 1.201 (2.3); 1.193 (3.8); 1.175 (4.5); 1.157 (2.2); 0.866 (2.9); 0.854 (5.0); 0.848 (6.7); 0.834 (5.9); 0.830 (5.6); 0.826 (4.7); 0.818 (3.9); 0.807 (2.8); 0.789 (0.7); 0.000 (0.5)

Example I-11: $^1$H-NMR (400.0 MHz, $d_6$-DMSO)

δ=8.054 (4.2); 8.023 (4.8); 7.511 (0.9); 7.507 (1.0); 7.503 (1.1); 7.494 (1.3); 7.486 (1.8); 7.466 (1.4); 7.462 (1.3); 7.451 (5.8); 7.447 (4.8); 7.436 (0.7); 7.432 (0.8); 7.425 (1.1); 7.419 (1.7); 7.413 (1.0); 7.402 (2.0); 7.394 (0.8); 7.385 (0.8); 7.378 (0.8); 7.268 (1.2); 7.244 (1.1); 7.218 (0.8); 7.212 (0.6); 7.205 (0.5); 7.137 (0.8); 7.111 (0.6); 7.083 (1.8); 7.077 (1.0); 7.069 (1.3); 7.058 (2.9); 6.947 (1.8); 6.942 (0.6); 6.934 (0.5); 6.834 (2.4); 6.789 (3.2); 6.008 (0.7); 5.999 (0.9); 5.989 (0.8); 5.980 (1.6); 5.971 (1.0); 5.961 (0.7); 5.951 (0.9); 5.756 (0.8); 4.453 (0.5); 4.420 (0.6); 4.398 (0.4); 4.366 (0.4); 4.257 (0.4); 4.248 (0.9); 4.240 (1.1); 4.230 (3.2); 4.226 (1.9); 4.223 (2.1); 4.213 (3.5); 4.208 (1.9); 4.205 (1.9); 4.195 (1.3); 4.191 (0.7); 4.178 (0.3); 4.038 (0.5); 4.020 (0.5); 3.994 (0.6); 3.968 (1.1); 3.950 (0.8); 3.941 (1.0); 3.925 (1.4); 3.897 (0.9); 3.795 (0.4); 3.761 (0.5); 3.744 (0.5); 3.707 (0.5); 3.553 (12.6); 3.547 (16.0); 3.365 (0.5); 3.358 (1.1); 3.338 (2.5); 3.324 (43.3); 3.295 (1.6); 3.274 (1.1); 3.236 (0.7); 3.206 (0.4); 2.956 (0.5); 2.925 (0.7); 2.893 (1.0); 2.869 (0.5); 2.861 (0.5); 2.671 (0.3); 2.525 (1.0); 2.511 (18.8); 2.507 (37.5); 2.502 (49.9); 2.497 (36.6); 2.493 (17.5); 2.329 (0.3); 2.120 (0.4); 2.085 (0.7); 2.051 (0.5); 1.989 (2.2); 1.952 (0.4); 1.856 (0.7); 1.850 (0.7); 1.825 (0.8); 1.504 (0.4); 1.495 (0.5); 1.473 (0.4); 1.464 (0.4); 1.222 (4.0); 1.217 (3.0); 1.205 (8.3); 1.199 (5.9); 1.193 (1.2); 1.187 (3.9); 1.182 (2.8); 1.175 (1.2); 1.157 (0.5); 0.918 (0.4); 0.910 (0.4); 0.888 (0.4); 0.879 (0.4); 0.000 (0.5)

Example I-12: $^1$H-NMR (601.6 MHz, CD3CN)

δ=7.926 (1.3); 7.725 (1.8); 7.695 (1.7); 7.617 (0.8); 7.615 (0.8); 7.582 (0.8); 7.581 (0.7); 7.558 (0.6); 7.546 (1.1); 7.533 (0.6); 7.439 (0.5); 7.436 (0.7); 7.434 (0.6); 7.426 (2.6); 7.422 (1.7); 7.416 (0.4); 7.403 (0.4); 7.399 (0.5); 7.396 (0.5); 7.391 (0.6); 7.386 (0.6); 7.383 (0.5); 6.050 (1.5); 6.024 (1.4); 6.017 (0.4); 6.003 (0.8); 5.998 (0.5); 5.990 (0.5); 5.985 (0.8); 5.971 (0.4); 4.512 (0.4); 4.278 (0.8); 4.270 (0.7); 4.266 (2.3); 4.259 (0.8); 4.254 (2.3); 4.247 (0.3); 4.242 (0.8); 4.065 (0.3); 4.053 (0.3); 3.950 (0.4); 3.932 (0.4); 3.922 (0.7); 3.904 (0.6); 3.895 (0.5); 3.876 (0.6); 3.383 (0.4); 3.369 (0.6); 3.357 (0.8); 3.354 (0.9); 3.350 (0.6); 3.344 (0.8); 3.340 (0.9); 3.335 (0.9); 3.329 (1.0); 3.324 (7.3); 3.317 (6.1); 3.237 (0.3); 2.905 (0.3); 2.887 (16.0); 2.771 (13.5); 2.770 (13.2); 2.750 (0.6); 2.749 (0.6); 2.352 (5.4); 2.346 (5.8); 2.338 (0.6); 2.163 (10.1); 2.137 (0.5); 1.971 (1.5); 1.964 (0.3); 1.956 (0.6); 1.952 (0.7); 1.948 (3.3); 1.944 (5.6); 1.940 (7.8); 1.935 (5.2); 1.931 (2.8); 1.275 (1.4); 1.269 (1.6); 1.263 (2.9); 1.257 (3.0); 1.252 (1.5); 1.245 (1.6); 1.228 (0.4); 1.215 (0.5); 1.203 (0.8); 1.191 (0.4); 0.000 (2.6)

Example I-13: $^1$H-NMR (400.0 MHz, $d_6$-DMSO)

δ=10.176 (12.1); 8.316 (0.4); 8.034 (3.5); 8.011 (9.1); 7.978 (5.8); 7.977 (6.0); 7.730 (1.0); 7.726 (0.9); 7.717 (1.8); 7.711 (2.7); 7.707 (2.3); 7.698 (1.4); 7.692 (1.9); 7.688 (1.6); 7.625 (2.5); 7.607 (6.2); 7.588 (3.4); 7.579 (1.8); 7.393 (1.1); 7.365 (0.9); 7.260 (1.8); 7.232 (1.7); 7.214 (1.1); 7.203 (0.8); 7.189 (0.7); 7.128 (1.3); 7.100 (1.0); 7.079 (2.6); 7.067 (1.8); 7.045 (5.7); 6.944 (1.2); 6.932 (0.9); 6.918 (0.8); 6.786 (3.5); 6.720 (4.8); 6.437 (1.2); 6.432 (1.5); 6.422 (1.3); 6.416 (1.7); 6.410 (1.4); 6.405 (1.6); 6.394 (1.2); 6.389 (1.5); 5.757 (1.2); 5.046 (0.5); 5.040 (0.7); 5.031 (1.3); 5.024 (1.8); 5.015 (1.8); 5.009 (2.4); 5.000 (1.4); 4.993 (1.8); 4.984 (0.5); 4.978 (0.7); 4.445 (0.9); 4.411 (0.9); 4.381 (0.7); 4.348 (0.7); 4.086 (0.9); 4.058 (2.2); 4.042 (1.2); 4.031 (1.6); 4.015 (2.5); 3.987 (1.4); 3.783 (0.6); 3.750 (0.7); 3.716 (0.8); 3.680 (0.9); 3.568 (2.6); 3.323 (52.8); 3.305 (1.3); 3.296 (1.5); 3.286 (1.1); 3.276 (0.7); 3.267 (0.7); 3.245 (0.7); 3.209 (1.8); 3.190 (2.5); 3.174 (2.0); 3.165 (1.1); 3.147 (2.1); 3.130 (1.6); 2.971 (0.4); 2.965 (0.5); 2.937 (0.8); 2.908 (1.4); 2.876 (1.9); 2.845 (1.0); 2.680 (0.4); 2.676 (0.8); 2.671 (1.1); 2.667 (0.8); 2.662 (0.4); 2.541 (9.4); 2.524 (3.2); 2.511 (66.0); 2.507 (133.0); 2.502 (174.8); 2.497 (125.9); 2.493 (60.4); 2.333 (0.9); 2.329 (1.2); 2.324 (0.9); 2.098 (0.6);

2.061 (1.2); 2.023 (0.9); 1.950 (0.4); 1.925 (0.7); 1.845 (0.6); 1.817 (1.2); 1.786 (1.0); 1.597 (0.5); 1.569 (0.5); 1.508 (0.4); 1.487 (0.7); 1.477 (0.8); 1.456 (0.8); 1.446 (0.7); 1.219 (15.6); 1.207 (15.4); 1.204 (16.0); 1.196 (9.0); 0.889 (0.7); 0.878 (0.7); 0.855 (0.7); 0.847 (0.7); 0.000 (2.9)

Example I-14: $^1$H-NMR (400.0 MHz, $d_6$-DMSO)

δ=10.177 (15.4); 8.034 (4.9); 8.012 (11.3); 7.979 (7.7); 7.731 (1.4); 7.717 (2.5); 7.712 (3.6); 7.693 (2.6); 7.626 (3.3); 7.607 (8.4); 7.589 (4.7); 7.580 (2.6); 7.398 (1.6); 7.375 (1.2); 7.264 (2.6); 7.242 (2.3); 7.218 (1.5); 7.206 (1.0); 7.193 (1.0); 7.132 (1.7); 7.109 (1.3); 7.082 (3.4); 7.071 (2.5); 7.053 (8.0); 6.947 (1.6); 6.936 (1.1); 6.922 (1.0); 6.828 (4.8); 6.809 (0.3); 6.782 (6.4); 6.434 (2.0); 6.423 (1.8); 6.418 (2.3); 6.412 (2.0); 6.406 (2.2); 6.395 (1.7); 6.390 (2.0); 4.440 (1.2); 4.407 (1.4); 4.385 (1.0); 4.351 (1.0); 4.255 (0.9); 4.245 (2.0); 4.238 (2.4); 4.228 (6.3); 4.221 (5.1); 4.210 (6.8); 4.204 (4.8); 4.192 (2.8); 4.176 (0.7); 4.086 (1.3); 4.060 (2.8); 4.043 (1.8); 4.038 (2.4); 4.033 (2.2); 4.020 (2.6); 4.016 (3.3); 4.003 (0.8); 3.989 (1.8); 3.784 (0.9); 3.732 (1.3); 3.695 (1.3); 3.325 (55.8); 3.303 (2.2); 3.273 (1.1); 3.262 (1.1); 3.255 (1.0); 3.224 (1.7); 3.213 (1.8); 3.192 (3.3); 3.176 (2.4); 3.169 (1.6); 3.149 (2.4); 3.132 (2.0); 2.975 (0.7); 2.946 (1.2); 2.914 (1.8); 2.882 (2.4); 2.857 (1.7); 2.850 (1.3); 2.676 (0.5); 2.672 (0.7); 2.668 (0.5); 2.507 (79.1); 2.503 (103.8); 2.498 (77.8); 2.334 (0.5); 2.329 (0.7); 2.325 (0.5); 2.102 (0.8); 2.065 (1.6); 2.028 (1.2); 1.990 (7.2); 1.960 (0.7); 1.933 (1.1); 1.862 (0.4); 1.833 (1.8); 1.801 (1.7); 1.626 (0.3); 1.596 (0.7); 1.575 (0.7); 1.567 (0.7); 1.519 (0.4); 1.509 (0.5); 1.488 (1.0); 1.478 (1.1); 1.457 (1.0); 1.447 (1.0); 1.427 (0.4); 1.416 (0.3); 1.397 (2.4); 1.337 (0.4); 1.250 (0.5); 1.230 (0.9); 1.220 (7.9); 1.212 (5.9); 1.202 (16.0); 1.194 (11.2); 1.185 (8.0); 1.175 (7.7); 1.157 (2.0); 0.933 (0.3); 0.924 (0.4); 0.902 (0.9); 0.895 (1.0); 0.871 (1.0); 0.864 (0.9); 0.841 (0.4); 0.008 (0.8); 0.000 (22.1); −0.008 (1.0)

Example I-15: $^1$H-NMR (400.0 MHz, $d_6$-DMSO)

δ=8.011 (6.5); 7.980 (6.2); 7.401 (1.2); 7.376 (1.0); 7.342 (1.7); 7.321 (5.3); 7.313 (2.9); 7.301 (4.7); 7.294 (2.9); 7.268 (2.4); 7.243 (2.1); 7.218 (1.4); 7.214 (1.1); 7.207 (1.0); 7.149 (4.8); 7.136 (1.9); 7.128 (4.1); 7.111 (1.2); 7.096 (0.4); 7.083 (3.3); 7.078 (2.4); 7.071 (2.3); 7.057 (5.9); 7.014 (2.1); 6.996 (3.6); 6.977 (1.6); 6.948 (1.6); 6.943 (1.2); 6.936 (1.0); 6.833 (4.1); 6.787 (5.3); 5.884 (1.2); 5.876 (1.5); 5.867 (1.4); 5.857 (2.7); 5.848 (1.7); 5.839 (1.2); 5.830 (1.5); 4.879 (6.3); 4.874 (12.5); 4.868 (8.0); 4.448 (0.9); 4.416 (1.1); 4.396 (0.9); 4.362 (0.8); 4.257 (0.7); 4.248 (1.7); 4.244 (1.3); 4.239 (1.9); 4.230 (5.4); 4.222 (3.8); 4.212 (5.9); 4.204 (3.3); 4.194 (2.4); 4.187 (1.1); 4.177 (0.6); 4.056 (0.5); 4.038 (1.5); 4.020 (1.5); 4.003 (0.5); 3.894 (1.0); 3.867 (2.2); 3.851 (1.4); 3.840 (1.7); 3.825 (2.6); 3.797 (2.1); 3.759 (0.9); 3.741 (1.0); 3.705 (1.0); 3.586 (1.5); 3.580 (3.5); 3.572 (4.4); 3.566 (1.9); 3.355 (0.8); 3.345 (1.1); 3.325 (61.6); 3.298 (1.2); 3.288 (1.0); 3.277 (0.7); 3.262 (2.0); 3.243 (2.6); 3.224 (2.4); 3.220 (1.7); 3.200 (2.6); 3.181 (1.4); 2.981 (0.5); 2.952 (0.9); 2.921 (1.3); 2.889 (1.8); 2.864 (0.9); 2.856 (0.9); 2.676 (0.4); 2.671 (0.6); 2.667 (0.4); 2.524 (1.7); 2.511 (34.4); 2.507 (69.0); 2.502 (90.9); 2.497 (66.4); 2.493 (32.6); 2.333 (0.5); 2.329 (0.6); 2.324 (0.5); 2.114 (0.7); 2.078 (1.4); 2.041 (1.0); 1.989 (6.7); 1.975 (0.6); 1.946 (0.8); 1.870 (1.4); 1.844 (1.4); 1.818 (1.4); 1.615 (0.6); 1.607 (0.6); 1.585 (0.6); 1.577 (0.6); 1.521 (0.3); 1.491 (0.8); 1.461 (0.7); 1.397 (1.7); 1.337 (0.5); 1.250 (0.7); 1.232 (0.7); 1.221 (8.0); 1.204 (16.0); 1.193 (3.1); 1.186 (7.8); 1.175 (3.9); 1.157 (1.8); 0.938 (0.3); 0.916 (0.7); 0.909 (0.8); 0.887 (0.7); 0.878 (0.7); 0.854 (0.4); 0.008 (0.7); 0.000 (21.8); −0.009 (0.8)

Example I-16: $^1$H-NMR (400.0 MHz, $d_6$-DMSO)

δ=7.958 (7.2); 7.931 (9.4); 7.407 (3.7); 7.387 (6.2); 7.366 (3.9); 7.272 (2.4); 7.247 (2.1); 7.221 (1.6); 7.216 (1.5); 7.158 (5.8); 7.149 (6.6); 7.138 (5.8); 7.129 (5.6); 7.115 (1.4); 7.086 (3.6); 7.080 (3.3); 7.063 (4.9); 6.950 (1.7); 6.945 (1.6); 6.837 (4.5); 6.795 (5.9); 6.231 (1.3); 6.219 (1.7); 6.206 (1.7); 6.200 (1.8); 6.194 (2.3); 6.188 (2.0); 6.176 (1.4); 6.163 (1.7); 4.833 (0.3); 4.826 (0.6); 4.819 (0.5); 4.793 (3.2); 4.785 (7.8); 4.779 (8.5); 4.772 (3.9); 4.745 (0.4); 4.738 (0.6); 4.731 (0.4); 4.456 (1.0); 4.423 (1.2); 4.401 (0.9); 4.368 (0.8); 4.260 (0.8); 4.250 (1.7); 4.242 (2.1); 4.233 (5.7); 4.228 (3.9); 4.225 (4.2); 4.215 (6.3); 4.210 (3.9); 4.207 (3.8); 4.197 (2.6); 4.180 (0.6); 4.038 (0.8); 4.020 (0.8); 3.804 (0.8); 3.758 (2.0); 3.731 (1.8); 3.727 (2.1); 3.716 (2.7); 3.701 (1.8); 3.690 (2.5); 3.659 (1.7); 3.575 (1.5); 3.551 (3.2); 3.533 (1.3); 3.526 (2.0); 3.509 (2.2); 3.484 (1.2); 3.440 (1.5); 3.434 (3.2); 3.429 (1.7); 3.419 (1.9); 3.415 (3.5); 3.409 (1.9); 3.373 (0.9); 3.365 (1.0); 3.355 (1.1); 3.345 (1.9); 3.336 (2.3); 3.322 (41.9); 3.309 (1.3); 3.277 (0.8); 3.247 (1.4); 3.217 (0.7); 2.998 (0.5); 2.969 (1.0); 2.942 (1.7); 2.910 (2.1); 2.891 (4.1); 2.878 (1.2); 2.732 (3.0); 2.675 (0.6); 2.671 (0.8); 2.666 (0.6); 2.524 (2.6); 2.510 (49.6); 2.506 (97.3); 2.502 (126.8); 2.497 (92.8); 2.493 (46.4); 2.333 (0.7); 2.328 (0.9); 2.324 (0.7); 2.140 (0.7); 2.104 (1.6); 2.069 (1.1); 1.996 (0.7); 1.989 (3.8); 1.973 (0.9); 1.882 (1.2); 1.854 (1.5); 1.639 (0.7); 1.608 (0.6); 1.541 (0.4); 1.518 (0.8); 1.509 (0.9); 1.487 (0.8); 1.479 (0.8); 1.455 (0.3); 1.398 (1.9); 1.336 (0.7); 1.250 (0.9); 1.224 (7.9); 1.220 (6.6); 1.206 (16.0); 1.202 (13.0); 1.188 (7.9); 1.184 (6.3); 1.175 (2.2); 1.157 (1.0); 0.973 (0.3); 0.945 (0.8); 0.914 (0.8); 0.890 (0.4); 0.146 (0.4); 0.008 (3.0); 0.000 (76.4); −0.008 (3.4); −0.150 (0.4)

Example I-17: $^1$H-NMR (400.0 MHz, $d_6$-DMSO)

δ=8.040 (3.7); 8.009 (5.0); 7.590 (0.7); 7.569 (1.6); 7.553 (1.6); 7.532 (0.9); 7.403 (0.7); 7.373 (0.5); 7.346 (1.1); 7.328 (3.6); 7.309 (2.5); 7.299 (1.1); 7.271 (1.2); 7.241 (1.1); 7.219 (0.8); 7.211 (0.7); 7.138 (0.8); 7.108 (0.6); 7.083 (1.7); 7.076 (1.4); 7.072 (1.3); 7.056 (2.6); 6.948 (0.8); 6.940 (0.7); 6.937 (0.6); 6.798 (2.3); 6.733 (3.1); 6.049 (0.6); 6.038 (0.7); 6.026 (0.8); 6.016 (1.2); 6.008 (0.9); 5.996 (0.7); 5.985 (0.8); 5.045 (0.4); 5.037 (0.8); 5.030 (1.1); 5.021 (1.1); 5.014 (1.4); 5.006 (0.9); 4.998 (1.0); 4.990 (0.4); 4.983 (0.4); 4.462 (0.6); 4.430 (0.6); 4.402 (0.5); 4.369 (0.5); 4.038 (0.9); 4.020 (0.9); 3.897 (0.4); 3.870 (0.8); 3.852 (0.5); 3.842 (0.6); 3.827 (1.0); 3.798 (0.8); 3.769 (0.5); 3.736 (0.7); 3.702 (0.6); 3.560 (0.7); 3.548 (11.5); 3.541 (14.3); 3.528 (0.8); 3.505 (1.3); 3.483 (1.3); 3.462 (1.2); 3.439 (1.0); 3.405 (6.2); 3.362 (0.9); 3.351 (0.9); 3.343 (0.8); 3.334 (1.0); 3.324 (0.7); 3.315 (0.5); 3.305 (0.4); 3.267 (0.5); 3.235 (0.8); 3.206 (0.5); 2.957 (0.6); 2.930 (0.9); 2.898 (1.3); 2.891 (2.4); 2.869 (0.7); 2.732 (1.5); 2.671 (0.4); 2.565 (0.5); 2.524 (1.2); 2.507 (56.4); 2.502 (72.2); 2.498 (51.5); 2.333 (0.4); 2.329 (0.5); 2.324 (0.4); 2.137 (0.4); 2.098 (0.8); 2.064 (0.6); 1.989 (4.0); 1.962 (0.6); 1.868 (0.7); 1.835 (0.7); 1.648 (0.6); 1.626 (0.8); 1.603 (0.4); 1.511 (0.5); 1.501 (0.4); 1.489 (0.3); 1.479 (0.5); 1.398 (1.0); 1.224 (16.0); 1.208 (15.9);

1.193 (1.6); 1.175 (2.1); 1.157 (1.0); 0.919 (0.5); 0.888 (0.5); 0.008 (1.6); 0.000 (42.7); −0.009 (1.4)

Example I-18: $^1$H-NMR (400.0 MHz, d$_6$-DMSO)

δ=14.144 (1.2); 8.316 (0.9); 7.977 (5.3); 7.942 (10.0); 7.432 (1.6); 7.415 (3.0); 7.411 (3.7); 7.394 (3.7); 7.373 (2.3); 7.356 (2.4); 7.284 (2.0); 7.242 (1.2); 7.235 (1.3); 7.221 (4.8); 7.212 (1.7); 7.204 (1.5); 7.173 (2.4); 7.153 (1.5); 7.110 (0.7); 7.102 (0.7); 7.085 (2.6); 7.076 (3.2); 7.065 (5.9); 7.060 (5.7); 7.036 (4.8); 7.008 (5.6); 6.987 (5.1); 6.942 (1.6); 6.934 (1.5); 6.906 (3.4); 6.901 (3.0); 6.880 (3.9); 6.873 (3.0); 6.859 (4.2); 6.850 (5.8); 6.763 (4.9); 6.072 (1.2); 6.059 (1.5); 6.050 (1.5); 6.037 (2.0); 6.028 (1.7); 6.019 (1.4); 6.006 (1.4); 4.885 (0.4); 4.879 (0.4); 4.839 (12.2); 4.825 (2.5); 4.808 (2.1); 4.467 (1.0); 4.435 (1.2); 4.406 (0.9); 4.375 (0.8); 4.038 (0.9); 4.020 (0.9); 3.815 (0.7); 3.802 (1.3); 3.775 (1.2); 3.759 (1.3); 3.746 (1.4); 3.733 (2.4); 3.703 (1.8); 3.586 (0.3); 3.536 (1.8); 3.531 (3.8); 3.525 (3.7); 3.521 (4.7); 3.520 (4.8); 3.495 (2.5); 3.472 (1.9); 3.452 (1.9); 3.429 (1.2); 3.357 (1.4); 3.349 (1.3); 3.323 (90.3); 3.302 (0.9); 3.272 (0.8); 3.240 (1.3); 3.210 (0.8); 2.996 (0.7); 2.968 (0.8); 2.931 (1.3); 2.899 (2.2); 2.891 (1.8); 2.870 (1.2); 2.731 (0.5); 2.680 (0.6); 2.676 (1.4); 2.671 (1.9); 2.666 (1.4); 2.662 (0.6); 2.524 (5.2); 2.520 (8.3); 2.511 (114.1); 2.507 (233.2); 2.502 (308.0); 2.497 (219.0); 2.493 (103.1); 2.421 (0.5); 2.338 (0.8); 2.333 (1.6); 2.329 (2.1); 2.324 (1.6); 2.320 (0.8); 2.139 (1.0); 2.095 (1.3); 2.060 (1.1); 1.989 (4.4); 1.964 (0.9); 1.888 (0.4); 1.854 (1.4); 1.825 (1.5); 1.619 (1.1); 1.613 (1.1); 1.600 (1.5); 1.594 (1.5); 1.581 (2.1); 1.577 (2.3); 1.564 (2.7); 1.558 (2.5); 1.546 (3.6); 1.526 (4.5); 1.508 (6.2); 1.491 (5.1); 1.398 (5.2); 1.298 (1.8); 1.236 (7.2); 1.226 (6.4); 1.217 (6.7); 1.196 (5.4); 1.193 (5.8); 1.175 (4.7); 1.157 (2.2); 0.868 (6.2); 0.855 (11.5); 0.849 (16.0); 0.836 (13.7); 0.831 (14.1); 0.822 (11.6); 0.805 (5.1); 0.008 (0.5); 0.000 (17.6); −0.009 (0.5)

Example I-19: $^1$H-NMR (400.0 MHz, d$_6$-DMSO)

δ=8.051 (3.7); 8.030 (5.0); 7.513 (0.9); 7.498 (1.5); 7.484 (1.8); 7.467 (1.4); 7.463 (1.6); 7.451 (5.3); 7.448 (5.9); 7.434 (1.0); 7.424 (1.0); 7.418 (1.5); 7.413 (0.9); 7.402 (1.4); 7.384 (0.6); 7.378 (0.4); 6.739 (2.5); 6.717 (3.4); 6.625 (3.6); 6.618 (1.8); 6.008 (0.7); 6.000 (0.9); 5.989 (0.8); 5.980 (1.7); 5.972 (1.0); 5.961 (0.7); 5.952 (0.9); 4.481 (0.6); 4.448 (0.6); 4.405 (0.4); 4.372 (0.4); 4.272 (0.5); 4.264 (0.9); 4.254 (1.5); 4.247 (2.7); 4.240 (2.1); 4.236 (1.8); 4.229 (2.9); 4.222 (1.8); 4.212 (1.1); 4.204 (0.6); 4.038 (0.7); 4.020 (0.7); 3.994 (0.6); 3.967 (1.1); 3.950 (0.8); 3.940 (0.9); 3.924 (1.3); 3.897 (0.8); 3.683 (0.4); 3.649 (0.9); 3.615 (0.6); 3.553 (11.9); 3.547 (16.0); 3.358 (0.9); 3.334 (2.2); 3.325 (31.8); 3.315 (2.9); 3.295 (1.3); 3.291 (1.4); 3.271 (0.9); 3.225 (0.5); 3.194 (0.8); 3.164 (0.4); 2.919 (0.8); 2.891 (2.3); 2.863 (0.6); 2.855 (0.8); 2.732 (0.9); 2.525 (0.9); 2.511 (17.7); 2.507 (35.2); 2.502 (46.8); 2.498 (34.8); 2.493 (17.3); 2.329 (0.3); 2.269 (9.9); 2.250 (7.2); 2.093 (0.8); 2.071 (0.6); 1.989 (3.0); 1.928 (0.4); 1.828 (0.7); 1.798 (0.7); 1.609 (0.3); 1.476 (0.5); 1.466 (0.3); 1.445 (0.5); 1.337 (0.7); 1.250 (1.2); 1.244 (5.0); 1.226 (10.0); 1.208 (4.9); 1.193 (1.1); 1.175 (1.7); 1.157 (0.8); 0.917 (0.5); 0.886 (0.4); 0.000 (0.4)

Example I-20: $^1$H-NMR (400.0 MHz, d$_6$-DMSO)

δ=8.051 (2.8); 8.027 (3.3); 7.953 (0.5); 7.509 (0.9); 7.504 (0.8); 7.488 (1.4); 7.468 (1.0); 7.464 (1.2); 7.453 (4.0); 7.448 (4.6); 7.434 (0.8); 7.422 (1.2); 7.418 (0.9); 7.405 (1.1); 7.389 (0.5); 7.383 (0.4); 6.636 (2.0); 6.624 (2.5); 6.007 (0.6); 6.001 (0.7); 5.988 (0.7); 5.980 (1.2); 5.973 (0.8); 5.960 (0.6); 5.953 (0.7); 4.437 (0.4); 4.406 (0.7); 4.375 (0.4); 4.248 (0.8); 4.231 (2.2); 4.214 (2.3); 4.196 (0.9); 3.994 (0.7); 3.977 (0.6); 3.965 (0.6); 3.949 (1.0); 3.932 (0.6); 3.922 (0.6); 3.904 (0.5); 3.725 (0.4); 3.704 (0.5); 3.675 (0.4); 3.552 (16.0); 3.358 (0.9); 3.340 (1.5); 3.324 (39.0); 3.297 (1.3); 3.278 (0.7); 3.191 (0.5); 2.939 (0.4); 2.910 (0.7); 2.891 (3.8); 2.879 (0.9); 2.849 (0.5); 2.731 (2.8); 2.671 (0.3); 2.524 (0.9); 2.511 (18.5); 2.507 (37.0); 2.502 (49.3); 2.497 (37.1); 2.493 (18.7); 2.329 (0.4); 2.284 (6.8); 2.263 (6.6); 2.250 (0.5); 2.178 (6.5); 2.167 (4.1); 2.155 (3.9); 2.119 (0.4); 2.081 (0.7); 2.048 (0.4); 1.989 (0.9); 1.950 (0.4); 1.857 (0.4); 1.825 (0.6); 1.511 (0.3); 1.336 (0.5); 1.299 (0.4); 1.259 (0.6); 1.250 (0.8); 1.241 (3.3); 1.238 (3.2); 1.223 (6.3); 1.220 (5.4); 1.205 (3.1); 1.202 (2.6); 1.191 (0.7); 1.175 (0.6); 0.000 (0.4)

Example I-21: $^1$H-NMR (400.0 MHz, d$_6$-DMSO)

δ=10.178 (5.6); 8.035 (1.5); 8.019 (2.8); 8.017 (2.8); 7.978 (2.6); 7.731 (0.7); 7.712 (1.6); 7.693 (1.2); 7.626 (1.2); 7.605 (3.2); 7.586 (1.7); 7.411 (0.5); 7.277 (0.8); 7.230 (0.4); 7.224 (0.5); 7.209 (0.5); 7.146 (0.6); 7.088 (0.5); 7.074 (1.2); 7.050 (3.0); 6.938 (0.5); 6.880 (0.6); 6.868 (0.8); 6.860 (0.6); 6.752 (2.0); 6.440 (0.6); 6.434 (0.7); 6.424 (0.7); 6.418 (0.9); 6.407 (0.8); 6.396 (0.6); 6.391 (0.7); 4.817 (1.0); 4.804 (0.8); 4.451 (0.5); 4.418 (0.5); 4.389 (0.4); 4.357 (0.4); 4.087 (0.4); 4.060 (1.0); 4.043 (0.5); 4.032 (0.7); 4.016 (1.1); 3.989 (0.6); 3.709 (0.4); 3.676 (0.4); 3.326 (14.8); 3.294 (0.7); 3.255 (0.4); 3.220 (0.6); 3.201 (0.6); 3.191 (1.2); 3.175 (0.9); 3.158 (0.5); 3.147 (0.9); 3.131 (0.7); 2.907 (0.5); 2.891 (1.1); 2.875 (1.0); 2.845 (0.5); 2.732 (0.7); 2.508 (29.1); 2.503 (37.8); 2.499 (27.8); 2.101 (0.3); 2.062 (0.5); 2.023 (0.5); 1.925 (0.3); 1.806 (0.6); 1.776 (0.5); 1.597 (0.5); 1.579 (0.8); 1.569 (0.9); 1.560 (1.1); 1.540 (1.5); 1.522 (2.1); 1.515 (1.8); 1.504 (2.4); 1.486 (2.3); 1.469 (1.2); 1.451 (0.7); 1.396 (16.0); 1.337 (0.6); 1.278 (1.0); 1.249 (2.2); 1.235 (2.5); 1.223 (2.3); 1.214 (2.4); 1.193 (2.1); 0.864 (2.8); 0.852 (4.8); 0.846 (5.9); 0.833 (5.3); 0.827 (4.8); 0.815 (3.4); 0.806 (3.1); 0.788 (1.7); 0.771 (0.5); 0.008 (0.6); 0.000 (15.4); −0.008 (0.6)

Example I-22: $^1$H-NMR (400.0 MHz, d$_6$-DMSO)

δ=8.208 (0.6); 8.034 (6.0); 7.590 (0.6); 7.574 (0.7); 7.569 (1.2); 7.553 (1.3); 7.548 (0.8); 7.532 (0.7); 7.346 (0.9); 7.329 (2.4); 7.322 (1.2); 7.308 (1.8); 7.300 (0.8); 6.045 (0.7); 6.022 (0.8); 6.015 (0.8); 5.992 (0.7); 4.756 (0.6); 4.742 (0.8); 4.728 (0.6); 4.447 (0.5); 4.414 (0.5); 4.038 (0.7); 4.020 (0.7); 3.896 (0.9); 3.865 (1.0); 3.862 (0.9); 3.853 (0.8); 3.848 (0.7); 3.822 (0.5); 3.818 (0.5); 3.645 (0.7); 3.606 (1.2); 3.546 (16.0); 3.523 (1.9); 3.500 (0.9); 3.490 (0.5); 3.482 (1.1); 3.457 (0.6); 3.390 (0.4); 3.371 (0.5); 3.361 (0.8); 3.353 (0.4); 3.322 (14.9); 3.234 (0.4); 3.204 (0.7); 3.175 (0.4); 2.799 (0.4); 2.770 (0.7); 2.741 (0.4); 2.732 (0.4); 2.671 (0.4); 2.524 (0.8); 2.520 (1.3); 2.511 (19.1); 2.507 (39.4); 2.502 (52.3); 2.497 (37.8); 2.493 (18.2); 2.329 (0.3); 2.089 (0.9); 2.056 (0.9); 1.989 (2.9); 1.744 (0.5); 1.713 (0.4); 1.574 (0.5); 1.558 (0.8); 1.545 (0.9); 1.539 (1.2); 1.527 (1.0); 1.517 (1.2); 1.507 (1.2); 1.499 (2.0); 1.481 (2.0); 1.463 (1.1); 1.446 (0.4); 1.231 (2.6); 1.216 (2.4); 1.193 (1.7); 1.175 (1.9); 1.157 (0.9); 0.849 (4.2); 0.839 (2.6); 0.831 (9.4); 0.813 (4.0); 0.000 (2.3)

Example I-23: ¹H-NMR (400.0 MHz, d₆-DMSO)

δ=8.038 (2.5); 8.035 (2.5); 7.590 (0.5); 7.574 (0.7); 7.569 (1.2); 7.554 (1.2); 7.549 (0.9); 7.533 (0.7); 7.348 (0.9); 7.330 (2.8); 7.309 (1.9); 7.302 (1.0); 6.046 (0.7); 6.023 (0.9); 6.017 (0.9); 5.993 (0.8); 5.934 (1.5); 5.894 (1.6); 5.004 (0.3); 4.989 (0.9); 4.973 (1.2); 4.958 (0.9); 4.942 (0.4); 4.381 (0.5); 4.353 (0.5); 4.056 (0.4); 4.038 (1.0); 4.020 (1.0); 4.003 (0.8); 3.972 (0.3); 3.899 (0.5); 3.868 (0.6); 3.864 (0.6); 3.855 (0.7); 3.851 (0.7); 3.821 (0.6); 3.547 (16.0); 3.528 (1.0); 3.504 (0.9); 3.484 (0.8); 3.460 (1.1); 3.430 (5.2); 3.379 (0.5); 3.369 (0.4); 3.282 (0.6); 3.247 (0.6); 2.908 (0.5); 2.876 (0.5); 2.565 (5.7); 2.524 (0.8); 2.511 (15.3); 2.507 (30.3); 2.502 (39.4); 2.498 (28.7); 2.493 (14.3); 2.121 (0.9); 2.099 (0.8); 1.989 (3.5); 1.979 (0.5); 1.750 (0.4); 1.646 (0.6); 1.574 (0.3); 1.543 (0.5); 1.237 (3.7); 1.233 (3.4); 1.222 (3.8); 1.217 (3.6); 1.210 (3.6); 1.202 (3.6); 1.194 (3.9); 1.186 (3.5); 1.175 (2.2); 1.169 (0.7); 1.157 (1.0); 0.008 (2.0); 0.000 (46.0); −0.009 (2.1)

Example I-24: ¹H-NMR (400.0 MHz, d₆-DMSO)

δ=8.316 (0.4); 8.021 (0.9); 7.979 (0.3); 7.971 (2.5); 7.965 (3.5); 7.958 (1.1); 7.945 (0.6); 7.432 (1.1); 7.415 (1.9); 7.411 (2.4); 7.394 (2.6); 7.373 (1.2); 7.147 (0.6); 7.009 (3.7); 6.987 (3.5); 6.945 (0.5); 6.933 (0.4); 6.924 (0.5); 6.908 (1.9); 6.887 (2.3); 6.868 (0.7); 6.861 (1.5); 6.080 (0.5); 6.067 (1.2); 6.045 (1.6); 6.037 (1.5); 6.027 (0.6); 6.013 (2.9); 5.997 (0.7); 5.980 (2.2); 5.966 (0.6); 4.964 (1.5); 4.889 (0.4); 4.883 (0.4); 4.849 (4.8); 4.843 (8.4); 4.838 (5.2); 4.803 (0.4); 4.797 (0.4); 4.370 (0.8); 4.345 (0.9); 4.335 (0.8); 4.323 (0.9); 4.312 (0.9); 4.304 (0.9); 4.293 (1.4); 4.281 (1.4); 4.271 (0.8); 4.250 (0.8); 4.239 (1.4); 4.227 (1.6); 4.216 (1.2); 4.210 (1.1); 4.197 (0.9); 4.186 (0.6); 4.171 (0.4); 4.160 (0.4); 4.056 (1.5); 4.038 (3.9); 4.020 (4.4); 4.002 (1.7); 3.984 (0.6); 3.874 (0.4); 3.843 (0.4); 3.830 (0.6); 3.820 (0.5); 3.804 (1.2); 3.790 (0.6); 3.774 (1.3); 3.762 (1.5); 3.732 (1.6); 3.699 (0.3); 3.687 (0.5); 3.674 (0.4); 3.669 (0.4); 3.657 (0.3); 3.635 (0.5); 3.623 (0.6); 3.616 (0.6); 3.593 (0.4); 3.580 (0.9); 3.558 (0.9); 3.541 (3.8); 3.535 (8.3); 3.529 (5.6); 3.526 (5.3); 3.516 (4.6); 3.495 (2.1); 3.475 (1.6); 3.453 (1.5); 3.432 (1.0); 3.403 (1.7); 3.389 (2.1); 3.354 (15.4); 3.292 (1.5); 3.254 (10.5); 3.246 (5.9); 3.231 (1.8); 3.213 (7.5); 3.204 (3.0); 3.175 (0.6); 3.168 (0.6); 3.157 (0.7); 3.146 (0.7); 3.140 (0.5); 2.940 (0.3); 2.913 (0.8); 2.883 (0.8); 2.858 (0.4); 2.805 (0.3); 2.798 (0.3); 2.675 (0.6); 2.671 (0.9); 2.666 (0.7); 2.565 (12.6); 2.524 (1.7); 2.519 (3.0); 2.511 (53.4); 2.506 (111.6); 2.502 (149.7); 2.497 (110.7); 2.493 (55.8); 2.411 (0.4); 2.338 (0.5); 2.333 (0.9); 2.329 (1.2); 2.324 (0.9); 2.103 (1.9); 2.025 (1.5); 2.009 (0.6); 1.989 (16.0); 1.909 (1.9); 1.825 (0.3); 1.790 (0.4); 1.763 (0.5); 1.736 (0.6); 1.705 (0.5); 1.673 (0.4); 1.653 (0.4); 1.641 (0.4); 1.620 (0.4); 1.612 (0.4); 1.591 (0.6); 1.583 (0.6); 1.562 (0.8); 1.553 (0.8); 1.532 (0.8); 1.523 (0.8); 1.502 (0.6); 1.298 (0.4); 1.259 (0.6); 1.235 (0.7); 1.202 (0.4); 1.193 (4.3); 1.175 (8.5); 1.157 (4.2); 0.008 (0.8); 0.000 (26.7); −0.008 (1.2)

Example I-25: ¹H-NMR (400.0 MHz, d₆-DMSO)

δ=10.177 (16.0); 8.032 (4.5); 8.011 (9.7); 8.006 (8.2); 7.735 (1.6); 7.732 (1.7); 7.716 (4.6); 7.698 (3.2); 7.694 (3.0); 7.625 (3.4); 7.607 (11.7); 7.588 (6.6); 6.440 (2.8); 6.424 (3.1); 6.412 (3.0); 6.396 (2.8); 5.956 (5.0); 5.932 (5.6); 4.371 (1.1); 4.360 (1.1); 4.343 (1.3); 4.227 (1.0); 4.218 (2.1); 4.210 (2.0); 4.200 (6.6); 4.195 (3.4); 4.192 (3.4); 4.183 (7.0); 4.178 (3.3); 4.174 (2.9); 4.165 (2.8); 4.147 (0.5); 4.084 (2.1); 4.056 (2.6); 4.039 (3.4); 4.021 (2.2); 4.012 (3.0); 4.003 (1.3); 3.990 (1.5); 3.961 (1.0); 3.568 (0.9); 3.400 (0.9); 3.369 (2.2); 3.354 (10.8); 3.304 (0.7); 3.274 (1.3); 3.258 (0.8); 3.244 (0.9); 3.228 (1.3); 3.216 (3.5); 3.200 (3.8); 3.173 (3.0); 3.157 (3.0); 2.923 (0.6); 2.917 (0.7); 2.892 (1.7); 2.861 (1.6); 2.836 (0.6); 2.677 (0.4); 2.672 (0.5); 2.668 (0.4); 2.566 (11.3); 2.525 (1.4); 2.512 (31.1); 2.508 (62.3); 2.503 (81.5); 2.498 (58.4); 2.494 (27.9); 2.334 (0.4); 2.330 (0.5); 2.325 (0.4); 2.087 (2.6); 1.990 (5.0); 1.776 (0.4); 1.755 (0.8); 1.746 (0.8); 1.724 (0.9); 1.713 (0.9); 1.701 (0.8); 1.695 (0.8); 1.671 (0.7); 1.576 (0.3); 1.556 (0.9); 1.546 (1.0); 1.525 (1.3); 1.517 (1.3); 1.494 (0.9); 1.486 (0.9); 1.465 (0.3); 1.259 (0.4); 1.236 (0.6); 1.223 (5.8); 1.216 (5.8); 1.205 (11.5); 1.198 (10.9); 1.193 (3.1); 1.187 (5.7); 1.181 (5.2); 1.175 (3.2); 1.157 (1.4); 0.008 (1.5); 0.000 (42.6); −0.009 (1.4)

Example I-26: ¹H-NMR (400.0 MHz, d₆-DMSO)

δ=7.970 (6.5); 7.966 (6.9); 7.433 (1.5); 7.415 (2.0); 7.412 (3.3); 7.395 (3.3); 7.391 (2.3); 7.374 (1.7); 7.009 (5.0); 6.988 (4.5); 6.909 (2.5); 6.884 (3.1); 6.862 (2.3); 6.068 (2.0); 6.046 (2.5); 6.038 (2.4); 6.015 (2.1); 5.967 (4.5); 5.941 (4.9); 4.890 (0.5); 4.884 (0.5); 4.850 (7.0); 4.844 (12.1); 4.839 (7.0); 4.804 (0.5); 4.798 (0.5); 4.377 (1.1); 4.354 (1.2); 4.232 (0.6); 4.223 (1.5); 4.214 (1.5); 4.205 (4.8); 4.196 (2.8); 4.187 (5.1); 4.178 (2.5); 4.169 (2.1); 4.151 (0.4); 4.056 (0.7); 4.038 (2.5); 4.020 (2.5); 4.002 (1.9); 3.979 (0.9); 3.805 (1.5); 3.774 (1.7); 3.762 (2.1); 3.732 (1.9); 3.541 (3.1); 3.535 (6.4); 3.529 (3.3); 3.519 (2.2); 3.496 (2.1); 3.476 (1.7); 3.454 (1.7); 3.432 (0.8); 3.404 (1.7); 3.375 (0.9); 3.323 (24.2); 3.293 (1.2); 3.264 (0.8); 3.248 (1.1); 3.219 (0.6); 2.938 (0.7); 2.913 (1.5); 2.882 (1.4); 2.858 (0.6); 2.675 (0.3); 2.671 (0.5); 2.666 (0.3); 2.524 (1.4); 2.511 (27.4); 2.506 (54.0); 2.502 (70.5); 2.497 (52.2); 2.333 (0.3); 2.329 (0.5); 2.324 (0.4); 2.126 (2.4); 1.989 (7.6); 1.781 (0.7); 1.757 (0.9); 1.728 (0.9); 1.699 (0.6); 1.588 (0.8); 1.579 (0.8); 1.556 (1.2); 1.549 (1.1); 1.525 (0.9); 1.517 (0.8); 1.397 (0.5); 1.226 (8.0); 1.208 (16.0); 1.191 (8.4); 1.175 (4.1); 1.157 (2.0); 0.008 (1.3); 0.000 (34.5); −0.008 (1.4)

Example I-27: ¹H-NMR (400.0 MHz, d₆-DMSO)

δ=8.038 (2.7); 8.035 (2.8); 7.591 (0.5); 7.575 (0.7); 7.570 (1.2); 7.554 (1.2); 7.549 (0.8); 7.533 (0.7); 7.348 (0.9); 7.330 (2.6); 7.309 (1.8); 7.302 (0.9); 6.047 (0.7); 6.024 (0.9); 6.017 (0.9); 5.994 (0.8); 5.966 (1.6); 5.940 (1.8); 4.377 (0.4); 4.360 (0.4); 4.223 (0.6); 4.214 (0.6); 4.205 (1.9); 4.201 (1.1); 4.196 (1.0); 4.187 (2.1); 4.178 (0.9); 4.169 (0.8); 4.056 (0.4); 4.038 (1.5); 4.020 (1.5); 4.003 (0.9); 3.977 (0.3); 3.900 (0.5); 3.869 (0.5); 3.866 (0.5); 3.857 (0.7); 3.853 (0.7); 3.824 (0.6); 3.547 (16.0); 3.530 (0.9); 3.507 (0.9); 3.486 (0.7); 3.463 (0.7); 3.437 (0.3); 3.407 (0.6); 3.378 (0.4); 3.323 (8.7); 3.293 (0.5); 3.247 (0.4); 2.912 (0.5); 2.880 (0.5); 2.566 (1.0); 2.524 (0.5); 2.511 (9.3); 2.507 (18.6); 2.502 (24.4); 2.498 (17.8); 2.493 (8.8); 2.124 (0.9); 2.119 (0.9); 1.989 (5.2); 1.552 (0.4); 1.397 (0.6); 1.226 (2.5); 1.208 (4.9); 1.192 (3.0); 1.175 (2.8); 1.157 (1.4); 0.008 (0.6); 0.000 (16.6); −0.009 (0.6)

Example I-28: ¹H-NMR (400.0 MHz, d₆-DMSO)

δ=10.177 (13.6); 8.034 (3.1); 8.017 (6.6); 8.006 (4.8); 7.778 (0.4); 7.733 (1.4); 7.730 (1.6); 7.714 (3.8); 7.711 (3.4);

7.695 (2.8); 7.692 (2.7); 7.624 (3.1); 7.606 (8.3); 7.586 (4.5); 6.439 (2.2); 6.423 (2.5); 6.411 (2.4); 6.395 (2.3); 6.034 (1.5); 6.026 (2.8); 5.961 (3.7); 4.778 (1.6); 4.765 (1.5); 4.372 (1.4); 4.340 (1.5); 4.082 (2.9); 4.054 (3.6); 4.038 (6.8); 4.020 (4.5); 4.010 (3.0); 4.003 (1.9); 3.985 (0.8); 3.408 (0.8); 3.400 (0.9); 3.380 (1.7); 3.370 (1.9); 3.346 (12.5); 3.293 (0.8); 3.275 (1.0); 3.262 (1.2); 3.246 (1.3); 3.215 (1.7); 3.198 (1.7); 3.179 (1.2); 3.172 (1.2); 3.154 (1.4); 3.136 (1.0); 2.908 (0.6); 2.891 (1.4); 2.882 (1.3); 2.851 (1.4); 2.823 (0.5); 2.731 (0.7); 2.676 (0.7); 2.671 (1.0); 2.667 (0.7); 2.566 (8.4); 2.546 (0.3); 2.525 (2.3); 2.511 (55.2); 2.507 (112.1); 2.502 (148.5); 2.498 (108.1); 2.493 (52.6); 2.338 (0.4); 2.334 (0.8); 2.329 (1.1); 2.325 (0.8); 2.320 (0.5); 2.091 (2.3); 2.060 (2.5); 1.989 (16.0); 1.789 (0.3); 1.758 (0.7); 1.735 (0.8); 1.727 (0.9); 1.696 (0.9); 1.665 (0.7); 1.632 (0.4); 1.626 (0.5); 1.610 (0.6); 1.591 (1.0); 1.551 (2.2); 1.544 (2.2); 1.509 (4.2); 1.503 (4.2); 1.492 (4.5); 1.474 (3.1); 1.397 (0.6); 1.348 (0.5); 1.298 (2.2); 1.259 (4.6); 1.235 (5.0); 1.221 (3.9); 1.193 (7.5); 1.175 (11.1); 1.157 (6.3); 0.907 (0.4); 0.875 (3.3); 0.858 (8.3); 0.839 (7.2); 0.831 (6.1); 0.821 (5.3); 0.812 (4.9); 0.805 (4.8); 0.800 (4.7); 0.793 (4.9); 0.781 (2.6); 0.775 (2.8); 0.761 (1.9); 0.743 (0.9); 0.146 (0.4); 0.008 (3.3); 0.000 (98.9); −0.009 (3.4); −0.150 (0.4)

Example I-29: $^1$H-NMR (400.0 MHz, d$_6$-DMSO)

δ=10.290 (1.5); 10.177 (15.0); 10.160 (1.0); 8.302 (1.3); 8.141 (0.4); 8.135 (0.4); 8.033 (4.4); 8.010 (9.5); 8.005 (7.7); 7.945 (0.4); 7.928 (0.8); 7.891 (0.4); 7.872 (0.6); 7.785 (0.4); 7.767 (0.6); 7.748 (0.4); 7.735 (1.8); 7.732 (1.8); 7.716 (4.7); 7.697 (3.4); 7.694 (3.1); 7.672 (0.4); 7.625 (3.3); 7.606 (11.8); 7.587 (6.7); 7.449 (0.7); 7.436 (0.7); 6.675 (0.6); 6.439 (2.8); 6.423 (3.1); 6.411 (3.1); 6.395 (2.8); 5.946 (0.6); 5.923 (4.7); 5.885 (5.3); 5.000 (1.2); 4.984 (2.5); 4.969 (3.1); 4.953 (2.2); 4.938 (0.9); 4.369 (1.6); 4.336 (1.6); 4.083 (2.3); 4.055 (2.8); 4.039 (3.9); 4.020 (2.2); 4.012 (3.1); 4.002 (1.4); 3.989 (2.0); 3.954 (1.1); 3.714 (0.3); 3.568 (11.7); 3.399 (1.2); 3.371 (2.5); 3.362 (1.7); 3.335 (30.9); 3.293 (0.9); 3.263 (2.0); 3.228 (2.0); 3.214 (2.3); 3.210 (2.1); 3.198 (2.6); 3.171 (1.8); 3.166 (1.7); 3.155 (1.7); 2.912 (0.9); 2.886 (1.9); 2.856 (1.9); 2.831 (0.7); 2.676 (0.7); 2.672 (1.0); 2.667 (0.7); 2.507 (121.1); 2.503 (151.9); 2.498 (110.7); 2.334 (0.8); 2.329 (1.1); 2.325 (0.8); 2.162 (0.4); 2.149 (0.4); 2.081 (3.2); 1.989 (3.8); 1.810 (0.4); 1.790 (0.4); 1.781 (0.5); 1.751 (1.1); 1.728 (1.1); 1.719 (1.3); 1.699 (0.9); 1.688 (0.8); 1.681 (0.8); 1.648 (0.4); 1.640 (0.4); 1.571 (0.5); 1.543 (1.1); 1.513 (1.5); 1.492 (1.1); 1.483 (1.0); 1.462 (0.4); 1.397 (1.0); 1.259 (0.6); 1.246 (3.2); 1.234 (11.4); 1.218 (15.6); 1.204 (13.9); 1.190 (16.0); 1.175 (9.5); 1.157 (1.5); 0.146 (0.4); 0.008 (4.8); 0.000 (98.8); −0.008 (4.2); −0.150 (0.5)

Example I-30: $^1$H-NMR (400.0 MHz, d$_6$-DMSO)

δ=8.263 (0.5); 8.010 (7.8); 8.006 (8.2); 7.346 (1.9); 7.342 (2.6); 7.321 (8.5); 7.302 (7.2); 7.273 (0.6); 7.268 (0.3); 7.149 (6.0); 7.129 (5.1); 7.018 (3.4); 6.999 (5.8); 6.981 (2.7); 5.962 (5.5); 5.935 (6.1); 5.883 (2.9); 5.865 (3.3); 5.855 (3.2); 5.837 (2.9); 5.758 (0.9); 4.879 (15.3); 4.873 (15.3); 4.785 (0.5); 4.367 (1.3); 4.350 (1.3); 4.341 (1.4); 4.229 (0.9); 4.220 (2.1); 4.216 (1.5); 4.211 (2.0); 4.202 (6.5); 4.193 (3.5); 4.184 (7.0); 4.175 (3.1); 4.167 (2.9); 4.158 (1.0); 4.148 (0.5); 4.056 (0.6); 4.038 (2.1); 4.020 (2.4); 4.002 (1.9); 3.995 (1.7); 3.965 (1.1); 3.893 (2.6); 3.865 (2.8); 3.850 (3.2); 3.822 (2.8); 3.585 (3.7); 3.579 (7.8); 3.574 (3.6); 3.413 (1.0); 3.384 (2.0); 3.354 (1.2); 3.329 (38.3); 3.311 (1.0); 3.279 (1.6); 3.263 (4.6); 3.245 (4.5); 3.234 (1.4); 3.220 (3.6); 3.203 (3.9); 2.928 (0.7); 2.923 (0.8); 2.897 (1.8); 2.866 (1.8); 2.841 (0.7); 2.676 (0.4); 2.671 (0.6); 2.667 (0.4); 2.525 (1.6); 2.520 (2.5); 2.511 (34.4); 2.507 (69.7); 2.502 (91.9); 2.498 (66.4); 2.493 (31.9); 2.334 (0.5); 2.329 (0.6); 2.324 (0.5); 2.100 (2.9); 2.095 (2.8); 1.989 (7.2); 1.795 (0.3); 1.785 (0.4); 1.763 (0.8); 1.754 (0.9); 1.733 (1.0); 1.722 (1.0); 1.706 (0.9); 1.685 (0.8); 1.587 (0.4); 1.566 (1.0); 1.556 (1.1); 1.535 (1.5); 1.526 (1.4); 1.504 (1.0); 1.494 (0.9); 1.474 (0.4); 1.258 (0.4); 1.249 (0.4); 1.224 (8.2); 1.206 (16.0); 1.188 (8.0); 1.175 (4.2); 1.157 (2.0); 0.008 (1.7); 0.000 (51.3); −0.009 (1.7)

Example I-31: $^1$H-NMR (400.0 MHz, d$_6$-DMSO)

δ=7.956 (5.7); 7.952 (6.1); 7.408 (2.8); 7.388 (5.8); 7.367 (4.1); 7.159 (5.5); 7.151 (6.2); 7.138 (4.7); 7.131 (5.2); 6.229 (2.1); 6.204 (2.7); 6.198 (2.6); 6.173 (2.1); 5.966 (4.1); 5.942 (4.6); 5.757 (0.8); 4.834 (0.7); 4.828 (0.7); 4.794 (5.5); 4.786 (7.4); 4.779 (5.4); 4.745 (0.7); 4.739 (0.7); 4.718 (0.3); 4.359 (1.2); 4.232 (0.7); 4.223 (1.6); 4.214 (1.7); 4.205 (4.7); 4.196 (3.0); 4.188 (5.1); 4.179 (2.7); 4.170 (2.2); 4.152 (0.5); 4.056 (0.6); 4.038 (1.9); 4.020 (2.0); 4.002 (1.8); 3.978 (1.0); 3.759 (1.7); 3.728 (2.0); 3.717 (2.8); 3.686 (2.4); 3.575 (2.3); 3.550 (2.3); 3.533 (1.6); 3.508 (1.5); 3.437 (4.7); 3.403 (1.7); 3.374 (1.0); 3.329 (19.8); 3.295 (1.3); 3.249 (1.2); 3.221 (0.6); 2.940 (0.7); 2.915 (1.4); 2.885 (1.3); 2.861 (0.6); 2.675 (0.4); 2.671 (0.5); 2.667 (0.4); 2.565 (1.2); 2.506 (63.4); 2.502 (81.7); 2.498 (61.1); 2.333 (0.5); 2.329 (0.6); 2.126 (2.5); 1.989 (4.9); 1.781 (0.7); 1.760 (0.9); 1.730 (0.9); 1.700 (0.7); 1.589 (0.9); 1.581 (0.8); 1.559 (1.2); 1.552 (1.1); 1.528 (0.9); 1.497 (0.3); 1.397 (0.4); 1.250 (0.5); 1.226 (8.2); 1.208 (16.0); 1.191 (8.4); 1.175 (2.9); 1.157 (1.4); 0.008 (1.9); 0.000 (36.0); −0.007 (1.6)

Example I-32: $^1$H-NMR (400.0 MHz, d$_6$-DMSO)

δ=8.260 (1.1); 8.010 (7.4); 8.005 (7.5); 7.990 (0.6); 7.986 (0.6); 7.950 (0.4); 7.946 (0.4); 7.931 (0.4); 7.927 (0.4); 7.547 (0.3); 7.345 (2.3); 7.341 (3.1); 7.321 (8.3); 7.307 (2.2); 7.302 (6.5); 7.300 (6.8); 7.268 (1.6); 7.188 (0.5); 7.149 (6.0); 7.129 (5.1); 7.055 (0.3); 7.036 (0.5); 7.018 (3.7); 6.999 (6.0); 6.980 (2.8); 5.956 (0.5); 5.930 (5.4); 5.911 (0.8); 5.889 (6.3); 5.884 (3.8); 5.865 (3.3); 5.855 (3.2); 5.837 (2.9); 5.077 (0.9); 5.018 (0.3); 5.002 (1.8); 4.987 (3.3); 4.971 (4.2); 4.955 (3.0); 4.940 (1.2); 4.878 (15.9); 4.872 (16.0); 4.784 (0.3); 4.373 (1.6); 4.358 (1.1); 4.342 (1.6); 4.056 (1.1); 4.038 (3.8); 4.020 (3.7); 4.002 (2.4); 3.996 (1.8); 3.959 (1.0); 3.892 (3.0); 3.877 (0.4); 3.864 (3.6); 3.849 (3.9); 3.834 (0.4); 3.821 (3.3); 3.656 (0.4); 3.650 (0.4); 3.585 (3.2); 3.579 (6.6); 3.574 (3.3); 3.420 (0.7); 3.412 (1.2); 3.402 (0.9); 3.392 (1.4); 3.383 (2.4); 3.374 (1.5); 3.363 (1.0); 3.354 (1.5); 3.336 (16.3); 3.300 (1.0); 3.261 (4.3); 3.243 (4.3); 3.218 (3.1); 3.200 (3.5); 2.925 (0.7); 2.918 (0.8); 2.893 (1.8); 2.862 (1.8); 2.837 (0.7); 2.676 (0.4); 2.671 (0.6); 2.667 (0.5); 2.525 (1.8); 2.520 (2.9); 2.511 (38.2); 2.507 (77.8); 2.502 (103.1); 2.498 (74.8); 2.493 (36.2); 2.333 (0.5); 2.329 (0.7); 2.324 (0.5); 2.149 (0.4); 2.094 (2.9); 2.072 (2.6); 1.989 (13.2); 1.799 (0.4); 1.791 (0.5); 1.768 (0.8); 1.760 (1.0); 1.738 (1.0); 1.729 (1.2); 1.697 (0.8); 1.691 (0.8); 1.579 (1.1); 1.553 (1.1); 1.523 (1.5); 1.501 (0.9); 1.493 (1.0); 1.472 (0.4); 1.397 (0.9); 1.299 (0.4); 1.259 (0.7); 1.249 (1.5); 1.235

(13.6); 1.220 (13.5); 1.208 (15.6); 1.198 (11.4); 1.193 (14.4); 1.183 (10.2); 1.175 (8.2); 1.157 (3.7); 0.008 (0.8); 0.000 (26.9); −0.009 (0.9)

Example I-33: $^1$H-NMR (400.0 MHz, d$_6$-DMSO)

δ=8.052 (2.3); 8.048 (2.5); 7.515 (0.9); 7.511 (1.0); 7.494 (1.5); 7.472 (0.3); 7.468 (0.8); 7.464 (1.0); 7.453 (3.2); 7.448 (3.7); 7.434 (0.6); 7.423 (1.1); 7.417 (0.8); 7.405 (0.9); 7.398 (0.6); 7.389 (0.4); 7.383 (0.4); 6.006 (0.8); 5.986 (0.9); 5.978 (0.9); 5.960 (2.1); 5.935 (1.6); 4.354 (0.3); 4.220 (0.6); 4.216 (0.3); 4.212 (0.5); 4.203 (1.9); 4.198 (0.9); 4.193 (0.9); 4.185 (2.1); 4.181 (0.9); 4.176 (0.8); 4.167 (0.8); 4.038 (0.7); 4.020 (0.8); 4.002 (0.6); 3.993 (1.0); 3.964 (1.0); 3.949 (0.9); 3.921 (0.7); 3.552 (16.0); 3.395 (0.5); 3.359 (1.2); 3.339 (1.2); 3.326 (13.0); 3.315 (1.3); 3.296 (1.1); 3.284 (0.4); 2.902 (0.5); 2.871 (0.4); 2.565 (1.9); 2.524 (0.5); 2.520 (0.8); 2.511 (11.8); 2.506 (24.1); 2.502 (32.7); 2.497 (24.0); 2.493 (11.4); 2.107 (0.7); 2.101 (0.7); 1.989 (2.7); 1.909 (0.4); 1.541 (0.4); 1.532 (0.4); 1.225 (1.8); 1.221 (1.8); 1.207 (3.7); 1.203 (3.5); 1.193 (1.2); 1.189 (1.8); 1.185 (1.7); 1.175 (1.5); 1.157 (0.7); 0.008 (0.4); 0.000 (11.8); −0.009 (0.4)

Example I-34: $^1$H-NMR (400.0 MHz, d$_6$-DMSO)

δ=8.049 (2.7); 8.046 (2.8); 7.584 (0.6); 7.579 (0.8); 7.564 (2.4); 7.559 (2.6); 7.556 (2.3); 7.536 (2.8); 7.516 (1.3); 7.488 (2.2); 7.483 (2.1); 7.469 (1.2); 7.464 (1.1); 6.188 (0.9); 6.160 (1.5); 6.130 (1.0); 5.965 (1.7); 5.939 (1.9); 5.756 (0.4); 4.359 (0.5); 4.222 (0.7); 4.213 (0.7); 4.204 (2.1); 4.199 (1.2); 4.195 (1.2); 4.186 (2.3); 4.182 (1.2); 4.178 (1.1); 4.168 (1.0); 4.038 (0.7); 4.020 (0.8); 4.002 (0.7); 3.975 (0.4); 3.856 (0.7); 3.825 (0.8); 3.813 (1.1); 3.782 (0.9); 3.586 (1.1); 3.559 (1.1); 3.543 (1.1); 3.528 (16.0); 3.516 (1.1); 3.437 (0.4); 3.407 (0.7); 3.378 (0.4); 3.322 (18.1); 3.290 (0.5); 3.262 (0.3); 3.246 (0.4); 2.910 (0.6); 2.879 (0.5); 2.565 (3.8); 2.524 (0.9); 2.511 (17.3); 2.506 (33.7); 2.502 (43.7); 2.497 (31.7); 2.493 (15.6); 2.124 (1.0); 2.095 (0.7); 1.989 (2.1); 1.740 (0.3); 1.580 (0.3); 1.549 (0.5); 1.520 (0.3); 1.397 (0.4); 1.225 (2.7); 1.208 (5.3); 1.190 (2.8); 1.175 (1.2); 1.157 (0.6); 0.008 (0.8); 0.000 (20.7); −0.008 (0.8)

Example I-35: $^1$H-NMR (400.0 MHz, d$_6$-DMSO)

δ=8.316 (0.4); 7.977 (4.5); 7.967 (8.4); 7.432 (1.7); 7.411 (3.8); 7.394 (4.0); 7.373 (2.0); 7.009 (5.9); 6.988 (5.5); 6.907 (2.7); 6.882 (3.7); 6.860 (2.6); 6.068 (2.3); 6.046 (3.0); 6.033 (3.8); 6.016 (2.7); 5.972 (3.4); 4.888 (0.5); 4.882 (0.5); 4.843 (12.8); 4.797 (1.7); 4.775 (1.9); 4.759 (1.7); 4.744 (1.2); 4.729 (0.7); 4.713 (0.3); 4.446 (0.6); 4.391 (1.4); 4.359 (1.5); 4.098 (0.7); 4.056 (1.7); 4.038 (4.1); 4.020 (3.9); 4.002 (1.9); 3.901 (0.5); 3.869 (0.6); 3.802 (1.6); 3.770 (1.8); 3.760 (2.3); 3.729 (2.0); 3.644 (0.7); 3.639 (0.7); 3.605 (1.3); 3.533 (7.5); 3.517 (3.3); 3.494 (3.2); 3.474 (2.3); 3.452 (2.4); 3.411 (1.6); 3.404 (1.6); 3.385 (1.4); 3.334 (69.6); 3.283 (1.5); 3.268 (1.5); 3.236 (1.2); 3.206 (0.9); 3.177 (0.5); 2.930 (0.6); 2.905 (1.2); 2.875 (1.3); 2.850 (0.6); 2.803 (0.4); 2.774 (0.7); 2.745 (0.4); 2.676 (0.9); 2.671 (1.2); 2.667 (0.9); 2.565 (14.7); 2.524 (3.0); 2.507 (148.5); 2.502 (193.1); 2.498 (143.4); 2.333 (1.0); 2.329 (1.3); 2.324 (1.1); 2.203 (0.3); 2.193 (0.3); 2.185 (0.5); 2.166 (0.5); 2.125 (2.3); 2.098 (2.9); 2.059 (1.3); 1.989 (15.1); 1.909 (0.4); 1.825 (0.4); 1.794 (0.7); 1.762 (0.9); 1.739 (1.1); 1.708 (1.0); 1.613 (0.8); 1.595 (1.6); 1.577 (2.3); 1.548 (3.5); 1.529 (4.6); 1.517 (5.8); 1.499 (6.5); 1.482 (4.9); 1.298 (2.4); 1.235 (8.3); 1.193 (8.4); 1.175 (10.4); 1.157 (5.1); 1.022 (0.4); 1.006 (0.4); 0.987 (0.3); 0.877 (3.3); 0.861 (9.4); 0.851 (10.6); 0.844 (10.5); 0.834 (16.0); 0.815 (10.1); 0.795 (3.3); 0.008 (1.2); 0.000 (30.0); −0.008 (1.2)

Example I-36: $^1$H-NMR (400.0 MHz, d$_6$-DMSO)

δ=8.053 (2.5); 8.049 (2.5); 7.510 (1.2); 7.492 (1.9); 7.468 (1.1); 7.464 (1.2); 7.452 (3.9); 7.448 (4.3); 7.434 (0.8); 7.423 (1.3); 7.417 (1.0); 7.405 (1.1); 7.389 (0.5); 7.383 (0.8); 6.006 (2.5); 5.987 (1.3); 5.977 (2.4); 5.959 (1.0); 4.370 (0.6); 4.334 (0.7); 4.321 (0.7); 4.309 (0.6); 4.303 (0.6); 4.291 (1.0); 4.279 (1.0); 4.267 (0.4); 4.248 (0.5); 4.237 (1.0); 4.225 (1.0); 4.213 (0.5); 4.207 (0.6); 4.195 (0.5); 4.038 (0.9); 4.020 (0.8); 4.003 (0.9); 3.993 (1.1); 3.965 (1.1); 3.950 (1.0); 3.922 (0.9); 3.552 (16.0); 3.533 (3.1); 3.523 (3.8); 3.511 (1.1); 3.424 (0.4); 3.414 (0.4); 3.395 (0.7); 3.386 (0.7); 3.376 (0.5); 3.359 (1.5); 3.339 (1.7); 3.325 (22.7); 3.296 (1.3); 3.284 (0.7); 3.253 (6.4); 3.209 (5.6); 2.903 (0.6); 2.873 (0.6); 2.506 (36.1); 2.502 (46.0); 2.498 (35.1); 2.329 (0.3); 2.114 (1.0); 2.092 (1.0); 1.989 (2.2); 1.769 (0.3); 1.747 (0.4); 1.739 (0.4); 1.718 (0.4); 1.576 (0.4); 1.568 (0.4); 1.546 (0.5); 1.538 (0.5); 1.515 (0.4); 1.506 (0.3); 1.336 (0.3); 1.250 (0.4); 1.193 (0.6); 1.175 (1.2); 1.157 (0.6); 0.000 (0.4)

Example I-37: $^1$H-NMR (400.0 MHz, d$_6$-DMSO)

δ=8.052 (2.3); 8.048 (2.3); 7.953 (0.5); 7.514 (0.9); 7.511 (1.0); 7.493 (1.6); 7.472 (0.3); 7.468 (0.8); 7.464 (1.0); 7.453 (3.2); 7.448 (3.7); 7.434 (0.6); 7.423 (1.2); 7.417 (0.8); 7.405 (0.9); 7.398 (0.6); 7.390 (0.4); 7.383 (0.4); 6.007 (0.8); 5.987 (0.9); 5.979 (0.9); 5.959 (0.8); 5.929 (1.5); 5.891 (1.6); 4.987 (0.7); 4.971 (0.9); 4.956 (0.7); 4.377 (0.4); 4.345 (0.4); 4.038 (0.8); 4.020 (0.7); 4.002 (0.7); 3.992 (1.2); 3.964 (1.2); 3.948 (1.1); 3.920 (0.9); 3.552 (16.0); 3.423 (0.3); 3.403 (0.4); 3.395 (0.7); 3.385 (0.4); 3.375 (0.3); 3.365 (0.4); 3.357 (1.1); 3.337 (1.1); 3.325 (11.9); 3.314 (1.0); 3.294 (0.9); 3.274 (0.5); 3.239 (0.5); 2.891 (4.5); 2.867 (0.5); 2.732 (3.4); 2.565 (1.3); 2.524 (0.6); 2.511 (12.3); 2.507 (24.0); 2.502 (31.2); 2.498 (22.6); 2.493 (11.0); 2.102 (0.8); 2.082 (0.7); 1.989 (2.6); 1.528 (0.4); 1.236 (2.9); 1.231 (2.4); 1.226 (2.1); 1.221 (3.2); 1.215 (2.4); 1.209 (3.5); 1.198 (2.9); 1.193 (3.7); 1.183 (2.5); 1.175 (1.6); 1.157 (0.7); 0.008 (0.6); 0.000 (14.8); −0.008 (0.5)

Example I-38: $^1$H-NMR (400.0 MHz, d$_6$-DMSO)

δ=7.971 (7.4); 7.965 (7.5); 7.432 (1.9); 7.415 (2.5); 7.411 (4.1); 7.394 (4.2); 7.390 (2.7); 7.373 (2.2); 7.009 (6.0); 6.988 (5.4); 6.908 (3.1); 6.887 (3.3); 6.883 (3.5); 6.861 (2.8); 6.069 (2.3); 6.046 (2.8); 6.038 (2.7); 6.016 (2.4); 5.933 (5.3); 5.895 (5.8); 5.006 (1.3); 4.990 (3.5); 4.974 (4.8); 4.959 (3.6); 4.943 (1.4); 4.889 (0.6); 4.883 (0.6); 4.849 (8.3); 4.843 (14.4); 4.838 (8.1); 4.804 (0.6); 4.798 (0.6); 4.382 (1.4); 4.354 (1.5); 4.056 (1.4); 4.038 (4.3); 4.020 (4.3); 4.002 (2.7); 3.972 (1.0); 3.805 (1.7); 3.803 (1.7); 3.775 (1.9); 3.772 (2.0); 3.763 (2.4); 3.760 (2.5); 3.730 (2.2); 3.540 (3.8); 3.534 (8.0); 3.528 (3.8); 3.518 (2.8); 3.496 (2.7); 3.475 (2.1); 3.453 (2.1); 3.440 (0.7); 3.431 (1.2); 3.421 (0.9); 3.411 (1.4); 3.402 (2.4); 3.393 (1.5); 3.383 (0.9); 3.374 (1.4); 3.365 (0.9); 3.338 (22.0); 3.314 (1.0); 3.283 (1.8); 3.249 (1.7); 3.220 (0.7); 2.933 (0.7); 2.909 (1.5); 2.878 (1.5); 2.854 (0.6); 2.676 (0.3); 2.671 (0.5); 2.667 (0.4); 2.565 (10.9); 2.524 (1.3); 2.511 (28.4);

2.507 (58.4); 2.502 (77.6); 2.497 (55.4); 2.493 (26.0); 2.333 (0.4); 2.329 (0.5); 2.324 (0.4); 2.122 (2.7); 2.099 (2.4); 1.989 (16.0); 1.909 (0.6); 1.825 (0.3); 1.815 (0.4); 1.784 (0.8); 1.762 (0.9); 1.755 (0.9); 1.735 (0.9); 1.706 (0.7); 1.607 (0.3); 1.576 (1.0); 1.554 (1.2); 1.546 (1.4); 1.523 (0.9); 1.515 (0.9); 1.494 (0.3); 1.237 (13.7); 1.221 (13.8); 1.210 (11.4); 1.204 (11.1); 1.193 (13.3); 1.189 (10.7); 1.175 (9.1); 1.157 (4.4); 0.146 (0.5); 0.008 (3.9); 0.000 (116.5); −0.009 (3.9); −0.150 (0.5)

Example I-39: $^1$H-NMR (400.0 MHz, $d_6$-DMSO)

δ=8.056 (2.2); 8.049 (2.1); 7.507 (0.8); 7.488 (1.4); 7.472 (0.5); 7.467 (1.1); 7.463 (1.4); 7.452 (4.1); 7.448 (4.9); 7.433 (0.9); 7.421 (1.3); 7.415 (1.0); 7.403 (1.2); 7.387 (0.6); 7.381 (0.5); 6.027 (1.2); 6.007 (0.8); 5.986 (0.9); 5.980 (1.0); 5.966 (1.8); 5.756 (3.6); 4.782 (0.7); 4.769 (0.7); 4.384 (0.6); 4.351 (0.6); 4.056 (0.4); 4.038 (0.3); 4.020 (0.4); 3.991 (1.1); 3.963 (1.0); 3.947 (1.1); 3.919 (0.9); 3.550 (16.0); 3.423 (0.3); 3.404 (0.6); 3.394 (0.6); 3.373 (0.5); 3.342 (10.9); 3.313 (0.8); 3.303 (0.9); 3.294 (0.8); 3.284 (0.8); 3.274 (0.6); 3.256 (0.5); 2.894 (0.6); 2.862 (0.5); 2.671 (0.4); 2.565 (8.3); 2.524 (0.7); 2.511 (23.2); 2.506 (47.9); 2.502 (64.8); 2.497 (48.9); 2.493 (24.6); 2.333 (0.4); 2.329 (0.5); 2.324 (0.4); 2.109 (0.9); 2.084 (1.0); 1.989 (0.7); 1.909 (0.6); 1.592 (0.5); 1.577 (0.7); 1.564 (0.8); 1.546 (1.1); 1.530 (1.3); 1.513 (1.9); 1.495 (1.7); 1.298 (0.8); 1.259 (1.8); 1.244 (1.9); 1.236 (1.9); 1.199 (1.5); 1.193 (1.6); 1.175 (1.4); 1.157 (0.8); 0.877 (1.2); 0.860 (3.2); 0.843 (2.7); 0.834 (2.7); 0.814 (2.3); 0.807 (2.3); 0.788 (1.5); 0.771 (0.4); 0.008 (1.2); 0.000 (35.3); −0.009 (1.2)

Example I-40: $^1$H-NMR (400.0 MHz, $d_6$-DMSO)

δ=7.978 (0.4); 7.967 (8.0); 7.432 (0.8); 7.411 (1.8); 7.394 (1.8); 7.373 (0.9); 7.008 (2.8); 6.987 (2.5); 6.906 (1.4); 6.881 (1.7); 6.859 (1.3); 6.067 (1.2); 6.044 (1.5); 6.037 (1.5); 6.014 (1.3); 4.847 (3.9); 4.842 (6.3); 4.837 (3.9); 4.774 (0.5); 4.757 (1.1); 4.743 (1.5); 4.728 (1.1); 4.712 (0.4); 4.445 (1.0); 4.413 (1.0); 4.038 (0.4); 4.020 (0.4); 3.900 (0.9); 3.866 (1.0); 3.800 (0.8); 3.769 (1.0); 3.757 (1.2); 3.727 (1.1); 3.643 (1.2); 3.639 (1.1); 3.604 (2.2); 3.600 (2.2); 3.539 (2.1); 3.533 (4.8); 3.527 (3.9); 3.516 (1.7); 3.492 (2.3); 3.487 (1.8); 3.473 (1.4); 3.461 (0.4); 3.451 (1.1); 3.395 (0.6); 3.386 (0.8); 3.377 (0.5); 3.366 (0.8); 3.357 (1.3); 3.347 (1.1); 3.334 (1.2); 3.322 (16.8); 3.243 (2.0); 3.235 (0.8); 3.205 (1.3); 3.176 (0.7); 2.802 (0.6); 2.773 (1.2); 2.743 (0.7); 2.675 (0.4); 2.670 (0.5); 2.666 (0.4); 2.506 (63.1); 2.502 (82.5); 2.497 (61.5); 2.333 (0.5); 2.328 (0.6); 2.324 (0.5); 2.090 (1.6); 2.058 (1.8); 1.989 (1.6); 1.769 (0.3); 1.740 (0.8); 1.710 (0.7); 1.594 (0.4); 1.576 (0.9); 1.559 (1.4); 1.546 (1.7); 1.540 (2.0); 1.528 (1.6); 1.518 (2.1); 1.508 (2.1); 1.499 (3.5); 1.481 (3.6); 1.464 (2.0); 1.446 (0.8); 1.428 (0.3); 1.398 (0.5); 1.233 (4.7); 1.219 (4.3); 1.193 (1.8); 1.175 (1.4); 1.157 (0.7); 0.875 (0.5); 0.850 (7.6); 0.833 (16.0); 0.815 (6.6); 0.008 (2.0); 0.000 (44.5); −0.008 (2.0)

Example I-41: $^1$H-NMR (400.0 MHz, $d_6$-DMSO)

δ=8.002 (9.7); 7.989 (0.3); 7.345 (0.9); 7.341 (1.2); 7.320 (4.5); 7.302 (3.9); 7.149 (3.1); 7.129 (2.6); 7.016 (1.7); 6.999 (3.0); 6.980 (1.4); 5.882 (1.5); 5.864 (1.7); 5.854 (1.7); 5.836 (1.5); 5.758 (3.5); 4.879 (8.1); 4.873 (8.1); 4.428 (1.0); 4.394 (1.1); 4.120 (2.3); 4.102 (7.3); 4.084 (7.4); 4.075 (0.5); 4.067 (2.4); 4.056 (0.5); 4.038 (1.1); 4.020 (1.1); 4.002 (0.4); 3.892 (1.6); 3.864 (2.3); 3.849 (2.9); 3.821 (2.8); 3.606 (0.9); 3.587 (2.1); 3.581 (4.4); 3.575 (2.4); 3.567 (6.5); 3.553 (6.3); 3.513 (0.9); 3.372 (0.4); 3.362 (0.7); 3.353 (0.6); 3.343 (0.9); 3.333 (2.2); 3.325 (22.4); 3.305 (0.9); 3.296 (0.5); 3.261 (2.0); 3.244 (2.0); 3.218 (2.4); 3.201 (1.9); 3.184 (1.5); 3.155 (0.8); 3.150 (0.7); 2.793 (0.8); 2.766 (1.4); 2.762 (1.4); 2.736 (0.8); 2.730 (0.7); 2.524 (0.8); 2.511 (15.6); 2.507 (30.6); 2.502 (39.8); 2.498 (29.4); 2.493 (14.8); 2.065 (1.8); 2.034 (2.1); 1.989 (4.8); 1.741 (0.4); 1.720 (0.8); 1.711 (0.9); 1.689 (0.8); 1.680 (0.8); 1.659 (0.3); 1.562 (0.3); 1.552 (0.4); 1.531 (0.8); 1.521 (0.9); 1.500 (0.9); 1.491 (0.8); 1.470 (0.4); 1.249 (0.3); 1.210 (7.4); 1.192 (16.0); 1.183 (1.0); 1.174 (9.4); 1.157 (1.4); 0.000 (2.8)

Example I-42: $^1$H-NMR (400.0 MHz, $d_6$-DMSO)

δ=7.963 (9.3); 7.432 (0.9); 7.415 (1.1); 7.411 (1.9); 7.395 (1.9); 7.391 (1.2); 7.374 (1.0); 7.009 (2.8); 6.988 (2.6); 6.909 (1.4); 6.887 (1.6); 6.884 (1.7); 6.862 (1.3); 6.067 (1.2); 6.045 (1.5); 6.036 (1.4); 6.014 (1.3); 4.849 (3.8); 4.843 (6.7); 4.838 (3.8); 4.436 (0.9); 4.403 (0.9); 4.123 (2.2); 4.105 (6.9); 4.087 (7.0); 4.070 (2.3); 4.056 (0.7); 4.038 (2.0); 4.020 (2.1); 4.002 (0.7); 3.866 (0.9); 3.831 (0.9); 3.805 (0.9); 3.774 (0.9); 3.762 (1.2); 3.760 (1.2); 3.731 (1.1); 3.610 (0.7); 3.571 (5.9); 3.559 (5.8); 3.541 (2.0); 3.535 (4.1); 3.529 (1.9); 3.518 (2.0); 3.495 (1.4); 3.475 (1.1); 3.452 (1.1); 3.392 (0.4); 3.382 (0.7); 3.373 (0.4); 3.363 (0.8); 3.353 (1.4); 3.344 (0.9); 3.322 (48.8); 3.235 (0.6); 3.229 (0.7); 3.199 (1.3); 3.170 (0.7); 3.164 (0.6); 2.810 (0.7); 2.779 (1.2); 2.753 (0.7); 2.747 (0.6); 2.675 (0.5); 2.671 (0.6); 2.666 (0.5); 2.524 (1.7); 2.519 (2.8); 2.511 (35.9); 2.506 (71.7); 2.502 (93.8); 2.497 (67.9); 2.493 (32.9); 2.333 (0.5); 2.328 (0.6); 2.324 (0.5); 2.089 (1.6); 2.063 (1.8); 1.989 (8.7); 1.733 (0.7); 1.703 (0.6); 1.555 (0.7); 1.545 (0.7); 1.524 (0.7); 1.514 (0.6); 1.213 (7.5); 1.195 (16.0); 1.177 (8.3); 1.175 (6.3); 1.157 (2.4); 0.008 (2.5); 0.000 (72.0); −0.008 (2.5)

Example I-43: $^1$H-NMR (400.0 MHz, $d_6$-DMSO)

δ=8.021 (0.4); 7.963 (3.6); 7.432 (0.5); 7.411 (1.0); 7.394 (1.1); 7.390 (0.8); 7.373 (0.6); 7.009 (1.6); 6.987 (1.4); 6.909 (0.8); 6.883 (1.0); 6.862 (0.8); 6.067 (0.6); 6.045 (0.8); 6.037 (0.8); 6.014 (0.7); 4.848 (2.1); 4.843 (3.6); 4.838 (2.3); 4.672 (0.3); 4.657 (0.7); 4.642 (0.5); 4.492 (0.4); 4.478 (0.9); 4.465 (0.5); 4.454 (0.3); 4.441 (0.9); 4.427 (0.5); 4.405 (0.4); 4.370 (0.4); 4.181 (1.3); 4.170 (1.6); 4.166 (1.2); 4.158 (1.5); 3.867 (0.4); 3.832 (0.4); 3.803 (0.6); 3.773 (0.6); 3.760 (0.8); 3.750 (0.4); 3.731 (0.7); 3.698 (0.5); 3.686 (0.8); 3.670 (0.9); 3.658 (1.3); 3.647 (1.0); 3.634 (0.7); 3.625 (0.6); 3.623 (0.6); 3.608 (2.0); 3.587 (2.0); 3.571 (1.2); 3.558 (1.0); 3.541 (1.7); 3.535 (2.8); 3.532 (2.9); 3.520 (2.5); 3.509 (1.9); 3.502 (0.8); 3.496 (1.2); 3.488 (1.0); 3.483 (0.7); 3.475 (1.3); 3.454 (2.8); 3.442 (3.2); 3.430 (1.6); 3.418 (0.4); 3.408 (0.4); 3.396 (1.8); 3.389 (1.3); 3.382 (1.9); 3.369 (0.5); 3.360 (1.3); 3.346 (1.9); 3.334 (1.3); 3.331 (1.6); 3.323 (10.2); 3.292 (0.3); 3.285 (0.3); 3.263 (1.9); 3.256 (1.4); 3.245 (16.0); 3.237 (11.2); 3.213 (0.6); 3.206 (0.8); 3.200 (0.8); 3.173 (0.4); 3.159 (0.3); 2.780 (0.5); 2.510 (13.8); 2.506 (26.5); 2.502 (34.4); 2.497 (25.4); 2.095 (0.7); 2.064 (0.8); 2.025 (0.7); 1.989 (1.2); 1.551 (0.4); 1.531 (0.4); 1.522 (0.4); 1.175 (0.6); 0.008 (0.8); 0.000 (18.9); −0.009 (0.9)

Example I-44: $^1$H-NMR (400.0 MHz, $d_6$-DMSO)

δ=7.963 (7.1); 7.432 (0.6); 7.415 (0.8); 7.411 (1.3); 7.394 (1.3); 7.390 (0.8); 7.373 (0.7); 7.009 (1.8); 6.988 (1.7);

6.909 (0.9); 6.887 (1.0); 6.884 (1.1); 6.862 (0.9); 6.067 (0.8); 6.045 (1.0); 6.037 (0.9); 6.014 (0.8); 4.949 (0.5); 4.933 (1.4); 4.918 (1.9); 4.902 (1.4); 4.886 (0.6); 4.849 (2.6); 4.843 (4.5); 4.838 (2.5); 4.440 (0.6); 4.406 (0.6); 4.056 (0.4); 4.038 (1.2); 4.020 (1.2); 4.002 (0.4); 3.860 (0.5); 3.824 (0.6); 3.804 (0.6); 3.773 (0.6); 3.770 (0.6); 3.761 (0.8); 3.758 (0.8); 3.729 (0.7); 3.577 (0.8); 3.538 (4.2); 3.534 (3.9); 3.528 (1.7); 3.515 (3.9); 3.495 (1.0); 3.475 (1.4); 3.452 (0.7); 3.382 (0.4); 3.363 (0.5); 3.353 (0.9); 3.344 (0.6); 3.323 (16.4); 3.232 (0.4); 3.226 (0.5); 3.196 (0.8); 3.167 (0.4); 2.805 (0.4); 2.775 (0.8); 2.748 (0.4); 2.742 (0.4); 2.524 (0.8); 2.519 (1.2); 2.511 (14.2); 2.506 (28.6); 2.502 (37.7); 2.497 (26.9); 2.493 (12.8); 2.088 (1.0); 2.062 (1.1); 1.989 (5.2); 1.738 (0.5); 1.708 (0.4); 1.551 (0.4); 1.542 (0.4); 1.522 (0.4); 1.513 (0.4); 1.204 (16.0); 1.189 (15.9); 1.175 (3.0); 1.157 (1.4); 0.000 (7.3)

Example I-45: $^1$H-NMR (400.0 MHz, $d_6$-DMSO)

δ=8.048 (5.6); 7.512 (0.8); 7.508 (0.9); 7.490 (1.3); 7.467 (0.9); 7.463 (1.0); 7.452 (2.9); 7.448 (3.7); 7.434 (0.6); 7.422 (1.1); 7.415 (0.8); 7.405 (0.7); 7.403 (0.8); 7.400 (0.7); 7.396 (0.6); 7.388 (0.4); 7.381 (0.4); 6.008 (0.8); 5.988 (0.9); 5.980 (0.9); 5.960 (0.8); 4.754 (0.5); 4.740 (0.7); 4.724 (0.4); 4.441 (0.4); 4.409 (0.4); 4.038 (0.7); 4.020 (0.7); 3.991 (0.7); 3.963 (0.8); 3.948 (0.9); 3.920 (0.8); 3.893 (0.4); 3.858 (0.4); 3.645 (0.4); 3.640 (0.5); 3.606 (0.7); 3.601 (1.0); 3.551 (16.0); 3.526 (0.7); 3.521 (1.1); 3.487 (0.4); 3.482 (0.6); 3.478 (0.4); 3.358 (0.4); 3.352 (1.3); 3.340 (0.5); 3.333 (1.2); 3.323 (15.6); 3.309 (1.0); 3.289 (0.9); 3.225 (0.4); 3.195 (0.6); 3.167 (0.3); 2.761 (0.5); 2.525 (0.4); 2.520 (0.7); 2.511 (8.9); 2.507 (18.1); 2.502 (24.1); 2.498 (17.5); 2.493 (8.3); 2.072 (0.7); 2.039 (0.7); 1.989 (3.1); 1.732 (0.3); 1.724 (0.3); 1.701 (0.3); 1.560 (0.5); 1.556 (0.6); 1.544 (0.6); 1.537 (0.7); 1.525 (0.8); 1.514 (0.9); 1.496 (1.6); 1.478 (1.4); 1.461 (0.9); 1.299 (0.4); 1.290 (0.3); 1.259 (0.8); 1.249 (1.1); 1.232 (1.7); 1.224 (1.7); 1.219 (1.7); 1.215 (1.6); 1.193 (1.7); 1.175 (2.0); 1.157 (0.9); 0.847 (2.8); 0.842 (1.6); 0.829 (6.4); 0.825 (3.4); 0.811 (2.8); 0.000 (7.8)

Example I-46: $^1$H-NMR (400.0 MHz, $d_6$-DMSO)

δ=8.045 (4.9); 7.514 (0.8); 7.510 (0.9); 7.492 (1.4); 7.472 (0.3); 7.468 (0.8); 7.463 (1.0); 7.452 (3.0); 7.448 (3.6); 7.433 (0.6); 7.423 (1.1); 7.417 (0.8); 7.404 (0.9); 7.398 (0.6); 7.389 (0.4); 7.382 (0.4); 6.005 (0.8); 5.986 (0.9); 5.977 (0.9); 5.958 (0.8); 4.429 (0.5); 4.397 (0.5); 4.178 (1.9); 4.170 (1.5); 4.167 (2.0); 4.163 (1.5); 4.155 (2.1); 4.038 (0.6); 4.020 (0.6); 3.992 (0.8); 3.964 (0.9); 3.949 (1.0); 3.921 (0.9); 3.857 (0.4); 3.822 (0.5); 3.644 (0.6); 3.631 (0.6); 3.604 (2.6); 3.583 (2.6); 3.570 (0.3); 3.552 (15.0); 3.544 (1.0); 3.529 (2.3); 3.520 (1.5); 3.517 (2.3); 3.506 (2.0); 3.454 (0.3); 3.442 (0.4); 3.370 (0.4); 3.356 (1.1); 3.351 (0.6); 3.337 (1.3); 3.331 (0.9); 3.322 (14.9); 3.313 (1.4); 3.303 (0.4); 3.294 (0.9); 3.258 (0.7); 3.245 (2.2); 3.234 (16.0); 3.220 (0.5); 3.190 (0.7); 3.161 (0.4); 3.156 (0.3); 2.799 (0.4); 2.772 (0.6); 2.768 (0.6); 2.742 (0.4); 2.524 (0.6); 2.511 (12.6); 2.506 (25.2); 2.502 (33.5); 2.497 (24.7); 2.493 (12.1); 2.075 (0.7); 2.043 (0.9); 1.989 (2.5); 1.737 (0.4); 1.728 (0.4); 1.706 (0.4); 1.697 (0.4); 1.543 (0.4); 1.534 (0.4); 1.512 (0.4); 1.503 (0.4); 1.193 (0.7); 1.175 (1.3); 1.157 (0.6); 0.000 (0.4)

Example I-47: $^1$H-NMR (400.0 MHz, $d_6$-DMSO)

δ=8.030 (5.7); 7.590 (0.5); 7.574 (0.7); 7.569 (1.2); 7.553 (1.2); 7.548 (0.9); 7.532 (0.7); 7.347 (0.9); 7.329 (2.7); 7.308 (1.9); 7.302 (1.0); 6.045 (0.7); 6.022 (1.0); 6.016 (0.9); 5.992 (0.8); 4.948 (0.5); 4.932 (1.2); 4.917 (1.6); 4.901 (1.2); 4.885 (0.5); 4.439 (0.6); 4.405 (0.7); 4.038 (0.8); 4.020 (0.9); 3.898 (0.5); 3.894 (0.5); 3.863 (1.0); 3.855 (1.2); 3.850 (1.1); 3.824 (1.2); 3.578 (0.9); 3.557 (0.9); 3.546 (16.0); 3.539 (3.9); 3.525 (1.2); 3.513 (3.2); 3.503 (1.1); 3.482 (0.8); 3.473 (0.9); 3.459 (0.7); 3.386 (0.4); 3.367 (0.6); 3.357 (0.9); 3.348 (0.5); 3.338 (0.4); 3.323 (15.9); 3.224 (0.5); 3.194 (0.9); 3.166 (0.5); 2.803 (0.5); 2.771 (0.8); 2.745 (0.5); 2.740 (0.4); 2.524 (0.6); 2.511 (13.1); 2.506 (26.6); 2.502 (35.3); 2.497 (26.5); 2.493 (13.5); 2.087 (1.1); 2.057 (1.2); 1.989 (3.7); 1.979 (0.6); 1.741 (0.5); 1.712 (0.5); 1.645 (0.7); 1.544 (0.5); 1.514 (0.5); 1.203 (14.3); 1.187 (14.4); 1.175 (2.7); 1.169 (0.9); 1.157 (1.1); 0.000 (6.1)

Example I-48: $^1$H-NMR (400.0 MHz, $d_6$-DMSO)

δ=8.034 (5.9); 7.968 (0.5); 7.590 (0.5); 7.574 (0.6); 7.569 (1.2); 7.553 (1.2); 7.548 (0.8); 7.532 (0.7); 7.346 (0.9); 7.329 (2.4); 7.322 (1.3); 7.308 (1.8); 7.300 (0.9); 6.045 (0.7); 6.022 (0.9); 6.016 (0.9); 5.992 (0.7); 4.756 (0.6); 4.742 (0.9); 4.728 (0.6); 4.447 (0.6); 4.413 (0.6); 4.056 (0.4); 4.038 (1.2); 4.020 (1.2); 4.002 (0.4); 3.896 (0.9); 3.865 (1.1); 3.853 (0.8); 3.848 (0.7); 3.818 (0.6); 3.643 (0.6); 3.604 (1.3); 3.546 (16.0); 3.523 (2.0); 3.501 (1.0); 3.488 (1.0); 3.482 (1.2); 3.475 (0.8); 3.457 (0.7); 3.391 (0.4); 3.371 (0.5); 3.362 (0.8); 3.352 (0.5); 3.348 (0.7); 3.334 (1.0); 3.322 (15.3); 3.243 (2.3); 3.234 (0.5); 3.204 (0.8); 3.175 (0.4); 2.799 (0.4); 2.769 (0.7); 2.741 (0.4); 2.671 (0.3); 2.524 (0.9); 2.511 (20.6); 2.506 (41.4); 2.502 (54.7); 2.497 (39.9); 2.493 (19.7); 2.329 (0.4); 2.090 (0.9); 2.056 (1.1); 1.989 (5.2); 1.744 (0.5); 1.713 (0.4); 1.575 (0.5); 1.558 (0.8); 1.545 (0.9); 1.539 (1.2); 1.527 (1.0); 1.517 (1.2); 1.499 (2.1); 1.481 (2.1); 1.464 (1.2); 1.446 (0.4); 1.298 (0.6); 1.290 (0.7); 1.231 (2.6); 1.216 (2.5); 1.193 (2.3); 1.175 (3.1); 1.157 (1.5); 1.031 (0.4); 1.016 (0.4); 0.849 (4.4); 0.831 (9.4); 0.813 (4.0); 0.008 (1.2); 0.000 (33.5); −0.009 (1.3)

Example I-49: $^1$H-NMR (400.0 MHz, $d_6$-DMSO)

δ=8.042 (6.1); 7.584 (0.6); 7.580 (0.9); 7.564 (2.6); 7.560 (2.7); 7.556 (2.3); 7.536 (2.9); 7.516 (1.4); 7.488 (2.3); 7.483 (2.1); 7.469 (1.3); 7.464 (1.1); 6.188 (1.0); 6.160 (1.6); 6.158 (1.5); 6.130 (1.1); 4.436 (0.6); 4.404 (0.7); 4.122 (3.8); 4.105 (4.6); 4.087 (4.7); 4.077 (0.3); 4.069 (1.6); 4.038 (0.6); 4.020 (0.6); 3.856 (1.3); 3.825 (1.6); 3.813 (1.4); 3.782 (1.1); 3.611 (0.6); 3.585 (1.3); 3.572 (4.0); 3.558 (5.0); 3.541 (1.8); 3.529 (16.0); 3.519 (1.1); 3.515 (1.3); 3.387 (0.5); 3.377 (0.3); 3.367 (0.6); 3.358 (1.0); 3.349 (0.6); 3.338 (0.5); 3.324 (14.5); 3.232 (0.4); 3.226 (0.5); 3.197 (0.9); 3.168 (0.5); 2.807 (0.5); 2.780 (0.9); 2.776 (0.9); 2.750 (0.5); 2.744 (0.4); 2.524 (0.6); 2.511 (11.9); 2.507 (22.8); 2.502 (29.4); 2.498 (21.5); 2.494 (10.6); 2.088 (1.2); 2.061 (1.3); 1.989 (2.4); 1.733 (0.5); 1.704 (0.5); 1.544 (0.5); 1.515 (0.5); 1.250 (0.3); 1.212 (5.0); 1.194 (10.3); 1.185 (0.8); 1.176 (5.4); 1.157 (0.7); 0.008 (0.4); 0.000 (8.1)

Example I-50: $^1$H-NMR (400.0 MHz, $d_6$-DMSO)

δ=8.044 (5.0); 7.515 (0.8); 7.511 (0.9); 7.494 (1.4); 7.472 (0.3); 7.468 (0.8); 7.463 (0.9); 7.452 (2.9); 7.448 (3.4); 7.434 (0.6); 7.423 (1.1); 7.417 (0.7); 7.405 (0.8); 7.398 (0.6); 7.389 (0.4); 7.383 (0.3); 6.005 (0.8); 5.986 (0.9); 5.977 (0.9); 5.958 (0.8); 4.431 (0.5); 4.398 (0.5); 4.120

(1.2); 4.103 (3.6); 4.085 (3.6); 4.067 (1.2); 4.056 (0.5); 4.038 (1.3); 4.020 (1.3); 4.002 (0.5); 3.992 (0.8); 3.964 (0.9); 3.948 (1.0); 3.920 (0.9); 3.858 (0.5); 3.823 (0.5); 3.607 (0.4); 3.568 (3.2); 3.552 (16.0); 3.514 (0.5); 3.374 (0.4); 3.363 (0.3); 3.356 (1.3); 3.345 (0.9); 3.336 (1.5); 3.323 (20.2); 3.313 (1.3); 3.293 (0.9); 3.225 (0.3); 3.219 (0.4); 3.189 (0.7); 3.160 (0.4); 2.798 (0.4); 2.772 (0.6); 2.767 (0.6); 2.741 (0.4); 2.524 (0.7); 2.511 (11.9); 2.507 (23.2); 2.502 (30.3); 2.498 (22.1); 2.493 (10.8); 2.072 (0.8); 2.042 (0.9); 1.989 (5.6); 1.726 (0.4); 1.717 (0.4); 1.695 (0.4); 1.687 (0.4); 1.537 (0.4); 1.528 (0.4); 1.507 (0.4); 1.498 (0.4); 1.210 (3.8); 1.192 (9.0); 1.175 (6.4); 1.157 (1.5); 0.000 (1.6)

Example I-51: $^1$H-NMR (400.0 MHz, $d_6$-DMSO)

δ=7.949 (9.4); 7.408 (1.9); 7.387 (3.8); 7.366 (2.8); 7.158 (3.4); 7.151 (3.9); 7.137 (2.8); 7.131 (3.3); 6.227 (1.5); 6.203 (2.0); 6.197 (1.8); 6.172 (1.6); 4.833 (0.4); 4.827 (0.4); 4.793 (3.5); 4.787 (4.5); 4.785 (4.5); 4.778 (3.4); 4.744 (0.4); 4.738 (0.4); 4.436 (0.9); 4.402 (1.0); 4.124 (2.3); 4.106 (7.1); 4.088 (7.3); 4.070 (2.4); 4.056 (0.7); 4.038 (2.0); 4.020 (2.0); 4.002 (0.7); 3.867 (0.9); 3.832 (1.0); 3.757 (1.2); 3.726 (1.5); 3.715 (2.1); 3.684 (1.7); 3.611 (0.8); 3.571 (6.9); 3.559 (6.2); 3.549 (2.3); 3.532 (1.4); 3.520 (0.9); 3.507 (1.3); 3.442 (1.9); 3.437 (4.2); 3.431 (2.0); 3.390 (0.4); 3.381 (0.7); 3.371 (0.5); 3.362 (0.8); 3.352 (1.4); 3.343 (0.9); 3.323 (22.6); 3.236 (0.7); 3.230 (0.8); 3.201 (1.3); 3.172 (0.8); 3.166 (0.6); 2.814 (0.7); 2.783 (1.3); 2.756 (0.7); 2.671 (0.3); 2.524 (0.9); 2.511 (19.4); 2.506 (38.8); 2.502 (51.0); 2.497 (37.8); 2.493 (18.9); 2.329 (0.4); 2.093 (1.7); 2.066 (1.9); 1.989 (8.4); 1.734 (0.8); 1.705 (0.7); 1.578 (0.3); 1.558 (0.7); 1.548 (0.8); 1.528 (0.7); 1.518 (0.7); 1.397 (0.5); 1.336 (0.4); 1.250 (0.5); 1.235 (0.3); 1.213 (7.7); 1.195 (16.0); 1.178 (8.1); 1.175 (6.6); 1.157 (2.3); 0.008 (0.5); 0.000 (14.3); −0.008 (0.5)

Example I-52: $^1$H-NMR (400.0 MHz, $d_6$-DMSO)

δ=8.002 (6.7); 7.345 (0.6); 7.341 (0.9); 7.320 (3.1); 7.301 (2.7); 7.149 (2.2); 7.129 (1.8); 7.016 (1.2); 6.998 (2.1); 6.979 (1.0); 5.882 (1.1); 5.864 (1.2); 5.854 (1.2); 5.836 (1.1); 4.945 (0.5); 4.929 (1.4); 4.914 (1.9); 4.898 (1.4); 4.879 (5.6); 4.873 (5.6); 4.430 (0.7); 4.397 (0.7); 4.056 (0.4); 4.038 (1.3); 4.020 (1.3); 4.003 (0.5); 3.891 (1.1); 3.863 (1.4); 3.848 (2.1); 3.820 (1.7); 3.587 (1.5); 3.581 (3.0); 3.575 (2.2); 3.535 (3.8); 3.506 (3.7); 3.467 (1.0); 3.362 (0.5); 3.353 (0.3); 3.343 (0.6); 3.333 (1.2); 3.324 (10.5); 3.305 (0.6); 3.260 (1.4); 3.242 (1.3); 3.217 (1.7); 3.199 (1.3); 3.181 (1.0); 3.152 (0.5); 2.787 (0.5); 2.761 (0.9); 2.756 (0.9); 2.730 (0.5); 2.724 (0.4); 2.524 (0.5); 2.511 (10.0); 2.507 (20.1); 2.502 (26.5); 2.498 (19.6); 2.493 (9.8); 2.062 (1.2); 2.032 (1.4); 1.989 (5.6); 1.726 (0.5); 1.717 (0.6); 1.695 (0.5); 1.687 (0.5); 1.528 (0.6); 1.518 (0.6); 1.496 (0.6); 1.487 (0.5); 1.397 (0.6); 1.200 (16.0); 1.193 (3.0); 1.185 (15.9); 1.175 (3.5); 1.157 (1.6); 0.000 (6.7)

Example I-53: $^1$H-NMR (400.0 MHz, $d_6$-DMSO)

δ=10.177 (9.2); 8.031 (2.9); 8.012 (3.2); 8.002 (10.5); 7.735 (1.1); 7.732 (1.1); 7.716 (2.8); 7.697 (2.0); 7.694 (1.9); 7.624 (2.1); 7.606 (7.2); 7.587 (4.1); 6.438 (1.6); 6.422 (1.8); 6.410 (1.8); 6.394 (1.6); 5.758 (1.9); 4.418 (1.1); 4.385 (1.2); 4.117 (2.6); 4.099 (7.7); 4.081 (9.3); 4.064 (2.7); 4.054 (2.4); 4.038 (3.7); 4.020 (1.6); 4.011 (2.0); 4.003 (0.7); 3.847 (1.1); 3.812 (1.2); 3.601 (0.9); 3.561 (7.0); 3.549 (6.8); 3.509 (0.9); 3.359 (0.5); 3.350 (0.9); 3.339 (0.8); 3.323 (30.5); 3.302 (0.7); 3.292 (0.9); 3.283 (0.5); 3.213 (2.9); 3.197 (2.3); 3.177 (1.7); 3.169 (2.6); 3.153 (2.4); 2.787 (0.9); 2.760 (1.5); 2.755 (1.5); 2.730 (0.9); 2.724 (0.8); 2.676 (0.4); 2.671 (0.6); 2.667 (0.4); 2.511 (32.8); 2.507 (62.6); 2.502 (80.3); 2.498 (58.4); 2.493 (28.7); 2.333 (0.4); 2.329 (0.5); 2.324 (0.4); 2.052 (1.9); 2.022 (2.2); 1.989 (6.4); 1.738 (0.3); 1.732 (0.4); 1.709 (0.8); 1.703 (0.9); 1.679 (0.8); 1.551 (0.4); 1.541 (0.4); 1.520 (0.9); 1.511 (1.0); 1.489 (0.9); 1.479 (0.8); 1.458 (0.4); 1.206 (7.9); 1.188 (16.0); 1.175 (4.6); 1.170 (7.8); 1.157 (1.8); 0.000 (0.8)

Example I-54: $^1$H-NMR (400.0 MHz, $d_6$-DMSO)

δ=8.031 (6.0); 7.590 (0.5); 7.574 (0.6); 7.569 (1.2); 7.553 (1.2); 7.548 (0.8); 7.532 (0.7); 7.348 (0.8); 7.329 (2.5); 7.324 (1.2); 7.309 (1.7); 7.302 (0.8); 6.046 (0.7); 6.023 (0.8); 6.016 (0.8); 5.993 (0.7); 4.437 (0.5); 4.403 (0.5); 4.123 (1.3); 4.105 (4.2); 4.087 (4.2); 4.069 (1.4); 4.038 (0.8); 4.020 (0.8); 3.899 (0.5); 3.895 (0.4); 3.868 (0.9); 3.865 (1.0); 3.856 (0.9); 3.852 (0.8); 3.826 (0.9); 3.822 (0.8); 3.611 (0.5); 3.572 (3.5); 3.558 (3.6); 3.547 (16.0); 3.527 (0.8); 3.519 (0.6); 3.504 (0.8); 3.483 (0.6); 3.460 (0.6); 3.387 (0.4); 3.368 (0.5); 3.358 (0.8); 3.348 (0.5); 3.338 (0.4); 3.323 (13.1); 3.233 (0.3); 3.227 (0.4); 3.198 (0.7); 3.169 (0.4); 3.164 (0.3); 2.808 (0.4); 2.781 (0.7); 2.777 (0.7); 2.751 (0.4); 2.745 (0.3); 2.524 (0.5); 2.511 (9.6); 2.506 (19.2); 2.502 (25.2); 2.497 (18.1); 2.493 (8.6); 2.088 (0.9); 2.059 (1.0); 1.989 (3.4); 1.735 (0.4); 1.706 (0.4); 1.552 (0.4); 1.546 (0.4); 1.543 (0.4); 1.518 (0.4); 1.212 (4.6); 1.194 (9.5); 1.176 (4.9); 1.157 (0.9); 0.008 (0.7); 0.000 (20.1); −0.009 (0.7)

Example I-55: $^1$H-NMR (400.0 MHz, $d_6$-DMSO)

δ=10.177 (10.8); 8.033 (3.4); 8.023 (1.0); 8.014 (4.0); 8.007 (11.0); 7.733 (1.2); 7.730 (1.3); 7.715 (3.3); 7.696 (2.4); 7.692 (2.3); 7.624 (2.6); 7.606 (8.4); 7.587 (4.7); 6.439 (1.8); 6.423 (2.1); 6.411 (2.0); 6.395 (1.9); 4.765 (0.5); 4.749 (1.5); 4.735 (1.9); 4.719 (1.4); 4.704 (0.5); 4.429 (1.3); 4.397 (1.3); 4.082 (2.0); 4.054 (2.5); 4.039 (6.0); 4.021 (3.8); 4.010 (2.2); 4.003 (1.4); 3.886 (1.2); 3.852 (1.3); 3.647 (1.0); 3.640 (1.6); 3.634 (1.0); 3.629 (0.6); 3.608 (1.6); 3.601 (2.8); 3.596 (1.7); 3.515 (1.6); 3.508 (2.7); 3.501 (1.5); 3.476 (1.0); 3.469 (1.6); 3.462 (0.9); 3.364 (0.5); 3.354 (0.9); 3.345 (0.9); 3.334 (1.4); 3.324 (24.1); 3.306 (0.8); 3.297 (1.0); 3.287 (0.6); 3.214 (1.2); 3.205 (2.7); 3.189 (3.8); 3.161 (2.7); 3.145 (2.6); 2.778 (0.9); 2.749 (1.6); 2.720 (0.9); 2.677 (0.3); 2.672 (0.4); 2.668 (0.3); 2.546 (0.4); 2.525 (1.4); 2.512 (26.4); 2.508 (51.5); 2.503 (66.4); 2.499 (47.6); 2.494 (22.8); 2.334 (0.4); 2.330 (0.5); 2.325 (0.4); 2.050 (2.0); 2.018 (2.2); 1.990 (16.0); 1.749 (0.5); 1.737 (0.5); 1.718 (1.1); 1.688 (1.0); 1.656 (0.4); 1.583 (0.5); 1.566 (0.9); 1.549 (1.6); 1.531 (2.0); 1.507 (2.9); 1.489 (4.3); 1.471 (5.2); 1.454 (3.3); 1.441 (1.5); 1.397 (0.5); 1.352 (0.5); 1.336 (0.6); 1.299 (1.1); 1.259 (2.4); 1.249 (2.9); 1.219 (5.2); 1.209 (5.4); 1.193 (8.3); 1.176 (10.4); 1.158 (5.0); 0.882 (0.5); 0.876 (0.5); 0.864 (1.2); 0.859 (1.4); 0.840 (7.8); 0.821 (14.5); 0.813 (7.6); 0.805 (6.3); 0.803 (6.3); 0.008 (1.4); 0.000 (36.4); −0.009 (1.3)

Example I-56: $^1$H-NMR (400.0 MHz, $d_6$-DMSO)

δ=10.176 (5.6); 8.032 (2.0); 8.013 (2.3); 8.002 (6.5); 7.732 (0.8); 7.716 (1.8); 7.697 (1.3); 7.694 (1.3); 7.624

(1.4); 7.606 (4.8); 7.587 (2.7); 7.349 (0.5); 6.437 (1.1); 6.421 (1.2); 6.410 (1.2); 6.394 (1.1); 5.678 (0.4); 4.941 (0.5); 4.925 (1.3); 4.910 (1.8); 4.894 (1.3); 4.878 (0.5); 4.421 (0.9); 4.387 (1.0); 4.082 (1.2); 4.054 (1.7); 4.038 (3.2); 4.020 (1.9); 4.010 (1.3); 4.003 (0.8); 3.841 (1.0); 3.807 (0.9); 3.630 (1.5); 3.584 (0.8); 3.568 (1.0); 3.529 (3.9); 3.502 (3.8); 3.463 (1.0); 3.349 (0.8); 3.324 (41.5); 3.292 (0.7); 3.283 (0.4); 3.210 (1.9); 3.194 (1.6); 3.173 (1.3); 3.167 (1.9); 3.151 (1.5); 2.781 (0.7); 2.750 (1.2); 2.723 (0.6); 2.671 (0.4); 2.507 (50.3); 2.502 (63.6); 2.498 (49.0); 2.329 (0.4); 2.325 (0.3); 2.049 (1.6); 2.019 (1.7); 1.989 (7.5); 1.710 (0.7); 1.682 (0.7); 1.536 (0.4); 1.505 (0.7); 1.485 (0.7); 1.476 (0.6); 1.397 (0.4); 1.195 (16.0); 1.179 (15.6); 1.157 (2.5); 1.095 (1.3); 1.079 (1.3); 0.000 (3.8)

Example I-57: $^1$H-NMR (400.0 MHz, d$_6$-DMSO)

δ=8.005 (9.6); 7.340 (1.8); 7.319 (4.3); 7.300 (3.7); 7.297 (4.3); 7.186 (0.3); 7.148 (4.4); 7.128 (3.7); 7.014 (2.4); 6.996 (4.1); 6.977 (2.0); 5.882 (1.9); 5.864 (2.3); 5.855 (2.2); 5.837 (2.0); 5.757 (0.4); 4.875 (10.0); 4.870 (10.0); 4.770 (0.5); 4.753 (1.4); 4.740 (1.9); 4.724 (1.4); 4.708 (0.5); 4.436 (1.3); 4.404 (1.4); 3.888 (2.9); 3.860 (3.2); 3.845 (2.9); 3.818 (2.0); 3.641 (1.5); 3.602 (2.8); 3.586 (2.9); 3.580 (5.0); 3.575 (2.7); 3.516 (2.7); 3.477 (1.5); 3.366 (1.0); 3.357 (0.8); 3.347 (1.3); 3.323 (40.9); 3.257 (2.3); 3.239 (2.4); 3.214 (2.4); 3.196 (3.2); 3.161 (1.9); 2.784 (0.9); 2.756 (1.7); 2.726 (1.4); 2.671 (0.9); 2.506 (98.0); 2.502 (122.7); 2.498 (90.8); 2.333 (0.7); 2.329 (0.9); 2.324 (0.7); 2.179 (0.4); 2.064 (2.1); 2.032 (2.4); 1.747 (0.5); 1.726 (1.1); 1.695 (1.1); 1.665 (0.5); 1.591 (0.6); 1.573 (0.9); 1.556 (1.7); 1.537 (1.9); 1.514 (3.0); 1.495 (4.6); 1.478 (4.9); 1.461 (3.1); 1.351 (1.6); 1.336 (2.6); 1.298 (2.0); 1.258 (4.2); 1.249 (6.1); 1.235 (10.6); 0.846 (7.8); 0.828 (16.0); 0.810 (7.3); 0.000 (23.9); −0.008 (1.2)

Example I-58: $^1$H-NMR (400.0 MHz, d$_6$-DMSO)

δ=8.045 (5.8); 7.515 (0.8); 7.511 (1.0); 7.494 (1.4); 7.473 (0.3); 7.468 (0.8); 7.464 (1.0); 7.453 (3.2); 7.449 (3.7); 7.434 (0.6); 7.424 (1.1); 7.417 (0.8); 7.405 (0.8); 7.402 (0.6); 7.398 (0.6); 7.390 (0.4); 7.383 (0.4); 6.005 (0.8); 5.986 (1.0); 5.978 (0.9); 5.958 (0.8); 5.758 (0.4); 4.945 (0.4); 4.929 (1.1); 4.914 (1.5); 4.898 (1.1); 4.882 (0.4); 4.433 (0.5); 4.400 (0.5); 4.038 (0.8); 4.020 (0.8); 3.991 (0.8); 3.963 (1.0); 3.948 (1.1); 3.920 (0.9); 3.851 (0.5); 3.816 (0.5); 3.575 (0.8); 3.553 (16.0); 3.536 (2.9); 3.509 (2.8); 3.470 (0.7); 3.375 (0.4); 3.355 (1.4); 3.345 (0.9); 3.336 (1.7); 3.325 (20.3); 3.312 (1.2); 3.293 (1.0); 3.221 (0.3); 3.215 (0.4); 3.185 (0.7); 3.157 (0.4); 2.792 (0.4); 2.766 (0.6); 2.761 (0.6); 2.735 (0.4); 2.524 (0.5); 2.520 (0.7); 2.511 (9.9); 2.507 (19.9); 2.502 (26.3); 2.497 (18.9); 2.493 (9.0); 2.070 (0.8); 2.039 (0.9); 1.989 (3.6); 1.731 (0.4); 1.722 (0.4); 1.700 (0.4); 1.691 (0.4); 1.533 (0.4); 1.523 (0.4); 1.502 (0.4); 1.493 (0.4); 1.200 (13.3); 1.193 (1.8); 1.185 (13.2); 1.175 (2.2); 1.157 (1.0); 0.008 (0.5); 0.000 (15.5); −0.009 (0.5)

Example I-59: $^1$H-NMR (400.0 MHz, d$_6$-DMSO)

δ=7.953 (5.2); 7.930 (6.7); 7.417 (1.0); 7.407 (2.0); 7.386 (5.5); 7.370 (16.0); 7.361 (3.9); 7.356 (3.3); 7.349 (6.4); 7.344 (4.4); 7.334 (3.8); 7.319 (1.0); 7.314 (1.4); 7.306 (1.1); 7.299 (0.8); 7.284 (1.7); 7.254 (1.4); 7.223 (1.1); 7.158 (3.9); 7.152 (4.3); 7.149 (4.5); 7.137 (3.3); 7.133 (3.2); 7.129 (3.5); 7.088 (2.7); 7.080 (3.6); 7.067 (2.6); 6.952 (1.5); 6.944 (3.5); 6.906 (3.9); 6.230 (0.9); 6.219 (1.1); 6.206 (1.2); 6.200 (1.2); 6.194 (1.6); 6.188 (1.4); 6.175 (0.9); 6.163 (1.1); 5.757 (0.5); 5.301 (1.4); 5.290 (0.9); 5.270 (3.7); 5.259 (3.1); 5.237 (6.2); 5.205 (2.1); 4.826 (0.4); 4.793 (2.2); 4.785 (5.3); 4.779 (5.8); 4.771 (2.6); 4.738 (0.4); 4.458 (0.7); 4.426 (0.8); 4.397 (0.6); 4.363 (0.6); 4.056 (0.5); 4.038 (1.5); 4.020 (1.5); 4.002 (0.5); 3.786 (0.5); 3.751 (1.4); 3.730 (1.3); 3.719 (0.9); 3.709 (1.6); 3.700 (1.6); 3.688 (1.6); 3.678 (0.9); 3.657 (1.2); 3.567 (1.0); 3.549 (1.4); 3.542 (1.2); 3.524 (1.8); 3.506 (0.9); 3.500 (0.8); 3.482 (0.9); 3.446 (1.2); 3.440 (2.4); 3.434 (1.2); 3.420 (1.3); 3.416 (2.5); 3.410 (1.3); 3.329 (36.5); 3.312 (1.1); 3.294 (0.7); 3.282 (0.6); 3.252 (0.5); 3.221 (0.9); 3.191 (0.5); 2.983 (0.4); 2.953 (0.7); 2.933 (0.8); 2.926 (0.9); 2.902 (1.3); 2.876 (0.6); 2.870 (0.7); 2.671 (0.4); 2.524 (1.2); 2.511 (24.6); 2.506 (49.8); 2.502 (65.0); 2.497 (47.0); 2.493 (22.7); 2.329 (0.4); 2.126 (0.5); 2.095 (1.1); 2.062 (0.7); 1.989 (6.5); 1.933 (0.4); 1.904 (0.6); 1.856 (0.6); 1.825 (0.7); 1.749 (0.5); 1.719 (0.4); 1.588 (0.4); 1.555 (0.5); 1.536 (0.4); 1.518 (0.6); 1.509 (0.6); 1.486 (0.5); 1.478 (0.5); 1.192 (1.7); 1.175 (3.5); 1.157 (1.7); 0.904 (0.6); 0.872 (0.5); 0.008 (1.8); 0.000 (50.4); −0.009 (1.9)

Example I-60: $^1$H-NMR (400.0 MHz, d$_6$-DMSO)

δ=8.049 (3.7); 8.022 (4.4); 7.502 (1.3); 7.485 (2.1); 7.463 (1.7); 7.450 (6.2); 7.436 (0.9); 7.432 (0.9); 7.418 (1.8); 7.413 (1.9); 7.401 (1.9); 7.383 (2.8); 7.369 (11.9); 7.360 (3.4); 7.344 (4.5); 7.329 (2.7); 7.307 (1.1); 7.281 (1.7); 7.250 (1.1); 7.220 (0.8); 7.208 (0.5); 7.148 (0.8); 7.118 (0.7); 7.085 (1.9); 7.080 (1.8); 7.072 (3.7); 6.950 (1.0); 6.939 (2.9); 6.901 (3.2); 6.010 (0.7); 5.998 (1.0); 5.991 (0.9); 5.979 (1.4); 5.970 (1.1); 5.963 (0.8); 5.951 (0.9); 5.299 (1.2); 5.286 (0.7); 5.267 (3.0); 5.255 (2.3); 5.232 (5.1); 5.201 (1.9); 4.454 (0.6); 4.423 (0.7); 4.393 (0.5); 4.358 (0.5); 4.056 (0.6); 4.038 (1.9); 4.020 (1.9); 4.002 (0.7); 3.991 (0.6); 3.966 (1.0); 3.948 (0.9); 3.939 (1.0); 3.923 (1.3); 3.895 (0.9); 3.772 (0.5); 3.735 (0.9); 3.695 (0.7); 3.552 (12.8); 3.548 (16.0); 3.353 (1.0); 3.329 (38.3); 3.316 (2.3); 3.291 (2.0); 3.272 (1.3); 3.241 (0.5); 3.210 (0.8); 3.179 (0.4); 2.936 (0.6); 2.918 (0.7); 2.908 (0.7); 2.887 (1.1); 2.862 (0.5); 2.854 (0.5); 2.671 (0.4); 2.507 (48.7); 2.502 (63.7); 2.498 (47.5); 2.329 (0.4); 2.110 (0.4); 2.075 (0.9); 2.043 (0.6); 1.989 (8.0); 1.915 (0.4); 1.886 (0.5); 1.826 (0.6); 1.799 (0.6); 1.738 (0.4); 1.731 (0.4); 1.709 (0.3); 1.701 (0.5); 1.565 (0.4); 1.534 (0.5); 1.502 (0.5); 1.494 (0.6); 1.472 (0.5); 1.463 (0.5); 1.397 (0.4); 1.193 (2.1); 1.175 (4.2); 1.157 (2.1); 0.875 (0.5); 0.868 (0.5); 0.845 (0.5); 0.837 (0.5); 0.008 (1.7); 0.000 (41.6); −0.008 (2.0)

Example I-61: $^1$H-NMR (400.0 MHz, d$_6$-DMSO)

δ=8.046 (3.0); 8.021 (3.9); 7.582 (0.8); 7.578 (0.7); 7.562 (3.0); 7.557 (3.1); 7.537 (2.0); 7.535 (2.2); 7.518 (0.9); 7.515 (1.1); 7.490 (1.3); 7.485 (2.5); 7.481 (1.5); 7.471 (0.8); 7.466 (1.4); 7.461 (0.8); 7.417 (0.6); 7.384 (1.7); 7.381 (1.5); 7.370 (9.4); 7.361 (2.4); 7.356 (1.9); 7.346 (3.7); 7.330 (2.3); 7.316 (0.6); 7.310 (0.9); 7.302 (0.8); 7.296 (0.6); 7.285 (1.3); 7.252 (0.9); 7.222 (0.6); 7.213 (0.5); 7.151 (0.6); 7.120 (0.5); 7.087 (1.4); 7.076 (2.8); 7.067 (1.7); 6.952 (0.8); 6.944 (2.3); 6.904 (2.4); 6.191 (0.5); 6.178 (0.7); 6.163 (0.9); 6.151 (1.2); 6.133 (0.6); 6.121 (0.5); 5.300 (0.9); 5.288 (0.6); 5.269 (2.3); 5.257 (1.9); 5.235 (4.3); 5.204 (1.5); 4.460 (0.4); 4.427 (0.5); 4.397 (0.4); 4.364 (0.4); 4.056 (1.2); 4.038 (3.8); 4.020

(3.8); 4.002 (1.3); 3.852 (0.4); 3.828 (0.5); 3.821 (0.6); 3.809 (0.7); 3.799 (0.6); 3.785 (1.0); 3.778 (0.9); 3.755 (0.9); 3.702 (0.5); 3.582 (0.6); 3.563 (0.8); 3.555 (0.7); 3.530 (8.5); 3.520 (9.9); 3.493 (0.6); 3.328 (24.0); 3.298 (0.5); 3.286 (0.4); 3.247 (0.3); 3.218 (0.6); 2.948 (0.5); 2.922 (0.5); 2.915 (0.5); 2.897 (0.7); 2.871 (0.4); 2.865 (0.4); 2.524 (0.7); 2.511 (17.2); 2.507 (34.5); 2.502 (45.1); 2.498 (32.8); 2.494 (16.3); 2.093 (0.7); 2.059 (0.5); 1.989 (16.0); 1.900 (0.4); 1.849 (0.4); 1.825 (0.4); 1.817 (0.4); 1.547 (0.3); 1.539 (0.3); 1.508 (0.4); 1.476 (0.4); 1.397 (0.9); 1.193 (4.3); 1.175 (8.6); 1.157 (4.2); 0.889 (0.4); 0.858 (0.4); 0.008 (1.2); 0.000 (33.2); −0.008 (1.4)

Example I-62: $^1$H-NMR (400.0 MHz, $d_6$-DMSO)

δ=8.006 (4.6); 7.979 (5.1); 7.413 (1.1); 7.403 (0.6); 7.382 (3.4); 7.369 (16.0); 7.359 (5.1); 7.341 (7.8); 7.322 (7.4); 7.302 (5.6); 7.293 (3.6); 7.280 (2.7); 7.268 (0.8); 7.250 (1.6); 7.220 (1.2); 7.210 (0.8); 7.148 (5.0); 7.128 (3.3); 7.117 (1.1); 7.099 (0.4); 7.084 (2.9); 7.068 (4.7); 7.014 (2.1); 6.995 (3.6); 6.976 (1.7); 6.964 (0.4); 6.949 (1.5); 6.939 (4.0); 6.922 (0.4); 6.898 (4.1); 5.886 (0.9); 5.875 (1.3); 5.869 (1.2); 5.858 (2.2); 5.848 (1.5); 5.842 (1.1); 5.830 (1.2); 5.298 (1.5); 5.286 (1.0); 5.267 (4.1); 5.255 (3.1); 5.232 (6.9); 5.201 (2.5); 5.074 (0.4); 5.071 (0.4); 4.873 (9.5); 4.452 (0.8); 4.419 (0.9); 4.389 (0.7); 4.356 (0.7); 4.056 (0.7); 4.038 (2.1); 4.020 (2.1); 4.002 (0.7); 3.890 (0.8); 3.866 (1.3); 3.847 (1.2); 3.839 (1.4); 3.823 (1.7); 3.796 (1.2); 3.769 (0.7); 3.732 (1.3); 3.692 (0.9); 3.581 (3.3); 3.574 (3.7); 3.330 (34.3); 3.302 (1.5); 3.291 (1.3); 3.274 (1.0); 3.259 (1.6); 3.241 (2.7); 3.222 (1.6); 3.215 (1.6); 3.198 (2.4); 3.179 (1.5); 2.963 (0.5); 2.933 (0.9); 2.914 (1.0); 2.904 (1.0); 2.883 (1.5); 2.857 (0.8); 2.849 (0.7); 2.672 (0.4); 2.506 (53.1); 2.502 (67.3); 2.329 (0.5); 2.103 (0.6); 2.070 (1.3); 2.038 (0.9); 1.989 (8.8); 1.907 (0.5); 1.876 (0.7); 1.825 (0.8); 1.793 (0.8); 1.725 (0.6); 1.702 (0.5); 1.559 (0.6); 1.528 (0.7); 1.493 (0.8); 1.461 (0.7); 1.397 (2.7); 1.193 (2.4); 1.175 (4.7); 1.157 (2.3); 0.870 (0.7); 0.846 (0.7); 0.008 (2.0); 0.000 (44.2); −0.009 (2.6)

Example I-63: $^1$H-NMR (400.0 MHz, $d_6$-DMSO)

δ=7.958 (1.5); 7.930 (2.2); 7.407 (0.7); 7.399 (0.4); 7.387 (1.7); 7.366 (1.0); 7.265 (0.6); 7.254 (0.5); 7.215 (0.3); 7.207 (0.3); 7.158 (1.5); 7.150 (1.6); 7.136 (1.4); 7.130 (1.5); 7.080 (0.7); 7.072 (0.7); 7.048 (1.6); 6.944 (1.5); 6.936 (0.4); 6.662 (0.9); 6.619 (1.4); 6.219 (0.4); 6.206 (0.4); 6.199 (0.4); 6.194 (0.6); 6.189 (0.5); 6.164 (0.4); 4.786 (1.9); 4.779 (2.0); 4.056 (0.5); 4.038 (1.6); 4.020 (1.6); 4.002 (0.6); 3.755 (0.5); 3.746 (0.5); 3.732 (0.5); 3.724 (0.5); 3.714 (0.6); 3.701 (0.5); 3.689 (0.6); 3.683 (0.4); 3.659 (0.4); 3.549 (0.7); 3.530 (0.3); 3.525 (0.5); 3.507 (0.5); 3.440 (0.4); 3.435 (0.7); 3.429 (0.4); 3.416 (0.9); 3.330 (20.6); 3.236 (0.3); 2.924 (0.3); 2.899 (0.4); 2.507 (18.4); 2.502 (23.6); 2.498 (17.3); 2.100 (0.4); 1.989 (7.1); 1.834 (0.4); 1.827 (0.3); 1.425 (16.0); 1.419 (11.9); 1.397 (3.8); 1.193 (1.9); 1.175 (3.7); 1.157 (1.8); 0.000 (5.9)

Example I-64: $^1$H-NMR (400.0 MHz, $d_6$-DMSO)

δ=8.051 (1.5); 8.021 (2.1); 7.581 (0.4); 7.579 (0.4); 7.562 (1.5); 7.558 (1.6); 7.535 (1.4); 7.515 (0.6); 7.485 (1.3); 7.466 (0.7); 7.264 (0.5); 7.252 (0.5); 7.133 (0.4); 7.078 (0.7); 7.065 (0.6); 7.046 (1.5); 6.943 (0.3); 6.663 (0.9); 6.615 (1.4); 6.178 (0.4); 6.159 (0.5); 6.150 (0.7); 6.120 (0.4); 4.056 (0.4); 4.038 (1.1); 4.020 (1.1); 4.002 (0.4); 3.811 (0.3); 3.798 (0.3); 3.785 (0.5); 3.780 (0.5); 3.755 (0.5); 3.742 (0.4); 3.563 (0.5); 3.555 (0.4); 3.531 (4.3); 3.520 (5.5); 3.493 (0.3); 3.329 (20.1); 3.231 (0.4); 2.918 (0.4); 2.891 (0.6); 2.507 (21.6); 2.502 (28.5); 2.498 (21.1); 2.094 (0.3); 1.989 (4.8); 1.851 (0.4); 1.826 (0.4); 1.424 (16.0); 1.418 (12.1); 1.397 (1.1); 1.193 (1.2); 1.175 (2.5); 1.157 (1.2); 0.000 (6.6)

Example I-65: $^1$H-NMR (400.0 MHz, $d_6$-DMSO)

δ=8.012 (1.5); 7.979 (1.6); 7.394 (0.3); 7.341 (0.5); 7.321 (1.1); 7.312 (0.9); 7.301 (0.9); 7.293 (0.9); 7.261 (0.6); 7.248 (0.4); 7.211 (0.3); 7.148 (1.2); 7.128 (1.3); 7.076 (0.7); 7.070 (0.6); 7.062 (0.5); 7.043 (1.8); 7.014 (0.6); 6.996 (1.0); 6.977 (0.5); 6.941 (0.3); 6.662 (0.9); 6.610 (1.3); 5.875 (0.4); 5.866 (0.3); 5.857 (0.7); 5.848 (0.4); 5.830 (0.4); 4.874 (3.1); 4.869 (2.2); 3.867 (0.4); 3.847 (0.3); 3.840 (0.4); 3.824 (0.5); 3.797 (0.4); 3.737 (0.4); 3.589 (0.4); 3.584 (0.9); 3.575 (1.1); 3.569 (0.5); 3.331 (28.3); 3.309 (0.5); 3.300 (0.3); 3.257 (0.5); 3.240 (0.7); 3.222 (0.7); 3.215 (0.5); 3.197 (0.7); 3.180 (0.5); 2.910 (0.4); 2.878 (0.5); 2.507 (21.9); 2.503 (28.1); 2.498 (20.5); 2.072 (0.4); 1.989 (1.2); 1.830 (0.4); 1.799 (0.4); 1.422 (16.0); 1.416 (11.6); 1.397 (1.3); 1.193 (0.3); 1.175 (0.7); 1.157 (0.3); 0.008 (0.6); 0.000 (15.0); −0.009 (0.6)

Example I-66: $^1$H-NMR (400.0 MHz, $d_6$-DMSO)

δ=8.054 (1.4); 8.023 (1.9); 7.508 (0.7); 7.487 (1.0); 7.463 (0.8); 7.451 (2.8); 7.433 (0.4); 7.419 (0.8); 7.399 (0.9); 7.385 (0.5); 7.263 (0.6); 7.250 (0.5); 7.212 (0.3); 7.130 (0.4); 7.077 (0.7); 7.069 (0.6); 7.062 (0.6); 7.045 (1.9); 6.942 (0.3); 6.663 (1.0); 6.613 (1.4); 6.000 (0.4); 5.990 (0.4); 5.981 (0.8); 5.972 (0.5); 5.962 (0.3); 5.953 (0.4); 4.038 (0.6); 4.020 (0.6); 3.969 (0.5); 3.948 (0.4); 3.941 (0.5); 3.925 (0.6); 3.898 (0.4); 3.739 (0.5); 3.701 (0.3); 3.554 (5.3); 3.549 (6.7); 3.353 (0.6); 3.332 (16.7); 3.293 (0.8); 3.275 (0.5); 3.225 (0.4); 2.913 (0.4); 2.884 (0.6); 2.853 (0.3); 2.507 (17.1); 2.503 (20.8); 2.499 (15.5); 2.080 (0.4); 1.990 (2.7); 1.837 (0.4); 1.805 (0.4); 1.423 (16.0); 1.416 (11.9); 1.193 (0.7); 1.175 (1.4); 1.157 (0.7); 0.000 (10.4)

Example I-67: $^1$H-NMR (400.0 MHz, $d_6$-DMSO)

δ=8.046 (5.0); 7.584 (0.6); 7.580 (0.8); 7.564 (2.2); 7.560 (2.4); 7.537 (2.3); 7.517 (1.0); 7.488 (1.8); 7.484 (1.7); 7.469 (1.0); 7.465 (0.9); 7.393 (2.5); 7.382 (5.0); 7.359 (2.4); 7.339 (1.8); 7.319 (0.7); 7.304 (0.6); 7.287 (0.5); 6.187 (1.0); 6.159 (1.5); 6.129 (1.0); 6.072 (1.7); 6.038 (1.7); 5.275 (0.5); 5.243 (1.7); 5.236 (1.7); 5.223 (1.7); 5.217 (1.7); 5.186 (0.5); 4.376 (0.5); 4.347 (0.5); 4.055 (0.4); 4.038 (1.1); 4.020 (1.3); 4.002 (0.7); 3.990 (0.5); 3.966 (0.4); 3.852 (0.6); 3.821 (0.7); 3.808 (0.9); 3.777 (0.8); 3.582 (0.7); 3.568 (1.0); 3.554 (0.8); 3.528 (16.0); 3.513 (0.7); 3.400 (0.4); 3.390 (0.6); 3.382 (0.5); 3.372 (0.6); 3.362 (0.5); 3.331 (46.4); 3.297 (0.3); 3.265 (0.5); 3.229 (0.5); 2.902 (0.6); 2.872 (0.6); 2.511 (15.9); 2.507 (30.8); 2.502 (39.7); 2.498 (28.8); 2.113 (1.0); 2.085 (1.1); 1.989 (4.3); 1.536 (0.4); 1.505 (0.4); 1.193 (1.1); 1.175 (2.3); 1.157 (1.1); 0.008 (1.8); 0.000 (39.6); −0.008 (1.7)

Example I-68: $^1$H-NMR (400.0 MHz, $d_6$-DMSO)

δ=8.049 (4.7); 7.510 (1.1); 7.492 (1.7); 7.468 (0.8); 7.464 (1.0); 7.452 (3.1); 7.448 (3.7); 7.434 (0.6); 7.422 (1.2); 7.416 (0.9); 7.403 (1.1); 7.392 (2.4); 7.381 (5.2); 7.360

(2.3); 7.339 (1.3); 7.322 (0.6); 7.306 (0.5); 7.288 (0.4); 6.067 (1.6); 6.036 (1.7); 6.007 (0.8); 5.987 (0.9); 5.979 (0.9); 5.960 (0.8); 5.758 (0.4); 5.274 (0.5); 5.242 (1.6); 5.236 (1.5); 5.222 (1.5); 5.215 (1.5); 5.184 (0.5); 4.370 (0.4); 4.343 (0.4); 4.038 (0.6); 4.020 (0.8); 4.002 (0.5); 3.990 (1.3); 3.962 (1.3); 3.947 (1.3); 3.919 (0.9); 3.568 (1.3); 3.552 (16.0); 3.389 (0.4); 3.379 (0.5); 3.370 (0.5); 3.357 (1.1); 3.330 (29.2); 3.313 (0.8); 3.293 (0.8); 3.259 (0.5); 3.220 (0.4); 2.896 (0.5); 2.866 (0.5); 2.525 (0.6); 2.511 (13.0); 2.507 (26.1); 2.502 (34.0); 2.498 (24.4); 2.494 (11.8); 2.098 (0.9); 2.068 (1.0); 1.989 (2.4); 1.528 (0.4); 1.498 (0.4); 1.193 (0.6); 1.175 (1.3); 1.157 (0.6); 0.008 (1.4); 0.000 (36.9); −0.009 (1.4)

Example I-69: $^1$H-NMR (400.0 MHz, d$_6$-DMSO)

δ=7.952 (11.5); 7.408 (3.0); 7.383 (16.0); 7.367 (9.9); 7.362 (8.1); 7.343 (4.9); 7.325 (2.2); 7.309 (1.5); 7.291 (1.2); 7.276 (0.5); 7.158 (6.2); 7.151 (6.7); 7.137 (5.3); 7.131 (5.7); 6.226 (2.7); 6.202 (3.6); 6.196 (3.4); 6.171 (2.9); 6.073 (4.7); 6.040 (5.0); 5.757 (1.2); 5.276 (1.5); 5.244 (5.2); 5.239 (5.4); 5.226 (4.6); 5.218 (4.6); 5.194 (0.9); 5.186 (1.5); 4.832 (0.7); 4.827 (0.7); 4.792 (6.0); 4.785 (8.5); 4.778 (6.3); 4.743 (0.7); 4.738 (0.8); 4.375 (1.4); 4.347 (1.5); 4.037 (0.9); 4.020 (1.5); 4.002 (1.5); 3.993 (1.4); 3.969 (1.0); 3.755 (1.0); 3.748 (1.0); 3.724 (1.2); 3.713 (2.2); 3.706 (1.6); 3.682 (1.5); 3.675 (1.4); 3.568 (1.8); 3.564 (1.8); 3.544 (1.7); 3.539 (1.8); 3.527 (1.2); 3.522 (1.2); 3.502 (1.2); 3.497 (1.2); 3.446 (3.5); 3.440 (7.3); 3.435 (3.7); 3.414 (0.7); 3.395 (1.1); 3.385 (1.5); 3.377 (1.4); 3.368 (1.5); 3.358 (1.3); 3.330 (91.1); 3.307 (1.0); 3.269 (1.5); 3.231 (1.4); 3.200 (0.7); 2.936 (0.7); 2.909 (1.7); 2.879 (1.7); 2.852 (0.6); 2.675 (0.4); 2.671 (0.6); 2.667 (0.4); 2.506 (75.4); 2.502 (99.6); 2.498 (75.3); 2.333 (0.5); 2.329 (0.7); 2.324 (0.6); 2.116 (2.9); 2.083 (3.4); 1.989 (2.8); 1.788 (0.4); 1.760 (0.8); 1.735 (0.7); 1.673 (0.3); 1.645 (0.7); 1.615 (0.7); 1.576 (0.7); 1.545 (1.4); 1.515 (1.3); 1.492 (0.5); 1.192 (0.8); 1.175 (1.5); 1.157 (0.8); 0.146 (0.4); 0.008 (3.4); 0.000 (94.9); −0.150 (0.5)

Example I-70: $^1$H-NMR (400.0 MHz, d$_6$-DMSO)

δ=8.261 (0.6); 8.005 (13.5); 7.391 (8.3); 7.380 (16.0); 7.358 (7.4); 7.350 (4.5); 7.345 (4.4); 7.340 (5.7); 7.333 (4.4); 7.320 (10.6); 7.301 (9.1); 7.287 (1.3); 7.274 (1.3); 7.149 (5.8); 7.128 (4.9); 7.015 (3.4); 6.997 (5.7); 6.978 (2.6); 6.088 (0.3); 6.066 (5.2); 6.033 (5.5); 5.883 (2.7); 5.865 (3.1); 5.856 (3.1); 5.838 (2.8); 5.273 (1.7); 5.266 (1.0); 5.241 (5.3); 5.235 (5.3); 5.221 (5.3); 5.215 (5.3); 5.189 (1.1); 5.183 (1.7); 5.075 (0.3); 4.876 (13.5); 4.870 (13.7); 4.366 (1.4); 4.341 (1.5); 4.055 (0.9); 4.038 (2.5); 4.020 (3.1); 4.002 (1.7); 3.980 (1.5); 3.954 (1.1); 3.889 (2.4); 3.861 (2.7); 3.846 (2.9); 3.818 (2.6); 3.585 (3.9); 3.579 (7.9); 3.573 (3.8); 3.568 (2.4); 3.396 (0.7); 3.386 (0.8); 3.376 (1.3); 3.367 (1.8); 3.358 (1.7); 3.332 (81.2); 3.285 (0.9); 3.260 (3.7); 3.243 (3.5); 3.217 (3.7); 3.200 (2.6); 3.185 (0.7); 2.918 (0.8); 2.890 (2.2); 2.860 (1.8); 2.835 (0.7); 2.731 (0.4); 2.676 (0.4); 2.671 (0.6); 2.667 (0.4); 2.524 (1.7); 2.511 (34.7); 2.507 (69.0); 2.502 (90.6); 2.498 (66.2); 2.494 (32.7); 2.333 (0.5); 2.329 (0.6); 2.324 (0.5); 2.091 (2.9); 2.061 (3.3); 1.989 (10.5); 1.762 (0.4); 1.732 (0.8); 1.709 (0.7); 1.679 (0.4); 1.655 (0.3); 1.648 (0.4); 1.618 (0.8); 1.593 (0.8); 1.563 (0.6); 1.554 (0.8); 1.523 (1.5); 1.493 (1.4); 1.461 (0.5); 1.397 (1.5); 1.193 (2.7); 1.175 (5.4); 1.157 (2.7); 0.146 (0.5); 0.008 (4.2); 0.000 (104.6); −0.008 (4.4); −0.150 (0.5)

Example I-71: $^1$H-NMR (400.0 MHz, d$_6$-DMSO)

δ=7.954 (3.5); 7.408 (1.1); 7.388 (2.3); 7.367 (1.6); 7.158 (2.1); 7.151 (2.5); 7.137 (1.7); 7.131 (2.1); 6.228 (0.9); 6.203 (1.2); 6.197 (1.1); 6.173 (0.9); 5.845 (1.5); 5.820 (1.5); 5.757 (0.5); 4.792 (1.9); 4.785 (2.8); 4.778 (1.9); 4.390 (0.5); 4.357 (0.6); 4.038 (0.5); 4.020 (0.5); 4.001 (0.5); 3.996 (0.5); 3.755 (0.6); 3.724 (0.7); 3.713 (1.0); 3.682 (0.8); 3.568 (4.0); 3.547 (1.1); 3.530 (0.7); 3.505 (0.7); 3.437 (2.1); 3.399 (0.7); 3.355 (8.1); 3.277 (0.5); 3.247 (0.5); 2.907 (0.5); 2.877 (0.5); 2.565 (3.0); 2.507 (22.4); 2.502 (29.0); 2.498 (21.0); 2.126 (0.9); 2.097 (0.8); 1.989 (1.4); 1.577 (0.3); 1.558 (0.4); 1.547 (0.4); 1.527 (0.3); 1.429 (16.0); 1.420 (15.5); 1.193 (0.4); 1.175 (0.7); 1.157 (0.4); 0.000 (3.1)

Example I-72: $^1$H-NMR (400.0 MHz, d$_6$-DMSO)

δ=8.047 (5.0); 7.585 (0.7); 7.580 (0.9); 7.565 (2.6); 7.560 (2.8); 7.556 (2.4); 7.537 (2.9); 7.517 (1.4); 7.488 (2.3); 7.483 (2.2); 7.469 (1.3); 7.464 (1.1); 6.188 (1.1); 6.160 (1.7); 6.130 (1.1); 5.848 (1.6); 5.818 (1.6); 5.757 (0.7); 4.390 (0.6); 4.358 (0.6); 4.056 (0.5); 4.038 (1.7); 4.020 (1.7); 4.002 (0.9); 3.853 (0.7); 3.823 (0.9); 3.810 (1.1); 3.779 (0.9); 3.582 (0.8); 3.568 (2.1); 3.555 (0.8); 3.530 (16.0); 3.514 (0.7); 3.448 (0.3); 3.438 (0.4); 3.431 (0.4); 3.411 (0.6); 3.404 (0.7); 3.375 (0.5); 3.347 (12.7); 3.274 (0.6); 3.244 (0.6); 2.901 (0.6); 2.870 (0.6); 2.566 (2.7); 2.507 (23.8); 2.503 (30.9); 2.498 (22.6); 2.149 (0.4); 2.122 (1.1); 2.092 (0.9); 1.989 (6.4); 1.721 (0.3); 1.551 (0.4); 1.539 (0.4); 1.520 (0.4); 1.509 (0.4); 1.485 (1.5); 1.429 (16.0); 1.417 (15.9); 1.193 (1.7); 1.175 (3.4); 1.157 (1.7); 0.000 (3.5)

Example I-73: $^1$H-NMR (400.0 MHz, d$_6$-DMSO)

δ=8.007 (4.1); 7.345 (0.6); 7.341 (0.8); 7.321 (2.1); 7.302 (1.8); 7.298 (1.8); 7.149 (2.0); 7.129 (1.7); 7.016 (1.1); 6.998 (1.9); 6.979 (0.9); 5.883 (1.0); 5.865 (1.1); 5.855 (1.3); 5.846 (1.8); 5.837 (1.2); 5.813 (1.7); 4.878 (4.9); 4.872 (4.8); 4.381 (0.6); 4.350 (0.7); 4.038 (0.4); 4.020 (0.6); 3.986 (0.6); 3.951 (0.6); 3.890 (0.7); 3.862 (0.7); 3.847 (0.8); 3.819 (0.7); 3.583 (1.9); 3.409 (0.4); 3.387 (0.7); 3.379 (0.7); 3.358 (0.4); 3.331 (21.5); 3.261 (1.1); 3.254 (0.9); 3.243 (0.8); 3.234 (1.0); 3.219 (0.6); 3.210 (0.6); 3.201 (0.7); 3.193 (0.6); 2.886 (0.6); 2.856 (0.6); 2.507 (21.5); 2.503 (27.2); 2.499 (19.8); 2.096 (1.1); 2.067 (1.0); 1.990 (1.3); 1.736 (0.3); 1.705 (0.3); 1.533 (0.5); 1.523 (0.4); 1.502 (0.4); 1.427 (16.0); 1.413 (12.4); 1.397 (2.8); 1.193 (0.4); 1.175 (0.7); 1.157 (0.3); 0.000 (14.1)

Example I-74: $^1$H-NMR (400.0 MHz, d$_6$-DMSO)

δ=8.050 (4.6); 7.511 (1.0); 7.492 (1.6); 7.468 (0.9); 7.464 (1.1); 7.453 (3.3); 7.449 (3.8); 7.435 (0.6); 7.424 (1.2); 7.417 (0.8); 7.405 (1.0); 7.398 (0.6); 7.390 (0.5); 7.383 (0.4); 6.007 (0.9); 5.988 (1.0); 5.979 (1.0); 5.960 (0.9); 5.845 (1.5); 5.815 (1.5); 4.385 (0.5); 4.354 (0.6); 4.038 (0.4); 4.020 (0.6); 4.002 (0.4); 3.990 (1.3); 3.962 (1.0); 3.947 (1.1); 3.919 (0.8); 3.553 (16.0); 3.398 (0.6); 3.392 (0.6); 3.357 (0.7); 3.351 (0.7); 3.331 (24.7); 3.314 (0.6); 3.307 (0.6); 3.294 (0.7); 3.267 (0.5); 3.235 (0.5); 2.891 (0.6); 2.861 (0.6); 2.507 (22.1); 2.503 (27.8); 2.499 (19.7); 2.103 (1.0); 2.074 (0.8); 1.990 (1.4); 1.538 (0.4); 1.529

(0.4); 1.507 (0.4); 1.427 (14.5); 1.412 (12.8); 1.397 (0.8); 1.193 (0.4); 1.175 (0.7); 1.157 (0.4); 0.008 (0.7); 0.000 (15.8); −0.008 (0.6)

Example I-75: $^1$H-NMR (400.0 MHz, d$_6$-DMSO)

δ=8.043 (5.6); 7.511 (1.2); 7.494 (1.7); 7.467 (0.9); 7.463 (1.1); 7.452 (3.2); 7.448 (4.2); 7.434 (0.7); 7.422 (1.2); 7.416 (0.9); 7.404 (1.0); 7.397 (0.8); 7.387 (1.2); 7.381 (1.1); 7.371 (6.5); 7.354 (3.5); 7.335 (1.2); 7.322 (0.8); 7.317 (1.1); 7.310 (0.8); 7.301 (1.0); 7.291 (0.3); 6.007 (0.9); 5.988 (1.1); 5.980 (1.1); 5.960 (1.0); 5.136 (8.9); 4.431 (0.6); 4.398 (0.7); 4.038 (0.7); 4.020 (0.8); 3.992 (0.9); 3.964 (1.0); 3.949 (1.2); 3.921 (1.0); 3.857 (0.6); 3.822 (0.7); 3.703 (0.7); 3.663 (3.3); 3.642 (3.2); 3.602 (0.7); 3.552 (16.0); 3.356 (1.3); 3.330 (30.5); 3.313 (1.6); 3.304 (0.5); 3.293 (1.4); 3.208 (0.4); 3.202 (0.5); 3.173 (0.9); 3.144 (0.5); 2.796 (0.5); 2.764 (0.8); 2.738 (0.5); 2.732 (0.4); 2.507 (19.3); 2.502 (25.1); 2.498 (18.2); 2.068 (0.6); 2.036 (1.1); 1.997 (0.7); 1.989 (3.5); 1.673 (0.5); 1.664 (0.6); 1.642 (0.5); 1.633 (0.5); 1.521 (0.5); 1.511 (0.6); 1.490 (0.5); 1.480 (0.5); 1.193 (0.8); 1.175 (1.6); 1.157 (0.8); 0.000 (0.5)

Example I-76: $^1$H-NMR (400.0 MHz, d$_6$-DMSO)

δ=8.039 (6.0); 7.583 (0.6); 7.579 (0.9); 7.563 (2.4); 7.558 (2.7); 7.555 (2.4); 7.535 (2.7); 7.516 (1.3); 7.488 (2.1); 7.484 (2.0); 7.469 (1.1); 7.465 (1.0); 7.393 (0.5); 7.388 (1.0); 7.371 (6.6); 7.354 (3.8); 7.335 (1.3); 7.323 (0.9); 7.318 (1.2); 7.311 (0.8); 7.301 (1.0); 7.292 (0.3); 7.286 (0.3); 6.189 (1.0); 6.161 (1.5); 6.131 (1.0); 5.138 (8.9); 4.436 (0.7); 4.404 (0.7); 4.038 (0.7); 4.020 (0.7); 3.854 (1.2); 3.823 (1.5); 3.811 (1.3); 3.780 (1.0); 3.707 (0.8); 3.667 (3.2); 3.643 (3.1); 3.603 (0.8); 3.583 (1.1); 3.556 (1.1); 3.539 (1.2); 3.527 (16.0); 3.513 (1.0); 3.363 (0.5); 3.353 (0.4); 3.328 (26.2); 3.306 (0.6); 3.210 (0.5); 3.180 (0.9); 3.151 (0.5); 2.803 (0.5); 2.772 (0.9); 2.746 (0.5); 2.740 (0.4); 2.507 (19.4); 2.502 (25.1); 2.498 (18.5); 2.086 (0.6); 2.052 (1.1); 2.017 (0.7); 1.989 (2.8); 1.676 (0.5); 1.646 (0.5); 1.526 (0.5); 1.497 (0.5); 1.193 (0.7); 1.175 (1.4); 1.157 (0.7); 0.000 (0.6)

Example I-77: $^1$H-NMR (400.0 MHz, d$_6$-DMSO)

δ=8.000 (11.3); 7.390 (1.0); 7.385 (1.7); 7.369 (10.9); 7.352 (6.1); 7.345 (2.2); 7.340 (2.0); 7.333 (2.4); 7.320 (6.9); 7.301 (6.3); 7.282 (0.5); 7.148 (3.3); 7.128 (2.8); 7.015 (1.8); 6.997 (3.2); 6.979 (1.5); 5.883 (1.6); 5.865 (1.9); 5.855 (1.8); 5.837 (1.7); 5.134 (16.0); 4.876 (8.8); 4.870 (8.8); 4.427 (1.1); 4.393 (1.1); 4.056 (0.9); 4.038 (2.6); 4.020 (2.6); 4.002 (0.9); 3.890 (1.8); 3.862 (2.5); 3.847 (3.0); 3.819 (2.9); 3.699 (1.3); 3.660 (6.0); 3.639 (5.9); 3.600 (1.3); 3.585 (2.5); 3.579 (5.0); 3.574 (2.3); 3.349 (0.5); 3.339 (1.2); 3.325 (49.6); 3.311 (1.8); 3.302 (1.0); 3.292 (0.6); 3.282 (0.8); 3.273 (0.5); 3.260 (2.0); 3.242 (2.0); 3.217 (1.8); 3.199 (2.4); 3.167 (1.5); 3.138 (0.8); 2.791 (0.8); 2.764 (1.3); 2.759 (1.4); 2.734 (0.9); 2.727 (0.7); 2.676 (0.3); 2.671 (0.5); 2.667 (0.3); 2.524 (1.4); 2.511 (28.6); 2.506 (57.0); 2.502 (74.4); 2.497 (53.2); 2.493 (25.4); 2.333 (0.4); 2.329 (0.5); 2.324 (0.3); 2.064 (1.0); 2.029 (1.9); 1.989 (12.2); 1.697 (0.4); 1.686 (0.4); 1.665 (0.9); 1.657 (1.0); 1.635 (0.9); 1.626 (0.9); 1.605 (0.4); 1.545 (0.4); 1.534 (0.4); 1.514 (0.9); 1.504 (1.0); 1.483 (0.9); 1.473 (0.9); 1.454 (0.4); 1.397 (0.9); 1.193 (3.1); 1.175 (6.1); 1.157 (3.0); 0.146 (0.3); 0.008 (3.2); 0.000 (80.6); −0.009 (3.1); −0.017 (0.4); −0.150 (0.4)

Example I-78: $^1$H-NMR (400.0 MHz, d$_6$-DMSO)

δ=7.948 (11.4); 7.940 (0.5); 7.408 (2.4); 7.395 (1.0); 7.387 (5.5); 7.374 (11.8); 7.370 (8.1); 7.357 (6.8); 7.351 (1.7); 7.342 (1.5); 7.339 (2.1); 7.337 (2.1); 7.326 (1.4); 7.321 (2.1); 7.314 (1.4); 7.308 (1.7); 7.305 (1.7); 7.295 (0.6); 7.289 (0.6); 7.159 (3.9); 7.151 (4.7); 7.137 (3.1); 7.131 (3.9); 6.228 (1.8); 6.203 (2.3); 6.197 (2.1); 6.172 (1.8); 5.757 (3.2); 5.140 (16.0); 4.833 (0.5); 4.827 (0.5); 4.793 (4.0); 4.787 (5.3); 4.778 (4.0); 4.744 (0.5); 4.738 (0.5); 4.436 (1.0); 4.403 (1.1); 3.867 (1.0); 3.832 (1.1); 3.753 (1.2); 3.722 (1.4); 3.710 (2.4); 3.680 (1.9); 3.667 (5.9); 3.646 (5.8); 3.606 (1.3); 3.569 (2.1); 3.545 (2.1); 3.527 (1.4); 3.503 (1.5); 3.446 (2.3); 3.440 (5.0); 3.434 (2.2); 3.369 (0.4); 3.360 (0.8); 3.350 (0.6); 3.340 (1.1); 3.327 (28.5); 3.312 (0.7); 3.302 (0.8); 3.293 (0.4); 3.221 (0.7); 3.214 (0.9); 3.185 (1.4); 3.156 (0.8); 3.151 (0.7); 2.810 (0.8); 2.784 (1.3); 2.779 (1.4); 2.753 (0.8); 2.748 (0.7); 2.524 (0.7); 2.511 (17.2); 2.507 (34.9); 2.502 (45.5); 2.497 (32.3); 2.493 (15.3); 2.093 (0.9); 2.089 (0.9); 2.057 (1.8); 2.021 (1.1); 1.989 (1.1); 1.710 (0.3); 1.681 (0.8); 1.655 (0.8); 1.571 (0.3); 1.561 (0.4); 1.540 (0.8); 1.531 (0.9); 1.510 (0.9); 1.500 (0.8); 1.480 (0.3); 1.175 (0.6); 0.008 (1.6); 0.000 (46.9); −0.009 (1.6)

Example I-79: $^1$H-NMR (400.0 MHz, d$_6$-DMSO)

δ=8.042 (1.9); 7.564 (0.9); 7.560 (1.0); 7.556 (0.8); 7.536 (1.0); 7.516 (0.5); 7.487 (0.8); 7.483 (0.7); 7.468 (0.5); 7.464 (0.4); 6.187 (0.4); 6.160 (0.6); 6.129 (0.4); 3.854 (0.4); 3.823 (0.5); 3.811 (0.7); 3.780 (0.4); 3.583 (0.4); 3.556 (0.5); 3.539 (0.5); 3.529 (5.3); 3.512 (0.4); 3.455 (1.5); 3.449 (1.4); 3.357 (0.4); 3.328 (5.2); 3.191 (0.3); 2.507 (8.6); 2.503 (10.7); 2.498 (7.7); 2.088 (0.4); 2.062 (0.5); 1.989 (1.1); 1.413 (16.0); 1.175 (0.6); 0.000 (7.4); −0.008 (0.4)

Example I-80: $^1$H-NMR (400.0 MHz, d$_6$-DMSO)

δ=7.949 (2.2); 7.408 (0.5); 7.387 (0.9); 7.367 (0.7); 7.159 (0.8); 7.151 (1.0); 7.137 (0.7); 7.131 (0.8); 6.228 (0.4); 6.203 (0.5); 6.197 (0.4); 6.172 (0.4); 4.793 (0.8); 4.786 (1.2); 4.778 (0.8); 3.724 (0.3); 3.713 (0.5); 3.682 (0.4); 3.573 (0.4); 3.548 (0.4); 3.455 (1.7); 3.451 (1.7); 3.443 (0.6); 3.437 (1.1); 3.431 (0.5); 3.351 (0.3); 3.328 (4.4); 2.511 (3.0); 2.507 (5.9); 2.502 (7.6); 2.498 (5.5); 2.494 (2.7); 2.094 (0.4); 2.067 (0.5); 1.989 (0.9); 1.414 (16.0); 1.406 (1.3); 1.175 (0.5); 0.000 (5.9)

Example I-81: $^1$H-NMR (400.0 MHz, d$_6$-DMSO)

δ=8.045 (2.1); 7.512 (0.5); 7.494 (0.7); 7.468 (0.4); 7.464 (0.4); 7.453 (1.4); 7.449 (1.7); 7.424 (0.5); 7.418 (0.4); 7.405 (0.4); 6.007 (0.4); 5.988 (0.4); 5.980 (0.4); 5.960 (0.4); 3.992 (0.4); 3.964 (0.4); 3.948 (0.5); 3.920 (0.4); 3.554 (6.2); 3.454 (1.5); 3.445 (1.5); 3.355 (0.6); 3.344 (0.5); 3.331 (5.3); 3.312 (0.5); 3.292 (0.4); 3.183 (0.4); 2.755 (0.4); 2.507 (6.6); 2.503 (8.2); 2.070 (0.5); 2.043 (0.6); 1.990 (1.2); 1.410 (16.0); 1.398 (1.0); 1.175 (0.6); 0.000 (2.0)

Example I-82: $^1$H-NMR (400.0 MHz, d$_6$-DMSO)

δ=8.001 (2.3); 7.319 (0.8); 7.299 (0.8); 7.149 (0.7); 7.128 (0.6); 7.016 (0.4); 6.998 (0.7); 5.881 (0.3); 5.864 (0.4);

5.854 (0.4); 5.836 (0.3); 4.878 (1.8); 4.872 (1.8); 4.038 (0.5); 4.020 (0.5); 3.889 (0.4); 3.861 (0.4); 3.846 (0.5); 3.819 (0.5); 3.588 (0.5); 3.582 (1.1); 3.576 (0.5); 3.451 (1.4); 3.440 (1.4); 3.329 (10.1); 3.257 (0.4); 3.240 (0.4); 3.214 (0.5); 3.197 (0.4); 2.511 (5.6); 2.507 (10.9); 2.502 (14.1); 2.498 (10.0); 2.494 (4.8); 2.063 (0.4); 2.035 (0.5); 1.989 (2.3); 1.409 (16.0); 1.193 (0.6); 1.175 (1.2); 1.157 (0.6); 0.000 (3.9)

Example II-01: $^1$H-NMR (400.0 MHz, $d_6$-DMSO)

δ=7.375 (1.3); 7.372 (1.3); 7.363 (5.7); 7.348 (0.7); 7.336 (0.4); 7.290 (0.6); 7.244 (0.6); 7.157 (1.6); 7.069 (0.7); 7.057 (0.8); 7.045 (0.7); 7.024 (2.2); 6.920 (0.4); 6.905 (1.4); 6.888 (0.8); 6.858 (1.0); 5.363 (3.5); 5.299 (0.3); 5.267 (0.9); 5.253 (0.9); 5.233 (0.9); 5.225 (0.9); 5.202 (0.3); 4.056 (1.2); 4.038 (3.7); 4.020 (3.7); 4.002 (1.2); 3.735 (0.4); 3.675 (0.4); 3.325 (15.5); 3.207 (0.3); 3.156 (0.4); 3.145 (0.5); 3.134 (0.4); 2.670 (0.8); 2.666 (0.7); 2.633 (0.4); 2.524 (0.4); 2.511 (8.6); 2.506 (17.6); 2.502 (23.2); 2.497 (16.6); 2.493 (8.0); 1.989 (16.0); 1.980 (0.4); 1.846 (0.4); 1.836 (0.3); 1.813 (0.4); 1.803 (0.4); 1.669 (0.3); 1.657 (0.5); 1.648 (0.4); 1.636 (0.4); 1.625 (0.4); 1.602 (0.4); 1.594 (0.4); 1.193 (4.2); 1.175 (8.4); 1.157 (4.1); 1.110 (0.4); 0.008 (0.8); 0.000 (22.3); −0.009 (0.8)

Example II-02: $^1$H-NMR (400.0 MHz, $d_6$-DMSO)

δ=9.438 (0.5); 9.387 (0.5); 9.162 (0.5); 9.074 (0.5); 7.381 (0.5); 7.352 (0.4); 7.248 (0.6); 7.219 (0.7); 7.195 (0.5); 7.184 (0.5); 7.115 (0.4); 7.087 (0.4); 7.059 (1.1); 7.048 (1.0); 7.037 (1.2); 7.023 (1.1); 6.924 (0.5); 6.912 (0.5); 6.625 (1.6); 6.583 (1.7); 4.450 (0.6); 4.417 (0.6); 4.038 (0.7); 4.020 (0.7); 3.736 (0.3); 3.713 (0.4); 3.326 (16.2); 3.049 (0.4); 2.716 (0.4); 2.707 (0.5); 2.700 (0.5); 2.677 (1.1); 2.658 (0.5); 2.650 (0.6); 2.642 (0.6); 2.609 (0.4); 2.602 (0.4); 2.507 (10.8); 2.502 (13.9); 2.498 (10.1); 1.989 (2.9); 1.723 (0.4); 1.664 (0.5); 1.633 (0.5); 1.603 (0.5); 1.572 (0.4); 1.499 (0.3); 1.462 (0.4); 1.431 (15.6); 1.414 (16.0); 1.193 (0.8); 1.175 (1.5); 1.157 (0.8); 0.008 (0.7); 0.000 (18.5); −0.008 (0.8)

Example IV-01: $^1$H-NMR (400.0 MHz, $d_6$-DMSO)

δ=8.315 (0.4); 7.385 (1.5); 7.370 (1.3); 7.252 (2.4); 7.239 (3.5); 7.220 (0.5); 7.208 (1.5); 7.120 (1.7); 7.104 (4.9); 7.073 (5.9); 7.049 (3.5); 7.024 (0.3); 6.969 (1.9); 6.938 (1.6); 6.849 (0.8); 6.791 (5.4); 6.771 (6.3); 5.755 (3.5); 5.362 (0.5); 4.259 (0.6); 4.249 (0.9); 4.240 (1.5); 4.231 (3.0); 4.227 (2.1); 4.222 (3.2); 4.216 (3.9); 4.213 (3.9); 4.209 (4.0); 4.205 (3.2); 4.199 (3.8); 4.192 (3.4); 4.181 (1.5); 4.174 (1.1); 4.165 (0.5); 4.099 (0.5); 4.081 (0.5); 3.954 (0.6); 3.944 (1.0); 3.932 (0.7); 3.921 (0.7); 3.909 (1.1); 3.899 (0.6); 3.792 (0.5); 3.783 (0.7); 3.777 (0.7); 3.767 (0.7); 3.759 (0.7); 3.750 (0.8); 3.743 (0.8); 3.733 (0.6); 3.535 (1.1); 3.523 (0.5); 3.515 (0.6); 3.508 (0.6); 3.498 (0.6); 3.488 (0.7); 3.475 (0.9); 3.464 (0.6); 3.420 (0.8); 3.409 (0.6); 3.394 (0.8); 3.384 (1.2); 3.355 (0.7); 3.347 (0.9); 3.324 (41.7); 3.300 (0.8); 3.292 (0.6); 3.267 (0.8); 3.260 (1.0); 3.242 (1.0); 3.234 (1.2); 3.224 (0.7); 3.207 (0.8); 3.199 (0.8); 3.193 (0.8); 3.185 (0.9); 3.168 (1.0); 3.159 (1.4); 3.151 (0.9); 3.134 (1.0); 3.126 (1.3); 3.117 (1.1); 3.089 (2.2); 3.078 (2.2); 3.068 (2.5); 3.058 (1.6); 3.044 (0.8); 3.034 (0.4); 2.671 (0.4); 2.524 (1.1); 2.511 (24.7); 2.506 (50.5); 2.502 (66.3); 2.497 (47.1); 2.493 (22.3); 2.328 (0.4); 1.989 (1.0); 1.935 (0.8); 1.925 (0.8); 1.913 (0.7); 1.901 (1.0); 1.889 (1.0); 1.879 (0.9); 1.869 (0.7); 1.861 (0.7); 1.852 (0.7); 1.844 (0.8); 1.835 (0.9); 1.826 (0.9); 1.813 (0.9); 1.803 (0.9); 1.790 (0.7); 1.779 (0.9); 1.769 (0.8); 1.735 (0.4); 1.714 (1.0); 1.702 (0.9); 1.688 (1.5); 1.675 (1.0); 1.662 (1.0); 1.641 (0.4); 1.586 (1.1); 1.571 (1.5); 1.561 (1.7); 1.546 (1.0); 1.537 (1.4); 1.528 (0.9); 1.513 (0.4); 1.218 (6.1); 1.207 (8.1); 1.200 (13.0); 1.190 (16.0); 1.182 (6.5); 1.172 (7.4); 1.157 (0.4); 1.083 (0.4); 1.074 (0.4); 1.059 (0.8); 1.050 (1.0); 1.040 (0.6); 1.026 (1.0); 1.017 (0.7); 1.002 (0.4); 0.008 (1.2); 0.000 (35.4); −0.009 (1.2)

Example IV-02: $^1$H-NMR (400.0 MHz, $d_6$-DMSO)

δ=7.385 (7.1); 7.373 (16.0); 7.362 (1.4); 7.352 (1.9); 7.344 (1.6); 7.331 (1.3); 7.324 (0.6); 7.318 (0.6); 7.310 (0.3); 5.133 (12.6); 4.055 (0.4); 4.038 (1.1); 4.020 (1.1); 4.002 (0.4); 3.801 (0.5); 3.786 (0.7); 3.776 (0.6); 3.767 (0.6); 3.757 (0.7); 3.753 (0.7); 3.743 (0.5); 3.626 (7.6); 3.623 (7.2); 3.571 (0.5); 3.561 (0.6); 3.557 (0.6); 3.547 (0.5); 3.536 (0.6); 3.526 (0.7); 3.512 (0.6); 3.327 (14.5); 3.299 (0.7); 3.291 (0.8); 3.277 (0.8); 3.268 (0.9); 3.256 (0.6); 3.242 (0.6); 3.234 (0.6); 3.220 (0.6); 3.212 (0.7); 3.198 (0.7); 3.188 (1.0); 3.178 (0.6); 3.164 (0.6); 3.156 (0.6); 3.110 (0.3); 3.100 (0.7); 3.089 (1.0); 3.078 (1.4); 3.068 (1.0); 3.056 (0.7); 3.046 (0.4); 2.510 (6.8); 2.506 (13.2); 2.501 (17.0); 2.497 (12.2); 1.988 (4.6); 1.852 (1.0); 1.842 (1.1); 1.827 (1.3); 1.818 (1.3); 1.795 (0.3); 1.686 (0.4); 1.677 (0.4); 1.664 (0.7); 1.654 (0.9); 1.642 (0.6); 1.631 (0.8); 1.621 (0.5); 1.609 (0.5); 1.601 (0.6); 1.588 (0.7); 1.578 (0.9); 1.567 (0.6); 1.555 (0.8); 1.545 (0.6); 1.192 (1.2); 1.175 (2.4); 1.157 (1.2); 0.000 (5.6)

Example IV-03: $^1$H-NMR (400.0 MHz, $d_6$-DMSO)

δ=7.411 (0.5); 7.383 (16.0); 7.378 (15.6); 7.368 (3.2); 7.346 (1.5); 7.334 (0.7); 6.028 (4.2); 6.009 (4.2); 5.274 (1.2); 5.267 (1.2); 5.243 (3.7); 5.236 (3.7); 5.217 (3.5); 5.208 (3.5); 5.186 (1.1); 5.177 (1.1); 4.055 (0.9); 4.038 (2.9); 4.020 (2.9); 4.002 (1.0); 3.834 (0.4); 3.824 (0.6); 3.811 (0.5); 3.799 (0.9); 3.789 (1.2); 3.766 (0.6); 3.751 (0.7); 3.741 (0.5); 3.683 (0.9); 3.672 (1.0); 3.661 (0.9); 3.648 (1.1); 3.638 (1.1); 3.391 (0.6); 3.383 (0.8); 3.370 (1.0); 3.358 (1.3); 3.349 (1.2); 3.324 (22.2); 3.272 (0.5); 3.264 (0.6); 3.240 (1.2); 3.211 (1.2); 3.186 (0.5); 3.178 (0.5); 3.139 (0.7); 3.129 (1.1); 3.118 (1.6); 3.108 (1.7); 3.097 (1.2); 3.086 (0.8); 2.524 (0.5); 2.510 (13.0); 2.506 (26.3); 2.501 (34.5); 2.497 (24.9); 2.493 (12.2); 1.988 (12.5); 1.883 (2.1); 1.850 (1.2); 1.825 (0.4); 1.735 (0.3); 1.721 (0.6); 1.712 (0.7); 1.699 (0.5); 1.688 (0.7); 1.679 (0.5); 1.666 (0.5); 1.658 (0.5); 1.645 (0.6); 1.635 (0.9); 1.620 (1.0); 1.606 (1.5); 1.596 (1.6); 1.584 (1.2); 1.573 (1.3); 1.563 (0.9); 1.550 (0.5); 1.541 (0.4); 1.398 (0.6); 1.193 (3.3); 1.175 (6.6); 1.157 (3.3); 0.008 (1.0); 0.000 (27.4); −0.008 (1.0)

Example IV-04: $^1$H-NMR (400.0 MHz, $d_6$-DMSO)

δ=7.952 (2.2); 7.396 (0.7); 7.386 (0.6); 7.377 (1.5); 7.368 (5.2); 7.360 (5.2); 7.356 (4.9); 7.345 (1.1); 7.335 (0.7); 7.321 (0.4); 7.309 (0.5); 7.263 (0.7); 7.242 (1.1); 7.209 (0.5); 7.131 (0.5); 7.106 (1.2); 7.089 (1.3); 7.074 (1.1); 7.058 (1.1); 6.971 (0.6); 6.939 (0.5); 6.897 (1.6); 6.877 (1.8); 5.293 (0.6); 5.284 (0.6); 5.262 (1.5); 5.253 (1.6); 5.229 (1.4); 5.218 (1.6); 5.198 (0.5); 5.187 (0.6); 3.366 (0.4); 3.329 (19.4); 3.212 (0.4); 3.182 (0.4); 3.156 (0.4); 3.078 (0.5); 3.068 (0.7); 3.058 (0.8); 3.045 (0.8); 3.036 (0.6); 2.890 (16.0); 2.731 (13.5); 2.524 (0.4); 2.510 (7.0); 2.506 (14.1); 2.502 (18.7); 2.497 (13.5); 2.493 (6.6); 1.871

(0.3); 1.633 (0.4); 1.622 (0.4); 1.611 (0.4); 1.599 (0.4); 1.588 (0.4); 1.578 (0.3); 1.553 (0.3); 1.529 (0.5); 1.520 (0.4)

Example IV-05: $^1$H-NMR (400.0 MHz, CD3CN)

δ=3.325 (3.4); 3.297 (0.3); 3.293 (0.4); 3.271 (0.3); 2.950 (0.4); 2.171 (3.6); 1.972 (1.3); 1.959 (0.4); 1.953 (1.6); 1.947 (2.8); 1.941 (3.8); 1.934 (2.7); 1.928 (1.5); 1.918 (0.3); 1.908 (0.3); 1.902 (0.4); 1.526 (0.4); 1.490 (1.4); 1.464 (1.2); 1.450 (1.4); 1.437 (16.0); 1.431 (4.2); 1.222 (0.4); 1.204 (0.7); 1.186 (0.4); 0.000 (5.2)

Example IV-06: $^1$H-NMR (400.0 MHz, $d_6$-DMSO)

δ=5.812 (1.6); 5.796 (1.6); 4.055 (0.4); 4.038 (1.3); 4.020 (1.3); 4.002 (0.4); 3.808 (0.4); 3.685 (0.4); 3.650 (0.5); 3.369 (6.2); 3.342 (0.5); 3.334 (0.3); 3.247 (0.3); 3.236 (0.4); 3.226 (0.3); 3.213 (0.3); 3.202 (0.4); 3.170 (0.4); 3.161 (0.5); 3.150 (0.6); 3.137 (0.6); 3.127 (0.4); 2.565 (4.0); 2.511 (6.5); 2.507 (13.2); 2.502 (17.2); 2.498 (12.1); 2.493 (5.6); 1.989 (6.0); 1.951 (0.4); 1.944 (0.4); 1.909 (0.6); 1.888 (0.4); 1.871 (0.5); 1.865 (0.5); 1.731 (0.3); 1.698 (0.4); 1.634 (0.3); 1.624 (0.4); 1.611 (0.4); 1.601 (0.5); 1.591 (0.4); 1.578 (0.4); 1.511 (1.3); 1.477 (2.4); 1.453 (1.0); 1.425 (16.0); 1.417 (15.0); 1.381 (0.4); 1.193 (1.6); 1.175 (3.2); 1.157 (1.5); 0.000 (5.4)

Example IV-07: $^1$H-NMR (400.0 MHz, $d_6$-DMSO)

δ=7.382 (0.4); 7.371 (0.3); 7.247 (0.6); 7.234 (0.7); 7.202 (0.4); 7.116 (0.4); 7.105 (0.4); 7.098 (1.0); 7.067 (1.6); 7.037 (0.9); 6.963 (0.5); 6.932 (0.4); 6.850 (0.4); 6.622 (1.3); 6.595 (1.6); 4.056 (0.4); 4.038 (1.1); 4.020 (1.1); 4.002 (0.5); 3.427 (0.4); 3.402 (0.4); 3.390 (0.5); 3.381 (0.4); 3.328 (11.1); 3.131 (0.4); 3.112 (0.5); 3.105 (0.7); 3.091 (0.5); 3.079 (0.7); 3.072 (0.6); 3.061 (0.4); 3.051 (0.4); 2.506 (14.4); 2.502 (18.6); 2.498 (13.6); 1.989 (4.6); 1.694 (0.4); 1.672 (0.4); 1.548 (0.5); 1.540 (0.4); 1.532 (0.3); 1.523 (0.4); 1.417 (13.8); 1.408 (16.0); 1.193 (1.2); 1.175 (2.4); 1.157 (1.2); 0.000 (4.5)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contain therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within patent applications" of the Research Disclosure Database Number 564025.

USE EXAMPLES

Example 1

*Phytophthora infestans* In Vitro Cell Test
Solvent: DMSO
Culture medium: 14.6 g anhydrous D-glucose (VWR), 7.1 g Mycological Peptone (Oxoid), 1.4 g granulated Yeast Extract (Merck), QSP liter Inoculum: sporocyste suspension Fungicides were solubilized in DMSO and the solution used to prepare the required range of concentrations. The final concentration of DMSO used in the assay was ≤1%.

A sporocyste suspension of *P. infestans* was prepared and diluted to the desired sporocyste density.

Fungicides were evaluated for their ability to inhibit sporocyste germination and mycelium growth in liquid culture assay. The compounds were added in the desired concentration to the culture medium with sporocystes. After 8 days incubation, fungi-toxicity of compounds was determined by spectrometric measurement of mycelium growth. Inhibition of fungal growth was determined by comparing the absorbance values in wells containing the fungicides with the absorbance in control wells without fungicides.

In this test, the following compounds showed an efficacy of 70% or even higher at a concentration of 20 μg/mL of active ingredient.

| Ex. | Eff. % |
|---|---|
| I-01 | 100 |
| I-03 | 99 |
| I-06 | 100 |
| I-08 | 99 |
| I-09 | 98 |
| I-10 | 97 |
| I-11 | 100 |
| I-16 | 100 |
| I-19 | 100 |
| I-20 | 100 |
| I-25 | 100 |
| I-26 | 100 |
| I-27 | 100 |
| I-28 | 100 |
| I-33 | 100 |
| I-34 | 100 |
| I-40 | 100 |
| I-41 | 100 |
| I-42 | 100 |
| I-44 | 100 |
| I-45 | 100 |
| I-46 | 100 |
| I-47 | 100 |
| I-49 | 100 |
| I-50 | 98 |
| I-51 | 100 |

-continued

| Ex. | Eff. % |
|---|---|
| I-52 | 87 |
| I-53 | 100 |
| I-55 | 100 |
| I-56 | 100 |
| I-58 | 100 |

In this test, the following compounds showed an efficacy of 70% or even higher at a concentration of 0.25 μg/mL of active ingredient.

| Ex. | Eff. % |
|---|---|
| I-02 | 100 |
| I-04 | 100 |
| I-05 | 100 |
| I-07 | 100 |
| I-13 | 94 |
| I-17 | 100 |
| I-23 | 100 |
| I-38 | 100 |
| I-59 | 100 |
| I-60 | 100 |
| I-61 | 100 |
| I-62 | 100 |
| I-63 | 100 |
| I-64 | 100 |
| I-65 | 100 |
| I-66 | 100 |
| I-71 | 100 |
| I-78 | 88 |
| I-80 | 100 |

Example 2

*Pythium ultimum* In Vitro Cell Test
Solvent: DMSO
Culture medium: 14.6 g anhydrous D-glucose (VWR), 7.1 g Mycological Peptone (Oxoid), 1.4 g granulated Yeast Extract (Merck), QSP liter
Inoculum: mycelial suspension Fungicides were solubilized in DMSO and the solution used to prepare the required range of concentrations. The final concentration of DMSO used in the assay was ≤1%.

Inoculum was prepared from a pre-culture of *P. ultimum* grown in liquid medium by homogenization using a blender. The concentration of ground mycelium in the inoculum was estimated and adjusted to the desired optical density (OD).

Fungicides were evaluated for their ability to inhibit mycelium growth in liquid culture assay. The compounds were added in the desired concentrations to culture medium containing the mycelial suspension. After 4 days of incubation, the fungicidal efficacy of compounds was determined by spectrometric measurement of mycelium growth. Inhibition of fungal growth was determined by comparing the absorbance values in wells containing the fungicides with the absorbance in control wells without fungicides.

In this test, the following compounds showed an efficacy of 70% or even higher at a concentration of 20 μg/mL of active ingredient.

| Ex. | Eff. % |
|---|---|
| I-01 | 95 |
| I-03 | 96 |
| I-04 | 92 |
| I-05 | 87 |

-continued

| Ex. | Eff. % |
|---|---|
| I-06 | 94 |
| I-08 | 87 |
| I-09 | 97 |
| I-11 | 97 |
| I-16 | 94 |
| I-20 | 87 |
| I-26 | 100 |
| I-27 | 100 |
| I-33 | 99 |
| I-34 | 94 |
| I-40 | 93 |
| I-41 | 99 |
| I-42 | 100 |
| I-44 | 99 |
| I-46 | 97 |
| I-47 | 93 |
| I-49 | 88 |
| I-50 | 94 |
| I-51 | 95 |
| I-52 | 86 |
| I-55 | 70 |
| I-56 | 84 |

In this test, the following compounds showed an efficacy of 70% or even higher at a concentration of 0.25 g/mL of active ingredient.

| Ex. | Eff. % |
|---|---|
| I-02 | 96 |
| I-07 | 97 |
| I-17 | 99 |
| I-38 | 99 |
| I-63 | 90 |
| I-65 | 91 |

Example 3

*Phytophthora* Test (Tomatoes)/Preventive
Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Phytophthora infestans*. The plants are then placed in an incubation cabinet at approximately 20° C. and a relative atmospheric humidity of 100%.

The test is evaluated 3 days after the inoculation. 0% means an efficacy which corresponds to that of the untreated control, while an efficacy of 100% means that no disease is observed.

In this test the following compounds according to the invention showed efficacy of 70% or even higher at a concentration of 100 ppm of active ingredient.

| Ex. | Eff. % |
|---|---|
| I-01 | 70 |
| I-02 | 96 |
| I-03 | 95 |
| I-05 | 96 |

-continued

| Ex. | Eff. % |
| --- | --- |
| I-08 | 95 |
| I-16 | 98 |

In this test the following compounds according to the invention showed efficacy of 70% or even higher at a concentration of 1 ppm of active ingredient.

| Ex. | Eff. % |
| --- | --- |
| I-41 | 94 |
| I-42 | 94 |

Example 4

*Plasmopara* Test (Grapevines)/Preventive

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Plasmopara viticola* and then remain for 1 day in an incubation cabinet at approximately 20° C. and a relative atmospheric humidity of 100%. The plant is subsequently placed for 4 days in a greenhouse at approximately 21° C. and a relative atmospheric humidity of approximately 90%. The plants are then misted and placed for 1 day in an incubation cabinet.

The test is evaluated 6 days after the inoculation. 0% means an efficacy which corresponds to that of the untreated control, while an efficacy of 100% means that no disease is observed.

In this test the following compounds according to the invention showed efficacy of 70% or even higher at a concentration of 100 ppm of active ingredient.

| Ex. | Eff. % |
| --- | --- |
| I-02 | 100 |
| I-03 | 98 |
| I-05 | 95 |
| I-08 | 98 |
| I-16 | 95 |

In this test the following compounds according to the invention showed efficacy of 70% or even higher at a concentration of 1 ppm of active ingredient.

| Ex. | Eff. % |
| --- | --- |
| I-38 | 93 |
| I-41 | 91 |
| I-42 | 99 |
| I-44 | 82 |
| I-51 | 94 |

The invention claimed is:
1. A compound of formula (I)

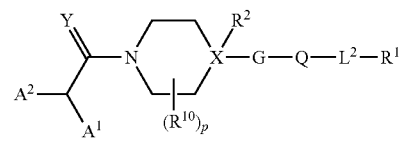

or a salt, metal complex, or N-oxide thereof, in which:
$A^1$ is —C(=O)$R^{L1}$,
$A^2$ is hydrogen, chloro, bromine, iodine, $C_1$-$C_4$-alkylsulphonyl, $C_1$-$C_4$-haloalkylsulphonyl, phenylsulphonyl, $C_1$-$C_4$-alkylsulphonyloxy, $C_1$-$C_4$-haloalkylsulphonyloxy, or phenyl-sulphonyloxy, wherein phenyl is optionally substituted by one, two or three groups independently selected from the group consisting of halogen, $C_1$-$C_4$-alkyl, $C_1$-$C_4$-haloalkyl, $C_1$-$C_4$-alkoxy, and $C_1$-$C_4$-haloalkoxy, or
$A^2$ is a heteroaromatic radical selected from the group consisting of furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,3-triazol-1-yl, 1,2,4-triazol-1-yl, pyridin-2-yl, pyridin-3-yl, pyridin-4-yl, pyridazin-3-yl, pyridazin-4-yl, pyrimidin-2-yl, pyrimidin-4-yl and pyrimidin-5-yl, which optionally contains one or two substituents, where the optional substituents on ring carbon atoms are the same or different and are each independently selected from the group consisting of fluorine, chlorine, bromine, iodine, cyano, nitro, methyl, ethyl, n-propyl, 1-methylethyl, 1,1-dimethylethyl, chlorofluoromethyl, dichloromethyl, dichlorofluoromethyl, difluoromethyl, trichloromethyl, trifluoromethyl, cyclopropyl, ethoxy, 1-methylethoxy, n-propoxy, methoxy, trifluoromethoxy, difluoromethoxy, 1-methylethylthio, methylthio, ethylthio, n-propylthio, difluoromethylthio, trifluoro-methylthio and phenyl and where the optional substituents on ring nitrogen atoms are the same or different and are each independently selected from the group consisting of methyl, ethyl, n-propyl, 1-methylethyl, methylsulphonyl, trifluoromethylsulphonyl, methylcarbonyl, trifluoromethylcarbonyl, chloromethylcarbonyl, 2,2,2-trifluoroethyl, 2,2-difluoroethyl, 2,2-dichloro-2-fluoroethyl, 2-chloro-2-difluoroethyl or 2-chloro-2-fluoroethyl, and trifluoromethyl,
Y is oxygen,
$R^{L1}$ is amino, ethoxy, n-propoxy, 1-methylethoxy, n-butoxy, 1,1-dimethylethoxy, 1,2-dimethylethoxy, n-pentyloxy, n-hexyloxy, n-octyloxy, 1-ethylhexyloxy, 2-ethyl-hexyloxy, 2,2,2-trifluoroethoxy, 2-methoxyethoxy, 2-ethoxyethoxy, allyloxy, but-2-en-1-yloxy, prop-2-yn-1-yloxy, phenoxy, 2,6-dimethylphenoxy, 2,6-diisopropylphenoxy, 2,6-di-tert-butylphenoxy, benzyloxy, 4-methoxybenzyloxy, or 3,4-dimethoxybenzyloxy,
X is carbon,
$R^2$ is hydrogen, fluorine, methoxy or hydroxyl,
$R^{10}$ is hydrogen, fluorine, methoxy or hydroxyl,
p is 0, G is

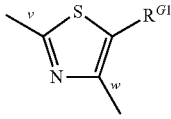   G¹ where the bond identified by v is bonded directly to X and the bond identified by w is bonded directly to Q,
$R^{G1}$ is hydrogen,
Q is

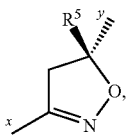   $Q^{24}$-1

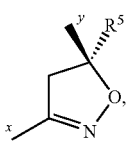   $Q^{24}$-2

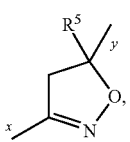   $Q^{24}$-3

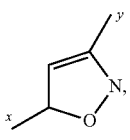   $Q^{24}$-4

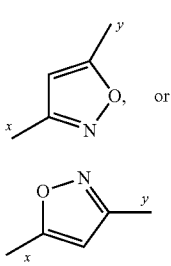   $Q^{11}$-1 or $Q^{11}$-2 where the bond identified by x is bonded directly to G and the bond identified by y is bonded directly to $L^2$,
$R^5$ is hydrogen, cyano, methyl, trifluoromethyl, difluoromethyl or methoxymethyl,
$L^2$ is a direct bond, —C(=O)—, —$CHR^{20}$— or —$NR^{21}$—,
$R^{20}$ is hydrogen, methyl, ethyl, trifluoromethyl,
$R^{21}$ is hydrogen or methyl,
$R^1$ is substituted cyclopentenyl, cyclohexenyl, cyclopentyl, cyclohexyl or cycloheptyl, each of which contains 1 or 2 substituents, where the substituents are each independently at least one substituent $Z^4$ and optionally also one substituent selected from the group consisting of methyl, ethyl, methoxy, ethoxy, trifluoro-methoxy, ethynyl, 2-propenyloxy, 2-propynyloxy, methylcarbonyloxy, ethylcarbonyloxy, trifluorocarbonyloxy, methylthio, ethylthio and trifluoromethylthio, or
$R^1$ is phenyl which contains 1, 2 or 3 substituents, where the substituents are each independently at least one substituent $Z^4$ and optionally also 1 or 2 substituents selected from the group consisting of fluorine, chlorine, bromine, iodine, cyano, nitro, hydroxyl, amino, —SH, —C(=O)H, methyl, ethyl, n-propyl, 1-methylethyl, n-butyl, 1,1-dimethylethyl, 1,2-dimethylethyl, ethenyl, ethynyl, trifluoromethyl, difluoromethyl, trichloromethyl, dichloromethyl, cyclopropyl, methoxy, ethoxy, n-propoxy, 1-methylethoxy, 1,1-dimethylethoxy, methylcarbonyl, ethylcarbonyl, trifluoromethylcarbonyl, methoxycarbonyl, ethoxycarbonyl, n-propoxycarbonyl, 1-methylethoxycarbonyl, 1,1-dimethylethoxycarbonyl, 1-ethenyloxy, 2-propenyloxy, 2-propynyloxy, methylcarbonyloxy, trifluoromethylcarbonyloxy, chloromethyl-carbonyloxy, methylthio, ethylthio, methylsulphonyl, or -$L^3Z^3$, or
$R^1$ is naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 2,3-dihydro-1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl or indan-5-yl, where each is substituted by at least one substituent $Z^4$ and optionally further substituents independently selected from $Z^4$ and the group consisting of methyl, methoxy, cyano, fluorine, chlorine, bromine and iodine, or
$R^1$ is furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl or pyrazin-2-yl, each of which contains 1 or 2 substituents, where the substituents are each independently at least one substituent $Z^4$ and a further optional substituent that is $Z^4$, oxo, or thio, or is a substituent on a ring carbon atom selected from the group consisting of fluorine, chlorine, bromine, iodine, cyano, nitro, hydroxyl, amino, methyl, ethyl, n-propyl, 1-methylethyl, n-butyl, 1,1-dimethylethyl, 1,2-dimethyl-ethyl, ethenyl, ethynyl, trifluoromethyl, difluoromethyl, trichloromethyl, dichloromethyl, cyclopropyl, methoxy, ethoxy, n-propoxy, 1-methylethoxy, 1,1-dimethylethoxy, methylcarbonyl, ethylcarbonyl, methoxycarbonyl, ethoxycarbonyl, n-propoxycarbonyl, 1-methylethoxycarbonyl, 1,1-dimethylethoxycarbonyl, methylcarbonyloxy, methylthio, ethylthio and methylsulphonyl, or is a substituent on a ring nitrogen atom selected from the group consisting of methyl, ethyl, n-propyl, —C(=O)H, methylcarbonyl, trifluoromethylcarbonyl, chloromethylcarbonyl, methylsulphonyl, trifluoromethyl-sulphonyl, phenylsulphonyl, phenyl and 2-propynyl, or R¹ is indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzo-furan-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl, each of which is substituted by at least one substituent $Z^4$ and further optional substituents independently selected from $Z^4$ and substituents on ring carbon atoms selected from the group consisting of fluorine, chlorine, bromine, iodine, methyl, and methoxy and substituents on ring nitrogen atoms selected from the group consisting of methyl, ethyl, n-propyl, —C(=O)H, methylcarbonyl, trifluoromethylcarbonyl, chloromethylcarbonyl, methylsulphonyl, trifluoromethyl-sulphonyl, phenylsulphonyl, phenyl and 2-propynyl, or R¹ is piperidin-1-yl, piperidin-2-yl, piperidin-3-yl, piperidin-4-yl, piperazin-1-yl, piperazin-2-yl, piperazin-3-yl, morpholin-1-yl, morpholin-2-yl, morpholin-3-yl, tetrahydropyran-2-yl, tetrahydropyran-3-yl, tetrahydropyran-4-yl, 1,2,3,4-tetrahydroquinolin-1-yl, 1,2,3,4-tetrahydroisoquinolin-2-yl, 1,2,3,4-tetrahydroquinoxalin-1-yl, indolin-1-yl, isoindolin-2-yl, decahydroquinolin-1-yl or decahydroisoquinolin-2-yl, each of which is substituted by at least one substituent $Z^4$ and further optional substituents independently selected from $Z^4$ and substituents on ring carbon atoms selected from the group consisting of fluorine, chlorine, bromine, iodine, methyl, and methoxy and substituents on ring nitrogen atoms selected from the group consisting of methyl, ethyl, n-propyl, —C(=O)H, methylcarbonyl, trifluoromethylcarbonyl, chloromethyl-carbonyl, methylsulphonyl, trifluoromethylsulphonyl, phenylsulphonyl, phenyl and 2-propynyl, $L^3$ is a direct bond, $Z^3$ is a phenyl radical which may contain up to two substituents, where the substituents are each independently selected from the group consisting of chlorine, bromine, iodine, fluorine, cyano, nitro, hydroxyl, amino, —SH, methyl, ethyl, n-propyl, 1-methylethyl, 1,1-dimethylethyl, ethenyl, propen-2-yl, ethynyl, propyn-2-yl, trifluoromethyl, difluoromethyl, methoxymethyl, methylcarbonyl, ethylcarbonyl, trifluoromethylcarbonyl, methoxycarbonyl, ethoxycarbonyl, n-propoxycarbonyl, 1-methylethoxycarbonyl, 1,1-dimethylethoxycarbonyl, methoxy, ethoxy, n-propoxy, 1-methylethoxy, 1,1-dimethylethoxy, trifluoromethoxy, ethenyloxy, 2-propenyloxy, ethynyloxy, 2-propynyloxy, methylthio, ethylthio, trifluoromethylthio, methylsulphonyl, ethylsulphonyl, propylthionyl, 1-methylethylthio, trifluoromethylsulphonyl, methyl-amino, ethylamino, n-propylamino, 1-methylethylamino, 1,1-dimethylethylamino and dimethylamino, or $Z^3$ is naphthalenyl, $Z^4$ is formyl, methoxymethoxy, 2-methoxyethoxy, allyloxy, 2-fluoroprop-2-en-1-yloxy, 2-chloroprop-2-en-1-yloxy, 3-chloroprop-2-en-1-yloxy, 2-bromoprop-2-en-1-yloxy, 2-methylprop-2-en-1-yloxy, 3,3-dichloroprop-2-en-1-yloxy, 3,3-dichloro-2-fluoroprop-2-en-1-yloxy, but-2-en-1-yloxy, but-3-en-2-yloxy, but-3-en-1-yloxy, 3-chlorobut-2-en-1-yloxy 3-methylbut-2-en-1-yloxy, 4,4,4-trifluorobut-2-en-1-yloxy, prop-2-yn-1-yloxy, 3-chloroprop-2-yn-1-yloxy, 3-bromoprop-2-yn-1-yloxy, but-2-yn-1-yloxy, pent-2-yn-1-yloxy, 2-fluoro-2-methylpropanoyloxy, 3,3,3-trifluoropropanoyloxy, cyclopropyl-carbonyloxy, cyclohexylcarbonyloxy, (1-chlorocyclopropyl)carbonyloxy, but-2-enoyloxy, acryloyloxy, cyanomethoxy, methylsulphonyloxy, ethylsulphonyloxy, trifluoromethylsulphonyloxy, cyclopropylsulphonyloxy, 2-methoxyethoxymethyl, allyloxymethyl, prop-2-yn-1-yloxymethyl, methylsulphonylmethyl, methylcarbonyl-aminomethyl, methylsulphonylaminomethyl, —C(=NOR⁹)R¹³, dimethylaminosulphonyl, ethylaminosulphonyl, trimethylsilylethynyl, diethylaminosulphonyl, methylamino-sulphonyl, trimethylsilyloxy, trimethylsilylprop-2-yn-1-yloxy, trifluoromethylamino, dimethylaminocarbonylamino, —C(=O)OH, —NHC(=O)H, —C(=O)NH₂, —C(=S)NR¹¹R¹² 1,1-dimethylethylcarbonylamino, chloromethylcarbonylamino, trifluoromethyl-carbonylamino, 1,1-dimethylethoxycarbonylamino, ethylcarbonylamino, 1-methylethoxycarbonylamino, trifluoromethylcarbonylamino, methylcarbonylamino, methoxycarbonylamino, ethoxycarbonylamino, iso-propoxycarbonylamino, 1-methylethylcarbonylamino, methylsulphonylamino, phenylsulphonylamino, 3-bromoprop-2-en-1-yloxy, or —L⁴Z³, $L^4$ is —C(=O)O—, —C(=O)NR³—, —OC(=O)—, —NR³C(=O)—, —OCH₂C≡C— or —OCH₂CH=CH—, R³ is hydrogen, alkyl, alkenyl, alkynyl, haloalkyl, cycloalkyl, benzyl or phenyl, R⁹ is hydrogen, alkyl, haloalkyl, benzyl or $Z^3$, R¹³ is hydrogen, methyl, ethyl, n-propyl, 1-methylethyl, n-butyl, 1,1-dimethylethyl or 2-methylpropyl, and R¹¹ and R¹² are the same or different and are hydrogen, $C_3$-$C_4$-alkenyl, $C_3$-$C_4$-alkynyl, cyano-$C_1$-$C_3$-alkyl, formyl, $C_1$-$C_3$-haloalkyl, phenyl, $C_1$-$C_3$-alkylcarbonyl, $C_3$-$C_8$-cycloalkoxy-carbonyl, $C_1$-$C_3$-alkoxycarbonyl, $C_3$-$C_4$-alkenyloxycarbonyl, $C_3$-$C_4$-alkynyloxycarbonyl, $C_1$-$C_3$-haloalkylcarbonyl, $C_3$-$C_8$-halocycloalkylcarbonyl, $C_3$-$C_8$-cycloalkoxycarbonyl, $C_3$-$C_8$-cycloalkylcarbonyl, or di($C_1$-$C_3$-alkyl)aminocarbonyl.

2. A method for controlling phytopathogenic harmful fungi, comprising applying a compound according to claim 1 to the phytopathogenic harmful fungi and/or a habitat thereof.

3. A composition for controlling phytopathogenic harmful fungi comprising a content of at least one compound according to claim 1 in addition to one or more extenders and/or surfactants.

4. A process for producing a composition for controlling phytopathogenic harmful fungi comprising mixing a compound of the formula (I) according to claim 1 with one or more extenders and/or surfactants.

5. A method for controlling phytopathogenic harmful fungi that infest transgenic plants comprising applying a compound according to claim 1 to a transgenic plant infested with a phytopathogenic harmful fungi and/or to a habitat of an infested transgenic plant.

6. A method for protecting seed from phytopathogenic harmful fungi comprising contacting the seed with a biologically effective amount of a compound according to claim 1.

7. A method according to claim 6 wherein the seed is the seed of a transgenic plant.

8. A compound of the formula (I) according to claim 1 or a salt, metal complex, or N-oxide thereof, in which
R$^1$ is phenyl substituted by at least one substituent selected from the group consisting of formyl, methoxymethoxy, 2-methoxyethoxy, allyloxy, 2-fluoroprop-2-en-1-yloxy, 2-chloroprop-2-en-1-yloxy, 3-chloroprop-2-en-1-yloxy, 2-bromoprop-2-en-1-yloxy, 2-methylprop-2-en-1-yloxy, 3,3-dichloroprop-2-en-1-yloxy, 3,3-dichloro-2-fluoroprop-2-en-1-yloxy, but-2-en-1-yloxy, but-3-en-2-yloxy, but-3-en-1-yloxy, 3-chlorobut-2-en-1-yloxy, 3-methylbut-2-en-1-yloxy, 4,4,4-trifluorobut-2-en-1-yloxy, prop-2-yn-1-yloxy, 3-chloroprop-2-yn-1-yloxy, 3-bromoprop-2-yn-1-yloxy, but-2-yn-1-yloxy, pent-2-yn-1-yloxy, 2-fluoro-2-methylpropanoyloxy, 3,3,3-trifluoropropanoyloxy, cyclopropyl-carbonyloxy, cyclohexylcarbonyloxy, (1-chlorocyclopropyl)carbonyloxy, but-2-enoyloxy, acryloyloxy, benzoyloxy, 2-fluorobenzoyloxy, 3-fluorobenzoyloxy, 4-fluorobenzoyloxy, cyanomethoxy, methylsulphonyloxy, ethylsulphonyloxy, trifluoromethylsulphonyloxy, cyclopropylsulphonyloxy, 2-methoxyethoxymethyl, allyloxymethyl, prop-2-yn-1-yloxymethyl, methylsulphonylmethyl, methylcarbonyl-aminomethyl, methylsulphonylaminomethyl, —C(=NOH)H, —C(=NOCH$_3$)H, —C(=NOCH$_2$CH$_3$)H, —C(=NOCH(CH$_3$)CH$_3$)H, —C(=NOH)CH$_3$, —C(=NOCH$_3$)CH$_3$, —C(=NOCH$_2$CH$_3$)CH$_3$, —C(=NOCH(CH$_3$)CH$_3$)CH$_3$, dimethylaminosulphonyl, —C(=O)NH$_2$, ethylaminosulphonyl, trimethylsilylethynyl, diethylaminosulphonyl, methylaminosulphonyl, trimethylsilyloxy, trimethylsilylprop-2-yn-1-yloxy, trifluoromethylamino, dimethylaminocarbonylamino, —C(=O)OH, 1,1-dimethyl-ethylcarbonylamino, chloromethylcarbonylamino, trifluoromethylcarbonylamino, 1,1-dimethylethoxycarbonylamino, ethylcarbonylamino, 1-methylethoxycarbonylamino, trifluoromethylcarbonylamino, methylcarbonylamino, methoxycarbonylamino, ethoxycarbonylamino, iso-propoxycarbonylamino, 1-methylethylcarbonylamino, methyl-sulphonylamino or phenylsulphonylamino, and 3-bromoprop-2-en-1-yloxy, and optionally further substituted with substituents selected from the group consisting of fluorine, chlorine, methyl, trifluoromethyl and methoxy.

9. A compound of the formula (I) according to claim 1 or a salt, metal complex, or N-oxide thereof, in which
A$^1$ is —C(=O)R$^{L1}$,
A$^2$ is hydrogen, chlorine, bromine, iodine, methylsulfonyloxy, trifluoromethylsulfonyloxy, phenylsulfonyloxy or 4-methylphenylsulfonyloxy, or
A$^2$ is pyrazol-1-yl which optionally contains one or two substituents, where the substituents are each independently selected from the group consisting of methyl, ethyl, chlorine, chloromethyl, dichloromethyl, bromine, fluorine, fluoromethyl, difluoromethyl and trifluoromethyl,
Y is oxygen,
R$^{L1}$ is amino, ethoxy, n-propoxy, 1-methylethoxy, n-butoxy, 1,1-dimethylethoxy, 1,2-dimethylethoxy, n-pentyloxy, n-hexyloxy, n-octyloxy, 1-ethylhexyloxy, 2-ethyl-hexyloxy, 2,2,2-trifluoroethoxy, 2-methoxyethoxy, 2-ethoxyethoxy, allyloxy, but-2-en-1-yloxy, prop-2-yn-1-yloxy, phenoxy, 2,6-dimethylphenoxy, 2,6-diisopropylphenoxy, 2,6-di-tert-butylphenoxy, benzyloxy, 4-methoxybenzyloxy or 3,4-dimethoxybenzyloxy,
X is carbon,
R$^2$ is hydrogen,
p is 0,
G is

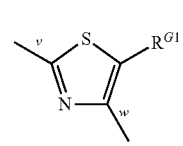

G$^1$ where the bond identified by v is bonded directly to X and the bond identified by w is bonded directly to Q,
R$^{G1}$ is hydrogen,
Q is

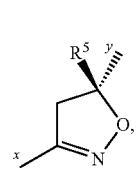

Q$^{24}$-1

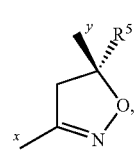

Q$^{24}$-2

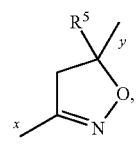

Q$^{24}$-3

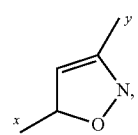

Q$^{24}$-4

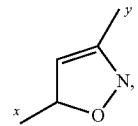

Q$^{11}$-1 or

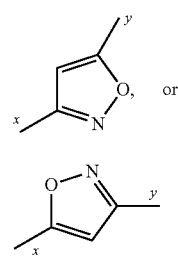

Q$^{11}$-2 where the bond identified by x is bonded directly to G and the bond identified by y is bonded directly to L$^2$,
R$^5$ is hydrogen,
L$^2$ is a direct bond,
R$^1$ is phenyl substituted by at least one substituent selected from the group consisting of formyl, methoxymethoxy, 2-methoxyethoxy, allyloxy, 2-fluoroprop-2-en-1-yloxy, 2-chloroprop-2-en-1-yloxy, 3-chloroprop-2-en-1-yloxy, 2-bromoprop-2-en-1-yloxy, 2-methylprop-2-en-1-yloxy, 3,3-dichloroprop-2-en-1-yloxy, 3,3-dichloro-2-fluoroprop-2-en-1-yloxy, but-2-en-1-yloxy, but-3-en-2-yloxy, but-3-en-1-yloxy, 3-chlorobut-2-en-1-yloxy, 3-methylbut-2-en-1-yloxy, 4,4,4-trifluorobut-2-en-1-yloxy, prop-2-yn-1-yloxy, 3-chloroprop-2-yn-1-yloxy, 3-bromoprop-2-yn-1-yloxy, but-2-yn-1-yloxy, pent-2-yn-1-yloxy, 2-fluoro-2-methylpropanoyloxy, 3,3,3-trifluoropropanoyloxy, cyclopropyl-carbonyloxy, cyclohexylcarbonyloxy, (1-chlorocyclopropyl)carbonyloxy, but-2-enoyloxy, acryloyloxy, benzoyloxy, 2-fluorobenzoyloxy, 3-fluorobenzoyloxy, 4-fluorobenzoyloxy, cyanomethoxy, methylsulphonyloxy, ethylsulphonyloxy, trifluoromethylsulphonyloxy, cyclopropylsulphonyloxy, 2-methoxyethoxymethyl, allyloxymethyl, prop-2-yn-1-yloxymethyl, methylsulphonylmethyl, methylcarbonyl-aminomethyl, methylsulphonylaminomethyl, —C(=NOH)H, —C(=NOCH$_3$)H, —C(=NOCH$_2$CH$_3$)H, —C(=NOCH(CH$_3$)CH$_3$)H, —C(=NOH)CH$_3$, —C(=NOCH$_3$)CH$_3$, —C(=NOCH$_2$CH$_3$)CH$_3$, —C(=NOCH(CH$_3$)CH$_3$)CH$_3$, dimethylaminosulphonyl, —C(=O)NH$_2$, ethylaminosulphonyl, trimethylsilylethynyl, diethylaminosulphonyl, methylaminosulphonyl, trimethylsilyloxy, trimethylsilylprop-2-yn-1-yloxy, trifluoromethylamino, dimethylaminocarbonylamino, —C(=O)OH, 1,1-dimethyl-ethylcarbonylamino, chloromethylcarbonylamino, trifluoromethylcarbonylamino, 1,1-dimethylethoxycarbonylamino, ethylcarbonylamino, 1-methylethoxycarbonylamino, trifluoromethylcarbonylamino, methylcarbonylamino, methoxycarbonylamino, ethoxy-carbonylamino, iso-propoxycarbonylamino, 1-methylethylcarbonylamino, methyl-sulphonylamino or phenylsulphonylamino, and 3-bromoprop-2-en-1-yloxy, and optionally further substituted with substituents selected from the group consisting of fluorine, chlorine, methyl, trifluoromethyl and methoxy.

10. A compound of the formula (I) according to claim 1 or a salt, metal complex, or N-oxide thereof, in which
A$^1$ is —C(=O)R$^{L1}$,
A$^2$ is hydrogen or bromine, or is pyrazol-1-yl which optionally contains one or two substituents, where the substituents on the pyrazol-1-yl are each independently selected from the group consisting of methyl, difluoromethyl and trifluoromethyl,
Y is oxygen,
R$^{L1}$ is ethoxy, 1-methylethoxy, 1,1-dimethylethoxy, 1-ethylhexyloxy, 2-methoxyethoxy, or benzyloxy,
X is carbon,
R$^2$ is hydrogen,
p is 0,
G is

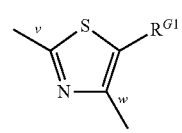

where the bond identified by v is bonded directly to X and the bond identified by w is bonded directly to Q,
R$^{G1}$ is hydrogen,
Q is

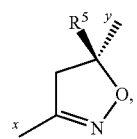

where the bond identified by x is bonded directly to G and the bond identified by y is bonded directly to L$^2$,
R$^5$ is hydrogen,
L$^2$ is a direct bond,
R$^1$ is phenyl substituted by at least one substituent selected from the group consisting of formyl, prop-2-yn-1-yloxy, and methylsulphonyloxy, and optionally further substituted with substituents selected from the group consisting of fluorine and chlorine.

11. A compound according to claim 1 having the formula

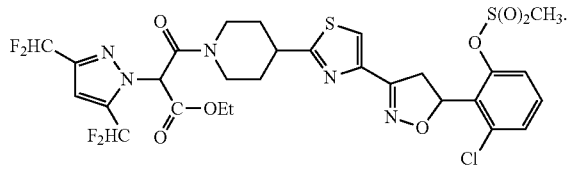

* * * * *